US007521048B2

(12) United States Patent
Gliniak et al.

(10) Patent No.: US 7,521,048 B2
(45) Date of Patent: Apr. 21, 2009

(54) TRAIL RECEPTOR-2 POLYPEPTIDES AND ANTIBODIES

(75) Inventors: Brian Gliniak, Seattle, WA (US); Xiao-Dong Yang, Palo Alto, CA (US); Sharon Wong-Madden, Bellevue, WA (US); Ian Foltz, Burnaby (CA); Xiao Feng, The Woodlands, TX (US); Alison Fitch, Vancouver (CA); Stephen Foster, Newbury Park, CA (US); Randal R. Ketchem, Snohomish, WA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 11/512,051

(22) Filed: Aug. 28, 2006

(65) Prior Publication Data

US 2007/0179086 A1 Aug. 2, 2007

Related U.S. Application Data

(60) Provisional application No. 60/713,478, filed on Aug. 31, 2005, provisional application No. 60/713,433, filed on Aug. 31, 2005.

(51) Int. Cl.
*C12P 21/08* (2006.01)
*A61K 39/00* (2006.01)

(52) U.S. Cl. .................... 424/133.1; 530/388.22
(58) Field of Classification Search ............ 424/133.1
See application file for complete search history.

(56) References Cited

U.S. PATENT DOCUMENTS

| | | | |
|---|---|---|---|
| 5,627,052 | A | 5/1997 | Schrader |
| 5,763,223 | A | 6/1998 | Wiley et al. |
| 6,313,269 | B1 | 11/2001 | Deen et al. |
| 6,342,363 | B1 | 1/2002 | Ni et al. |
| 6,342,369 | B1 | 1/2002 | Ashkenazi |
| 6,417,328 | B2 | 7/2002 | Alnemri |
| 6,433,147 | B1 | 8/2002 | Ni et al. |
| 6,461,823 | B1 | 10/2002 | Ni et al. |
| 6,872,568 | B1 | 3/2005 | Ni et al. |
| 2001/0010924 | A1 | 8/2001 | Deen et al. |
| 2002/0048785 | A1 | 4/2002 | Holtzman |
| 2002/0072091 | A1 | 6/2002 | Ni et al. |
| 2002/0098550 | A1 | 7/2002 | Ni et al. |
| 2002/0150985 | A1 | 10/2002 | Adams et al. |
| 2002/0161202 | A1 | 10/2002 | Ashkenazi et al. |
| 2003/0017161 | A1 | 1/2003 | Ashkenazi et al. |
| 2003/0157109 | A1* | 8/2003 | Corvalan et al. ......... 424/146.1 |
| 2004/0009552 | A1 | 1/2004 | Adams et al. |
| 2004/0141969 | A1* | 7/2004 | Floege et al. ............ 424/145.1 |
| 2006/0035334 | A1 | 2/2006 | Adams et al. |
| 2006/0073570 | A1 | 4/2006 | Adams et al. |
| 2006/0084147 | A1 | 4/2006 | Adams et al. |
| 2006/0115484 | A1 | 6/2006 | Adams et al. |
| 2006/0251647 | A1 | 11/2006 | Adams et al. |
| 2007/0004910 | A1* | 1/2007 | Sexton et al. .......... 530/388.26 |
| 2007/0217997 | A1* | 9/2007 | Devy et al. ............... 424/1.49 |

FOREIGN PATENT DOCUMENTS

| | | |
|---|---|---|
| EP | 0 870 827 A2 | 10/1998 |
| WO | WO 98/32856 A1 | 7/1998 |
| WO | WO 98/41629 A3 | 9/1998 |
| WO | WO 98/46643 A1 | 10/1998 |
| WO | WO 98/51793 A1 | 11/1998 |
| WO | WO 98/58062 A1 | 12/1998 |
| WO | WO 99/02653 A1 | 1/1999 |
| WO | WO 99/09165 A1 | 2/1999 |
| WO | WO 99/11791 A3 | 3/1999 |
| WO | WO 99/12963 A3 | 3/1999 |
| WO | WO 99/13078 A1 | 3/1999 |
| WO | WO 99/64461 A3 | 12/1999 |
| WO | WO 00/66156 A1 | 11/2000 |
| WO | WO 01/19861 A3 | 3/2001 |
| WO | WO 01/83560 A1 | 11/2001 |
| WO | WO 02/053727 A1 | 7/2002 |
| WO | WO 03/054216 A2 | 7/2003 |
| WO | WO 03/054216 A3 | 7/2003 |
| WO | WO 2004/106380 A2 | 12/2004 |
| WO | WO 2004/106380 A3 | 12/2004 |
| WO | WO 2005/100399 A2 | 10/2005 |
| WO | WO 2005/100399 A3 | 10/2005 |

OTHER PUBLICATIONS

Paul, Fundamental Immunology, 3rd Edition, 1993, pp. 292-295, under the heading "Fv Structure and Diversity in Three Dimensions".*
MacCallum et al. (J. Mol. Biol. (1996) 262:732-745).*
Pascalis et al. The Journal of Immunology (2002) 169, 3076-3084.*
Casset et al. (2003) BBRC 307, 198-205.*
Vajdos et al. ((2002) J. Mol. Biol. 320, 415-428).*
Holm et al (2007) Mol. Immunol. 44: 1075-1084.*
Chen et al. J. Mol. Bio. (1999) 293, 865-881.*
Wu et al. J. Mol. Biol. (1999) 294, 151-162.*
Smith-Gill et al. (J. Immunol. 139:4135-4144 (1987)).*
Kumar et al. (J. Biol. Chem. 275:35129-35136 (2000)).*

(Continued)

*Primary Examiner*—David J. Blanchard
*Assistant Examiner*—Lynn Bristol
(74) *Attorney, Agent, or Firm*—Rebecca B. Scarr; David B. Ran

(57) ABSTRACT

Polypeptides are provided. Antibodies or antigen binding domains are provided which bind such polypeptides. Also provided are methods of obtaining an antibody that binds tumor necrosis factor (TNF)-related apoptosis-inducing ligand ("TRAIL") Receptor-2 (TR-2) comprising administering at least one of such polypeptides to an animal and obtaining an antibody that binds TR-2 from the animal. Antibodies reactive with TR-2 are provided. Also provided are cells producing antibodies reactive with TR-2, pharmaceutical compositions comprising antibodies reactive with TR-2, methods using antibodies reactive with TR-2, and kits comprising antibodies reactive with TR-2. Also provided are methods of decreasing or preventing binding of an antibody to TR-2 by administering such a polypeptide.

37 Claims, 29 Drawing Sheets

OTHER PUBLICATIONS

Song et al. (Biochem Biophys Res Comm 268:390-394 (2000)).*
BCPCP Meeting, USPTO Presentation: "Enablement Issues in the Examination of Antibodies" (Jun. 13, 2007) (pp. 1-28).*
U.S. Patent and Trademark Office, Before the Board of Patent Appeals and Interferences: *Human Genome Sciences, Inc.* v. *Immunex Corp.*, Patent Interference No. 105,240 (RES), Decision—Motions—Bd.R. 125(a), Paper 133, filed Jul. 26, 2007 (73 pages).
U.S. Patent and Trademark Office, Before the Board of Patent Appeals and Interferences: *Human Genome Sciences, Inc.* v. *Immunex Corp.*, Patent Interference No. 105,240 (RES), Interference File Contents as of Sep. 11, 2008 (9 pages).
U.S. Patent and Trademark Office, Before the Board of Patent Appeals and Interferences: *Human Genome Sciences, Inc.* v. *Immunex Corp.*, Patent Interference No. 105,381 (RES); Decision—Order to Show Cause, Paper 134, filed Jul. 27, 2007 (13 pages).
U.S. Patent and Trademark Office, Before the Board of Patent Appeals and Interferences: *Human Genome Sciences, Inc.* v. *Immunex Corp.*, Patent Interference No. 105,381 (RES); Interference File Contents as of Sep. 11, 2008 (8 pages).
Civil Docket for Case # : 1:07-cv-00780-SLR from the U.S. District Court District of Delaware (Wilmington), *Human Genome Sciences Inc.* v. *Immunex Corp et al.*, docket as of Sep. 10, 2008 (5 pages).
Civil Docket for Case # : 1:07-cv-00526-SLR-MPT from the U.S. District Court District of Delaware (Wilmington), *Human Genome Sciences Inc.* v. *Amgen Inc. et al.*, docket as of Sep. 10, 2008 (5 pages).
Civil Docket for Case # : 1:08-cv-00166-SLR from the U.S. District Court District of Delaware (Wilmington), *Human Genome Sciences Inc.* v. *Genentech Inc.*, docket as of Sep. 11, 2008 (3 pages).
U.S. Patent and Trademark Office, Before the Board of Patent Appeals and Interferences: *Human Genome Sciences, Inc.* v. *Genentech, Inc.*, Patent Interference No. 105,361 (RES), Decision on Motions, filed Nov. 28, 2007 (28 pages).
U.S. Patent and Trademark Office, Before the Board of Patent Appeals and Interferences: *Human Genome Sciences, Inc.* v. *Genentech, Inc.*, Patent Interference No. 105,361 (RES), Order—Miscellaneous—Bd.R. 104(a), filed Feb. 20, 2008 (4 pages).
U.S. Patent and Trademark Office, Before the Board of Patent Appeals and Interferences: *Human Genome Sciences, Inc.* v. *Genentech, Inc.*, Patent Interference No. 105,361 (RES), Judgment—Request for Adverse—Bd.R. 127(b), filed Feb. 20, 2008 (4 pages).
U.S. Patent and Trademark Office, Before the Board of Patent Appeals and Interferences: *Human Genome Sciences, Inc.* v. *Genentech, Inc.*, Patent Interference No. 105,361 (RES), Interference File Contents as of Sep. 11, 2008 (7 pages).
PCT Notification Concerning Transmittal of International Preliminary Report on Patentability, International Preliminary Report on Patentability, and Written Opinion of the International Searching Authority, mailed Mar. 13, 2008, for International Application No. PCT/US2006/033736.
U.S. Appl. No. 60/041,230, filed Mar. 14, 1997, Deen et al.
U.S. Appl. No. 60/040,846, filed Mar. 17, 1997, Ni et al.
U.S. Appl. No. 08/843,652, filed Apr. 16, 1997, Holtzman.
U.S. Appl. No. 08/853,684, filed May 9, 1997, Deen et al.
U.S. Appl. No. 08/857,216, filed May 15, 1997, Ashkenazi.
U.S. Appl. No. 60/054,021, filed Jul. 29, 1997, Ni et al.
U.S. Appl. No. 60/055,906, filed Aug. 15, 1997, Alnemri.
U.S. Appl. No. 08/916,625, filed Aug. 22, 1997, Deen et al.
U.S. Appl. No. 60/058,631, filed Sep. 12, 1997, Tschopp.
U.S. Appl. No. 09/020,746, filed Feb. 9, 1998, Ashkenazi et al.
U.S. Appl. No. 60/084,422, filed May 6, 1998, Tschopp et al.
U.S. Appl. No. 60/037,829, filed Feb. 5, 1997, Ni et al.
U.S. Appl. No. 09/042,583, filed Mar. 17, 1998, Ni et al.
U.S. Appl. No. 60/132,498, filed May 4, 1999, Ni et al.
U.S. Appl. No. 60/133,238, filed May 7, 1999, Ni et al.
U.S. Appl. No. 60/148,939, filed Aug. 13, 1999, Ni et al.
U.S. Appl. No. 11/483,978, filed Jul. 11, 2006, Adams.
Bowie et al., "Deciphering the Message in Protein Sequences: Tolerance to Amino Acid Substitutions," Science, 247:1306-1310, 1990.
Cross et al., "Purification of CpG islands using a methylated DNA binding column," Nature Genetics, 6:236-244, 1994.
Database record for Genbank Accession No. AA223122, "zr06g05.r1, Stratagene NT2 neuronal precursor 937230 *Homo sapiens* cDNA Clone 650744 5' mRNA Sequence," Submitted by R.K. Wilson Feb. 19, 1997.
Database record for GenBank Accession No. AA232440, "zr27h05.r1, Stratagene NT2 neuronal precursor 937230 *Homo sapiens* cDNA Clone 664665 5' mRNA Sequence," Submitted by R. K. Wilson Feb. 28, 1997.
Database record for GenBank Accession No. Z66083, "*H. sapiens* CpG Island DNA Genomic MseI Fragment, Clone 75a7, Reverse Read cpg75a7.rt1a," Locus HS75A7R, Submitted by Cross et al. 1994 and Macdonald et al. Oct. 1995.
Degli-Esposti, et al., "Cloning and Characterization of TRAIL-R3, a Novel Member of the Emerging TRAIL Receptor Family," J. Exp. Med. 186(7); 1165-1170, 1997.
George et al., "12. Current Methods in Sequence Comparison and Analysis," from *Macromolecular Sequencing and Synthesis, Selected Methods and Applications*, (David H. Schlesinger, ed.), Alan R. Liss, Inc., New York, pp. 127-149, 1988.
Pan et al., "The Receptor for the Cytotoxic Ligand TRAIL," Science 276:111-113, 1997.
Schneider et al., "Characterization of two receptors for TRAIL," FEBS Letters 416(3):329-334, 1997.
Screaton et al., "TRICK2, a new alternatively spliced receptor that transduces the cytotoxic signal from TRAIL," Current Biology 7(9): 693-696, 1997.
Shatzman et al., "[69] Expression, Identification, and Characterization of Recombinant Gene Products in *Escherichia coli*," from *Methods in Enzymology* vol. 152: *Guide to Molecular Cloning Techniques*, (Berger et al., eds.), Academic Press, Inc., New York, pp. 661-673, 1987.
Walczak et al., "TRAIL-R2: a novel apoptosis-mediating receptor for TRAIL," EMBO J. 16(17); 5386-5397, 1997.
White et al., *Principles of Biochemistry, Sixth Edition*, pp. 155-158, McGraw-Hill, Inc., New York, 1978.
Wiley et al., "Identification and Characterization of a New Member of the TNF Family that Induces Apoptosis," Immunity 3: 673-682, 1995.
Almasan et al., "Apo2L/TRAIL: apoptosis signaling, biology, and potential for cancer therapy," *Cytokine & Growth Factor Reviews*, 14: 337-348 (2003).
Babcook et al., "A novel strategy for generating monoclonal antibodies from single, isolated lymphocytes producing antibodies of defined specificities," *Proc. Natl. Acad. Sci. USA*, 93:7843-7848 (1996).
Daigle et al., "Alternative functions for TRAIL receptors in eosinophils and neutrophils," *Swiss Med. Wkly*, 131:231-237 (2001).
Griffith et al., "Functional analysis of TRAIL receptors using monoclonal antibodies," *J. of Immun.*, 162:2597-2605 (1999).
Hymowitz et al., "Triggering cell death: the crystal structure of Apo2L/TRAIL in a complex with Death Receptor 5," *Mol. Cell*, 4:563-571 (1999).
Ichikawa et al., "Tumoricidal activity of a novel anti-human DR5 monoclonal antibody without hepatocyte cytotoxicity," *Nat. Med.*, 7:954-960 (2001).
Spierings et al., "Tissue distribution of the death ligand TRAIL and its receptors," *J. Histochem. Cytochem.*, 52: 821-831 (2004).
Walczak et al., "TRAIL-R2: a novel apoptosis-mediating receptor for TRAIL," *The EMBO Journal*, 16:5386-5397(1997).
Database Uniprot, "Tumor necrosis factor receptor superfamily member 10B precursor (death receptor inducing ligand receptor 2) (TRAIL receptor 2) (TRAIL-R2) (CD262 antigen)," Database accession No. O14763 (2001).
Database Geneseq, "Human anti-TNFa antibody light chain variable region cDNA SEQ ID No. 139," EBI acession No. GSN: ADP22233 (2004).
Database Geneseq, "Human anti-TNFa antibody light chain variable region SEQ ID No. 140," EBI acession No. GSN: ADP22234 (2004).

Database Geneseq, "Anti-human PDGF-D antibody light chain protein sequence," EBI acession No. GSP: ADK18608 (2004).

Database Geneseq, "Anti-human PDGF-D antibody light chain gene sequence," EBI acession No. GSP: ADK18650 (2004).

Database Geneseq, "Human mAb 1.33 light chain variable region encoding cDNA SEQ ID No. 43," EBI acession No. GSP: ADL25433 (2004).

Database Geneseq, "Human mAb 1.33 light chain variable protein region SEQ ID No. 44," EBI acession No. GSN: ADL25434 (2004).

PCT Notification of Transmittal of the International Search Report and the Written Opinion of the Internaional Searching Authority, or the Declaration, mailed Apr. 2, 2007, in International Application No. PCT/US2006/033763.

* cited by examiner

FIGURE 1

Group 1 Immunized XenoMice

| Mouse ID | Day 18 bleed (after 4 inj.) | Day 28 bleed (after 6 inj.) | Day 46 fusion (after 10 inj.) |
|---|---|---|---|
| | Reactivity to TR-2 Titers via hIgG | | |
| M560-1 | 60 | 1,000 | - |
| M560-2 | 24,000 | 40,000 | 73,000 |
| M560-3 | 400 | 12,000 | 80,000 |
| M560-4 | 2,500 | 16,000 | 80,000 |
| M560-5 | 200 | 16,000 | 150,000 |
| M560-6 | 1,200 | 50,000 | 300,000 |
| M560-7 | <100 | 1,000 | - |
| NC | 40 | 50 | 210 |
| PC | 4,100 | 3,500 | 24,000 |

Group 2 Immunized XenoMice

| Mouse ID | Day 14 bleed (after 4 inj.) | Day 23 bleed (after 6 inj.) |
|---|---|---|
| | Reactivity to TR-2 Titers via hIgG | |
| L475-6 | 75 | 350 |
| L568-7 | 50 | 175 |
| L569-7 | 50 | <100 |
| M050-4 | 50 | 25 |
| M057-6 | 50 | 40 |
| M184-3 | 50 | 110 |
| M230-5 | 50 | 25 |
| M365-4 | 50 | <100 |
| NC | 50 | <100 |
| PC | 3,500 | 11,000 |

Group 3 Immunized XenoMice

| Mouse ID | Day 21 bleed (after 4 inj.) |
|---|---|
| | Reactivity to TR-2 Titers via hIgG |
| M712-1 | 75 |
| M712-2 | 2,400 |
| M712-3 | 800 |
| M712-4 | 2,700 |
| M712-5 | 1,800 |
| M712-6 | 290 |
| M712-7 | 7,500 |
| M712-8 | 800 |
| NC | <100 |
| PC | 24,000 |

Group 5 Immunized XenoMice

| Mouse ID | Day 37 bleed (after 3 inj.) |
|---|---|
| | Reactivity to TR-2 Titers via hIgG |
| M564-1 | 100 |
| M564-2 | 100,000 |
| M564-3 | 200 |
| M564-4 | 60 |
| M564-5 | 60 |
| NC | 210 |
| PC | 24,000 |

Group 4 Immunized XenoMice

| Mouse ID | Day 37 bleed (after 3 inj.) |
|---|---|
| | Reactivity to TR-2 Titers via hIgG |
| M563-1 | 300 |
| M563-2 | 100 |
| M563-3 | 200 |
| M563-4 | 250,000 |
| M563-5 | 700 |
| M563-6 | <100 |
| M563-7 | 120 |
| M563-8 | 130 |
| M563-9 | <100 |
| M563-10 | <100 |
| NC | 225 |
| PC | 36,000 |

Negative Control (NC)
bleed from mouse
not immunized with
TR-2

Positive Control (PC)
TR-2+ 1:50 bleed
from group 1 mouse

FIGURE 2

ANTIBODY A

Nucleotide sequence of the heavy chain variable region:
CAGGTGCAGCTGGTGCAGTCTGGGGCTGAGGTGAAGAAGCCTGGGGCCTC
AGTGAAGGTCTCCTGCAAGGCTTCTGGATACACCTTCACCAGTTATGATAT
CAACTGGGTGCGACAGGCCACTGGACAAGGGCTTGAGTGGATGGGATGG
ATGAACCCTAACAGTGATAACACAGGCTATGCACAGAAGTTCCAGGGCAG
AGTCACCATGACCAGGAACACCTCCATAAGCACAGCCTACATGGAGTTGA
GCAGCCTGAGATCTGAGGACACGGCCGTGTATTACTGTGCGAGATGGAAT
CACTATGGTTCGGGGAGTCATTTTGACTACTGGGGCCAGGGAACCCTGGT
CACCGTCTCCTCA (SEQ ID NO: 1)

Protein sequence of the heavy chain variable region:
QVQLVQSGAEVKKPGASVKVSCKASGYTFTSYDINWVRQATGQGLEWMGW
MNPNSDNTGYAQKFQGRVTMTRNTSISTAYMELSSLRSEDTAVYYCARWNH
YGSGSHFDYWGQGTLVTVSS (SEQ ID NO: 2)

Nucleotide sequence of the light chain variable region:
GACATCCAGATGACCCAGTCTCCATCCTCCCTGTCTGCATCTGTAGGAGAC
AGAGTCACCATCACTTGCCGGGCAAGTCAGAGCATTAGCATTTATTTAAA
TTGGTATCAGCAGAAACCAGGGAAAGCCCCTAAGCTCCTGATCTATGCTG
CATCCAGTTTGCAAAGTGGGGTCCCATTAAGGTTCAGTGGCAGTGGATCT
GGGACAGATTTCACTCTCACCATCAGCAGTCTGCAACCTGAAGATATTGC
AACTTACTACTGTCAACAGAGTTACAAAACCCCGCTCACTTTCGGCGGAG
GGACCAAGGTGGAGATCAAA (SEQ ID NO: 35)

Protein sequence of the light chain variable region:
DIQMTQSPSSLSASVGDRVTITCRASQSISIYLNWYQQKPGKAPKLLIYAASSL
QSGVPLRFSGSGSGTDFTLTISSLQPEDIATYYCQQSYKTPLTFGGGTKVEIK
(SEQ ID NO: 36)

FIGURE 3

ANTIBODY B

Nucleotide sequence of the heavy chain variable region:
CAGGTGCAGCTGCAGGAGTCGGGCCCAGGACTGGTGAAGCCTTCACAGAC
CCTGTCCCTCACCTGCACTGTCTCTGGTGGCTCCATCAGCAGTGGTGGTCA
CTACTGGAGCTGGATCCGCCAGCACCCAGGGAAGGGCCTGGAGTGGATTG
GGTACATCTATTACAGTGGGAGCACCTACTACAACCCGTCCCTCAAGAGT
CGAGTTACCATATCAGTAGACACGTCTAAGAACCAGTTCTCCCTGAAGCT
GAGCTCTGTGACTGCCGCGGACACGGCCGTGTATTATTGTGCGAGAGATG
ACAGCAGTGGCTGGGGTTTTGACTACTGGGGCCAGGGAATCCTGGTCACC
GTCTCCTCA (SEQ ID NO: 3)

Protein sequence of the heavy chain variable region:
QVQLQESGPGLVKPSQTLSLTCTVSGGSISSGGHYWSWIRQHPGKGLEWIGYI
YYSGSTYYNPSLKSRVTISVDTSKNQFSLKLSSVTAADTAVYYCARDDSSGW
GFDYWGQGILVTVSS (SEQ ID NO: 4)

Nucleotide sequence of the light chain variable region:
GACATCCAGATGACCCAGTCTCCATCCTCCCTGTCTGCATCTGTTGGAGAC
AGAGTCACCATCACTTGCCGGGCAAGTCAGGGCCTTAGAAATGATTTAGG
CTGGTTTCAGCAGAAACCAGGGAAAGTCACTAAGCGCCTGATCTATGCTG
CATCCAGTTTGCAAAGAGGGGTCCCATCAAGGTTCAGCGGCAGTGGATCT
GGGACAGAATTCACTCTCACAATCAGCAGCCTGCAGCCTGAAGATTTTGC
AACTTATTACTGTCTACAGCATTATAGTTTCCCGTGGACGTTCGGCCAAGG
GACCAAGGTGGAGATCAAA (SEQ ID NO: 37)

Protein sequence of the light chain variable region:
DIQMTQSPSSLSASVGDRVTITCRASQGLRNDLGWFQQKPGKVTKRLIYAASS
LQRGVPSRFSGSGSGTEFTLTISSLQPEDFATYYCLQHYSFPWTFGQGTKVEIK
(SEQ ID NO: 38)

FIGURE 4

ANTIBODY C

Nucleotide sequence of the heavy chain variable region:
CAGGTGCAGCTGCAGGAGTCGGGCCCAGGACTGGTGAAGCCTTCACAGAC
CCTGTCCCTCACCTGCACTGTCTCTGGTGGCTCCATCAGCAGTGGTGGTCA
CTACTGGAGCTGGATCCGCCAGCACCCAGGGAAGGGCCTGGAGTGGATTG
GGTACATCTATTACAGTGGGAGCGCCTACTACAACCCGTCCCTCAAGAGT
CGAGTTACCATATCAGTAGACACGTCTAAGAACCAGTTCTCCCTGAAGCT
GAGCTCTGTGACTGCCGCGGACACGGCCGTGTATTACTGTGCGAGAGATG
ACAGCAGTGGCTGGGGTTTTGACTACTGGGGCCAGGGAATCCTGGTCACC
GTCTCCTCA (SEQ ID NO: 5)

Protein sequence of the heavy chain variable region:
QVQLQESGPGLVKPSQTLSLTCTVSGGSISSGGHYWSWIRQHPGKGLEWIGYI
YYSGSAYYNPSLKSRVTISVDTSKNQFSLKLSSVTAADTAVYYCARDDSSGW
GFDYWGQGILVTVSS (SEQ ID NO: 6)

Nucleotide sequence of the light chain variable region:
GACATCCAGATGACCCAGTCTCCATCCTCCCTGTCTGCATCTGTTGGAGAC
AGAGTCACCATCACTTGCCGGGCAAGTCAGGGCCTTAGAAATGATTTAGG
CTGGTTTCAGCAGAAACCAGGGAAAGCCCCTAAGCGCCTGATCTATGCTG
CATCCAGTTTGCAAAGAGGGGTCCCATCAAGGTTCAGCGGCAGTGGATCT
GGGACAGAATTCACTCTCACAATCAGCAGCCTGCAGCCTGAAGATTTTAC
AACTTATTTCTGTCTACAGCATAATAGTTTCCCGTGGACGTTCGGCCAAGG
GACCAAGGTGGAAATCAAA (SEQ ID NO: 39)

Protein sequence of the light chain variable region:
DIQMTQSPSSLSASVGDRVTITCRASQGLRNDLGWFQQKPGKAPKRLIYAASS
LQRGVPSRFSGSGSGTEFTLTISSLQPEDFTTYFCLQHNSFPWTFGQGTKVEIK
(SEQ ID NO: 40)

FIGURE 5

ANTIBODY D

Nucleotide sequence of the heavy chain variable region:
CAGGTGCAGCTGCAGGAGTCGGGCCCAGGACTGGTGAAGCCTTCACAGAC
CCTGTCCCTCACCTGCACTGTCTCTGGTGGCTCCATCAGCAGTGGTGGTCA
CTACTGGAGCTGGATCCGCCAGCACCCAGGGAAGGGCCTGGAGTGGATTG
GGTACATCTATTACAGTGGGAGCGCCTACTACAACCCGTCCCTCAAGAGT
CGAGTTACCATATCAGTAGACACGTCTAAGAACCAGTTCTCCCTGAAGCT
GAGCTCTGTGACTGCCGCGGACACGGCCGTGTATTACTGTGCGAGAGATG
ACAGCAGTGGCTGGGGTTTTGACTACTGGGGCCAGGGAATCCTGGTCACC
GTCTCCTCA (SEQ ID NO: 7)

Protein sequence of the heavy chain variable region:
QVQLQESGPGLVKPSQTLSLTCTVSGGSISSGGHYWSWIRQHPGKGLEWIGYI
YYSGSAYYNPSLKSRVTISVDTSKNQFSLKLSSVTAADTAVYYCARDDSSGW
GFDYWGQGILVTVSS (SEQ ID NO: 8)

Nucleotide sequence of the light chain variable region:
GACATCCAGATGACCCAGTCTCCATCCTCCCTGTCTGCATCTGTTGGAGAC
AGAGTCACCATCACTTGCCGGGCAAGTCAGGGCCTTAGAAATGATTTAGG
CTGGTTTCAGCAGAAACCAGGGAAAGCCCCTAAGCGCCTGATCTATGCTG
CATCCAGTTTGCAAAGAGGGGTCCCATCAAGGTTCAGCGGCAGTGGATCT
GGGACAGAATTCACTCTCACAATCAGCAGCCTGCAGCCTGAAGATTTTAC
AACTTATTTCTGTCTACAGCATAATAGTTTCCCGTGGACGTTCGGCCAAGG
GACCAAGGTGGAAATCAAA (SEQ ID NO: 41)

Protein sequence of the light chain variable region:
DIQMTQSPSSLSASVGDRVTITCRASQGLRNDLGWFQQKPGKAPKRLIYAASS
LQRGVPSRFSGSGSGTEFTLTISSLQPEDFTTYFCLQHNSFPWTFGQGTKVEIK
(SEQ ID NO: 42)

FIGURE 6

ANTIBODY E

Nucleotide sequence of the heavy chain variable region:
CAGGTGCAGCTGGTGGAGTCTGGGGGAGGCTTGGTCAAGCCTGGAGGGTC
CCTGAGACTCTCCTGTGCAGCCTCTGGATTCACCTTCAGTGACTACTACAT
GAACTGGATCCGCCAGGCTCCAGGGAAGGGACTGGAGTGGGTTTCACACA
TTAGTAGTAGTGGTAGTATCTTAGACTACGCAGACTCTGTGAAGGGCCGA
TTCACCATCTCCAGGGACAACGCCAAGAACTCACTGTATCTGCAAATGAA
CAGCCTGAGAGTCGAGGACACGGCCGTGTATTACTGTGCGAGAGATGGGG
CTGCAGCTGGTACGGATGCTTTTGATCTCTGGGGCCAAGGGACAATGGTC
ACCGTCTCTTCA (SEQ ID NO: 9)

Protein sequence of the heavy chain variable region:
QVQLVESGGGLVKPGGSLRLSCAASGFTFSDYYMNWIRQAPGKGLEWVSHIS
SSGSILDYADSVKGRFTISRDNAKNSLYLQMNSLRVEDTAVYYCARDGAAAG
TDAFDLWGQGTMVTVSS (SEQ ID NO: 10)

Nucleotide sequence of the light chain variable region:
GACATCCAGATGACCCAGTCTCCATCCTCCCTGTCTGCATCTGTAGGAGAC
AGAGTCACCATCACTTGCCGGTCAAGTCAGAGCATTAGTAACTATATAAA
TTGGTATCAACAGAGACCAGGGAAAGCCCCGAACCTCCTGATCCATGATG
TATCCAGTTTCCAAAGTGCGGTCCCATCAAGGTTCAGTCGCAGTGGATCTG
GGACAGTTTTCACTCTCACCATCAGCAGTCTGCAACCTGAAGATTTTGCAA
CTTACTTCTGTCAACAGACTTACATTACCCCATTCACTTTCGGCCCTGGGA
CCAAAGTGGATATCAAA (SEQ ID NO: 43)

Protein sequence of the light chain variable region:
DIQMTQSPSSLSASVGDRVTITCRSSQSISNYINWYQQRPGKAPNLLIHDVSSF
QSAVPSRFSRSGSGTVFTLTISSLQPEDFATYFCQQTYITPFTFGPGTKVDIK
(SEQ ID NO: 44)

FIGURE 7

ANTIBODY F

Nucleotide sequence of the heavy chain variable region:
CAGGTGCAGCTGGTGGAGTCTGGGGGAGGCGTGGTCCAGCCTGGGAGGTC
CCTGAGACTCTCCTGTGCAGCGTCTGGATTCACCTTCAGTTACTATGGCAT
ACACTGGGTCCGCCAGGCTCCAGGCAAGGGGCTGGAGTGGGTGGCAGTTA
TATGGTATGATGGAAGTAATAAATACTATGCAGACTCCGTGAAGGGCCGA
TTCACCATCTCCAGAGACAATTCCAAGAACACGCTGTATCTGCAAATGAA
CAGCCTGAGAGCCGAGGACACGGCTGTGTATTACTGTGCGAGAGGGAGGT
ATAGCAGCTCGTCCTGGTGGTACTTCGATCTCTGGGGCCGTGGCACCCTGG
TCACTGTCTCCTCA (SEQ ID NO: 11)

Protein sequence of the heavy chain variable region:
QVQLVESGGGVVQPGRSLRLSCAASGFTFSYYGIHWVRQAPGKGLEWVAVI
WYDGSNKYYADSVKGRFTISRDNSKNTLYLQMNSLRAEDTAVYYCARGRYS
SSSWWYFDLWGRGTLVTVSS (SEQ ID NO: 12)

Nucleotide sequence of the light chain variable region:
GACATCCAGATGACCCAGTCTCCATCCTCCCTGTCTGCATCTGTAGGAGAC
AGAGTCACCATCACTTGCCGGGCGAGTCAGGGCATTAGCAATTATTTAGC
CTGGTATCAGCAGAAACCAGGGAAAGTTCCTAAGCTCCTGATCTATGCTG
CATCCACTTTGCAATCAGGGGTCCCATCTCGGTTCAGTGGCAGTGGATCTG
GGACAGATTTCACTCTCACCATCAGCAGCCTGCAGCCTGAAGATGTTGCA
ACTTATTACTGTCAAAAGTATAACAGTGCCCCGCTCACTTTCGGCGGAGG
GACCAAGGTGGAGATCAAA (SEQ ID NO: 45)

Protein sequence of the light chain variable region:
DIQMTQSPSSLSASVGDRVTITCRASQGISNYLAWYQQKPGKVPKLLIYAAST
LQSGVPSRFSGSGSGTDFTLTISSLQPEDVATYYCQKYNSAPLTFGGGTKVEIK
(SEQ ID NO: 46)

FIGURE 8

ANTIBODY G

Nucleotide sequence of the heavy chain variable region:
CAGGTGCAGGCTGAGCAGTCGGGCCCAGGACTGGTGAAGCCTTCGGAGAC
CCTGTCCCTCACCTGCACTGTCTCTGGTGGCTCCATCAGTAATTACTACTG
GAGCTGGATCCGGCAGCCCCAGGGAAGGGACTGGAGTGGATTGGGTAT
ATCTATTACAGTGGGAGCACCAAGTACAACCCCTCCCTCAAGAGTCGAGT
CACCATATCAGTAGACACGTCCAAGAACCAGTTCTCCCTGAAGCTAACCT
CTGTGACCACTGCGGACACGGCCGTGTATTACTGTGCGAGAGACTCCCCT
CGTGGATTTAGTGGCTACGAGGCTTTTGACTCCTGGGGCCAGGGAACCCT
GGTCACCGTCTCCTCA (SEQ ID NO: 13)

Protein sequence of the heavy chain variable region:
QVQAEQSGPGLVKPSETLSLTCTVSGGSISNYYWSWIRQPPGKGLEWIGYIYY
SGSTKYNPSLKSRVTISVDTSKNQFSLKLTSVTTADTAVYYCARDSPRGFSGY
EAFDSWGQGTLVTVSS (SEQ ID NO: 14)

Nucleotide sequence of the light chain variable region:
GACATCGTGATGACCCAGTCTCCAGACTCCCTGGCTGTGTCTCTGGGCGAG
AGGGCCACCATCAACTGCAAGTCCAGCCAGAGTGTTTTATACAGGTCCAA
CAATAAGATCTACTTAGCTTGGTACCAGCAGAAACCAGGACAGCCTCCTA
AGCTGCTCATTTACTGGGCATCGACCCGGGAATCCGGGGTCCCTGACCGA
TTCAGTGGCAGCGGGTCTGGGACAGATTTCACTCTCACCATCAGCAGCCT
GCTGGCTGAAGATGTGGCAGTTTATTACTGTCAGCAATATTATAGTACTCC
ATTCACTTTCGGCCCTGGGACCAAAGTGGATATCAAA (SEQ ID NO: 47)

Protein sequence of the light chain variable region:
DIVMTQSPDSLAVSLGERATINCKSSQSVLYRSNNKIYLAWYQQKPGQPPKLL
IYWASTRESGVPDRFSGSGSGTDFTLTISSLLAEDVAVYYCQQYYSTPFTFGPG
TKVDIK (SEQ ID NO: 48)

FIGURE 9

ANTIBODY H

Nucleotide sequence of the heavy chain variable region:
CAGGTGCAGCTGCAGGAGTCGGGCCCAGGACTGGTGAAGCCTTCACAGAC
CCTGTCCCTCACCTGCACTGTCTCTGGTGGCTCCATCAGCAGTGATAATTA
CTACTGGAGCTGGATCCGCCAGCACCCAGGGAAGGGCCTGGAGTGGATTG
GGTACATCTATTACAGTGGGAGCACCTACTACAACCCGTCCCTCAAGAGT
CGAGTTACCATATCAGTAGACACGTCTAAGAACCAGTTCTCCCTGAAGCT
GAGCTCTGTGACTGCCGCGGACACGGCCGTGTATTACTGTGCGAGAGGAG
TTAACTGGAACTTTCTTTTTGATATCTGGGGCCAAGGGACAATGGTCACCG
TCTCTTCA (SEQ ID NO: 15)

Protein sequence of the heavy chain variable region:
QVQLQESGPGLVKPSQTLSLTCTVSGGSISSDNYYWSWIRQHPGKGLEWIGYI
YYSGSTYYNPSLKSRVTISVDTSKNQFSLKLSSVTAADTAVYYCARGVNWNF
LFDIWGQGTMVTVSS (SEQ ID NO: 16)

Nucleotide sequence of the light chain variable region:
GATATTGTGATGACTCAGTCTCCACTCTCCCTGCCCGTCACCCCTGGAGAG
CCGGCCTCCATCTCCTGCAGGTCTAGTCAGAGCCTCCTGCGTCGTAATGGA
TACAACTATTTGGATTGGTACCTGCAGAAGCCAGGGCAGTCTCCACAACT
CCTGATCTATTTGGGTTCTAATCGGGCCTCCGGGGTCCCAGACAGGTTCAG
TGGCAGTGGATCAGGCACAGATTTTACACTGAAAATCAGCAGAGTGGAGG
CTGAGGATGTTGGGGTTTATTACTGCATGCAAGCTCTACAAACTCCGCTCA
CTTTCGGCGGAGGGACCGAGGTGGAGATCAAA (SEQ ID NO: 49)

Protein sequence of the light chain variable region:
DIVMTQSPLSLPVTPGEPASISCRSSQSLLRRNGYNYLDWYLQKPGQSPQLLIY
LGSNRASGVPDRFSGSGSGTDFTLKISRVEAEDVGVYYCMQALQTPLTFGGG
TEVEIK (SEQ ID NO: 50)

FIGURE 10

ANTIBODY I

Nucleotide sequence of the heavy chain variable region:
CAGGTGCAGCTGGTGGAGTCTGGGGGAGGCTTGGTCAAGCCTGGAGGGTC
CCTGAGACTCTCCTGTGCAGCCTCTGGATTCACCTTCAGTGACTACTACAT
GAGCTGGATCCGCCAGGCTCCAGGGAAGGGGCTGGAGTGGGTTTCATACA
TTAGTAGAAGTGGTAGTACCATATACTACGCAGACTCTGTGAAGGGCCGA
TTCACCATCTCCAGGGACAACGCCAAGAACTCACTGTATCTGCAAATGAA
CAGCCTGAGAGCCGAGGACACGGCCGTGTATTACTGTGCGAGATCTTTAG
GCGGTATGGACGTCTGGGGCCAAGGGACCACGGTCACCGTCTCCTCA
(SEQ ID NO: 17)

Protein sequence of the heavy chain variable region:
QVQLVESGGGLVKPGGSLRLSCAASGFTFSDYYMSWIRQAPGKGLEWVSYIS
RSGSTIYYADSVKGRFTISRDNAKNSLYLQMNSLRAEDTAVYYCARSLGGMD
VWGQGTTVTVSS (SEQ ID NO: 18)

Nucleotide sequence of the light chain variable region:
GACATCGTGATGACCCAGTTTCCAGACTCCCTGGCTGTGTCTCTGGGCGAG
AGGGCCACCATCAACTGCAAGTCCAGCCAGAGTGTTTTACACAGCTCCAA
CAATAAGAACTACTTAACTTGGTACCAGCTGAAACCAGGACAGCCTCCTA
AGTTGCTCATTTACTGGGCATCTACCCGGGAATCCGGGGTCCCTGACCGAT
TCAGTGGCAGCGGGTCTGGGACAGATTTCACTCTCACCATCAGCAGCCTG
CAGGCTGAAGATGTGGCAGTTTATTACTGTCACCAATATTATAGTACTCCG
TCCAGTTTTGGCCAGGGGACCAAGCTGGAGATCAAA (SEQ ID NO: 51)

Protein sequence of the light chain variable region:
DIVMTQFPDSLAVSLGERATINCKSSQSVLHSSNNKNYLTWYQLKPGQPPKLL
IYWASTRESGVPDRFSGSGSGTDFTLTISSLQAEDVAVYYCHQYYSTPSSFGQ
GTKLEIK (SEQ ID NO: 52)

FIGURE 11

ANTIBODY J

Nucleotide sequence of the heavy chain variable region:
CAGGTGCAGCTGGTGGAGTCTGGGGGAGGCGTGGTCCAGCCTGGGAGGTC
CCTGAGACTCTCCTGTGCAGCGTCTGGATTCACCTTCAATAACTATGGCAT
GCACTGGGTCCGCCAGGCTCCAGGCAAGGGGCTGGAGTGGGTGGCAGTTA
TATGGTATGATGGAAGTAATAAATACTATGCAGACTCCGTGAAGGGCCGA
TTCACCATCTCCAGAGACAATTCCAAGAACACGCTGTATCTGCAAATGAA
CAGCCTGAGAGCCGAGGACACGGCTGTGTATTACTGTGCGAGAGATAGGA
CCGTATATAGCAACTCGTCACCCTTTTACTACTACTACTACGGTATGGACG
TCTGGGGCCAAGGGACCACGGTCACCGTCTCCTCA (SEQ ID NO: 19)

Protein sequence of the heavy chain variable region:
QVQLVESGGGVVQPGRSLRLSCAASGFTFNNYGMHWVRQAPGKGLEWVAV
IWYDGSNKYYADSVKGRFTISRDNSKNTLYLQMNSLRAEDTAVYYCARDRT
VYSNSSPFYYYYYGMDVWGQGTTVTVSS (SEQ ID NO: 20)

Nucleotide sequence of the light chain variable region:
GACATCCAGATGACCCAGTCTCCATCCTCCCTGTCTGCATCTGTTGGAGAC
AGAGTCACCATCACTTGCCGGACAAGTCAGAGCATTAGCACCTATTTAAA
TTGGTATCAGCAGAAACCAGGGAAAGCCCCTAAGCTCCTGATCTCTGCTA
CATCCAGTTTGCAAAGTGGGGTCCCATCAAGGTTCAGTGGCAGTGGATCT
GGGACAGATTTCACTCTCACCATCAGCAGTCTGCAACCTGAAGATTTTGCA
ACTTACTACTGTCAACAGAGTTACAGTACCCCGCTCACTTTCGGCGGAGG
GACCAAGGTGGAGATCAAA (SEQ ID NO: 53)

Protein sequence of the light chain variable region:
DIQMTQSPSSLSASVGDRVTITCRTSQSISTYLNWYQQKPGKAPKLLISATSSL
QSGVPSRFSGSGSGTDFTLTISSLQPEDFATYYCQQSYSTPLTFGGGTKVEIK
(SEQ ID NO: 54)

FIGURE 12

ANTIBODY K

Nucleotide sequence of the heavy chain variable region:
CAGGTGCAGCTGGTGGAGTCTGGGGGAGGCGTGGTCCAGCCTGGGAGGTC
CCTGAGACTCTCCTGTGCAGCGTCTGGATTCACCTTCAGTACCTATGGCAT
GCACTGGGTCCGCCAGGCTCCAGGCAAGGGGCTGGAGTGGGTGGCAGTTA
TATGGTATGATGGAAGTAATAAATACTATGCAGACTCCGTGAAGGGCCGA
TTCACCATCTCCAGAGACAATTCCAAGAACACGCTGTATCTGCAAATGAA
CAGCCTGAGAGCCGAGGACACGGCTGTGTATTATTGTGCGAGAGATAGGA
CCGTATATAGCAGCTCGTCACCCTTTTACTACTACTACGGTATGGACG
TCTGGGGCCAAGGGACCACGGTCACCGTCTCCTCA (SEQ ID NO: 21)

Protein sequence of the heavy chain variable region:
QVQLVESGGGVVQPGRSLRLSCAASGFTFSTYGMHWVRQAPGKGLEWVAVI
WYDGSNKYYADSVKGRFTISRDNSKNTLYLQMNSLRAEDTAVYYCARDRTV
YSSSSPFYYYYYGMDVWGQGTTVTVSS (SEQ ID NO: 22)

Nucleotide sequence of the light chain variable region:
GACATCCAGATGACCCAGTCTCCATCCTCCCTGTCTGCATCTGTAGGAGAC
AGAGTCACCATCACTTGCCGGGCAAGTCAGAGCATTAGCAGCTATTTAAA
TTGGTATCAGCAGAAACCAGGGAAAGCCCCTAAGCTCCTGATCTCTGCTA
CATCCAGTTTTCAAAGTGGGGTCCCATCAAGGTTCAGTGGCAGTGGATCT
GGGACAGATTTCACTCTCACCATCAGCAGTCTGCAACCTGAAGATTTTGCA
GCTTACTACTGTCAACAGAGTTACAGTACCCCGCTCACTTTCGGCGGAGG
GACCAAGGTGGAGATCAAA (SEQ ID NO: 55)

Protein sequence of the light chain variable region:
DIQMTQSPSSLSASVGDRVTITCRASQSISSYLNWYQQKPGKAPKLLISATSSF
QSGVPSRFSGSGSGTDFTLTISSLQPEDFAAYYCQQSYSTPLTFGGGTKVEIK
(SEQ ID NO: 56)

FIGURE 13

ANTIBODY L

Nucleotide sequence of the heavy chain variable region:
CAGGTGCAGCTACAGCAGTGGGGCGCACGACTGTTGAAGCCTTCGGAGAC
CCTGTCCCTCACCTGCGCTGTCTATGGTGGGTCCTTCAGTGGTTACTACTG
GAGCTGGATCCGCCAGCCCCCAGGGAAGGGGCTGGAGTGGATTGGGGAA
ATCAATCATAGTGGAAGCACCAACTACAACCCGTCCCTCAAGAGTCGAGT
CACCATATCAGTAGACACGTCCAAGAACCAGTTCTCCCTGAAGCTGAGGT
CTGTGACCGCCGCGGACACGGCTGTGTATTACTGTGCGAGAGGGGGAAGC
AGTGGCTACTGGTACTTCGATCTCTGGGGCCGTGGCACCCTGGTCACTGTC
TCCTCA (SEQ ID NO: 23)

Protein sequence of the heavy chain variable region:
QVQLQQWGARLLKPSETLSLTCAVYGGSFSGYYWSWIRQPPGKGLEWIGEIN
HSGSTNYNPSLKSRVTISVDTSKNQFSLKLRSVTAADTAVYYCARGGSSGYW
YFDLWGRGTLVTVSS (SEQ ID NO: 24)

Nucleotide sequence of the light chain variable region:
GACATCGTGATGACCCAGTCTCCAGACTCCCTGGCTGTGTCTCTGGGCGAG
AGGGCCACCATCAACTGCAAGTCCAGCCAGAGTGTTTTACACAGCTCCAA
CAATAAGAATTATTTAGTTTGGTACCAGCAGAAACCAGGACAGCCTCCTA
AGCTGCTCATTTACTGGGCATCTACCCGGGAATCCGGGGTCCCTGACCGAT
TCAGTGGCAGCGGGTCTGGGACAGATTTCACTCTCACCATCAGCAGCCTG
CAGGCTGAAGATGTGGCAGTTTATTACTGTCAGCAATATTATAGTACTCCT
CTCACTTTCGGCGGAGGGACCAAGGTGGAGATCAAA (SEQ ID NO: 57)

Protein sequence of the light chain variable region:
DIVMTQSPDSLAVSLGERATINCKSSQSVLHSSNNKNYLVWYQQKPGQPPKL
LIYWASTRESGVPDRFSGSGSGTDFTLTISSLQAEDVAVYYCQQYYSTPLTFG
GGTKVEIK (SEQ ID NO: 58)

FIGURE 14

ANTIBODY M

Nucleotide sequence of the heavy chain variable region:
GAGGTGCAGGTGGTGGAGTCTGGGGGAGGCCTGGTCAAGCCTGGGGGGT
CCCTGAGACTCTCCTGTGCAGCCTCTGGATTCACCTTCAGTAGCTATAGCA
TGAACTGGGTCCGCCAGGCTCCAGGGAAGGGGCTGGAGTGGGTCTCATCC
ATTAGTAGTAGTAGTAGTTACATATACTACGCAGACTCAGTGAAGGGCCG
ATTCACCATCTCCAGAGACAACGCCAAGAACTCACTGTATCTGCAAATGA
ACAGCCTGAGAGCCGAGGACACGGCTGTGTATTACTGTGCGAGGGGGGGC
AGCAGCTGGTACGGGGACTGGTTCGACCCCTGGGGCCAGGGAACCCTGGT
CACCGTCTCCTCA (SEQ ID NO: 25)

Protein sequence of the heavy chain variable region:
EVQVVESGGGLVKPGGSLRLSCAASGFTFSSYSMNWVRQAPGKGLEWVSSIS
SSSSYIYYADSVKGRFTISRDNAKNSLYLQMNSLRAEDTAVYYCARGGSSWY
GDWFDPWGQGTLVTVSS (SEQ ID NO: 26)

Nucleotide sequence of the light chain variable region:
GACATCCAGATGACCCAGTCTCCATCTTCCGTGTCTGCATCTGTAGGAGAC
AGAGTCACCATCACTTGTCGGGCGAGTCAGGGTATTAGCAGCTGGTTAGT
CTGGTATCAGCAGAAACCAGGGAAAGCCCCTAAGCTCCTGATCTATGCTG
CATCCAGTTTGCAAAGTGGGGTCCCATCAAGGTTCAGCGGCAGTGGATCT
GGGACAGATTTCACTCTCACCATCAGCAGCCTGCAGCCTGAAGATTTTGC
AACTTACTATTGTCAGCAGGCTAACAGTTTCCCTTTCACTTTCGGCGGAGG
GACCAAGGTGGAGATCAAA (SEQ ID NO: 59)

Protein sequence of the light chain variable region:
DIQMTQSPSSVSASVGDRVTITCRASQGISSWLVWYQQKPGKAPKLLIYAASS
LQSGVPSRFSGSGSGTDFTLTISSLQPEDFATYYCQQANSFPFTFGGGTKVEIK
(SEQ ID NO: 60)

FIGURE 15

ANTIBODY N

Nucleotide sequence of the heavy chain variable region:
CAGCTGGTGGAGTCTGGGGGAGGCGTGGTCCAGCCTGGGAGGTCCCTGAG
ACTCTCCTGTGCAGCGTCTGGATTCACCTTCAGTAGCTATGGCATGCACTG
GGTCCGCCAGGCTCCAGGCAAGGGGCTGGAGTGGGTGGCAGTTATATGGT
ATGATGGAAGAAATAAATACTATGCAGACTCCGTGAAGGGCCGATTCACC
ATCTCCAGAGACAATTCCAAGAACACGCTGTATCTGCAAATGAACAGCCT
GAGAGCCGAGGACACGGCTGTGTATTACTGTGCGAGAGAAGTGGGATATT
GTACTAATGGTGTATGCTCCTACTACTACTACGGTATGGACGTCTGGGGCC
AAGGGACCACGGTCACCGTCTCCTCA (SEQ ID NO: 27)

Protein sequence of the heavy chain variable region:
QLVESGGGVVQPGRSLRLSCAASGFTFSSYGMHWVRQAPGKGLEWVAVIWY
DGRNKYYADSVKGRFTISRDNSKNTLYLQMNSLRAEDTAVYYCAREVGYCT
NGVCSYYYYGMDVWGQGTTVTVSS (SEQ ID NO: 28)

Nucleotide sequence of the light chain variable region:
GACATCCAGATGACCCAGTCTCCATCCTCACTGTCTGCATCTGTAGGAGAC
AGAGTCACCATCACTTGTCGGGCGAGTCAGGGCATTAGCAATTATTTAGC
CTGGTTTCAGCAGAAACCAGGGAAAGCCCCTAAGTCCCTGATCTATGCTG
CATCCAGTTTGCAAAGTGGGGTCCCATCAAAATTCAGCGGCAGTGGATCT
GGGACAGATTTCACTCTCACCATCAGCAGCCTGCAGCCTGAAGATTTTGC
AACTTATTACTGCCAACAGTATAATAGTTACCCTCTCACTTTCGGCGGAGG
GACCAAGGTGGAGATCAAA (SEQ ID NO: 61)

Protein sequence of the light chain variable region:
DIQMTQSPSSLSASVGDRVTITCRASQGISNYLAWFQQKPGKAPKSLIYAASSL
QSGVPSKFSGSGSGTDFTLTISSLQPEDFATYYCQQYNSYPLTFGGGTKVEIK
(SEQ ID NO: 62)

FIGURE 16

ANTIBODY O

Nucleotide sequence of heavy chain variable region:

CAGGTGCAGCTGCAGGAGTCGGGCCCAGGACTGGTGAAGCCTTCACAGAC
CCTGTCCCTCACCTGCACTGTCTCTGGTGGCTCCATCAGCAGTGGTGATTA
CTTCTGGAGCTGGATCCGCCAGCTCCCAGGGAAGGGCCTGGAGTGCATTG
GGCACATCCATAACAGTGGGACCACCTACTACAATCCGTCCCTCAAGAGT
CGAGTTACCATATCAGTAGACACGTCTAAGAAGCAGTTCTCCCTGAGGCT
GAGTTCTGTGACTGCCGCGGACACGGCCGTATATTACTGTGCGAGAGATC
GAGGGGGTGACTACTACTATGGTATGGACGTCTGGGGCCAAGGGACCACG
GTCACCGTCTCCTCA (SEQ ID NO: 29)

Amino acid sequence of heavy chain variable region:

QVQLQESGPGLVKPSQTLSLTCTVSGGSISSGDYFWSWIRQLPGKGLECIGHIH
NSGTTYYNPSLKSRVTISVDTSKKQFSLRLSSVTAADTAVYYCARDRGGDYY
YGMDVWGQGTTVTVSS (SEQ ID NO: 30)

Nucleotide sequence of light chain variable region:

GAAATTGTGTTGACGCAGTCTCCAGGCACCCTGTCTTTGTCTCCAGGGGAA
AGAGCCACCCTCTCCTGCAGGGCCAGTCAGGGTATTAGTAGAAGCTACTT
AGCCTGGTACCAGCAGAAACCTGGCCAGGCTCCCAGCCTCCTCATCTATG
GTGCATCCAGCAGGGCCACTGGCATCCCAGACAGGTTCAGTGGCAGTGGG
TCTGGG
ACAGACTTCACTCTCACCATCAGCAGACTGGAGCCTGAAGATTTTGCAGT
GTATTACTGTCAACAATTTGGTAGTTCACCGTGGACGTTCGGCCAAGGGA
CCAAGGTGGAAATCAAA (SEQ ID NO: 63)

Amino acid sequence of light chain variable region:

EIVLTQSPGTLSLSPGERATLSCRASQGISRSYLAWYQQKPGQAPSLLIYGASS
RATGIPDRFSGSGSGTDFTLTISRLEPEDFAVYYCQQFGSSPWTFGQGTKVEIK
(SEQ ID NO: 64)

FIGURE 17

ANTIBODY P

Nucleotide sequence of heavy chain variable region:

CAGGTGCAGCTGCAGGAGTCGGGCCCAGGACTGGTGAAGCCTTCACAGAC
CCTGTCCCTCACCTGCAGTGTCTCTGGTGGCTCCATCAGCAGTGGTGGTTA
CTACTGGAGCTGGATCCGCCAGCACCCAGGGAAGGGCCTGGAGTGGATTG
GGTACATCTATTACAGTGGGAGCACCTACTGCAACCCGTCCCTCAAGAGT
CGAGTTACCATATCAGTCGACACGTCTAAGAACCAGTTCTCCCTGAAGCT
GAGCTCTGTGACTGCCGCGGACACGGCCGTGTATTACTGTGCGAGAGACA
ATGGTTCGGGGAGTTATGACTGGTTCGACCCCTGGGGCCAGGGAATCCTG
GTCACCGTCTCCTCA (SEQ ID NO: 31)

Amino acid sequence of heavy chain variable region:

QVQLQESGPGLVKPSQTLSLTCSVSGGSISSGGYYWSWIRQHPGKGLEWIGYI
YYSGSTYCNPSLKSRVTISVDTSKNQFSLKLSSVTAADTAVYYCARDNGSGSY
DWFDPWGQGILVTVSS (SEQ ID NO: 32)

Nucleotide sequence of light chain variable region:

GACATTCAGATGACCCAGTCTCCATCCTCCGTGTCTGCATCTGTAGGAGAC
AGAGTCACCATCACTTGTCGGGCGAGTCAGGGTATTAGCAGCTGGTTAGC
CTGGTATCAGCAGAAACCAGGGAAAGCCCCAAAGTTCCTGATCTTTGTTG
CATCCAGTTTCCAAAGTGGGGTCCCATCAAGGTTCAGCGGCAGTGGATCT
GGGACAGATTTCACTCTCACCATCAGCAGCCTGCAGCCTGAAGATTTTGC
AACTTACTATTGTCAACAGGCTAACAGTTTCCCTCGGACGTTCGGCCAAGG
GACCAAGGTGGAAATCAAA (SEQ ID NO: 65)

Amino acid sequence of light chain variable region:

DIQMTQSPSSVSASVGDRVTITCRASQGISSWLAWYQQKPGKAPKFLIFVASS
FQSGVPSRFSGSGSGTDFTLTISSLQPEDFATYYCQQANSFPRTFGQGTKVEIK
(SEQ ID NO: 66)

FIGURE 18

ANTIBODY Q

Nucleotide sequence of heavy chain variable region:

CAGGTGCAGATGCAGGAGTCGGGCCCAGGACTGGTGAAGCCTTCACAGAC
CCTGTCCCTCACCTGCACTGTCTCTGGTGGCTCCATCAGCAGTGGTGATTA
CTACTGGAGCTGGATCCGCCAGCACCCAGGGAAGAACCTGGAGTGGATTG
GGTACATCTATTACAGTGGGAGCACCTACTACAACCCGTCCCTCAAGAGT
CGAGT
TACCATATCAGTAGACACGTCTAAGAACCAGTTCTCCCTGAAGCTGAGCT
CTGTGACTGCCGCGGACACGGCCGTGTATTACTGTGCGAGAGACAATGGT
TCGGGGAGTTATGACTGGTTCGACCCCTGGGGCCAGGGAACCCTGGTCAC
CGTCTCCTCA (SEQ ID NO: 33)

Amino acid sequence of heavy chain variable region:

QVQMQESGPGLVKPSQTLSLTCTVSGGSISSGDYYWSWIRQHPGKNLEWIGYI
YYSGSTYYNPSLKSRVTISVDTSKNQFSLKLSSVTAADTAVYYCARDNGSGS
YDWFDPWGQGTLVTVSS (SEQ ID NO: 34)

Nucleotide sequence of light chain variable region:

GACATCCAGATGACCCAGTCTCCATCTTCCGTGTCTGCATCTGTTGGAGAC
AGAGTCACCATCACTTGTCGGGCGAGTCAGGGTATTAGCAGCTGGTTAGC
CTGGTATCAGCAGAAACCAGGGAAAGCCCCTAAGTTCCTGATCTTTGTTG
CATCCAGTTTGCAAAGTGGGGTCCCATCAAGGTTCAGCGGCAGTGGATCT
GGG
ACAGATTTCACTCTCACCATCAGCAGCCTGCAGCCTGAAGATTTTGCAACT
TACTATTGTCAACAGGCTAACAGTTTCCCTCGGACGTTCGGCCAAGGGAC
CAAGGTGGAAATCAAA (SEQ ID NO: 67)

Amino acid sequence of light chain variable region:
DIQMTQSPSSVSASVGDRVTITCRASQGISSWLAWYQQKPGKAPKFLIFVASS
LQSGVPSRFSGSGSGTDFTLTISSLQPEDFATYYCQQANSFPRTFGQGTKVEIK
(SEQ ID NO: 68)

FIGURE 19

| Antibody | V | D | J | Seq. ID No | FR1 | CDR1 | FR2 |
|---|---|---|---|---|---|---|---|
| A | VH1-8 | Germline | | 177 | QVQLVQSGAEVKKPGASVKVSCKAS | GYTFTSYDIN | WVRQATGQGLEWMG |
| | | D3-10 | JH4B | 2 | --------------------------- | ---------- | --------------- |
| B | VH4-31 | Germline | | 178 | QVQLQESGPGLVKPSQTLSLTCTVS | GGSISSGGYYWS | WIRQHPGKGLEWIG |
| | | D6-19 | JH4B | 4 | --------------------------- | ------H--- | --------------- |
| C | " | " | " | 6 | --------------------------- | ------H--- | --------------- |
| D | " | " | " | 8 | --------------------------- | ------H--- | --------------- |
| E | | Germline | | 179 | QVQLVESGGGLVKPGGSLRLSCAAS | GFTFSDYYMS | WVRQAPGKGLEWVS |
| | VH3-11 | D6-13 | JH3B | 10 | --------------------------- | -------N-- | --------------- |
| F | VH3-33 | Germline | | 180 | QVQLVESGGGVVQPGRSLRLSCAAS | GFTFSSYGMH | WVRQAPGKGLEWVA |
| | | D6-6 | JH2 | 12 | --------------------------- | ---Y--I-- | --------------- |
| G | VH4-59 | Germline | | 181 | QVQLQESGPGLVKPSETLSLTCTVS | GGSISSYYWS | WIRQPPGKGLEWIG |
| | | D5-12 | JH4B | 14 | --AEQ----------------------- | ----N---- | --------------- |
| H | VH4-31 | Germline | | 182 | QVQLQESGPGLVKPSQTLSLTCTVS | GGSISSGGYYWS | WIRQHPGKGLEWIG |
| | | D1-7 | JH3B | 16 | --------------------------- | ------DN-- | --------------- |
| I | VH3-11 | Germline | | 183 | QVQLVESGGGLVKPGGSLRLSCAAS | GFTFSDYYMS | WIRQAPGKGLEWVS |
| | | - NA - | JH6B | 18 | --------------------------- | ---------- | --------------- |
| J | VH3-33 | Germline | | 184 | QVQLVESGGGVVQPGRSLRLSCAAS | GFTFSSYGMH | WVRQAPGKGLEWVA |
| | | D6-6 | JH6B | 20 | --------------------------- | ----NN---- | --------------- |
| K | " | " | " | 22 | --------------------------- | ----T----- | --------------- |
| L | VH4-34 | Germline | | 185 | QVQLQQWGAGLLKPSETLSLTCAVY | GGSFSGYYWS | WIRQPPGKGLEWIG |
| | | D6-19 | JH2 | 24 | -----R--------------------- | ---------- | --------------- |
| M | VH3-21 | Germline | | 186 | EVQLVESGGGLVKPGGSLRLSCAAS | GFTFSSYSMN | WVRQAPGKGLEWVS |
| | | D6-13 | JH5B | 26 | ---V----------------------- | ---------- | --------------- |
| N | VH3-33 | Germline | | 187 | QVQLVESGGGVVQPGRSLRLSCAAS | GFTFSSYGMH | WVRQAPGKGLEWVA |
| | | D2-8 | JH6B | 28 | ##-------------------------- | ---------- | --------------- |
| O | VH4-31 | Germline | | 188 | QVQLQESGPGLVKPSQTLSLTCTVS | GGSISSGGYYWS | WIRQHPGKGLEWIG |
| | | - NA - | JH6B | 30 | --------------------------- | ----D-F--- | ----L-----C--- |
| P | VH4-31 | Germline | | 189 | QVQLQESGPGLVKPSQTLSLTCTVS | GGSISSGGYYWS | WIRQHPGKGLEWIG |
| | | D3-10 | JH5B | 32 | ---M----------------------- | -----D---- | --------------- |
| Q | " | " | " | 34 | -----S--------------------- | -----D---- | -------N------- |

| Antibody | V | J | Seq.ID No | FR1 | CDR1 | FR2 |
|---|---|---|---|---|---|---|
| | Germline | | 190 | DIQMTQSPSSLSASVGDRVTITC | RASQSISSYLN | WYQQKPGKAPKLLIY |
| J | O12 | JK4 | 54 | ---------------------- | -T-----T--- | ---------------S |
| K | " | " | 56 | ---------------------- | ----------- | ---------------S |
| A | " | " | 36 | ---------------------- | ----I------ | ---------------- |
| | Germline | | 191 | DIQMTQSPSSLSASVGDRVTITC | RASQSISSYLN | WYQQKPGKAPKLLIY |
| E | O12 | JK3 | 44 | ---------------------- | -S-----N-I- | ---R-----N---H |
| | Germline | | 192 | DIVMTQSPLSLPVTPGEPASISC | RSSQSLLHSNGYNYLD | WYLQKPGQSPQLLIY |
| H | A3 | JK4 | 50 | ---------------------- | -----RR---------- | ---------------- |
| | Germline | | 193 | DIQMTQSPSSVSASVGDRVTITC | RASQGISSWLA | WYQQKPGKAPKLLIY |
| M | L5 | JK4 | 60 | ---------------------- | ----------V | ---------------- |
| | Germline | | 194 | DIQMTQSPSSLSASVGDRVTITC | RASQGIRNDLG | WYQQKPGKAPKRLIY |
| D | A30 | JK1 | 42 | ---------------------- | --L-------- | -F-------------- |
| C | " | " | 40 | ---------------------- | --L-------- | -F-------------- |
| B | " | " | 38 | ---------------------- | --L-------- | -F-----VT------ |
| | Germline | | 195 | DIQMTQSPSSLSASVGDRVTITC | RASQGISNYLA | WFQQKPGKAPKSLIY |
| N | L1 | JK4 | 62 | ---------------------- | ----------- | ---------------- |
| | Germline | | 196 | DIVMTQSPDSLAVSLGERATINC | KSSQSVLYSSNNKNYLA | WYQQKPGQPPKLLIY |
| L | B3 | JK4 | 58 | ---------------------- | -------------V--- | ---------------- |
| | Germline | | 197 | DIVMTQSPDSLAVSLGERATINC | KSSQSVLYSSNNKNYLA | WYQQKPGQPPKLLIY |
| G | B3 | JK3 | 48 | ---------------------- | -------R--------- | ---------------- |
| | Germline | | 198 | DIQMTQSPSSLSASVGDRVTITC | RASQGISNYLA | WYQQKPGKVPKLLIY |
| F | A20 | JK4 | 46 | ---------------------- | ----------- | ---------------- |
| | Germline | | 199 | DIVMTQSPDSLAVSLGERATINC | KSSQSVLYSSNNKNYLA | WYQQKPGQPPKLLIY |
| I | B3 | JK1 | 52 | ------F--------------- | -----H-------T--- | --L------------- |
| | Germline | | 200 | BIVLTQSPGTLSLSPGERATLSC | RASQSVSSSYLA | WYQQKPGQAPRLLIY |
| O | A27 | JK1 | 64 | ---------------------- | ----GI-R--- | ---------S------ |
| | Germline | | 201 | DIQMTQSPSSVSASVGDRVTITC | RASQGISSWLA | WYQQKPGKAPKLLIY |
| P | L5 | JK1 | 66 | ---------------------- | ----------- | ---------F--F |
| Q | " | " | 68 | ---------------------- | ----------- | ---------F--F |

FIGURE 21A

| CDR2 | FR3 | CDR3 | FR4 |
|---|---|---|---|
| AASSLQS | GVPSRFSGSGSGTDFTLTISSLQPEDFATYYC | QQSYST#T | FGGGTKVEIKR |
| -T- | ---------------------------- | ---PL- | ---------- |
| -T--F- | ----A---------- | ---PL- | ---------- |
| AASSLQS | GVPSRFSGSGSGTDFTLTISSLQPEDFATYYC | QQSYSTPFT | FGPGTKVDIKR |
| DV--F- | A-----R---V---- | --T-I--- | ---------- |
| LGSNRAS | GVPDRFSGSGSGTDFTLKISRVEAEDVGVYYC | MQALQT##T | FGGGTKVEIKR |
| --- | ------ | ---PL- | --E------- |
| AASSLQS | GVPSRFSGSGSGTDFTLTISSLQPEDFATYYC | QQANSFP#T | FGGGTKVEIK# |
| --- | --- | --F--- | -----R |
| AASSLQS | GVPSRFSGSGSGTBFTLTISSLQPEDFATYYC | LQHNS##WT | FGQGTKVEIKR |
| ---R | ------------------- | ---FP- | ---------- |
| ---R | ---T--F- | ---FP- | ---------- |
| ---R | ---T--P- | --Y-FP- | ---------- |
| AASSLQS | GVPDRFSGSGSGTDFTLTISSLQPEDFATYYC | QQYNSYPLT | FGGGTKVEIKR |
| --- | --K--- | ------ | ---------- |
| WASTRES | GVPDRFSGSGSGTDFTLTISSLQAEDVAVYYC | QQYYSTPLT | FGGGTKVEIKR |
| --- | ------ | ------ | ---------- |
| WASTRES | GVPDRFSGSGSGTDFTLTISSLQAEDVAVYYC | QQYYSTPFT | FGPGTKVDIKR |
| AASTLQS | GVPSRFSGSGSGTDFTLTISSLQPEDVATYYC | QKYNSA##T | FGGGTKVEIKR |
| --- | ----L--- | ---PL- | ---------- |
| WASTRES | GVPSRFSGSGSGTDFTLTISSLQAEDVAVYYC | QQYYST### | FGQGTKLEIKR |
| --- | ------ | H----PSS | ---------- |
| GASSRAT | GIPDRFSGSGSGTDFTLTISRLEPEDFAVYYC | QQYGSSPWT | FGQGTKVEIKR |
| --- | ------ | --F--- | ---------- |
| AASSLQS | GVPSRFSGSGSGTDFTLTISSLQPEDFATYYC | QQANSFPRT | FGQGTKVEIKR |
| V--F- | --- | --- | --- |
| V----- | --- | --- | --- |

FIGURE 21B

Epitope Binding Groups of Certain Human Anti-TR-2 Antibodies

| Group 1 | Group 2 | Group 3 | Group 4 |
|---------|---------|---------|---------|
| Ab B | Ab A | Ab G | Ab N |
| Ab C | Ab E | Ab O | |
| Ab D | Ab H | | |
| Ab F | | | |
| Ab I | | | |
| Ab J | | | |
| Ab K | | | |
| Ab L | | | |
| Ab M | | | |

FIGURE 22

Cyno Truncations and Cyno/Human TR-2 Chimeras

Cyno TR-2 (short)        1 APIT ———————— RIQT 132

Cyno TR-2 (long)         1 APIT ———————————————————————— TPAS 154

Cyno TR-2 1-85           1 APIT ———————— TVCQ 85

Cyno TR-2 16-85                          16 PQQK ———— TVCQ 85

Cyno TR-2 16-154 (long)                  16 PQQK ———————————————— TPAS 154

CynoTR-2 1-16, hu17-85   1 APIT AAP 16 ═══ 17 QQKR ═══ TVCQ 85

CynoTR-2 1-16, hu17-154  1 APIT AAP 16 ═══ 17 QQKR ═══════════════ TPAS 154

Hu TR-2 1-16, Cyno TR-2 17-85   1 ALIT ═══ AAP 16 ——— 17 QQKR ——— TVCQ 85

Hu TR-2 1-16, Cyno TR-2 17-end (long)  1 ALIT ═══ AAP 16 ——— 17 QQKR ——————————— TPAS 154

Legend: Cyno sequences are single line, human are double line.

FIGURE 25

```
                1                                                              50
Cyno_TR2_Pep  -APITRQSLD PQRRAAPQQK RSSPTEGLCP PGHHISEDSR DCISCKYGQD
huTR2_ECD_Pe  -ALITQQDLA PQQRAAPQQK RSSPSEGLCP PGHHISEDGR DCISCKYGQD
   muTR2_ECD  --PVTANP.A HNRPAGLQRP EESPSRGPCL AGQYLSE..G NCKPCREGID 51                                                             100
Cyno_TR2_Pep  YSTHWNDFL. FCLRCTKCDS GEVEVSSCTT TRNTVCQCEE GTFREEDSPE
huTR2_ECD_Pe  YSTHWNDLL. FCLRCTRCDS GEVELSPCTT TRNTVCQCEE GTFREEDSPE
   muTR2_ECD  YTSHSNHSLD SCILCTVCKE DKVVETRCNI TTNTVCRCKP GTFEDKDSPE 101                                                             150
Cyno_TR2_Pep  ICRKCRTGCP RGMVKVKDCT PWSDIECVHK E--------- ----------
huTR2_ECD_Pe  MCRKCRTGCP RGMVKVGDCT PWSDIECVHK ESGTKHSGEA PAVEETVTSS
   muTR2_ECD  ICQSC.SNCT DGEEELTSCT PRENRKCVSK TAWASWHKL- ----------

151
Cyno_TR2_Pep  ------  SEQ ID NO: 202
huTR2_ECD_Pe  PGTPAS  SEQ ID NO: 203
   muTR2_ECD  ------  SEQ ID NO: 204
```

FIGURE 26

SEQUENCE LISTING

```
<160> NUMBER OF SEQ ID NOS: 204

<210> SEQ ID NO 1
<211> LENGTH: 363
<212> TYPE: DNA
<213> ORGANISM: Homo sapiens

<400> SEQUENCE: 1
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag ggcttgagtg gatgggatgg atgaaccctaacagtgataa cacaggctat     180 gcacagaagt tccagggcag agtcaccatg accaggaaca cctccataag cacagcctac    240
atggagttga gcagcctgag atctgaggac acggccgtgt attactgtgc gagatggaat    300
cactatggtt cggggagtca ttttgactac tggggccagg gaaccctggt caccgtctcc    360
tca                                                                  363

<210> SEQ ID NO 2
<211> LENGTH: 121
<212> TYPE: PRT
<213> ORGANISM: Homo sapiens

<400> SEQUENCE: 2

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30
```

```
Asp Ile Asn Trp Val Arg Gln Ala Thr Gly Gln Gly Leu Glu Trp Met
            35                  40                  45

Gly Trp Met Asn Pro Asn Ser Asp Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Trp Asn His Tyr Gly Ser Gly Ser His Phe Asp Tyr Trp Gly
            100                 105                 110

Gln Gly Thr Leu Val Thr Val Ser Ser
            115                 120
```

```
<210> SEQ ID NO 3
<211> LENGTH: 360
<212> TYPE: DNA
<213> ORGANISM: Homo sapiens

<400> SEQUENCE: 3
caggtgcagc tgcaggagtc gggcccagga ctggtgaagc cttcacagac cctgtccctc    60
acctgcactg tctctggtgg ctccatcagc agtggtggtc actactgag ctggatccgc    120 cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattattg cgcgagagat    300
gacagcagtg gctggggttt tgactactgg ggccagggaa tcctggtcac cgtctcctca    360
```

```
<210> SEQ ID NO 4
<211> LENGTH: 120
<212> TYPE: PRT
<213> ORGANISM: Homo sapiens

<400> SEQUENCE: 4

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
             20                  25                  30

Gly His Tyr Trp Ser Trp Ile Arg Gln His Pro Gly Lys Gly Leu Glu
         35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Asp Asp Ser Ser Gly Trp Gly Phe Asp Tyr Trp Gly Gln
            100                 105                 110

Gly Ile Leu Val Thr Val Ser Ser
            115                 120
```

```
<210> SEQ ID NO 5
<211> LENGTH: 360
<212> TYPE: DNA
<213> ORGANISM: Homo sapiens

<400> SEQUENCE: 5
```

```
caggtgcagc tgcaggagtc gggcccagga ctggtgaagc cttcacagac cctgtccctc    60
acctgcactg tctctggtgg ctccatcagc agtggtggtc actactggag ctggatccgc   120
cagcacccag ggaagggcct ggagtggatt gggtacatct attacagtgg gagcgcctac   180
tacaacccgt ccctcaagag tcgagttacc atatcagtag acacgtctaa gaaccagttc   240
tccctgaagc tgagctctgt gactgccgcg gacacggccg tgtattactg tgcgagagat   300
gacagcagtg ctggggtttt gactactgg ggccagggaa tcctggtcac cgtctcctca   360
```

<210> SEQ ID NO 6
<211> LENGTH: 120
<212> TYPE: PRT
<213> ORGANISM: Homo sapiens

<400> SEQUENCE: 6

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
        35                  40                  45

Trp Ile Gly Tyr Ile Tyr Tyr Ser Gly Ser Ala Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Asp Ser Ser Gly Trp Gly Phe Asp Tyr Trp Gly Gln
            100                 105                 110

Gly Ile Leu Val Thr Val Ser Ser
        115                 120
```

<210> SEQ ID NO 7
<211> LENGTH: 360
<212> TYPE: DNA
<213> ORGANISM: Homo sapiens

<400> SEQUENCE: 7

```
caggtgcagc tgcaggagtc gggcccagga ctggtgaagc cttcacagac cctgtccctc    60
acctgcactg tctctggtgg ctccatcagc agtggtggtc actactggag ctggatccgc   120
cagcacccag ggaagggcct ggagtggatt gggtacatct attacagtgg gagcgcctac   180
tacaacccgt ccctcaagag tcgagttacc atatcagtag acacgtctaa gaaccagttc   240
tccctgaagc tgagctctgt gactgccgcg gacacggccg tgtattactg tgcgagagat   300
gacagcagtg ctggggtttt gactactgg ggccagggaa tcctggtcac cgtctcctca   360
```

<210> SEQ ID NO 8
<211> LENGTH: 120
<212> TYPE: PRT
<213> ORGANISM: Homo sapiens

<400> SEQUENCE: 8

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly His Tyr Trp Ser Trp Ile Arg Gln His Pro Gly Lys Gly Leu Glu
```

```
            35                  40                  45
Trp Ile Gly Tyr Ile Tyr Tyr Ser Gly Ser Ala Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Asp Ser Ser Gly Trp Gly Phe Asp Tyr Trp Gly Gln
                100                 105                 110

Gly Ile Leu Val Thr Val Ser Ser
            115                 120

<210> SEQ ID NO 9
<211> LENGTH: 363
<212> TYPE: DNA
<213> ORGANISM: Homo sapiens

<400> SEQUENCE: 9
caggtgcagc tggtggagtc tgggggaggc ttggtcaagc ctggagggtc cctgagactc      60
tcctgtgcag cctctggatt caccttcagt gactactaca tgaactggat ccgccaggct    120
ccagggaagg gactggagtg ggtttcacac attagtagta gtggtagtat cttagactac    180
gcagactctg tgaagggccg attcaccatc tccagggaca acgccaagaa ctcactgtat    240
ctgcaaatga acagcctgag agtcgaggac acggccgtgt attactgtgc gagagatggg    300
gctgcagctg gtacggatgc ttttgatctc tggggccaag gacaatggt caccgtctct    360 tca                                                                  363

<210> SEQ ID NO 10
<211> LENGTH: 121
<212> TYPE: PRT
<213> ORGANISM: Homo sapiens

<400> SEQUENCE: 10

Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Asn Trp Ile Arg Gln Ala Pro Gly Lys Gly Leu Glu Trp Val
         35                  40                  45

Ser His Ile Ser Ser Ser Gly Ser Ile Leu Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Val Tyr Tyr Cys
                 85                  90                  95

Ala Arg Asp Gly Ala Ala Ala Gly Thr Asp Ala Phe Asp Leu Trp Gly
                100                 105                 110

Gln Gly Thr Met Val Thr Val Ser Ser
            115                 120

<210> SEQ ID NO 11
<211> LENGTH: 366
<212> TYPE: DNA
<213> ORGANISM: Homo sapiens

<400> SEQUENCE: 11
```

```
caggtgcagc tggtggagtc tgggggaggc gtggtccagc ctggggaggtc cctgagactc     60 tcctgtgcag cgtctggatt caccttcagt tactatggca tactgggt ccgccaggct       120 ccaggcaagg ggctggagtg ggtggcagtt atatggtatg atggaagtaa taaatactat    180
gcagactccg tgaagggccg attcaccatc tccagagaca attccaagaa cacgctgtat    240
ctgcaaatga acagcctgag agccgaggac acggctgtgt attactgtgc gagagggagg    300
tatagcagct cgtcctggtg gtacttcgat ctctggggcc gtggcaccct ggtcactgtc    360
tcctca                                                                366
```

<210> SEQ ID NO 12
<211> LENGTH: 122
<212> TYPE: PRT
<213> ORGANISM: Homo sapiens

<400> SEQUENCE: 12

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Tyr Tyr
             20                  25                  30

Gly Ile His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Tyr Ser Ser Ser Ser Trp Trp Tyr Phe Asp Leu Trp
            100                 105                 110

Gly Arg Gly Thr Leu Val Thr Val Ser Ser
        115                 120

<210> SEQ ID NO 13
<211> LENGTH: 366
<212> TYPE: DNA
<213> ORGANISM: Homo sapiens

<400> SEQUENCE: 13

```
caggtgcagg ctgagcagtc gggcccagga ctggtgaagc cttcggagac cctgtccctc     60
acctgcactg tctctggtgg ctccatcagt aattactact ggagctggat ccggcagccc    120
ccagggaagg gactggagtg gattgggtat atctattaca gtgggagcac caagtacaac    180
ccctccctca agagtcgagt caccatatca gtagacacgt ccaagaacca gttctccctg    240
aagctaacct ctgtgaccac tgcggacacg gccgtgtatt actgtgcgag agactcccct    300
cgtggattta gtggctacga ggcttttgac tcctggggcc agggaaccct ggtcaccgtc    360
tcctca                                                                366
```

<210> SEQ ID NO 14
<211> LENGTH: 122
<212> TYPE: PRT
<213> ORGANISM: Homo sapiens

<400> SEQUENCE: 14

Gln Val Gln Ala Glu Gln Ser Gly Pro Gly Leu Val Lys Pro Ser Glu
 1               5                  10                  15

```
Thr Leu Ser Leu Thr Cys Thr Val Ser Gly Gly Ser Ile Ser Asn Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Thr Ala Asp Thr Ala Val Tyr Tyr Cys Ala
                85                  90                  95

Arg Asp Ser Pro Arg Gly Phe Ser Gly Tyr Glu Ala Phe Asp Ser Trp
            100                 105                 110

Gly Gln Gly Thr Leu Val Thr Val Ser Ser
        115                 120
```

<210> SEQ ID NO 15
<211> LENGTH: 360
<212> TYPE: DNA
<213> ORGANISM: Homo sapiens

<400> SEQUENCE: 15

```
caggtgcagc tgcaggagtc gggcccagga ctggtgaagc cttcacagac cctgtccctc     60
acctgcactg tctctggtgg ctccatcagc agtgataatt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagga    300
gttaactgga actttctttt tgatatctgg ggccaaggga caatggtcac cgtctcttca    360
```

<210> SEQ ID NO 16
<211> LENGTH: 120
<212> TYPE: PRT
<213> ORGANISM: Homo sapiens

<400> SEQUENCE: 16

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Asp
            20                  25                  30

Asn Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Asn Trp Asn Phe Leu Phe Asp Ile Trp Gly Gln
            100                 105                 110

Gly Thr Met Val Thr Val Ser Ser
        115                 120
```

<210> SEQ ID NO 17
<211> LENGTH: 348
<212> TYPE: DNA
<213> ORGANISM: Homo sapiens

<400> SEQUENCE: 17

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagaa gtggtagtac catatactac     180
gcagactctg tgaagggccg attcaccatc tccaggaca acgccaagaa ctcactgtat      240
ctgcaaatga acagcctgag agccgaggac acggccgtgt attactgtgc gagatcttta     300
ggcggtatgg acgtctgggg ccaagggacc acggtcaccg tctcctca                  348
```

<210> SEQ ID NO 18
<211> LENGTH: 116
<212> TYPE: PRT
<213> ORGANISM: Homo sapiens

<400> SEQUENCE: 18

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Arg Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Gly Gly Met Asp Val Trp Gly Gln Gly Thr Thr Val
            100                 105                 110

Thr Val Ser Ser
        115
```

<210> SEQ ID NO 19
<211> LENGTH: 387
<212> TYPE: DNA
<213> ORGANISM: Homo sapiens

<400> SEQUENCE: 19

```
caggtgcagc tggtggagtc tgggggaggc gtggtccagc ctggagggtc cctgagactc      60
tcctgtgcag cgtctggatt caccttcaat aactatggca tgcactgggt ccgccaggct     120
ccaggcaagg ggctggagtg ggtggcagtt atatggtatg atggaagtaa taaatactat     180
gcagactccg tgaagggccg attcaccatc tccagagaca attccaagaa cacgctgtat     240
ctgcaaatga acagcctgag agccgaggac acggctgtgt attactgtgc gagagatagg     300
accgtatata gcaactcgtc accctttac tactactact acggtatgga cgtctggggc      360
caagggacca cggtcaccgt ctcctca                                         387
```

<210> SEQ ID NO 20
<211> LENGTH: 129
<212> TYPE: PRT
<213> ORGANISM: Homo sapiens

<400> SEQUENCE: 20

```
Gln Val Gln Leu Val Glu Ser Gly Gly Gly Val Val Gln Pro Gly Arg
  1               5                  10                  15
```

```
Ser Leu Arg Leu Ser Cys Ala Ala Ser Gly Phe Thr Phe Asn Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Val Tyr Ser Asn Ser Ser Pro Phe Tyr Tyr
            100                 105                 110

Tyr Tyr Gly Met Asp Val Trp Gly Gln Gly Thr Val Thr Val Ser
        115                 120                 125

Ser
```

<210> SEQ ID NO 21
<211> LENGTH: 387
<212> TYPE: DNA
<213> ORGANISM: Homo sapiens

<400> SEQUENCE: 21

```
caggtgcagc tggtggagtc tggggggaggc gtggtccagc ctggggaggtc cctgagactc      60
tcctgtgcag cgtctggatt caccttcagt acctatggca tgcactgggt ccgccaggct      120
ccaggcaagg ggctggagtg ggtggcagtt atatggtatg atggaagtaa taaatactat      180
gcagactccg tgaagggccg attcaccatc tccagagaca attccaagaa cacgctgtat      240
ctgcaaatga acagcctgag agccgaggac acggctgtgt attattgtgc gagagatagg      300
accgtatata gcagctcgtc accctttttac tactactact acggtatgga cgtctggggc      360
caagggacca cggtcaccgt ctcctca                                           387
```

<210> SEQ ID NO 22
<211> LENGTH: 129
<212> TYPE: PRT
<213> ORGANISM: Homo sapiens

<400> SEQUENCE: 22

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Thr Val Tyr Ser Ser Ser Ser Pro Phe Tyr Tyr
            100                 105                 110

Tyr Tyr Gly Met Asp Val Trp Gly Gln Gly Thr Thr Val Thr Val Ser
        115                 120                 125

Ser
```

<210> SEQ ID NO 23
<211> LENGTH: 357
<212> TYPE: DNA
<213> ORGANISM: Homo sapiens

<400> SEQUENCE: 23

```
caggtgcagc tacagcagtg gggcgcacga ctgttgaagc cttcggagac cctgtccctc      60
acctgcgctg tctatggtgg gtccttcagt ggttactact ggagctggat ccgccagccc     120
ccagggaagg ggctggagtg gattggggaa atcaatcata gtggaagcac caactacaac     180
ccgtccctca gagtcgagt caccatatca gtagacacgt ccaagaacca gttctccctg      240
aagctgaggt ctgtgaccgc cgcggacacg gctgtgtatt actgtgcgag agggggaagc     300
agtggctact ggtacttcga tctctggggc cgtggcaccc tggtcactgt ctcctca        357
```

<210> SEQ ID NO 24
<211> LENGTH: 119
<212> TYPE: PRT
<213> ORGANISM: Homo sapiens

<400> SEQUENCE: 24

Gln Val Gln Leu Gln Gln Trp Gly Ala Arg Leu Leu Lys Pro Ser Glu
 1               5                  10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Arg Ser Val Thr Ala Ala Asp Thr Ala Val Tyr Tyr Cys Ala
                85                  90                  95
Arg Gly Gly Ser Ser Gly Tyr Trp Tyr Phe Asp Leu Trp Gly Arg Gly
            100                 105                 110
Thr Leu Val Thr Val Ser Ser
        115

<210> SEQ ID NO 25
<211> LENGTH: 363
<212> TYPE: DNA
<213> ORGANISM: Homo sapiens

<400> SEQUENCE: 25

```
gaggtgcagg tggtggagtc tgggggaggc ctggtcaagc ctgggggtc cctgagactc       60
tcctgtgcag cctctggatt caccttcagt agctatagca tgaactgggt ccgccaggct    120
ccagggaagg ggctggagtg ggtctcatcc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gaggggggc     300
agcagctggt acggggactg gttcgacccc tggggccagg gaaccctggt caccgtctcc    360
tca                                                                  363
```

<210> SEQ ID NO 26
<211> LENGTH: 121
<212> TYPE: PRT
<213> ORGANISM: Homo sapiens

<400> SEQUENCE: 26

Glu Val Gln Val Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ser Ser Trp Tyr Gly Asp Trp Phe Asp Pro Trp Gly
            100                 105                 110

Gln Gly Thr Leu Val Thr Val Ser Ser
        115                 120

<210> SEQ ID NO 27
<211> LENGTH: 378
<212> TYPE: DNA
<213> ORGANISM: Homo sapiens

<400> SEQUENCE: 27

```
cagctggtgg agtctggggg aggcgtggtc cagcctggga ggtccctgag actctcctgt      60
gcagcgtctg gattcacctt cagtagctat ggcatgcact gggtccgcca ggctccaggc     120
aaggggctgg agtgggtggc agttatatgg tatgatggaa gaataaata ctatgcagac     180
tccgtgaagg gccgattcac catctccaga gacaattcca agaacacgct gtatctgcaa     240
atgaacagcc tgagagccga ggacacggct gtgtattact gtgcgagaga gtgggatat     300
tgtactaatg gtgtatgctc ctactactac tacggtatgg acgtctgggg ccaagggacc     360
acggtcaccg tctcctca                                                    378
```

<210> SEQ ID NO 28
<211> LENGTH: 126
<212> TYPE: PRT
<213> ORGANISM: Homo sapiens

<400> SEQUENCE: 28

Gln Leu Val Glu Ser Gly Gly Gly Val Val Gln Pro Gly Arg Ser Leu
1               5                   10                  15

Arg Leu Ser Cys Ala Ala Ser Gly Phe Thr Phe Ser Ser Tyr Gly Met
            20                  25                  30

His Trp Val Arg Gln Ala Pro Gly Lys Gly Leu Glu Trp Val Ala Val
        35                  40                  45

Ile Trp Tyr Asp Gly Arg Asn Lys Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Glu Val Gly Tyr Cys Thr Asn Gly Val Cys Ser Tyr Tyr Tyr Tyr Gly
            100                 105                 110

Met Asp Val Trp Gly Gln Gly Thr Thr Val Thr Val Ser Ser

<210> SEQ ID NO 29
<211> LENGTH: 366
<212> TYPE: DNA
<213> ORGANISM: Homo sapiens

<400> SEQUENCE: 29

```
caggtgcagc tgcaggagtc gggcccagga ctggtgaagc cttcacagac cctgtccctc      60
acctgcactg tctctggtgg ctccatcagc agtggtgatt acttctggag ctggatccgc     120
cagctcccag ggaagggcct ggagtgcatt gggcacatcc ataacagtgg accacctac      180
tacaatccgt ccctcaagag tcgagttacc atatcagtag acacgtctaa gaagcagttc     240
tccctgaggc tgagttctgt gactgccgcg gacacggccg tatattactg tgcgagagat     300
cgagggggtg actactacta tggtatggac gtctggggcc aagggaccac ggtcaccgtc     360
tcctca                                                                366
```

<210> SEQ ID NO 30
<211> LENGTH: 122
<212> TYPE: PRT
<213> ORGANISM: Homo sapiens

<400> SEQUENCE: 30

```
Gln Val Gln Leu Gln Glu Ser Gly Pro Gly Leu Val Lys Pro Ser Gln
  1               5                  10                  15
Thr Leu Ser Leu Thr Cys Thr Val Ser Gly Gly Ser Ile Ser Ser Gly
             20                  25                  30
Asp Tyr Phe Trp Ser Trp Ile Arg Gln Leu Pro Gly Lys Gly Leu Glu
         35                  40                  45
Cys Ile Gly His Ile His Asn Ser Gly Thr Thr Tyr Tyr Asn Pro Ser
     50                  55                  60
Leu Lys Ser Arg Val Thr Ile Ser Val Asp Thr Ser Lys Lys Gln Phe
 65                  70                  75                  80
Ser Leu Arg Leu Ser Ser Val Thr Ala Ala Asp Thr Ala Val Tyr Tyr
                 85                  90                  95
Cys Ala Arg Asp Arg Gly Gly Asp Tyr Tyr Tyr Gly Met Asp Val Trp
            100                 105                 110
Gly Gln Gly Thr Thr Val Thr Val Ser Ser
            115                 120
```

<210> SEQ ID NO 31
<211> LENGTH: 366
<212> TYPE: DNA
<213> ORGANISM: Homo sapiens

<400> SEQUENCE: 31

```
caggtgcagc tgcaggagtc gggcccagga ctggtgaagc cttcacagac cctgtccctc      60
acctgcagtg tctctggtgg ctccatcagc agtggtggtt actactggag ctggatccgc     120
cagcacccag ggaagggcct ggagtggatt gggtacatct attacagtgg gagcacctac     180
tgcaacccgt ccctcaagag tcgagttacc atatcagtcg acacgtctaa gaaccagttc     240
tccctgaagc tgagctctgt gactgccgcg gacacggccg tgtattactg tgcgagagac     300
aatggttcgg ggagttatga ctggttcgac ccctgggcc agggaatcct ggtcaccgtc     360
tcctca                                                                366
```

<210> SEQ ID NO 32
<211> LENGTH: 122
<212> TYPE: PRT
<213> ORGANISM: Homo sapiens

<400> SEQUENCE: 32

Gln Val Gln Leu Gln Glu Ser Gly Pro Gly Leu Val Lys Pro Ser Gln
1               5                   10                  15

Thr Leu Ser Leu Thr Cys Ser Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Cys Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Asn Gly Ser Gly Ser Tyr Asp Trp Phe Asp Pro Trp
            100                 105                 110

Gly Gln Gly Ile Leu Val Thr Val Ser Ser
        115                 120

<210> SEQ ID NO 33
<211> LENGTH: 366
<212> TYPE: DNA
<213> ORGANISM: Homo sapiens

<400> SEQUENCE: 33
caggtgcaga tgcaggagtc gggcccagga ctggtgaagc cttcacagac cctgtccctc      60
acctgcactg tctctggtgg ctccatcagc agtggtgatt actactggag ctggatccgc     120
cagcacccag gaagaacct gagtggatt gggtacatct attacagtgg gagcacctac       180
tacaacccgt ccctcaagag tcgagttacc atatcagtag acacgtctaa gaaccagttc     240
tccctgaagc tgagctctgt gactgccgcg gacacggccg tgtattactg tgcgagagac     300
aatggttcgg ggagttatga ctggttcgac ccctgggggcc agggaaccct ggtcaccgtc    360
tcctca                                                                366

<210> SEQ ID NO 34
<211> LENGTH: 122
<212> TYPE: PRT
<213> ORGANISM: Homo sapiens

<400> SEQUENCE: 34

Gln Val Gln Met Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Asn Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Asn Gly Ser Gly Ser Tyr Asp Trp Phe Asp Pro Trp
            100                 105                 110

Gly Gln Gly Thr Leu Val Thr Val Ser Ser
        115                 120

<210> SEQ ID NO 35
<211> LENGTH: 321
<212> TYPE: DNA
<213> ORGANISM: Homo sapiens

<400> SEQUENCE: 35
gacatccaga tgacccagtc tccatcctcc ctgtctgcat ctgtaggaga cagagtcacc      60
atcacttgcc gggcaagtca gagcattagc atttatttaa attggtatca gcagaaacca    120
gggaaagccc ctaagctcct gatctatgct gcatccagtt tgcaaagtgg ggtcccatta    180
aggttcagtg gcagtggatc tgggacagat ttcactctca ccatcagcag tctgcaacct    240
gaagatattg caacttacta ctgtcaacag agttacaaaa ccccgctcac tttcggcgga    300
gggaccaagg tggagatcaa a                                              321

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ile Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Leu Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Ile Ala Thr Tyr Tyr Cys Gln Gln Ser Tyr Lys Thr Pro Leu
                 85                  90                  95

Thr Phe Gly Gly Gly Thr Lys Val Glu Ile Lys
            100                 105

<210> SEQ ID NO 37
<211> LENGTH: 321
<212> TYPE: DNA
<213> ORGANISM: Homo sapiens

<400> SEQUENCE: 37
gacatccaga tgacccagtc tccatcctcc ctgtctgcat ctgttggaga cagagtcacc      60
atcacttgcc gggcaagtca gggccttaga aatgatttag ctggtttca gcagaaacca     120 gggaaagtca ctaagcgcct gatctatgct gcatccagtt tgcaaagagg ggtcccatca    180
aggttcagcg gcagtggatc tgggacagaa ttcactctca caatcagcag cctgcagcct    240
gaagattttg caacttatta ctgtctacag cattatagtt cccgtggacg ttcggccaa     300 gggaccaagg tggagatcaa a                                              321

<210> SEQ ID NO 38
<211> LENGTH: 107
<212> TYPE: PRT

-continued

<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Leu Arg Asn Asp
            20                  25                  30

Leu Gly Trp Phe Gln Gln Lys Pro Gly Lys Val Thr Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Tyr Ser Phe Pro Trp
                85                  90                  95

Thr Phe Gly Gln Gly Thr Lys Val Glu Ile Lys
            100                 105

<210> SEQ ID NO 39
<211> LENGTH: 321
<212> TYPE: DNA
<213> ORGANISM: Homo sapiens

<400> SEQUENCE: 39
gacatccaga tgacccagtc tccatcctcc ctgtctgcat ctgttggaga cagagtcacc      60
atcacttgcc gggcaagtca gggcttaga aatgatttag ctggtttca gcagaaacca      120 gggaaagccc ctaagcgcct gatctatgct gcatccagtt tgcaaagagg ggtcccatca      180
aggttcagcg gcagtggatc tgggacagaa ttcactctca caatcagcag cctgcagcct      240
gaagatttta caacttattt ctgtctacag cataatagtt tcccgtggac gttcggccaa      300
gggaccaagg tggaaatcaa a                                                321

<210> SEQ ID NO 40
<211> LENGTH: 107
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Leu Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Phe Cys Leu Gln His Asn Ser Phe Pro Trp
                85                  90                  95

Thr Phe Gly Gln Gly Thr Lys Val Glu Ile Lys
            100                 105

<210> SEQ ID NO 41
<211> LENGTH: 321
<212> TYPE: DNA
<213> ORGANISM: Homo sapiens

<400> SEQUENCE: 41

```
gacatccaga tgacccagtc tccatcctcc ctgtctgcat ctgttggaga cagagtcacc      60
atcacttgcc gggcaagtca gggccttaga aatgatttag ctggtttca gcagaaacca     120
gggaaagccc ctaagcgcct gatctatgct gcatccagtt tgcaaagagg ggtcccatca    180
aggttcagcg gcagtggatc tgggacagaa ttcactctca caatcagcag cctgcagcct    240
gaagatttta caacttattt ctgtctacag cataatagtt tcccgtggac gttcggccaa    300
gggaccaagg tggaaatcaa a                                              321
```

<210> SEQ ID NO 42
<211> LENGTH: 107
<212> TYPE: PRT
<213> ORGANISM: Homo sapiens

<400> SEQUENCE: 42

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Leu Arg Asn Asp
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Thr Thr Tyr Phe Cys Leu Gln His Asn Ser Phe Pro Trp
                85                  90                  95

Thr Phe Gly Gln Gly Thr Lys Val Glu Ile Lys
            100                 105
```

<210> SEQ ID NO 43
<211> LENGTH: 321
<212> TYPE: DNA
<213> ORGANISM: Homo sapiens

<400> SEQUENCE: 43

```
gacatccaga tgacccagtc tccatcctcc ctgtctgcat ctgtaggaga cagagtcacc      60
atcacttgcc ggtcaagtca gagcattagt aactatataa attggtatca acagagacca    120
gggaaagccc cgaacctcct gatccatgat gtatccagtt tccaaagtgc ggtcccatca    180
aggttcagtc gcagtggatc tgggacagtt ttcactctca ccatcagcag tctgcaacct    240
gaagattttg caacttactt ctgtcaacag acttacatta ccccattcac tttcggccct    300
gggaccaaag tggatatcaa a                                              321
```

<210> SEQ ID NO 44
<211> LENGTH: 107
<212> TYPE: PRT
<213> ORGANISM: Homo sapiens

<400> SEQUENCE: 44

```
Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Ser Asn Tyr
            20                  25                  30

Ile Asn Trp Tyr Gln Gln Arg Pro Gly Lys Ala Pro Asn Leu Leu Ile
```

-continued

```
                 35                  40                  45
His Asp Val Ser Ser Phe Gln Ser Ala Val Pro Ser Arg Phe Ser Arg
        50                  55                  60

Ser Gly Ser Gly Thr Val Phe Thr Leu Thr Ile Ser Ser Leu Gln Pro
65                  70                  75                  80

Glu Asp Phe Ala Thr Tyr Phe Cys Gln Gln Thr Tyr Ile Thr Pro Phe
                85                  90                  95

Thr Phe Gly Pro Gly Thr Lys Val Asp Ile Lys
            100                 105
```

<210> SEQ ID NO 45
<211> LENGTH: 321
<212> TYPE: DNA
<213> ORGANISM: Homo sapiens

<400> SEQUENCE: 45

```
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctatgct gcatccactt tgcaatcagg ggtcccatct   180
cggttcagtg gcagtggatc tgggacagat ttcactctca ccatcagcag cctgcagcct   240
gaagatgttg caactattta ctgtcaaaag tataacagtg ccccgctcac tttcggcgga   300
gggaccaagg tggagatcaa a                                             321
```

<210> SEQ ID NO 46
<211> LENGTH: 107
<212> TYPE: PRT
<213> ORGANISM: Homo sapiens

<400> SEQUENCE: 46

```
Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys
            100                 105
```

<210> SEQ ID NO 47
<211> LENGTH: 339
<212> TYPE: DNA
<213> ORGANISM: Homo sapiens

<400> SEQUENCE: 47

```
gacatcgtga tgacccagtc tccagactcc ctggctgtgt ctctgggcga gagggccacc    60
atcaactgca agtccagcca gagtgtttta tacaggtcca acaataagat ctacttagct   120
tggtaccagc agaaaccagg acagcctcct aagctgctca tttactgggc atcgacccgg   180
gaatccgggg tccctgaccg attcagtggc agcgggtctg gacagattt cactctcacc    240
```

```
atcagcagcc tgctggctga agatgtggca gtttattact gtcagcaata ttatagtact    300
ccattcactt tcggccctgg gaccaaagtg gatatcaaa                            339
```

<210> SEQ ID NO 48
<211> LENGTH: 113
<212> TYPE: PRT
<213> ORGANISM: Homo sapiens

<400> SEQUENCE: 48

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Arg
            20                  25                  30

Ser Asn Asn Lys Ile Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Leu Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
            100                 105                 110

Lys
```

<210> SEQ ID NO 49
<211> LENGTH: 336
<212> TYPE: DNA
<213> ORGANISM: Homo sapiens

<400> SEQUENCE: 49

```
gatattgtga tgactcagtc tccactctcc ctgcccgtca cccctggaga gccggcctcc     60
atctcctgca ggtctagtca gagcctcctg cgtcgtaatg gatacaacta tttggattgg    120
tacctgcaga agccagggca gtctccacaa ctcctgatct atttgggttc taatcgggcc    180
tccggggtcc cagacaggtt cagtggcagt ggatcaggca cagatttac actgaaaatc     240 agcagagtgg aggctgagga tgttgggggtt attactgca tgcaagctct acaaactccg    300
ctcactttcg gcggagggac cgaggtggag atcaaa                              336
```

<210> SEQ ID NO 50
<211> LENGTH: 112
<212> TYPE: PRT
<213> ORGANISM: Homo sapiens

<400> SEQUENCE: 50

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Arg Arg
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

85                  90                  95
Leu Gln Thr Pro Leu Thr Phe Gly Gly Gly Thr Glu Val Glu Ile Lys
            100                 105                 110

<210> SEQ ID NO 51
<211> LENGTH: 339
<212> TYPE: DNA
<213> ORGANISM: Homo sapiens

<400> SEQUENCE: 51
gacatcgtga tgacccagtt tccagactcc ctggctgtgt ctctgggcga gagggccacc    60
atcaactgca agtccagcca gagtgtttta cacagctcca acaataagaa ctacttaact   120
tggtaccagc tgaaaccagg acagcctcct aagttgctca tttactgggc atctacccgg   180
gaatccgggg tccctgaccg attcagtggc agcgggtctg ggacagattt cactctcacc   240
atcagcagcc tgcaggctga agatgtggca gtttattact gtcaccaata ttatagtact   300
ccgtccagtt ttggccaggg gaccaagctg gagatcaaa                          339

<210> SEQ ID NO 52
<211> LENGTH: 113
<212> TYPE: PRT
<213> ORGANISM: Homo sapiens

<400> SEQUENCE: 52

Asp Ile Val Met Thr Gln Phe Pro Asp Ser Leu Ala Val Ser Leu Gly
 1               5                  10                  15

Glu Arg Ala Thr Ile Asn Cys Lys Ser Ser Gln Ser Val Leu His Ser
            20                  25                  30

Ser Asn Asn Lys Asn Tyr Leu Thr Trp Tyr Gln Leu Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
 65                 70                  75                  80

Ile Ser Ser Leu Gln Ala Glu Asp Val Ala Val Tyr Tyr Cys His Gln
                85                  90                  95

Tyr Tyr Ser Thr Pro Ser Ser Phe Gly Gln Gly Thr Lys Leu Glu Ile
            100                 105                 110

Lys

<210> SEQ ID NO 53
<211> LENGTH: 321
<212> TYPE: DNA
<213> ORGANISM: Homo sapiens

<400> SEQUENCE: 53
gacatccaga tgacccagtc tccatcctcc ctgtctgcat ctgttggaga cagagtcacc    60
atcacttgcc ggacaagtca gagcattagc acctatttaa attggtatca gcagaaacca   120
gggaaagccc ctaagctcct gatctctgct acatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac tttcggcgga   300
gggaccaagg tggagatcaa a                                             321

<210> SEQ ID NO 54
<211> LENGTH: 107

```
<212> TYPE: PRT
<213> ORGANISM: Homo sapiens

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Ser Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 55
<211> LENGTH: 321
<212> TYPE: DNA
<213> ORGANISM: Homo sapiens

<400> SEQUENCE: 55
gacatccaga tgacccagtc tccatcctcc ctgtctgcat ctgtaggaga cagagtcacc        60
atcacttgcc gggcaagtca gagcattagc agctatttaa attggtatca gcagaaacca       120
gggaaagccc ctaagctcct gatctctgct catccagtt ttcaaagtgg ggtcccatca        180
aggttcagtg gcagtggatc tgggacagat ttcactctca ccatcagcag tctgcaacct       240
gaagattttg cagcttacta ctgtcaacag agttacagta ccccgctcac tttcggcgga       300
gggaccaagg tggagatcaa a                                                 321

<210> SEQ ID NO 56
<211> LENGTH: 107
<212> TYPE: PRT
<213> ORGANISM: Homo sapiens

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Ser Ala Thr Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 57
<211> LENGTH: 339
<212> TYPE: DNA
```

<213> ORGANISM: Homo sapiens

<400> SEQUENCE: 57

```
gacatcgtga tgacccagtc tccagactcc ctggctgtgt ctctgggcga gagggccacc    60
atcaactgca agtccagcca gagtgtttta cacagctcca acaataagaa ttatttagtt   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctctcactt tcggcggagg gaccaaggtg gagatcaaa                           339
```

<210> SEQ ID NO 58
<211> LENGTH: 113
<212> TYPE: PRT
<213> ORGANISM: Homo sapiens

<400> SEQUENCE: 58

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu His Ser
            20                  25                  30

Ser Asn Asn Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```

<210> SEQ ID NO 59
<211> LENGTH: 321
<212> TYPE: DNA
<213> ORGANISM: Homo sapiens

<400> SEQUENCE: 59

```
gacatccaga tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcactctca ccatcagcag cctgcagcct   240
gaagattttg caacttacta ttgtcagcag gctaacagtt tccctttcac tttcggcgga   300
gggaccaagg tggagatcaa a                                             321
```

<210> SEQ ID NO 60
<211> LENGTH: 107
<212> TYPE: PRT
<213> ORGANISM: Homo sapiens

<400> SEQUENCE: 60

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
```

-continued

```
                    20                  25                  30
Leu Val Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Phe
                 85                  90                  95

Thr Phe Gly Gly Gly Thr Lys Val Glu Ile Lys
            100                 105
```

<210> SEQ ID NO 61
<211> LENGTH: 321
<212> TYPE: DNA
<213> ORGANISM: Homo sapiens

<400> SEQUENCE: 61

| | | | | | |
|---|---|---|---|---|---|
| gacatccaga | tgacccagtc | tccatcctca | ctgtctgcat | ctgtaggaga | cagagtcacc | 60 |
| atcacttgtc | gggcgagtca | gggcattagc | aattatttag | cctggtttca | gcagaaacca | 120 |
| gggaaagccc | ctaagtccct | gatctatgct | gcatccagtt | tgcaaagtgg | ggtcccatca | 180 |
| aaattcagcg | gcagtggatc | tgggacagat | ttcactctca | ccatcagcag | cctgcagcct | 240 |
| gaagattttg | caacttatta | ctgccaacag | tataatagtt | accctctcac | tttcggcgga | 300 |
| gggaccaagg | tggagatcaa | a | | | | 321 |

<210> SEQ ID NO 62
<211> LENGTH: 107
<212> TYPE: PRT
<213> ORGANISM: Homo sapiens

<400> SEQUENCE: 62

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Ser Asn Tyr
                 20                  25                  30

Leu Ala Trp Phe Gln Gln Lys Pro Gly Lys Ala Pro Lys Ser Leu Ile
         35                  40                  45

Tyr Ala Ala Ser Ser Leu Gln Ser Gly Val Pro Ser Lys Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Leu
                 85                  90                  95

Thr Phe Gly Gly Gly Thr Lys Val Glu Ile Lys
            100                 105
```

<210> SEQ ID NO 63
<211> LENGTH: 324
<212> TYPE: DNA
<213> ORGANISM: Homo sapiens

<400> SEQUENCE: 63

| | | | | | |
|---|---|---|---|---|---|
| gaaattgtgt | tgacgcagtc | tccaggcacc | ctgtctttgt | ctccagggga | aagagccacc | 60 |
| ctctcctgca | gggccagtca | gggtattagt | agaagctact | tagcctggta | ccagcagaaa | 120 |
| cctggccagg | ctcccagcct | cctcatctat | ggtgcatcca | gcagggccac | tggcatccca | 180 |

```
gacaggttca gtggcagtgg gtctgggaca gacttcactc tcaccatcag cagactggag    240
cctgaagatt ttgcagtgta ttactgtcaa caatttggta gttcaccgtg gacgttcggc    300
caagggacca aggtggaaat caaa                                           324
```

<210> SEQ ID NO 64
<211> LENGTH: 108
<212> TYPE: PRT
<213> ORGANISM: Homo sapiens

<400> SEQUENCE: 64

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Gly Ile Ser Arg Ser
            20                  25                  30

Tyr Leu Ala Trp Tyr Gln Gln Lys Pro Gly Gln Ala Pro Ser Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Phe Gly Ser Ser Pro
                85                  90                  95

Trp Thr Phe Gly Gln Gly Thr Lys Val Glu Ile Lys
           100                 105
```

<210> SEQ ID NO 65
<211> LENGTH: 321
<212> TYPE: DNA
<213> ORGANISM: Homo sapiens

<400> SEQUENCE: 65

```
gacattcaga tgacccagtc tccatcctcc gtgtctgcat ctgtaggaga cagagtcacc    60
atcacttgtc gggcgagtca gggtattagc agctggttag cctggtatca gcagaaacca    120
gggaaagccc caaagttcct gatctttgtt gcatccagtt tccaaagtgg ggtcccatca    180
aggttcagcg gcagtggatc tgggacagat tcactctcac ccatcagcag cctgcagcct    240
gaagattttg caacttacta ttgtcaacag gctaacagtt tccctcggac gttcggccaa    300
gggaccaagg tggaaatcaa a                                              321
```

<210> SEQ ID NO 66
<211> LENGTH: 107
<212> TYPE: PRT
<213> ORGANISM: Homo sapiens

<400> SEQUENCE: 66

```
Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Phe Leu Ile
        35                  40                  45

Phe Val Ala Ser Ser Phe Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 67
<211> LENGTH: 321
<212> TYPE: DNA
<213> ORGANISM: Homo sapiens

<400> SEQUENCE: 67
gacatccaga tgacccagtc tccatcttcc gtgtctgcat ctgttggaga cagagtcacc     60
atcacttgtc gggcgagtca gggtattagc agctggttag cctggtatca gcagaaacca    120
gggaaagccc ctaagttcct gatctttgtt gcatccagtt tgcaaagtgg ggtcccatca    180
aggttcagcg gcagtggatc tgggacagat ttcactctca ccatcagcag cctgcagcct    240
gaagattttg caacttacta ttgtcaacag gctaacagtt ccctcggac gttcggccaa     300 gggaccaagg tggaaatcaa a                                               321

<210> SEQ ID NO 68
<211> LENGTH: 107
<212> TYPE: PRT
<213> ORGANISM: Homo sapiens

<400> SEQUENCE: 68

Asp Ile Gln Met Thr Gln Ser Pro Ser Ser Val Ser Ala Ser Val Gly
  1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Gly Lys Ala Pro Lys Phe Leu Ile
         35                  40                  45

Phe Val Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Arg
                85                  90                  95

Thr Phe Gly Gln Gly Thr Lys Val Glu Ile Lys
            100                 105

<210> SEQ ID NO 69
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 69

Met Val His Ala Thr Ser Pro Leu Leu Leu Leu Leu Leu Leu Ser Leu
  1               5                  10                  15

Ala Leu Val Ala Pro Gly Leu Ser Ala Arg Lys Cys Ser Leu Thr Gly
             20                  25                  30

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
     50                  55                  60

Ser Asn Glu Ile Lys Glu Ser Pro Leu His Gly Thr Gln Asn Thr Ile
```

```
                65                  70                  75                  80
Asn Lys Arg Thr Gln Pro Thr Phe Gly Phe Thr Val Asn Trp Lys Phe
                        85                  90                  95

Ser Glu Ser Thr Thr Val Phe Thr Gly Gln Cys Phe Ile Asp Arg Asn
                    100                 105                 110

Gly Lys Glu Val Leu Lys Thr Met Trp Leu Leu Arg Ser Ser Val Asn
                115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Leu
145                 150                 155                 160

Ile Thr Gln Gln Asp Leu Ala Pro Gln Gln Arg Ala Ala Pro Gln Gln
                    165                 170                 175

Lys Arg Ser Ser Pro Ser Glu Gly Leu Cys Pro Pro Gly His His Ile
                180                 185                 190

Ser Glu Asp Gly Arg Asp Cys Ile Ser Cys Lys Tyr Gly Gln Asp Tyr
            195                 200                 205

Ser Thr His Trp Asn Asp Leu Leu Phe Cys Leu Arg Cys Thr Arg Cys
        210                 215                 220

Asp Ser Gly Glu Val Glu Leu Ser Pro Cys Thr Thr Thr Arg Asn Thr
225                 230                 235                 240

Val Cys Gln Cys Glu Glu Gly Thr Phe Arg Glu Asp Ser Pro Glu
                    245                 250                 255

Met Cys Arg Lys Cys Arg Thr Gly Cys Pro Arg Gly Met Val Lys Val
                260                 265                 270

Gly Asp Cys Thr Pro Trp Ser Asp Ile Glu Cys Val His Lys Glu Ser
            275                 280                 285

Gly Thr Lys His Ser Gly Glu Ala Pro Ala Val Glu Glu Thr Val Thr
        290                 295                 300

Ser Ser Pro Gly Thr Pro Ala Ser
305                 310

<210> SEQ ID NO 70
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 70

Met Val His Ala Thr Ser Pro Leu Leu Leu Leu Leu Leu Ser Leu
  1               5                  10                  15

Ala Leu Val Ala Pro Gly Leu Ser Ala Arg Lys Cys Ser Leu Thr Gly
                20                  25                  30

Lys Trp Thr Asn Asp Leu Gly Ser Asn Met Thr Ile Gly Ala Val Asn
            35                  40                  45

Ser Lys Gly Glu Phe Thr Gly Thr Tyr Thr Thr Ala Val Thr Ala Thr
        50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                    85                  90                  95

Ser Glu Ser Thr Thr Val Phe Thr Gly Gln Cys Phe Ile Asp Arg Asn
                100                 105                 110
```

```
Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Leu
145                 150                 155                 160

Ile Thr Gln Gln Asp Leu Ala Pro Gln Gln Arg Ala Ala Pro Gln Gln
                165                 170                 175

Lys Arg Ser Ser Pro Ser Glu Gly Leu Cys Pro Pro Gly His His Ile
                180                 185                 190

Ser Glu Asp Gly Arg Asp Cys Ile Ser
                195                 200

<210> SEQ ID NO 71
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 71

Met Val His Ala Thr Ser Pro Leu Leu Leu Leu Leu Leu Ser Leu
  1               5                  10                  15

Ala Leu Val Ala Pro Gly Leu Ser Ala Arg Lys Cys Ser Leu Thr Gly
                 20                  25                  30

Lys Trp Thr Asn Asp Leu Gly Ser Asn Met Thr Ile Gly Ala Val Asn
             35                  40                  45

Ser Lys Gly Glu Phe Thr Gly Thr Tyr Thr Thr Ala Val Thr Ala Thr
     50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Leu
145                 150                 155                 160

Ile Thr Gln Gln Asp Leu Ala Pro Gln Gln Arg Ala Ala Pro Gln Gln
                165                 170                 175

Lys Arg Ser Ser Pro Ser Glu Gly Leu Cys Pro Pro Gly His His Ile
                180                 185                 190

Ser Glu Asp Gly Arg Asp Cys Ile Ser Cys Lys Tyr Gly Gln Asp Tyr
                195                 200                 205

Ser Thr His Trp Asn Asp Leu Leu Phe Cys Leu Arg Cys Thr Arg Cys
        210                 215                 220

Asp Ser Gly Glu Val Glu Leu Ser Pro Cys Thr Thr Thr Arg Asn Thr
225                 230                 235                 240

Val Cys Gln

<210> SEQ ID NO 72
<211> LENGTH: 284
```

<212> TYPE: PRT
<213> ORGANISM: Artificial Sequence
<220> FEATURE:
<223> OTHER INFORMATION: Description of Artificial Sequence: Synthetic polypeptide sequence

<400> SEQUENCE: 72

```
Met Val His Ala Thr Ser Pro Leu Leu Leu Leu Leu Ser Leu
 1               5                  10                  15
Ala Leu Val Ala Pro Gly Leu Ser Ala Arg Lys Cys Ser Leu Thr Gly
             20                  25                  30
Lys Trp Thr Asn Asp Leu Gly Ser Asn Met Thr Ile Gly Ala Val Asn
         35                  40                  45
Ser Lys Gly Glu Phe Thr Gly Thr Tyr Thr Thr Ala Val Thr Ala Thr
     50                  55                  60
Ser Asn Glu Ile Lys Glu Ser Pro Leu His Gly Thr Gln Asn Thr Ile
 65                  70                  75                  80
Asn Lys Arg Thr Gln Pro Thr Phe Gly Phe Thr Val Asn Trp Lys Phe
                 85                  90                  95
Ser Glu Ser Thr Thr Val Phe Thr Gly Gln Cys Phe Ile Asp Arg Asn
            100                 105                 110
Gly Lys Glu Val Leu Lys Thr Met Trp Leu Leu Arg Ser Ser Val Asn
        115                 120                 125
Asp Ile Gly Asp Asp Trp Lys Ala Thr Arg Val Gly Ile Asn Ile Phe
    130                 135                 140
Thr Arg Leu Arg Thr Gln Lys Glu Gln Leu Leu Ala Ser Leu Ala Leu
145                 150                 155                 160
Ile Thr Gln Gln Asp Leu Ala Pro Gln Gln Arg Ala Ala Pro Gln Gln
                165                 170                 175
Lys Arg Ser Ser Pro Ser Glu Gly Leu Cys Pro Pro Gly His His Ile
            180                 185                 190
Ser Glu Asp Gly Arg Asp Cys Ile Ser Cys Lys Tyr Gly Gln Asp Tyr
        195                 200                 205
Ser Thr His Trp Asn Asp Leu Leu Phe Cys Leu Arg Cys Thr Arg Cys
    210                 215                 220
Asp Ser Gly Glu Val Glu Leu Ser Pro Cys Thr Thr Thr Arg Asn Thr
225                 230                 235                 240
Val Cys Gln Cys Glu Glu Gly Thr Phe Arg Glu Glu Asp Ser Pro Glu
                245                 250                 255
Met Cys Arg Lys Cys Arg Thr Gly Cys Pro Arg Gly Met Val Lys Val
            260                 265                 270
Gly Asp Cys Thr Pro Trp Ser Asp Ile Glu Cys Val
        275                 280
```

<210> SEQ ID NO 73
<211> LENGTH: 186
<212> TYPE: PRT
<213> ORGANISM: Artificial Sequence
<220> FEATURE:
<223> OTHER INFORMATION: Description of Artificial Sequence: Synthetic polypeptide sequence

<400> SEQUENCE: 73

```
Met Val His Ala Thr Ser Pro Leu Leu Leu Leu Leu Ser Leu
 1               5                  10                  15
Ala Leu Val Ala Pro Gly Leu Ser Ala Arg Lys Cys Ser Leu Thr Gly
             20                  25                  30
```

```
Lys Trp Thr Asn Asp Leu Gly Ser Asn Met Thr Ile Gly Ala Val Asn
            35                  40                  45

Ser Lys Gly Glu Phe Thr Gly Thr Tyr Thr Thr Ala Val Thr Ala Thr
    50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
            115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Pro Gln
145                 150                 155                 160

Gln Lys Arg Ser Ser Pro Ser Glu Gly Leu Cys Pro Pro Gly His His
                165                 170                 175

Ile Ser Glu Asp Gly Arg Asp Cys Ile Ser
                180                 185

<210> SEQ ID NO 74
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 74

Met Val His Ala Thr Ser Pro Leu Leu Leu Leu Leu Leu Leu Ser Leu
  1               5                  10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
            35                  40                  45

Ser Lys Gly Glu Phe Thr Gly Thr Tyr Thr Thr Ala Val Thr Ala Thr
    50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
            115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Pro Gln
145                 150                 155                 160

Gln Lys Arg Ser Pro Ser Glu Gly Leu Cys Pro Pro Gly His His
                165                 170                 175

Ile Ser Glu Asp Gly Arg Asp Cys Ile Ser Cys Lys Tyr Gly Gln Asp
                180                 185                 190

Tyr Ser Thr His Trp Asn Asp Leu Leu Phe Cys Leu Arg Cys Thr Arg
                195                 200                 205
```

-continued

Cys Asp Ser Gly Glu Val Glu Leu Ser Pro Cys Thr Thr Thr Arg Asn
    210                 215                 220

Thr Val Cys Gln
225

<210> SEQ ID NO 75
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 75

Met Val His Ala Thr Ser Pro Leu Leu Leu Leu Leu Leu Leu Ser Leu
  1               5                  10                  15

Ala Leu Val Ala Pro Gly Leu Ser Ala Arg Lys Cys Ser Leu Thr Gly
             20                  25                  30

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
     50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
            115                 120                 125

Asp Ile Gly Asp Asp Trp Lys Ala Thr Arg Val Gly Ile Asn Ile Phe
        130                 135                 140

Thr Arg Leu Arg Thr Gln Lys Glu Gln Leu Leu Ala Ser Leu Pro Gln
145                 150                 155                 160

Gln Lys Arg Ser Ser Pro Ser Glu Gly Leu Cys Pro Pro Gly His His
                165                 170                 175

Ile Ser Glu Asp Gly Arg Asp Cys Ile Ser Cys Lys Tyr Gly Gln Asp
            180                 185                 190

Tyr Ser Thr His Trp Asn Asp Leu Leu Phe Cys Leu Arg Cys Thr Arg
        195                 200                 205

Cys Asp Ser Gly Glu Val Glu Leu Ser Pro Cys Thr Thr Thr Arg Asn
    210                 215                 220

Thr Val Cys Gln Cys Glu Glu Gly Thr Phe Arg Glu Glu Asp Ser Pro
225                 230                 235                 240

Glu Met Cys Arg Lys Cys Arg Thr Gly Cys Pro Arg Gly Met Val Lys
                245                 250                 255

Val Gly Asp Cys Thr Pro Trp Ser Asp Ile Glu Cys Val
            260                 265

<210> SEQ ID NO 76
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 76

```
Met Val His Ala Thr Ser Pro Leu Leu Leu Leu Leu Leu Ser Leu
  1               5                  10                  15

Ala Leu Val Ala Pro Gly Leu Ser Ala Arg Lys Cys Ser Leu Thr Gly
             20                  25                  30

Lys Trp Thr Asn Asp Leu Gly Ser Asn Met Thr Ile Gly Ala Val Asn
             35                  40                  45

Ser Lys Gly Glu Phe Thr Gly Thr Tyr Thr Thr Ala Val Thr Ala Thr
 50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
                115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Ile Ser
145                 150                 155                 160

Cys Lys Tyr Gly Gln Asp Tyr Ser Thr His Trp Asn Asp Leu Leu Phe
                165                 170                 175

Cys Leu Arg Cys Thr Arg Cys Asp Ser Gly Glu Val Glu Leu Ser Pro
                180                 185                 190

Cys Thr Thr Thr Arg Asn Thr Val Cys Gln
                195                 200

<210> SEQ ID NO 77
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 77

Met Val His Ala Thr Ser Pro Leu Leu Leu Leu Leu Leu Ser Leu
  1               5                  10                  15

Ala Leu Val Ala Pro Gly Leu Ser Ala Arg Lys Cys Ser Leu Thr Gly
             20                  25                  30

Lys Trp Thr Asn Asp Leu Gly Ser Asn Met Thr Ile Gly Ala Val Asn
             35                  40                  45

Ser Lys Gly Glu Phe Thr Gly Thr Tyr Thr Thr Ala Val Thr Ala Thr
 50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
                115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Ile Ser
```

```
                145                 150                 155                 160
Cys Lys Tyr Gly Gln Asp Tyr Ser Thr His Trp Asn Asp Leu Leu Phe
                    165                 170                 175

Cys Leu Arg Cys Thr Arg Cys Asp Ser Gly Glu Val Glu Leu Ser Pro
                    180                 185                 190

Cys Thr Thr Thr Arg Asn Thr Val Cys Gln Cys Glu Glu Gly Thr Phe
                    195                 200                 205

Arg Glu Glu Asp Ser Pro Glu Met Cys Arg Lys Cys Arg Thr Gly Cys
                    210                 215                 220

Pro Arg Gly Met Val Lys Val Gly Asp Cys Thr Pro Trp Ser Asp Ile
225                 230                 235                 240

Glu Cys Val

<210> SEQ ID NO 78
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 78

Met Val His Ala Thr Ser Pro Leu Leu Leu Leu Leu Leu Ser Leu
1               5                   10                  15

Ala Leu Val Ala Pro Gly Leu Ser Ala Arg Lys Cys Ser Leu Thr Gly
                    20                  25                  30

Lys Trp Thr Asn Asp Leu Gly Ser Asn Met Thr Ile Gly Ala Val Asn
                    35                  40                  45

Ser Lys Gly Glu Phe Thr Gly Thr Tyr Thr Thr Ala Val Thr Ala Thr
                50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                    85                  90                  95

Ser Glu Ser Thr Thr Val Phe Thr Gly Gln Cys Phe Ile Asp Arg Asn
                    100                 105                 110

Gly Lys Glu Val Leu Lys Thr Met Trp Leu Leu Arg Ser Ser Val Asn
                    115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Gln Cys
145                 150                 155                 160

Glu Glu Gly Thr Phe Arg Glu Glu Asp Ser Pro Glu Met Cys Arg Lys
                    165                 170                 175

Cys Arg Thr Gly Cys Pro Arg Gly Met Val Lys Val Gly Asp Cys Thr
                    180                 185                 190

Pro Trp Ser Asp Ile Glu Cys Val His Lys Glu Ser Gly Thr Lys His
                    195                 200                 205

Ser Gly Glu Ala Pro Ala Val Glu Glu Thr Val Thr Ser Ser Pro Gly
                    210                 215                 220

Thr Pro Ala Ser
225

<210> SEQ ID NO 79
<211> LENGTH: 271
<212> TYPE: PRT
```

<213> ORGANISM: Artificial Sequence
<220> FEATURE:
<223> OTHER INFORMATION: Description of Artificial Sequence: Synthetic
      polypeptide sequence

<400> SEQUENCE: 79

```
Met Val His Ala Thr Ser Pro Leu Leu Leu Leu Leu Leu Ser Leu
 1               5                  10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
        35                  40                  45

Ser Lys Gly Glu Phe Thr Gly Thr Tyr Thr Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ile Ser
145                 150                 155                 160

Cys Lys Tyr Gly Gln Asp Tyr Ser Thr His Trp Asn Asp Leu Leu Phe
                165                 170                 175

Cys Leu Arg Cys Thr Arg Cys Asp Ser Gly Glu Val Glu Leu Ser Pro
            180                 185                 190

Cys Thr Thr Thr Arg Asn Thr Val Cys Gln Cys Glu Glu Gly Thr Phe
        195                 200                 205

Arg Glu Glu Asp Ser Pro Glu Met Cys Arg Lys Cys Arg Thr Gly Cys
    210                 215                 220

Pro Arg Gly Met Val Lys Val Gly Asp Cys Thr Pro Trp Ser Asp Ile
225                 230                 235                 240

Glu Cys Val His Lys Glu Ser Gly Thr Lys His Ser Gly Glu Ala Pro
                245                 250                 255

Ala Val Glu Glu Thr Val Thr Ser Ser Pro Gly Thr Pro Ala Ser
            260                 265                 270
```

<210> SEQ ID NO 80
<211> LENGTH: 209
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 80

```
Met Val His Ala Thr Ser Pro Leu Leu Leu Leu Leu Leu Ser Leu
 1               5                  10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
        35                  40                  45

Ser Lys Gly Glu Phe Thr Gly Thr Tyr Thr Thr Ala Val Thr Ala Thr
```

```
                    50                  55                  60
Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
                115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Pro Gln
145                 150                 155                 160

Gln Lys Arg Ser Ser Pro Ser Glu Gly Leu Cys Pro Pro Gly His His
                165                 170                 175

Ile Ser Glu Asp Gly Arg Asp Cys Ile Ser Tyr Lys Tyr Gly Gln Asp
                180                 185                 190

Tyr Ser Thr His Trp Asn Asp Leu Leu Phe Cys Leu Arg Cys Thr Arg
                195                 200                 205

Cys

<210> SEQ ID NO 81
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 81

Met Val His Ala Thr Ser Pro Leu Leu Leu Leu Leu Leu Ser Leu
  1               5                  10                  15

Ala Leu Val Ala Pro Gly Leu Ser Ala Arg Lys Cys Ser Leu Thr Gly
                 20                  25                  30

Lys Trp Thr Asn Asp Leu Gly Ser Asn Met Thr Ile Gly Ala Val Asn
                 35                  40                  45

Ser Lys Gly Glu Phe Thr Gly Thr Tyr Thr Thr Ala Val Thr Ala Thr
 50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
                115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Pro Gln
145                 150                 155                 160

Gln Lys Arg Ser Ser Pro Ser Glu Gly Leu Cys Pro Pro Gly His His
                165                 170                 175

Ile Ser Glu Asp Gly Arg Asp Cys Ile Ser Cys Lys Tyr Gly Gln Asp
                180                 185                 190

Tyr Ser Thr His Trp Asn Asp Leu Leu Phe Cys Leu Arg Cys Thr Arg
```

```
                195                 200                 205
Cys Asp Ser Gly Glu Val Glu Leu Ser
    210                 215

<210> SEQ ID NO 82
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 82

Met Val His Ala Thr Ser Pro Leu Leu Leu Leu Leu Leu Ser Leu
  1               5                  10                  15

Ala Leu Val Ala Pro Gly Leu Ser Ala Arg Lys Cys Ser Leu Thr Gly
                 20                  25                  30

Lys Trp Thr Asn Asp Leu Gly Ser Asn Met Thr Ile Gly Ala Val Asn
                 35                  40                  45

Ser Lys Gly Glu Phe Thr Gly Thr Tyr Thr Thr Ala Val Thr Ala Thr
     50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
                115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Pro
145                 150                 155                 160

Ile Thr Arg Gln Ser Leu Asp Pro Gln Arg Arg Ala Ala Pro Gln Gln
                165                 170                 175

Lys Arg Ser Ser Pro Thr Glu Gly Leu Cys Pro Pro Gly His His Ile
                180                 185                 190

Ser Glu Asp Ser Arg Asp Cys Ile Ser Cys Lys Tyr Gly Gln Asp Tyr
                195                 200                 205

Ser Thr His Trp Asn Asp Phe Leu Phe Cys Leu Arg Cys Thr Lys Cys
    210                 215                 220

Asp Ser Gly Glu Val Glu Val Ser Ser Cys Thr Thr Arg Asn Thr
225                 230                 235                 240

Val Cys Gln Cys Glu Glu Gly Thr Phe Arg Glu Glu Asp Ser Pro Glu
                245                 250                 255

Ile Cys Arg Lys Cys Arg Thr Gly Cys Pro Arg Gly Met Val Lys Val
                260                 265                 270

Lys Asp Cys Thr Pro Trp Ser Asp Ile Glu Cys Pro Gln Arg Arg Ile
    275                 280                 285

Gln Thr
    290

<210> SEQ ID NO 83
<211> LENGTH: 312
<212> TYPE: PRT
<213> ORGANISM: Artificial Sequence
<220> FEATURE:
```

<223> OTHER INFORMATION: Description of Artificial Sequence: Synthetic
      polypeptide sequence

<400> SEQUENCE: 83

Met Val His Ala Thr Ser Pro Leu Leu Leu Leu Leu Leu Ser Leu
 1               5                  10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
        35                  40                  45

Ser Lys Gly Glu Phe Thr Gly Thr Tyr Thr Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Pro
145                 150                 155                 160

Ile Thr Arg Gln Ser Leu Asp Pro Gln Arg Arg Ala Ala Pro Gln Gln
                165                 170                 175

Lys Arg Ser Ser Pro Thr Glu Gly Leu Cys Pro Pro Gly His His Ile
            180                 185                 190

Ser Glu Asp Ser Arg Asp Cys Ile Ser Cys Lys Tyr Gly Gln Asp Tyr
        195                 200                 205

Ser Thr His Trp Asn Asp Phe Leu Phe Cys Leu Arg Cys Thr Lys Cys
    210                 215                 220

Asp Ser Gly Glu Val Glu Val Ser Ser Cys Thr Thr Thr Arg Asn Thr
225                 230                 235                 240

Val Cys Gln Cys Glu Glu Gly Thr Phe Arg Glu Glu Asp Ser Pro Glu
                245                 250                 255

Ile Cys Arg Lys Cys Arg Thr Gly Cys Pro Arg Gly Met Val Lys Val
            260                 265                 270

Lys Asp Cys Thr Pro Trp Ser Asp Ile Glu Cys Val His Lys Glu Ser
        275                 280                 285

Gly Thr Lys His Thr Gly Glu Val Pro Ala Val Glu Lys Thr Val Thr
    290                 295                 300

Thr Ser Pro Gly Thr Pro Ala Ser
305                 310

<210> SEQ ID NO 84
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 84

Met Val His Ala Thr Ser Pro Leu Leu Leu Leu Leu Leu Ser Leu
 1               5                  10                  15

```
Ala Leu Val Ala Pro Gly Leu Ser Ala Arg Lys Cys Ser Leu Thr Gly
             20                  25                  30

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
 50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
             85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
            115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Ala Pro
145                 150                 155                 160

Ile Thr Arg Gln Ser Leu Asp Pro Gln Arg Arg Ala Ala Pro Gln Gln
                165                 170                 175

Lys Arg Ser Ser Pro Thr Glu Gly Leu Cys Pro Pro Gly His His Ile
            180                 185                 190

Ser Glu Asp Ser Arg Asp Cys Ile Ser Cys Lys Tyr Gly Gln Asp Tyr
            195                 200                 205

Ser Thr His Trp Asn Asp Phe Leu Phe Cys Leu Arg Cys Thr Lys Cys
            210                 215                 220

Asp Ser Gly Glu Val Glu Val Ser Ser Cys Thr Thr Thr Arg Asn Thr
225                 230                 235                 240

Val Cys Gln

<210> SEQ ID NO 85
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 85

Met Val His Ala Thr Ser Pro Leu Leu Leu Leu Leu Leu Ser Leu
 1               5                  10                  15

Ala Leu Val Ala Pro Gly Leu Ser Ala Arg Lys Cys Ser Leu Thr Gly
             20                  25                  30

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
 50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
             85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
            115                 120                 125
```

```
Asp Ile Gly Asp Asp Trp Lys Ala Thr Arg Val Gly Ile Asn Ile Phe
        130                 135                 140

Thr Arg Leu Arg Thr Gln Lys Glu Gln Leu Leu Ala Ser Leu Pro Gln
145                 150                 155                 160

Gln Lys Arg Ser Ser Pro Ile Glu Gly Leu Cys Pro Pro Gly His His
                165                 170                 175

Ile Ser Glu Asp Ser Arg Asp Cys Ile Ser Cys Lys Tyr Gly Gln Asp
                180                 185                 190

Tyr Ser Thr His Trp Asn Asp Phe Leu Phe Cys Leu Arg Cys Thr Lys
        195                 200                 205

Cys Asp Ser Gly Glu Val Glu Val Ser Ser Cys Thr Thr Thr Arg Asn
    210                 215                 220

Thr Val Cys Gln
225

<210> SEQ ID NO 86
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 86

Met Val His Ala Thr Ser Pro Leu Leu Leu Leu Leu Leu Leu Ser Leu
  1               5                  10                  15

Ala Leu Val Ala Pro Gly Leu Ser Ala Arg Lys Cys Ser Leu Thr Gly
                 20                  25                  30

Lys Trp Thr Asn Asp Leu Gly Ser Asn Met Thr Ile Gly Ala Val Asn
             35                  40                  45

Ser Lys Gly Glu Phe Thr Gly Thr Tyr Thr Thr Ala Val Thr Ala Thr
 50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
            115                 120                 125

Asp Ile Gly Asp Asp Trp Lys Ala Thr Arg Val Gly Ile Asn Ile Phe
        130                 135                 140

Thr Arg Leu Arg Thr Gln Lys Glu Gln Leu Leu Ala Ser Leu Ala Pro
145                 150                 155                 160

Ile Thr Arg Gln Ser Leu Asp Pro Gln Arg Arg Ala Ala Pro Gln Gln
                165                 170                 175

Lys Arg Ser Ser Pro Ser Glu Gly Leu Cys Pro Pro Gly His His Ile
            180                 185                 190

Ser Glu Asp Gly Arg Asp Cys Ile Ser Cys Lys Tyr Gly Gln Asp Tyr
        195                 200                 205

Ser Thr His Trp Asn Asp Leu Leu Phe Cys Leu Arg Cys Thr Arg Cys
    210                 215                 220

Asp Ser Gly Glu Val Glu Leu Ser Pro Cys Thr Thr Thr Arg Asn Thr
225                 230                 235                 240

Val Cys Gln
```

```
<210> SEQ ID NO 87
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 87

Met Val His Ala Thr Ser Pro Leu Leu Leu Leu Leu Leu Leu Ser Leu
 1               5                  10                  15

Ala Leu Val Ala Pro Gly Leu Ser Ala Arg Lys Cys Ser Leu Thr Gly
             20                  25                  30

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
     50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Pro
145                 150                 155                 160

Ile Thr Arg Gln Ser Leu Asp Pro Gln Arg Arg Ala Ala Pro Gln Gln
                165                 170                 175

Lys Arg Ser Ser Pro Ser Glu Gly Leu Cys Pro Pro Gly His His Ile
            180                 185                 190

Ser Glu Asp Gly Arg Asp Tyr Ile Ser Cys Lys Tyr Gly Gln Asp Tyr
        195                 200                 205

Ser Thr His Trp Asn Asp Leu Leu Phe Cys Leu Arg Cys Thr Arg Cys
    210                 215                 220

Asp Ser Gly Glu Val Glu Leu Ser Pro Cys Thr Thr Thr Arg Asn Thr
225                 230                 235                 240

Val Cys Gln Cys Glu Glu Gly Thr Phe Arg Glu Glu Asp Ser Pro Glu
                245                 250                 255

Met Cys Arg Lys Cys Arg Thr Gly Cys Pro Arg Gly Met Val Lys Val
            260                 265                 270

Gly Asp Cys Thr Pro Trp Ser Asp Ile Glu Cys Val His Lys Glu Ser
        275                 280                 285

Gly Thr Lys His Ser Gly Glu Ala Pro Ala Val Glu Glu Thr Val Thr
    290                 295                 300

Ser Ser Pro Gly Thr Pro Ala Ser
305                 310

<210> SEQ ID NO 88
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide sequence
```

<400> SEQUENCE: 88

```
Met Val His Ala Thr Ser Pro Leu Leu Leu Leu Leu Leu Ser Leu
 1               5                  10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
     50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Leu
145                 150                 155                 160

Ile Thr Gln Gln Asp Leu Ala Pro Gln Gln Arg Ala Ala Pro Gln Gln
                165                 170                 175

Lys Arg Ser Ser Pro Thr Glu Gly Leu Cys Pro Pro Gly His His Ile
            180                 185                 190

Ser Glu Asp Ser Arg Asp Cys Ile Ser Cys Lys Tyr Gly Gln Asp Tyr
        195                 200                 205

Ser Thr His Trp Asn Asp Phe Leu Phe Cys Leu Arg Cys Thr Lys Cys
    210                 215                 220

Asp Ser Gly Glu Val Glu Val Ser Ser Cys Thr Thr Arg Asn Thr
225                 230                 235                 240

Val Cys Gln
```

<210> SEQ ID NO 89
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 89

```
Met Val His Ala Thr Ser Pro Leu Leu Leu Leu Leu Leu Ser Leu
 1               5                  10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
         35                  40                  45

Ser Lys Gly Glu Phe Thr Gly Thr Tyr Thr Thr Ala Val Thr Ala Thr
     50                  55                  60

Ser Asn Glu Ile Lys Glu Ser Pro Leu His Gly Thr Gln Asn Thr Ile
 65                  70                  75                  80

Asn Lys Arg Thr Gln Pro Thr Phe Gly Phe Thr Val Asn Trp Lys Phe
                 85                  90                  95
```

```
Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Leu
145                 150                 155                 160

Ile Thr Gln Gln Asp Leu Ala Pro Gln Gln Arg Ala Ala Pro Gln Gln
                165                 170                 175

Lys Arg Ser Ser Pro Thr Glu Gly Leu Cys Pro Pro Gly His His Ile
            180                 185                 190

Ser Glu Asp Ser Arg Asp Cys Ile Ser Cys Lys Tyr Gly Gln Asp Tyr
        195                 200                 205

Ser Thr His Trp Asn Asp Phe Leu Phe Cys Leu Arg Cys Thr Lys Cys
    210                 215                 220

Asp Ser Gly Glu Val Glu Val Ser Ser Cys Thr Thr Thr Arg Asn Thr
225                 230                 235                 240

Val Cys Gln Cys Glu Glu Gly Thr Phe Arg Glu Glu Asp Ser Pro Glu
                245                 250                 255

Ile Cys Arg Lys Cys Arg Thr Gly Cys Pro Arg Gly Met Val Lys Val
            260                 265                 270

Lys Asp Cys Thr Pro Trp Ser Asp Ile Glu Cys Val His Lys Glu Ser
        275                 280                 285

Gly Thr Lys His Thr Gly Glu Val Pro Ala Val Glu Lys Thr Val Thr
    290                 295                 300

Thr Ser Pro Gly Thr Pro Ala Ser
305                 310

<210> SEQ ID NO 90
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 90

Met Val His Ala Thr Ser Pro Leu Leu Leu Leu Leu Leu Leu Ser Leu
1               5                   10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
        35                  40                  45

Ser Lys Gly Glu Phe Thr Gly Thr Tyr Thr Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140
```

```
Thr Arg Leu Arg Thr Gln Lys Glu Gln Leu Leu Ala Ser Leu Val Pro
145                 150                 155                 160

Val Thr Ala Asn Pro Ala His Asn Arg Pro Ala Gly Leu Gln Arg Pro
                165                 170                 175

Glu Glu Ser Pro Ser Glu Gly Leu Cys Pro Pro Gly His His Ile Ser
            180                 185                 190

Glu Asp Gly Arg Asp Cys Ile Ser Cys Lys Tyr Gly Gln Asp Tyr Ser
        195                 200                 205

Thr His Trp Asn Asp Leu Leu Phe Cys Leu Arg Cys Thr Arg Cys Asp
    210                 215                 220

Ser Gly Glu Val Glu Leu Ser Pro Cys Thr Thr Arg Asn Thr Val
225                 230                 235                 240

Cys Gln Cys Glu Glu Gly Thr Phe Arg Glu Glu Asp Ser Pro Glu Met
                245                 250                 255

Cys Arg Lys Cys Arg Thr Gly Cys Pro Arg Gly Met Val Lys Val Gly
            260                 265                 270

Asp Cys Thr Pro Trp Ser Asp Ile Glu Cys Val His Lys Glu Ser Gly
        275                 280                 285

Thr Lys His Ser Gly Glu Ala Pro Ala Val Glu Glu Thr Val Thr Ser
    290                 295                 300

Ser Pro Gly Thr Pro Ala Ser
305                 310

<210> SEQ ID NO 91
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 91

Met Val His Ala Thr Ser Pro Leu Leu Leu Leu Leu Leu Leu Ser Leu
 1               5                  10                  15

Ala Leu Val Ala Pro Gly Leu Ser Ala Arg Lys Cys Ser Leu Thr Gly
                20                  25                  30

Lys Trp Thr Asn Asp Leu Gly Ser Asn Met Thr Ile Gly Ala Val Asn
            35                  40                  45

Ser Lys Gly Glu Phe Thr Gly Thr Tyr Thr Thr Ala Val Thr Ala Thr
        50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu Gln Leu Leu Ala Ser Leu Ala Leu
145                 150                 155                 160

Ile Thr Gln Gln Asp Leu Ala Pro Gln Gln Arg Ala Ala Pro Gln Gln
                165                 170                 175

Lys Arg Ser Ser Pro Ser Glu Gly Leu Cys Leu Ala Gly Gln Tyr Leu
```

-continued

```
                180                 185                 190
Ser Glu Asp Gly Arg Asp Cys Ile Ser Cys Lys Tyr Gly Gln Asp Tyr
        195                 200                 205
Ser Thr His Trp Asn Asp Leu Leu Phe Cys Leu Arg Cys Thr Arg Cys
        210                 215                 220
Asp Ser Gly Glu Val Glu Leu Ser Pro Cys Thr Thr Arg Asn Thr
225                 230                 235                 240
Val Cys Gln Cys Glu Glu Gly Thr Phe Arg Glu Asp Ser Pro Glu
                245                 250                 255
Met Cys Arg Lys Cys Arg Thr Gly Cys Pro Arg Gly Met Val Lys Val
        260                 265                 270
Gly Asp Cys Thr Pro Trp Ser Asp Ile Glu Cys Val His Lys Glu Ser
        275                 280                 285
Gly Thr Lys His Ser Gly Glu Ala Pro Ala Val Glu Thr Val Thr
        290                 295                 300
Ser Ser Pro Gly Thr Pro Ala Ser
305                 310

<210> SEQ ID NO 92
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 92

Met Val His Ala Thr Ser Pro Leu Leu Leu Leu Leu Leu Ser Leu
  1               5                  10                  15
Ala Leu Val Ala Pro Gly Leu Ser Ala Arg Lys Cys Ser Leu Thr Gly
                 20                  25                  30
Lys Trp Thr Asn Asp Leu Gly Ser Asn Met Thr Ile Gly Ala Val Asn
         35                  40                  45
Ser Lys Gly Glu Phe Thr Gly Thr Tyr Thr Thr Ala Val Thr Ala Thr
    50                  55                  60
Ser Asn Glu Ile Lys Glu Ser Pro Leu His Gly Thr Gln Asn Thr Ile
65                  70                  75                  80
Asn Lys Arg Thr Gln Pro Thr Phe Gly Phe Thr Val Asn Trp Lys Phe
                 85                  90                  95
Ser Glu Ser Thr Thr Val Phe Thr Gly Gln Cys Phe Ile Asp Arg Asn
                100                 105                 110
Gly Lys Glu Val Leu Lys Thr Met Trp Leu Leu Arg Ser Ser Val Asn
        115                 120                 125
Asp Ile Gly Asp Asp Trp Lys Ala Thr Arg Val Gly Ile Asn Ile Phe
130                 135                 140
Thr Arg Leu Arg Thr Gln Lys Glu Gln Leu Leu Ala Ser Leu Ala Leu
145                 150                 155                 160
Ile Thr Gln Gln Asp Leu Ala Pro Gln Gln Arg Ala Ala Pro Gln Gln
                165                 170                 175
Lys Arg Ser Ser Pro Ser Glu Gly Leu Cys Pro Pro Gly His His Ile
                180                 185                 190
Ser Glu Asp Gly Arg Asp Cys Ile Ser Cys Lys Tyr Gly Gln Asp Tyr
        195                 200                 205
Ser Thr His Trp Asn Asp Leu Leu Phe Cys Leu Arg Cys Thr Arg Cys
        210                 215                 220
```

```
Asp Ser Gly Glu Val Glu Leu Ser Pro Cys Thr Thr Thr Arg Asn Thr
225                 230                 235                 240

Val Cys Gln Cys Glu Glu Gly Thr Phe Arg Glu Asp Ser Pro Glu
            245                 250                 255

Met Cys Arg Lys Cys Arg Thr Gly Cys Pro Arg Gly Met Val Lys Val
            260                 265                 270

Gly Asp Cys Thr Pro Trp Ser Asp Ile Glu Cys Val His Lys Glu Ser
            275                 280                 285

Gly Thr Lys His Ser Gly Glu Ala Pro Ala Val Glu Glu Thr Val Thr
            290                 295                 300

Ser Ser Pro Gly Thr Pro Ala Ser
305                 310

<210> SEQ ID NO 93
<211> LENGTH: 313
<212> TYPE: PRT
<213> ORGANISM: Artificial Sequence
<220> FEATURE:
<223> OTHER INFORMATION: Description of Artificial Sequence: Synthetic
      polypeptide sequence

<400> SEQUENCE: 93

Met Val His Ala Thr Ser Pro Leu Leu Leu Leu Leu Leu Ser Leu
1               5                   10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
            35                  40                  45

Ser Lys Gly Glu Phe Thr Gly Thr Tyr Thr Thr Ala Val Thr Ala Thr
        50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
130                 135                 140

Thr Arg Leu Arg Thr Gln Lys Glu Gln Leu Leu Ala Ser Leu Ala Leu
145                 150                 155                 160

Ile Thr Gln Gln Asp Leu Ala Pro Gln Gln Arg Ala Ala Pro Gln Gln
                165                 170                 175

Lys Arg Ser Ser Pro Ser Glu Gly Leu Cys Pro Pro Gly His His Ile
            180                 185                 190

Ser Glu Asp Gly Arg Asp Cys Ile Ser Cys Lys Tyr Gly Gln Asp Tyr
        195                 200                 205

Ser Thr His Ser Asn His Ser Leu Asp Ser Cys Leu Arg Cys Thr Arg
    210                 215                 220

Cys Asp Ser Gly Glu Val Glu Leu Ser Pro Cys Thr Thr Thr Arg Asn
225                 230                 235                 240

Thr Val Cys Gln Cys Glu Glu Gly Thr Phe Arg Glu Glu Asp Ser Pro
                245                 250                 255

Glu Met Cys Arg Lys Cys Arg Thr Gly Cys Pro Arg Gly Met Val Lys
            260                 265                 270
```

```
Val Gly Asp Cys Thr Pro Trp Ser Asp Ile Glu Cys Val His Lys Glu
        275                 280                 285

Ser Gly Thr Lys His Ser Gly Glu Ala Pro Ala Val Glu Glu Thr Val
        290                 295                 300

Thr Ser Ser Pro Gly Thr Pro Ala Ser
305                 310

<210> SEQ ID NO 94
<211> LENGTH: 15
<212> TYPE: PRT
<213> ORGANISM: Homo sapiens

<400> SEQUENCE: 94

Ala Leu Ile Thr Gln Gln Asp Leu Ala Pro Gln Gln Arg Ala Ala
1               5                   10                  15

<210> SEQ ID NO 95
<211> LENGTH: 42
<212> TYPE: PRT
<213> ORGANISM: Homo sapiens

<400> SEQUENCE: 95

Cys Lys Tyr Gly Gln Asp Tyr Ser Thr His Trp Asn Asp Leu Leu Phe
1               5                   10                  15

Cys Leu Arg Cys Thr Arg Cys Asp Ser Gly Glu Val Glu Leu Ser Pro
                20                  25                  30

Cys Thr Thr Thr Arg Asn Thr Val Cys Gln
            35                  40

<210> SEQ ID NO 96
<211> LENGTH: 85
<212> TYPE: PRT
<213> ORGANISM: Homo sapiens

<400> SEQUENCE: 96

Ala Leu Ile Thr Gln Gln Asp Leu Ala Pro Gln Gln Arg Ala Ala Pro
1               5                   10                  15

Gln Gln Lys Arg Ser Ser Pro Ser Glu Gly Leu Cys Pro Pro Gly His
                20                  25                  30

His Ile Ser Glu Asp Gly Arg Asp Cys Ile Ser Cys Lys Tyr Gly Gln
            35                  40                  45

Asp Tyr Ser Thr His Trp Asn Asp Leu Leu Phe Cys Leu Arg Cys Thr
        50                  55                  60

Arg Cys Asp Ser Gly Glu Val Glu Leu Ser Pro Cys Thr Thr Thr Arg
65                  70                  75                  80

Asn Thr Val Cys Gln
            85

<210> SEQ ID NO 97
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gtaggtgctg tcct                                                         14

<210> SEQ ID NO 98
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
tgagttccac gaca                                                       14

<210> SEQ ID NO 99
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cttccaagcc act                                                        13

<210> SEQ ID NO 100
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cargcactgt ca                                                         12

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gtaggtgctg tccttgct                                                   18

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ctctgtgaca ctctcctggg a                                               21

<210> SEQ ID NO 103
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gctctagatt ggagggcgtt atccaccttc cact                                 34

<210> SEQ ID NO 104
<211> LENGTH: 39
```

<210> SEQ ID NO 104
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
aactagctag cagttccaga tttcaactgc tcatcagat                    39

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
gctcccgggt agaagtca                                           18

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
acyagtgtgg ccttgttggc tt                                      22

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
gctctagagg gygggaacag agtgac                                  26

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 108
acgacaccgt caccggtt                                           18

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 109
aagtagtcct tgaccaggca gccca                                   25

<210> SEQ ID NO 110
<211> LENGTH: 30
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 110
gctctagagg gtgccagggg gaagaccgat                                       30

<210> SEQ ID NO 111
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gctctagagc agggcgccag ggggaaga                                         28

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
atgaggstcc cygctcagct                                                  20

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
atggaarccc cagckcagct t                                                21

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
atggtgttgc agacccaggt ct                                               22

<210> SEQ ID NO 115
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gaagatctca ccatgaggst cccygctcag ctyct                                 35

<210> SEQ ID NO 116
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gaagatctca ccatggaarc cccagckcag cttctctt                            38

<210> SEQ ID NO 117
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gaagatctca ccatggtgtt gcagacccag gtcttcat                            38

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
crtcwccacc atgrcmwg                                                  18

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
caccatgrcc wgstyccct                                                 19

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
accatggcct ggrctcykct                                                20

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
caccatggcm tggrycvyt                                                 19

<210> SEQ ID NO 122
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 122
caccatggcy tggryccmay t                                              21

<210> SEQ ID NO 123
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gaagatctca ccatgrccwg styccctct                                      29

<210> SEQ ID NO 124
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gaagatctca ccatggcctg grctcykcts yt                                  32

<210> SEQ ID NO 125
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gaagatctca ccatggcmtg grycvytctc                                     30

<210> SEQ ID NO 126
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gaagatctca ccatggcytg gryccmaytc                                     30

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)
<223> OTHER INFORMATION: a, c, g or t

<400> SEQUENCE: 127
caccatggas tggacctgga gvntc                                          25

<210> SEQ ID NO 128
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
caccatggac atactttgyt ccacgctc                                          28

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
caccatggar ttkggrctbh gct                                               23

<210> SEQ ID NO 130
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
caccatgaar cayctgtggt tcttcctyct                                        30

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
caccatgggg tcaaccgyca tcct                                              24

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
caccatgtct gtctccttcc tcatcttc                                          28

<210> SEQ ID NO 133
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (30)
<223> OTHER INFORMATION: a, c, g or t

<400> SEQUENCE: 133
gaagatctca ccatggastg gacctggagv ntcc                                   34
```

<210> SEQ ID NO 134
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gaagatctca ccatggacat actttgytcc acgctcc                              37

<210> SEQ ID NO 135
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gaagatctca ccatggartt kggrctbhgc tggvttttyc t                         41

<210> SEQ ID NO 136
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gaagatctca ccatgaarca yctgtggttc ttcctyctc                            39

<210> SEQ ID NO 137
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gaagatctca ccatggggtc aaccgycatc ct                                   32

<210> SEQ ID NO 138
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gaagatctca ccatgtctgt ctccttcctc atcttct                              37

<210> SEQ ID NO 139
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gaagatctca ccatggactg gacctggagg atcctcttct tggt                      44

-continued

```
<210> SEQ ID NO 140
<211> LENGTH: 165
<212> TYPE: PRT
<213> ORGANISM: Homo sapiens

<400> SEQUENCE: 140

Ala Leu Ile Thr Gln Gln Asp Leu Ala Pro Gln Gln Arg Ala Pro
 1               5                  10                  15

Gln Gln Lys Arg Ser Ser Pro Ser Glu Gly Leu Cys Pro Pro Gly His
             20                  25                  30

His Ile Ser Glu Asp Gly Arg Asp Cys Ile Ser Cys Lys Tyr Gly Gln
             35                  40                  45

Asp Tyr Ser Thr His Trp Asn Asp Leu Leu Phe Cys Leu Arg Cys Thr
 50                  55                  60

Arg Cys Asp Ser Gly Glu Val Glu Leu Ser Pro Cys Thr Thr Thr Arg
 65                  70                  75                  80

Asn Thr Val Cys Gln Cys Glu Glu Gly Thr Phe Arg Glu Glu Asp Ser
             85                  90                  95

Pro Glu Met Cys Arg Lys Cys Arg Thr Gly Cys Pro Arg Gly Met Val
             100                 105                 110

Lys Val Gly Asp Cys Thr Pro Trp Ser Asp Ile Glu Cys Val His Lys
             115                 120                 125

Glu Ser Gly Thr Lys His Ser Gly Glu Ala Pro Ala Val Glu Glu Thr
 130                 135                 140

Val Thr Ser Ser Pro Gly Thr Pro Ala Ser Arg Ser Gly Ser Ser His
145                 150                 155                 160

His His His His His
             165

<210> SEQ ID NO 141
<211> LENGTH: 119
<212> TYPE: PRT
<213> ORGANISM: Mus sp.

<400> SEQUENCE: 141

Met Glu Val Gln Leu Val Glu Ser Gly Gly Gly Leu Val Gln Pro Gly
 1               5                  10                  15

Gly Ser Leu Lys Leu Ser Cys Ala Ala Ser Gly Phe Thr Phe Ser Thr
             20                  25                  30

Tyr Gly Met Ser Trp Val Arg Gln Thr Pro Asp Lys Arg Leu Glu Leu
             35                  40                  45

Val Ala Leu Ile Asn Ser Gln Gly Gly Ser Thr Tyr Asn Ser Asp Ser
 50                  55                  60

Val Lys Gly Arg Phe Thr Ile Ser Arg Asp Asn Ala Arg Asn Thr Leu
 65                  70                  75                  80

Tyr Leu Gln Met Ser Ser Leu Lys Ser Glu Asp Thr Ala Met Tyr Tyr
             85                  90                  95

Cys Ala Arg Arg Asp Tyr Glu Ser Leu Asp Ser Trp Gly Gln Gly Thr
             100                 105                 110

Ser Val Thr Val Ser Ser Gly
             115

<210> SEQ ID NO 142
<211> LENGTH: 122
<212> TYPE: PRT
<213> ORGANISM: Mus sp.

<400> SEQUENCE: 142
```

```
Asp Ile Val Leu Thr Gln Ser Pro Ala Ser Leu Pro Val Ser Leu Gly
  1               5                  10                  15

Gln Arg Ala Thr Ile Ser Cys Arg Ala Ser Glu Ser Val Glu Tyr Ser
                 20                  25                  30

Gly Thr Ser Leu Ile Gln Trp Tyr Arg Gln Lys Pro Gly Gln Pro Pro
             35                  40                  45

Lys Leu Leu Ile Tyr Ala Ala Ser Asn Val Asp Ser Glu Val Pro Ala
         50                  55                  60

Arg Phe Ser Gly Ser Gly Ser Gly Thr Asp Phe Ser Leu Tyr Ile His
 65                  70                  75                  80

Pro Val Glu Glu Asp Asp Ile Ala Met Tyr Phe Cys Gln Gln Ser Arg
                 85                  90                  95

Lys Val Pro Trp Thr Phe Gly Gly Gly Thr Lys Leu Glu Ile Lys Arg
                100                 105                 110

Thr Asp Ala Ala Pro Gly Leu Glu Ala Ala
            115                 120
```

<210> SEQ ID NO 143
<211> LENGTH: 119
<212> TYPE: PRT
<213> ORGANISM: Mus sp.

<400> SEQUENCE: 143

```
Lys Val Gln Leu Gln Gln Ser Gly Thr Glu Leu Val Lys Pro Gly Ala
  1               5                  10                  15

Ser Val Lys Leu Ser Cys Lys Ala Ser Gly Tyr Thr Phe Thr Glu Tyr
                 20                  25                  30

Ile Ile His Trp Val Lys Gln Arg Ser Gly Gln Gly Leu Glu Trp Ile
             35                  40                  45

Gly Trp Phe Tyr Pro Gly Ser Gly Tyr Ile Lys Tyr Asn Glu Lys Phe
         50                  55                  60

Lys Asp Lys Ala Thr Met Thr Ala Asp Lys Ser Ser Ser Thr Val Tyr
 65                  70                  75                  80

Met Glu Leu Ser Arg Leu Thr Ser Glu Asp Ser Ala Val Tyr Phe Cys
                 85                  90                  95

Thr Arg His Glu Glu Asp Gly Tyr Tyr Ala Ala Tyr Trp Gly Gln Gly
                100                 105                 110

Thr Leu Val Thr Val Ser Ala
            115
```

<210> SEQ ID NO 144
<211> LENGTH: 108
<212> TYPE: PRT
<213> ORGANISM: Mus sp.

<400> SEQUENCE: 144

```
Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Ser Ser Ala
                 20                  25                  30

Val Ala Trp Tyr Gln Gln Lys Pro Gly Gln Ser Pro Lys Leu Leu Ile
             35                  40                  45

Tyr Trp Ala Ser Thr Arg His Thr Gly Val Pro Asp Arg Phe Thr Gly
         50                  55                  60

Ser Gly Ser Gly Thr Asp Tyr Thr Leu Thr Ile Ser Ser Val Gln Ala
 65                  70                  75                  80
```

```
Glu Asp Leu Ala Leu Tyr Tyr Cys Gln Gln His Tyr Ser Thr Pro Tyr
            85                  90                  95
Thr Phe Gly Gly Gly Thr Lys Leu Glu Ile Lys Arg
            100                 105

<210> SEQ ID NO 145
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gtaagcaagc ttggctctga tcacccaaca aga                                33

<210> SEQ ID NO 146
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gattagggat ccagaggcag gagtccctgg                                    30

<210> SEQ ID NO 147
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
tagttgggat cctcaggaga tgcaatctct accgt                              35

<210> SEQ ID NO 148
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ggtagtggat cctcactgac acactgtgtt tctgg                              35

<210> SEQ ID NO 149
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gtaatgggat cctcagacac attcgatgtc actcc                              35

<210> SEQ ID NO 150
<211> LENGTH: 33
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 150
gtaatgaagc ttgccacaac aaaagaggtc cag                          33

<210> SEQ ID NO 151
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gattgaaagc ttgatctcct gcaaatatgg acag                         34

<210> SEQ ID NO 152
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gtaatgaagc ttgcagtgcg aagaaggcac ct                           32

<210> SEQ ID NO 153
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
gatggaggat cctcaacacc tggtgcagcg caag                         34

<210> SEQ ID NO 154
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gtaagtggat cctcagcagg gacttagctc cact                         34

<210> SEQ ID NO 155
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gttagtaagc ttggctccaa tcacccgac                               29

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gttgatggat ccttctttgt ggacactcga t                          31

<210> SEQ ID NO 157
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gtagttggat cctcaagaag caggagtccc aggg                       34

<210> SEQ ID NO 158
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gtatgaggga tcctcactga cacaccgtgt ttctgg                     36

<210> SEQ ID NO 159
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gtatggaagc ttgccacaac aaaagagatc cagc                       34

<210> SEQ ID NO 160
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
cagcgaagag cggctccaca acaaaagagg tccag                      35

<210> SEQ ID NO 161
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ggatctcttt tgttgtgggg ccgctctctg ctggg                      35

<210> SEQ ID NO 162
<211> LENGTH: 36
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 162
cagcagagag cggccccaca acaaaagaga tccagc                                36

<210> SEQ ID NO 163
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
cagcggccgg aggagagccc ctcagaggga ttgt                                  34

<210> SEQ ID NO 164
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gattgaggat ccctaagagg caggagtccc tgg                                   33

<210> SEQ ID NO 165
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tgaatgaagc ttggttccag taacagctaa ccca                                  34

<210> SEQ ID NO 166
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tccctctgag gggctctcct ccggccgctg tag                                   33

<210> SEQ ID NO 167
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
caggtactgg cctgctagac acaatccctc tgagggg                               37

<210> SEQ ID NO 168
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
```
ctagcaggcc agtacctgtc agaagacggt agagattgc        39

<210> SEQ ID NO 169
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
caggtactgg cctgctagac acaatccctc tgagggg        37

<210> SEQ ID NO 170
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ctagcaggcc agtacctgtc agaagacggt agagattgc        39

<210> SEQ ID NO 171
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
tgaatccaga gaatggttgg agtgagtgct atagtcctgt c        41

<210> SEQ ID NO 172
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
tccaaccatt ctctggattc atgcttgcgc tgcaccagg        39

<210> SEQ ID NO 173
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gattgaggat ccctaagagg caggagtccc tgg        33

<210> SEQ ID NO 174
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
tcgggtttct acgactttat cttccttaca cctggtgcag cgcaag 46

<210> SEQ ID NO 175
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
aaggaagata aagtcgtaga aacccgatgc accacgacca gaaacac 47

<210> SEQ ID NO 176
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gattgaggat ccctaagagg caggagtccc tgg 33

<210> SEQ ID NO 177
<211> LENGTH: 118
<212> TYPE: PRT
<213> ORGANISM: Homo sapiens

<400> SEQUENCE: 177

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
    65                  70                  75                  80

Met Glu Leu Ser Ser Leu Arg Ser Glu Asp Thr Ala Val Tyr Tyr Cys
                85                  90                  95

Ala Arg Tyr Gly Ser Gly Ser Phe Asp Tyr Trp Gly Gln Gly Thr Leu
            100                 105                 110

Val Thr Val Ser Ser Ala
        115

<210> SEQ ID NO 178
<211> LENGTH: 118
<212> TYPE: PRT
<213> ORGANISM: Homo sapiens

<400> SEQUENCE: 178

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

```
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
             85                  90                  95

Cys Ala Arg Ser Ser Gly Trp Phe Asp Tyr Trp Gly Gln Gly Thr Leu
            100                 105                 110

Val Thr Val Ser Ser Ala
        115
```

```
<210> SEQ ID NO 179
<211> LENGTH: 117
<212> TYPE: PRT
<213> ORGANISM: Homo sapiens

<400> SEQUENCE: 179

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Thr Ile Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Ala Ala Gly Ala Phe Asp Ile Trp Gly Gln Gly Thr Met Val
            100                 105                 110

Thr Val Ser Ser Ala
        115
```

```
<210> SEQ ID NO 180
<211> LENGTH: 119
<212> TYPE: PRT
<213> ORGANISM: Homo sapiens

<400> SEQUENCE: 180

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Tyr Ser Ser Ser Trp Tyr Phe Asp Leu Trp Gly Arg Gly Thr
            100                 105                 110

Leu Val Thr Val Ser Ser Ala
        115
```

```
<210> SEQ ID NO 181
```

```
<211> LENGTH: 117
<212> TYPE: PRT
<213> ORGANISM: Homo sapiens

<400> SEQUENCE: 181

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Ser Gly Tyr Phe Asp Tyr Trp Gly Gln Gly Thr Leu Val
            100                 105                 110

Thr Val Ser Ser Ala
        115

<210> SEQ ID NO 182
<211> LENGTH: 117
<212> TYPE: PRT
<213> ORGANISM: Homo sapiens

<400> SEQUENCE: 182

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asn Trp Asn Phe Asp Ile Trp Gly Gln Gly Thr Met Val
            100                 105                 110

Thr Val Ser Ser Ala
        115

<210> SEQ ID NO 183
<211> LENGTH: 114
<212> TYPE: PRT
<213> ORGANISM: Homo sapiens

<400> SEQUENCE: 183

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45
```

```
Ser Tyr Ile Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Met Asp Val Trp Gly Gln Gly Thr Thr Val Thr Val Ser
             100                 105                 110

Ser Ala
```

<210> SEQ ID NO 184
<211> LENGTH: 123
<212> TYPE: PRT
<213> ORGANISM: Homo sapiens

<400> SEQUENCE: 184

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Ser Ser Tyr Tyr Tyr Tyr Gly Met Asp Val Trp
             100                 105                 110

Gly Gln Gly Thr Thr Val Thr Val Ser Ser Ala
             115                 120
```

<210> SEQ ID NO 185
<211> LENGTH: 118
<212> TYPE: PRT
<213> ORGANISM: Homo sapiens

<400> SEQUENCE: 185

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ser Ser Gly Tyr Trp Tyr Phe Asp Leu Trp Gly Arg Gly Thr Leu
             100                 105                 110

Val Thr Val Ser Ser Ala
             115
```

<210> SEQ ID NO 186
<211> LENGTH: 117
<212> TYPE: PRT
<213> ORGANISM: Homo sapiens

<400> SEQUENCE: 186

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Ser Trp Tyr Trp Phe Asp Pro Trp Gly Gln Gly Thr Leu Val
            100                 105                 110

Thr Val Ser Ser Ala
        115

<210> SEQ ID NO 187
<211> LENGTH: 126
<212> TYPE: PRT
<213> ORGANISM: Homo sapiens

<400> SEQUENCE: 187

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Cys Thr Asn Gly Val Cys Tyr Tyr Tyr Gly Met
            100                 105                 110

Asp Val Trp Gly Gln Gly Thr Val Thr Val Ser Ser Ala
        115                 120                 125

<210> SEQ ID NO 188
<211> LENGTH: 118
<212> TYPE: PRT
<213> ORGANISM: Homo sapiens

<400> SEQUENCE: 188

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

```
Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Tyr Tyr Gly Met Asp Val Trp Gly Gln Gly Thr Thr
                100                 105                 110

Val Thr Val Ser Ser Ala
        115
```

<210> SEQ ID NO 189
<211> LENGTH: 120
<212> TYPE: PRT
<213> ORGANISM: Homo sapiens

<400> SEQUENCE: 189

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Gly Ser Tyr Trp Phe Asp Pro Trp Gly Gln Gly
                100                 105                 110

Thr Leu Val Thr Val Ser Ser Ala
        115                 120
```

<210> SEQ ID NO 190
<211> LENGTH: 106
<212> TYPE: PRT
<213> ORGANISM: Homo sapiens

<400> SEQUENCE: 190

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Thr Phe
                85                  90                  95

Gly Gly Gly Thr Lys Val Glu Ile Lys Arg
                100                 105
```

<210> SEQ ID NO 191

```
<211> LENGTH: 108
<212> TYPE: PRT
<213> ORGANISM: Homo sapiens

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg
            100                 105

<210> SEQ ID NO 192
<211> LENGTH: 111
<212> TYPE: PRT
<213> ORGANISM: Homo sapiens

<400> SEQUENCE: 192

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Thr Phe Gly Gly Gly Thr Lys Val Glu Ile Lys Arg
            100                 105                 110

<210> SEQ ID NO 193
<211> LENGTH: 106
<212> TYPE: PRT
<213> ORGANISM: Homo sapiens

<400> SEQUENCE: 193

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ala Asn Ser Phe Pro Thr
                85                  90                  95

Phe Gly Gly Gly Thr Lys Val Glu Ile Lys
            100                 105

<210> SEQ ID NO 194
<211> LENGTH: 106
<212> TYPE: PRT
<213> ORGANISM: Homo sapiens

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Trp Thr Phe
                85                  90                  95

Gly Gln Gly Thr Lys Val Glu Ile Lys Arg
            100                 105

<210> SEQ ID NO 195
<211> LENGTH: 108
<212> TYPE: PRT
<213> ORGANISM: Homo sapiens

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 196
<211> LENGTH: 114
<212> TYPE: PRT
<213> ORGANISM: Homo sapiens

<400> SEQUENCE: 196

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln

```
                35                  40                  45
Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Leu Thr Phe Gly Gly Gly Thr Lys Val Glu Ile
            100                 105                 110

Lys Arg

<210> SEQ ID NO 197
<211> LENGTH: 114
<212> TYPE: PRT
<213> ORGANISM: Homo sapiens

<400> SEQUENCE: 197

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Phe Thr Phe Gly Pro Gly Thr Lys Val Asp Ile
            100                 105                 110

Lys Arg

<210> SEQ ID NO 198
<211> LENGTH: 106
<212> TYPE: PRT
<213> ORGANISM: Homo sapiens

<400> SEQUENCE: 198

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
             20                  25                  30

Leu Ala Trp Tyr Gln Gln Lys Pro Gly Lys Val Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Thr Phe
                 85                  90                  95

Gly Gly Gly Thr Lys Val Glu Ile Lys Arg
            100                 105

<210> SEQ ID NO 199
<211> LENGTH: 111
```

```
<212> TYPE: PRT
<213> ORGANISM: Homo sapiens

<400> SEQUENCE: 199

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Phe Gly Gln Gly Thr Lys Leu Glu Ile Lys Arg
            100                 105                 110

<210> SEQ ID NO 200
<211> LENGTH: 109
<212> TYPE: PRT
<213> ORGANISM: Homo sapiens

<400> SEQUENCE: 200

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg
            100                 105

<210> SEQ ID NO 201
<211> LENGTH: 108
<212> TYPE: PRT
<213> ORGANISM: Homo sapiens

<400> SEQUENCE: 201

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Arg
```

```
                85                  90                  95

Thr Phe Gly Gln Gly Thr Lys Val Glu Ile Lys Arg
            100                 105

<210> SEQ ID NO 202
<211> LENGTH: 129
<212> TYPE: PRT
<213> ORGANISM: Macaca fascicularis

<400> SEQUENCE: 202

Ala Pro Ile Thr Arg Gln Ser Leu Asp Pro Gln Arg Arg Ala Ala Pro
  1               5                  10                  15

Gln Gln Lys Arg Ser Ser Pro Thr Glu Gly Leu Cys Pro Pro Gly His
             20                  25                  30

His Ile Ser Glu Asp Ser Arg Asp Cys Ile Ser Cys Lys Tyr Gly Gln
         35                  40                  45

Asp Tyr Ser Thr His Trp Asn Asp Phe Leu Phe Cys Leu Arg Cys Thr
     50                  55                  60

Lys Cys Asp Ser Gly Glu Val Glu Val Ser Cys Thr Thr Thr Arg
 65                  70                  75                  80

Asn Thr Val Cys Gln Cys Glu Glu Gly Thr Phe Arg Glu Glu Asp Ser
                 85                  90                  95

Pro Glu Ile Cys Arg Lys Cys Arg Thr Gly Cys Pro Arg Gly Met Val
            100                 105                 110

Lys Val Lys Asp Cys Thr Pro Trp Ser Asp Ile Glu Cys Val His Lys
        115                 120                 125

Glu

<210> SEQ ID NO 203
<211> LENGTH: 154
<212> TYPE: PRT
<213> ORGANISM: Homo sapiens

<400> SEQUENCE: 203

Ala Leu Ile Thr Gln Gln Asp Leu Ala Pro Gln Gln Arg Ala Ala Pro
  1               5                  10                  15

Gln Gln Lys Arg Ser Ser Pro Ser Glu Gly Leu Cys Pro Pro Gly His
             20                  25                  30

His Ile Ser Glu Asp Gly Arg Asp Cys Ile Ser Cys Lys Tyr Gly Gln
         35                  40                  45

Asp Tyr Ser Thr His Trp Asn Asp Leu Leu Phe Cys Leu Arg Cys Thr
     50                  55                  60

Arg Cys Asp Ser Gly Glu Val Glu Leu Ser Pro Cys Thr Thr Thr Arg
 65                  70                  75                  80

Asn Thr Val Cys Gln Cys Glu Glu Gly Thr Phe Arg Glu Glu Asp Ser
                 85                  90                  95

Pro Glu Met Cys Arg Lys Cys Arg Thr Gly Cys Pro Arg Gly Met Val
            100                 105                 110

Lys Val Gly Asp Cys Thr Pro Trp Ser Asp Ile Glu Cys Val His Lys
        115                 120                 125

Glu Ser Gly Thr Lys His Ser Gly Glu Ala Pro Ala Val Glu Glu Thr
    130                 135                 140

Val Thr Ser Ser Pro Gly Thr Pro Ala Ser
145                 150

<210> SEQ ID NO 204
```

-continued

```
<211> LENGTH: 133
<212> TYPE: PRT
<213> ORGANISM: Mus sp.

<400> SEQUENCE: 204

Pro Val Thr Ala Asn Pro Ala His Asn Arg Pro Ala Gly Leu Gln Arg
 1               5                  10                  15

Pro Glu Glu Ser Pro Ser Arg Gly Pro Cys Leu Ala Gly Gln Tyr Leu
            20                  25                  30

Ser Glu Gly Asn Cys Lys Pro Cys Arg Glu Gly Ile Asp Tyr Thr Ser
        35                  40                  45

His Ser Asn His Ser Leu Asp Ser Cys Ile Leu Cys Thr Val Cys Lys
    50                  55                  60

Glu Asp Lys Val Val Glu Thr Arg Cys Asn Ile Thr Thr Asn Thr Val
65                  70                  75                  80

Cys Arg Cys Lys Pro Gly Thr Phe Glu Asp Lys Asp Ser Pro Glu Ile
                85                  90                  95

Cys Gln Ser Cys Ser Asn Cys Thr Asp Gly Glu Glu Glu Leu Thr Ser
            100                 105                 110

Cys Thr Pro Arg Glu Asn Arg Lys Cys Val Ser Lys Thr Ala Trp Ala
        115                 120                 125

Ser Trp His Lys Leu
    130
```

TRAIL RECEPTOR-2 POLYPEPTIDES AND ANTIBODIES

This application claims the benefit of U.S. Provisional Application No. 60/713,433, filed Aug. 31, 2005, and U.S. Provisional Application No. 60/713,478, filed Aug. 31, 2005. U.S. Provisional Application Nos. 60/713,433 and 60/713,478 are incorporated by reference herein in their entirety for any purpose.

FIELD

Polypeptides are provided. Antibodies or antigen binding domains are provided which bind such polypeptides. Also provided are methods of obtaining an antibody that binds tumor necrosis factor (TNF)-related apoptosis-inducing ligand ("TRAIL") Receptor-2 (TR-2) comprising administering at least one of such polypeptides to an animal and obtaining an antibody that binds TR-2 from the animal. Antibodies reactive with TR-2 are provided. Also provided are cells producing antibodies reactive with TR-2, pharmaceutical compositions comprising antibodies reactive with TR-2, methods using antibodies reactive with TR-2, and kits comprising antibodies reactive with TR-2. Also provided are methods of decreasing or preventing binding of an antibody to TR-2 by administering such a polypeptide.

BACKGROUND

The interaction between TR-2 and its ligand, TRAIL, plays a role in the induction of apoptosis (see, for example, Almasan et al., Cytokine & Growth Factor Reviews 14: 337-348 (2003)). TRAIL, also known as Apo2 ligand, is a homomeric ligand that interacts with four members of the TNF-receptor superfamily (TRAIL receptors ("TR") 1 to 4), as well as with the related, soluble, opsteoprotegerin ("OPG") receptor. Binding of TRAIL to TR-1 or TR-2 at the surface of a cell triggers apoptosis of that cell. After initial binding of TRAIL to TR-1 or TR-2, intracellular proteins are recruited to the intracellular death domain of the receptor, forming a signaling complex. Certain intracellular caspases are recruited to the complex; where they autoactivate and in turn activate additional caspases and the intracellular apoptosis cascade. TR-3 and TR-4 and OPG lack the intracellular domain responsible for transmitting the apoptosis signal. Thus, binding of TRAIL to TR-3, TR-4, or OPG does not trigger apoptosis. TR-3 and TR-4 are also referred to as "decoy" receptors, and their overexpression has been shown to protect cells from apoptotic induction by TRAIL. TR-2 is expressed in a variety of cells, including liver, brain, breast, kidney, colon, lung, spleen, thymus, peripheral blood lymphocytes, prostate, testis, ovary, uterus, and various tissues along the gastro-intestinal tract. (See, for example, Walczak et al., EMBO J. 16: 5386-5397 (1997); Spierings et al., J. Histochem. Cytochem. 52: 821-831 (2004)). Though TRAIL and TRAIL receptors are widely expressed, they are most active in inducing apoptosis in transformed cells. (See, for example, Daigle et al., Swiss Med. Wkly. 131: 231-237 (2001)).

SUMMARY

In certain embodiments, an isolated polypeptide is provided comprising at least one complementarity determining region (CDR) selected from CDR1a, CDR2a, and CDR3a:

wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present;

wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present; wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; and wherein the polypeptide, in association with an antibody light chain, binds TRAIL receptor-2 (TR-2).

In certain embodiments, an isolated polypeptide is provided comprising at least one complementarity determining region (CDR) selected from:
  amino acids 26 to 35 of SEQ ID NO: 2;
  amino acids 50 to 66 of SEQ ID NO: 2;
  amino acids 99 to 110 of SEQ ID NO: 2;
  amino acids 26 to 37 of SEQ ID NO: 4;
  amino acids 52 to 67 of SEQ ID NO: 4;
  amino acids 100 to 109 of SEQ ID NO: 4;
  amino acids 26 to 37 of SEQ ID NO: 6;
  amino acids 52 to 67 of SEQ ID NO: 6;
  amino acids 100 to 109 of SEQ ID NO: 6;
  amino acids 26 to 37 of SEQ ID NO: 8;
  amino acids 52 to 67 of SEQ ID NO: 8;
  amino acids 100 to 109 of SEQ ID NO: 8;
  amino acids 26 to 35 of SEQ ID NO: 10;
  amino acids 50 to 66 of SEQ ID NO: 10;
  amino acids 99 to 110 of SEQ ID NO: 10;
  amino acids 26 to 35 of SEQ ID NO: 12;
  amino acids 50 to 66 of SEQ ID NO: 12;
  amino acids 99 to 111 of SEQ ID NO: 12;
  amino acids 26 to 35 of SEQ ID NO: 14;
  amino acids 50 to 65 of SEQ ID NO: 14;
  amino acids 98 to 111 of SEQ ID NO: 14;
  amino acids 26 to 37 of SEQ ID NO: 16;
  amino acids 52 to 67 of SEQ ID NO: 16;
  amino acids 100 to 109 of SEQ ID NO: 16;
  amino acids 26 to 35 of SEQ ID NO: 18;
  amino acids 50 to 66 of SEQ ID NO: 18;
  amino acids 99 to 105 of SEQ ID NO: 18;
  amino acids 26 to 35 of SEQ ID NO: 20;
  amino acids 50 to 66 of SEQ ID NO: 20;
  amino acids 99 to 118 of SEQ ID NO: 20;
  amino acids 26 to 35 of SEQ ID NO: 22;
  amino acids 50 to 66 of SEQ ID NO: 22;
  amino acids 99 to 118 of SEQ ID NO: 22;
  amino acids 26 to 35 of SEQ ID NO: 24;
  amino acids 50 to 65 of SEQ ID NO: 24;
  amino acids 98 to 108 of SEQ ID NO: 24;
  amino acids 26 to 35 of SEQ ID NO: 26;
  amino acids 50 to 66 of SEQ ID NO: 26;
  amino acids 99 to 110 of SEQ ID NO: 26;
  amino acids 26 to 35 of SEQ ID NO: 28;
  amino acids 50 to 66 of SEQ ID NO: 28;
  amino acids 99 to 117 of SEQ ID NO: 28;
  amino acids 26 to 37 of SEQ ID NO: 30;
  amino acids 52 to 67 of SEQ ID NO: 30;
  amino acids 100 to 111 of SEQ ID NO: 30;
  amino acids 26 to 37 of SEQ ID NO: 32;
  amino acids 52 to 67 of SEQ ID NO: 32;
  amino acids 100 to 111 of SEQ ID NO: 32;
  amino acids 26 to 37 of SEQ ID NO: 34;
  amino acids 52 to 67 of SEQ ID NO: 34; and
  amino acids 100 to 111 of SEQ ID NO: 34;

wherein the polypeptide, in association with an antibody light chain, binds TR-2.

In certain embodiments, an isolated polypeptide is provided comprising at least one complementarity determining region (CDR) selected from CDR1b, CDR2b, and CDR3b:
  wherein CDR1b comprises the amino acid sequence a1 b1 c1 d1 e1 f1 g1 h1 i1 j1 k1 l1 m1 n1 o1 p1 q1, wherein amino acid a1 is selected from arginine or lysine; amino acid b1 is selected from threonine, alanine, or serine; amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid l1 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present;
  wherein CDR2b comprises the amino acid sequence r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine;
  wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; and wherein the polypeptide, in association with an antibody heavy chain, binds TR-2.

In certain embodiments, an isolated polypeptide is provided comprising at least one complementarity determining region (CDR) selected from:
  amino acids 24 to 34 of SEQ ID NO: 36;
  amino acids 50 to 56 of SEQ ID NO: 36;
  amino acids 89 to 97 of SEQ ID NO: 36;
  amino acids 24 to 34 of SEQ ID NO: 38;
  amino acids 50 to 56 of SEQ ID NO: 38;
  amino acids 89 to 97 of SEQ ID NO: 38;
  amino acids 24 to 34 of SEQ ID NO: 40;
  amino acids 50 to 56 of SEQ ID NO: 40;
  amino acids 89 to 97 of SEQ ID NO: 40;
  amino acids 24 to 34 of SEQ ID NO: 42;
  amino acids 50 to 56 of SEQ ID NO: 42;

amino acids 89 to 97 of SEQ ID NO: 42;
amino acids 24 to 34 of SEQ ID NO: 44;
amino acids 50 to 56 of SEQ ID NO: 44;
amino acids 89 to 97 of SEQ ID NO: 44;
amino acids 24 to 34 of SEQ ID NO: 46;
amino acids 50 to 56 of SEQ ID NO: 46;
amino acids 89 to 97 of SEQ ID NO: 46;
amino acids 24 to 40 of SEQ ID NO: 48;
amino acids 56 to 62 of SEQ ID NO: 48;
amino acids 95 to 103 of SEQ ID NO: 48;
amino acids 24 to 39 of SEQ ID NO: 50;
amino acids 55 to 61 of SEQ ID NO: 50;
amino acids 94 to 102 of SEQ ID NO: 50;
amino acids 24 to 40 of SEQ ID NO: 52;
amino acids 56 to 62 of SEQ ID NO: 52;
amino acids 95 to 103 of SEQ ID NO: 52;
amino acids 24 to 34 of SEQ ID NO: 54;
amino acids 50 to 56 of SEQ ID NO: 54;
amino acids 89 to 97 of SEQ ID NO: 54;
amino acids 24 to 34 of SEQ ID NO: 56,
amino acids 50 to 56 of SEQ ID NO: 56;
amino acids 89 to 97 of SEQ ID NO: 56;
amino acids 24 to 40 of SEQ ID NO: 58;
amino acids 56 to 62 of SEQ ID NO: 58;
amino acids 95 to 103 of SEQ ID NO: 58;
amino acids 24 to 34 of SEQ ID NO: 60;
amino acids 50 to 56 of SEQ ID NO: 60;
amino acids 89 to 97 of SEQ ID NO: 60;
amino acids 24 to 34 of SEQ ID NO: 62;
amino acids 50 to 56 of SEQ ID NO: 62;
amino acids 89 to 97 of SEQ ID NO: 62;
amino acids 24 to 35 of SEQ ID NO: 64;
amino acids 51 to 57 of SEQ ID NO: 64;
amino acids 90 to 88 of SEQ ID NO: 64;
amino acids 24 to 34 of SEQ ID NO: 66;
amino acids 50 to 57 of SEQ ID NO: 66;
amino acids 89 to 97 of SEQ ID NO: 66;
amino acids 24 to 34 of SEQ ID NO: 68;
amino acids 50 to 56 of SEQ ID NO: 68; and
amino acids 89 to 97 of SEQ ID NO: 68;

wherein the polypeptide, in association with an antibody heavy chain, binds TR-2.

In certain embodiments, an isolated polynucleotide is provided comprising a sequence encoding a polypeptide comprising at least one complementarity determining region (CDR) selected from CDR1a, CDR2a, and CDR3a:

wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present;

wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present;

wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; and wherein the polypeptide, in association with an antibody light chain, binds TR-2.

In certain embodiments, an isolated polynucleotide is provided comprising a sequence encoding a polypeptide comprising at least one complementarity determining region (CDR) selected from CDR1b, CDR2b, and CDR3b:

wherein CDR1b comprises the amino acid sequence a1 b1 c1 d1 e1 f1 g1 h1 i1 j1 k1 l1 m1 n1 o1 p1 q1, wherein amino acid a1 is selected from arginine or lysine; amino acid b1 is selected from threonine, alanine, or serine;

amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid l1 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present;

wherein CDR2b comprises the amino acid sequence r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine; wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; and wherein the polypeptide, in association with an antibody heavy chain, binds TR-2.

In certain embodiments, an isolated anti-TR-2 antibody comprising a variable region and a constant region is provided, wherein the antibody comprises:

(i) a first polypeptide comprising at least one complementarity determining region (CDR) selected from CDR1a, CDR2a, and CDR3a, wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present;

wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present;

wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; and wherein the first polypeptide, in association with an antibody light chain, binds TR-2; and (ii) a second polypeptide comprising at least one complementarity determining region (CDR) selected from CDR1b, CDR2b, and CDR3b wherein CDR1b comprises the amino acid sequence a1 b1 c1 d1 e1 f1 g1 h1 i1 j1 k1 l1 m1 n1 o1 p1 q1, wherein amino acid a1 is selected from arginine or lysine; amino acid b1 is selected from threonine, alanine, or serine; amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid l1 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present;

wherein CDR2b comprises the amino acid sequence r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine;

wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; and wherein the second polypeptide, in association with an antibody heavy chain, binds TR-2.

In certain embodiments, an isolated anti-TR-2 antibody comprising a variable region and a constant region is provided, wherein the antibody comprises:

a first polypeptide comprising complementary determining regions (CDRs) as set forth in SEQ ID NO: 2 and a second polypeptide comprising CDRs as set forth in SEQ ID NO: 36; a first polypeptide comprising complementarity determining regions (CDRs) as set forth in SEQ ID NO: 4 and a second polypeptide comprising CDRs as set forth in SEQ ID NO: 38; a first polypeptide comprising complementarity determining regions (CDRs) as set forth in SEQ ID NO: 6 and a second polypeptide comprising CDRs as set forth in SEQ ID NO: 40; a first polypeptide comprising complementarity determining regions (CDRs) as set forth in SEQ ID NO: 8 and a second polypeptide comprising CDRs as set forth in SEQ ID NO: 42; a first polypeptide comprising complementarity determining regions (CDRs) as set forth in SEQ ID NO: 10 and a second polypeptide comprising CDRs as set forth in SEQ ID NO: 44; a first polypeptide comprising complementarity determining regions (CDRs) as set forth in SEQ ID NO: 12 and a second polypeptide comprising CDRs as set forth in SEQ ID NO: 46; a first polypeptide comprising complementarity determining regions (CDRs) as set forth in SEQ ID NO: 14 and a second polypeptide comprising CDRs as set forth in SEQ ID NO: 48; a first polypeptide comprising complementarity determining regions (CDRs) as set forth in SEQ ID NO: 16 and a second polypeptide comprising CDRs as set forth in SEQ ID NO: 50; a first polypeptide comprising complementarity determining regions (CDRs) as set forth in SEQ ID NO: 18 and a second polypeptide comprising CDRs as set forth in SEQ ID NO: 52; a first polypeptide comprising complementarity determining regions (CDRs) as set forth in SEQ ID NO: 20 and a second polypeptide comprising CDRs as set forth in SEQ ID NO: 54; a first polypeptide comprising complementarity determining regions (CDRs) as set forth in SEQ ID NO: 22 and a second polypeptide comprising CDRs as set forth in SEQ ID NO: 56; a first polypeptide comprising complementarity determining regions (CDRs) as set forth in SEQ ID NO: 24 and a second polypeptide comprising CDRs as set forth in SEQ ID NO: 58; a first polypeptide comprising complementarity determining regions (CDRs) as set forth in SEQ ID NO: 26 and a second polypeptide comprising CDRs as set forth in SEQ ID NO: 60; a first polypeptide comprising complementarity determining regions (CDRs) as set forth in SEQ ID NO: 28 and a second polypeptide comprising. CDRs as set forth in SEQ ID NO: 62; a first polypeptide comprising complementarity determining regions (CDRs) as set forth in SEQ ID NO: 30 and a second polypeptide comprising CDRs as set forth in SEQ ID NO: 64; a first polypeptide comprising complementarity determining regions (CDRs) as set forth in SEQ ID NO: 32 and a second polypeptide comprising CDRs as set forth in SEQ ID NO: 66; or a first polypeptide comprising complementarity determining regions (CDRs) as set forth in SEQ ID NO: 34 and a second polypeptide comprising CDRs as set forth in SEQ ID NO: 68.

In certain embodiments, a cell is provided, comprising:

(a) a first polynucleotide comprising a sequence encoding a first polypeptide comprising at least one complementarity determining region (CDR) selected from CDR1a, CDR2a, and CDR3a, wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present;

wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present;

wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; wherein the first polypeptide, in association with an antibody light chain, binds TR-2; and (b) a second polynucleotide comprising a sequence encoding a second polypeptide comprising at least one complementarity determining region (CD R) selected from CDR1b, CDR2b, and CDR3b, wherein CDR1b comprises the amino acid sequence a1 b1 c1 d1 e1 f1 g1 h1 i1 j1 k1 l1 ml n1 o1 p1 q1, wherein amino acid a1 is selected from arginine or lysine; amino acid b1 is selected from threonine, alanine, or serine; amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid l1 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present;

wherein CDR2b comprises the amino acid sequence r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine;

wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; wherein the second polypeptide, in association with an antibody heavy chain, binds TR-2.

In certain embodiments, an isolated antibody is provided that specifically binds to an epitope that is specifically bound by at least one antibody selected from: Ab A, Ab B, Ab C, Ab D, Ab E, Ab F, Ab G, Ab H, Ab I, Ab J, Ab K, Ab L, Ab M, Ab N, Ab O, Ab P, and Ab Q.

In certain embodiments, a polypeptide is provided comprising at least one amino acid sequence selected from SEQ ID NO: 94, SEQ ID NO: 95, and SEQ ID NO: 96.

In certain embodiments, a polypeptide is provided consisting essentially of at least one amino acid sequence selected from SEQ ID NO: 94, SEQ ID NO: 95, and SEQ ID NO: 96.

In certain embodiments, an antibody or antigen binding domain is provided which binds at least one amino acid sequence selected from SEQ ID NO: 94, SEQ ID NO: 95, and SEQ ID NO: 96.

In certain embodiments, a method of obtaining an antibody that binds TR-2 is provided comprising administering at least one polypeptide selected from SEQ ID NO: 94, SEQ ID NO: 95, and SEQ ID NO: 96 to an animal and obtaining an antibody that binds TR-2 from the animal.

In certain embodiments, a method of decreasing or preventing binding of an antibody to TR-2 by administering a polypeptide comprising at least one amino acid sequence selected from SEQ ID NO: 94, SEQ ID NO: 95, and SEQ ID NO: 96 is provided.

In certain embodiments, a method of decreasing or preventing binding of an antibody to TR-2 by administering a polypeptide consisting of at least one amino acid sequence selected from SEQ ID NO: 94, SEQ ID NO: 95, and SEQ ID NO: 96 is provided.

BRIEF DESCRIPTION OF THE FIGURES

FIG. 1 shows the immunization schedule used in Example 1 for a TR-2-His construct in transgenic mice expressing human immunoglobulin genes, via either footpad inoculation (groups 1, 2, and 3) or via intraperitoneal injection (groups 4 and 5).

FIG. 2 shows the results of an ELISA assay to measure the reactivity of certain blood samples from selected mice described in FIG. 1 to the antigen TR-2, according to work described in Example 1.

FIG. 3 shows the nucleotide sequences encoding the heavy chain (SEQ ID NO: 1) and light chain (SEQ ID NO: 35) variable regions of anti-TR-2 antibody A, and the amino acid sequences of the heavy chain (SEQ ID NO: 2) and the light chain (SEQ ID NO: 36) variable regions of that antibody.

FIG. 4 shows the nucleotide sequences encoding the heavy chain (SEQ ID NO: 3) and light chain (SEQ ID NO: 37) variable regions of anti-TR-2 antibody B, and the amino acid sequences of the heavy chain (SEQ ID NO: 4) and the light chain (SEQ ID NO: 38) variable regions of that antibody.

FIG. 5 shows the nucleotide sequences encoding the heavy chain (SEQ ID NO: 5) and light chain (SEQ ID NO: 39) variable regions of anti-TR-2 antibody C, and the amino acid sequences of the heavy chain (SEQ ID NO: 6) and the light chain (SEQ ID NO: 40) variable regions of that antibody.

FIG. 6 shows the nucleotide sequences encoding the heavy chain (SEQ ID NO: 7) and light chain (SEQ ID NO: 41) variable regions of anti-TR-2 antibody D, and the amino acid sequences of the heavy chain (SEQ ID NO: 8) and the light chain (SEQ ID NO: 42) variable regions of that antibody.

FIG. 7 shows the nucleotide sequences encoding the heavy chain (SEQ ID NO: 9) and light chain (SEQ ID NO: 43) variable regions of anti-TR-2 antibody E, and the amino acid sequences of the heavy chain (SEQ ID NO: 10) and the light chain (SEQ ID NO: 44) variable regions of that antibody.

FIG. 8 shows the nucleotide sequences encoding the heavy chain (SEQ ID NO: 11) and light chain (SEQ ID NO: 45) variable regions of anti-TR-2 antibody F, and the amino acid sequences of the heavy chain (SEQ ID NO: 12) and the light chain (SEQ ID NO: 46) variable regions of that antibody.

FIG. 9 shows the nucleotide sequences encoding the heavy chain (SEQ ID NO: 13) and light chain (SEQ ID NO: 47) variable regions of anti-TR-2 antibody G, and the amino acid sequences of the heavy chain (SEQ ID NO: 14) and the light chain (SEQ ID NO: 48) variable regions of that antibody.

FIG. 10 shows the nucleotide sequences encoding the heavy chain (SEQ ID NO: 15) and light chain (SEQ ID NO: 49) variable regions of anti-TR-2 antibody H, and the amino acid sequences of the heavy chain (SEQ ID NO: 16) and the light chain (SEQ ID NO: 50) variable regions of that antibody.

FIG. 11 shows the nucleotide sequences encoding the heavy chain (SEQ ID NO: 17) and light chain (SEQ ID NO: 51) variable regions of anti-TR-2 antibody I, and the amino acid sequences of the heavy chain (SEQ ID NO: 18) and the light chain (SEQ ID NO: 52) variable regions of that antibody.

FIG. 12 shows the nucleotide sequences encoding the heavy chain (SEQ ID NO: 19) and light chain (SEQ ID NO: 53) variable regions of anti-TR-2 antibody J, and the amino acid sequences of the heavy chain (SEQ ID NO: 20) and the light chain (SEQ ID NO: 54) variable regions of that antibody.

FIG. 13 shows the nucleotide sequences encoding the heavy chain (SEQ ID NO: 21) and light chain (SEQ ID NO: 55) variable regions of anti-TR-2 antibody K, and the amino acid sequences of the heavy chain (SEQ ID NO: 22) and the light chain (SEQ ID NO: 56) variable regions of that antibody.

FIG. 14 shows the nucleotide sequences encoding the heavy chain (SEQ ID NO: 23) and light chain (SEQ ID NO: 57) variable regions of anti-TR-2 antibody L, and the amino acid sequences of the heavy chain (SEQ ID NO: 24) and the light chain (SEQ ID NO: 58) variable regions of that antibody.

FIG. 15 shows the nucleotide sequences encoding the heavy chain (SEQ ID NO: 25) and light chain (SEQ ID NO: 59) variable regions of anti-TR-2 antibody M, and the amino acid sequences of the heavy chain (SEQ ID NO: 26) and the light chain (SEQ ID NO: 60) variable regions of that antibody.

FIG. 16 shows the nucleotide sequences encoding the heavy chain (SEQ ID NO: 27) and light chain (SEQ ID NO: 61) variable regions of anti-TR-2 antibody N, and the amino acid sequences of the heavy chain (SEQ ID NO: 28) and the light chain (SEQ ID NO: 62) variable regions of that antibody.

FIG. 17 shows the nucleotide sequences encoding the heavy chain (SEQ ID NO: 29) and light chain (SEQ ID NO: 63) variable regions of anti-TR-2 antibody 0, and the amino acid sequences of the heavy chain (SEQ ID NO: 30) and the light chain (SEQ ID NO: 64) variable regions of that antibody.

FIG. 18 shows the nucleotide sequences encoding the heavy chain (SEQ ID NO: 31) and light chain (SEQ ID NO: 65) variable regions of anti-TR-2 antibody P, and the amino acid sequences of the heavy chain (SEQ ID NO: 32) and the light chain (SEQ ID NO: 66) variable regions of that antibody.

FIG. 19 shows the nucleotide sequences encoding the heavy chain (SEQ ID NO: 33) and light chain (SEQ ID NO: 67) variable regions of anti-TR-2 antibody Q, and the amino acid sequences of the heavy chain (SEQ ID NO: 34) and the light chain (SEQ ID NO: 68) variable regions of that antibody.

FIG. 20 is an alignment of the amino acid sequences of the heavy chain variable regions for anti-TR-2 antibodies A to Q (SEQ ID NOs: 2, 4, 6, 8, 10, 12, 14, 16, 18, 20, 22, 24, 26, 28, 30, 32, and 34). Framework regions 1 through 3 (FR1, FR2, and FR3) and complementarity determining regions 1 through 3 (CDR1, CDR2, and CDR3) for each sequence are shown.

FIG. 21 is an alignment of the amino acid sequences of the light chain variable regions for anti-TR-2 antibodies A to Q (SEQ ID NOs: 36, 38, 40, 42, 44, 46, 48, 50, 52, 54, 56, 58, 60, 62, 64, 66, and 68). Framework regions 1 through 3 (FR1, FR2, and FR3) and complementarity determining regions 1 through 3 (CDR1, CDR2, and CDR3) for each sequence are shown.

FIG. 22 is a table showing the classification of certain human anti-TR-2 antibodies into one of four reactivity groups according to the ability of each to bind to the truncated and chimeric N-avidin TR-2 proteins, according to work described in Example 5.

FIG. 23 shows schematic representations of the thirteen truncations of human N-avidin-TR-2 used in epitope mapping, according to the work described in Example 6.

FIG. 25 shows schematic representations of N-avidin-cyno TR-2 truncations and N-avidin-cyno/human TR-2 chimeras used in epitope mapping, according to work described in Example 6.

FIG. 26 is an alignment of the human TR-2, cyno TR-2 (short form), and mouse TR-2 sequences, according to work described in Example 6.

DETAILED DESCRIPTION OF CERTAIN EMBODIMENTS

Figure 23:
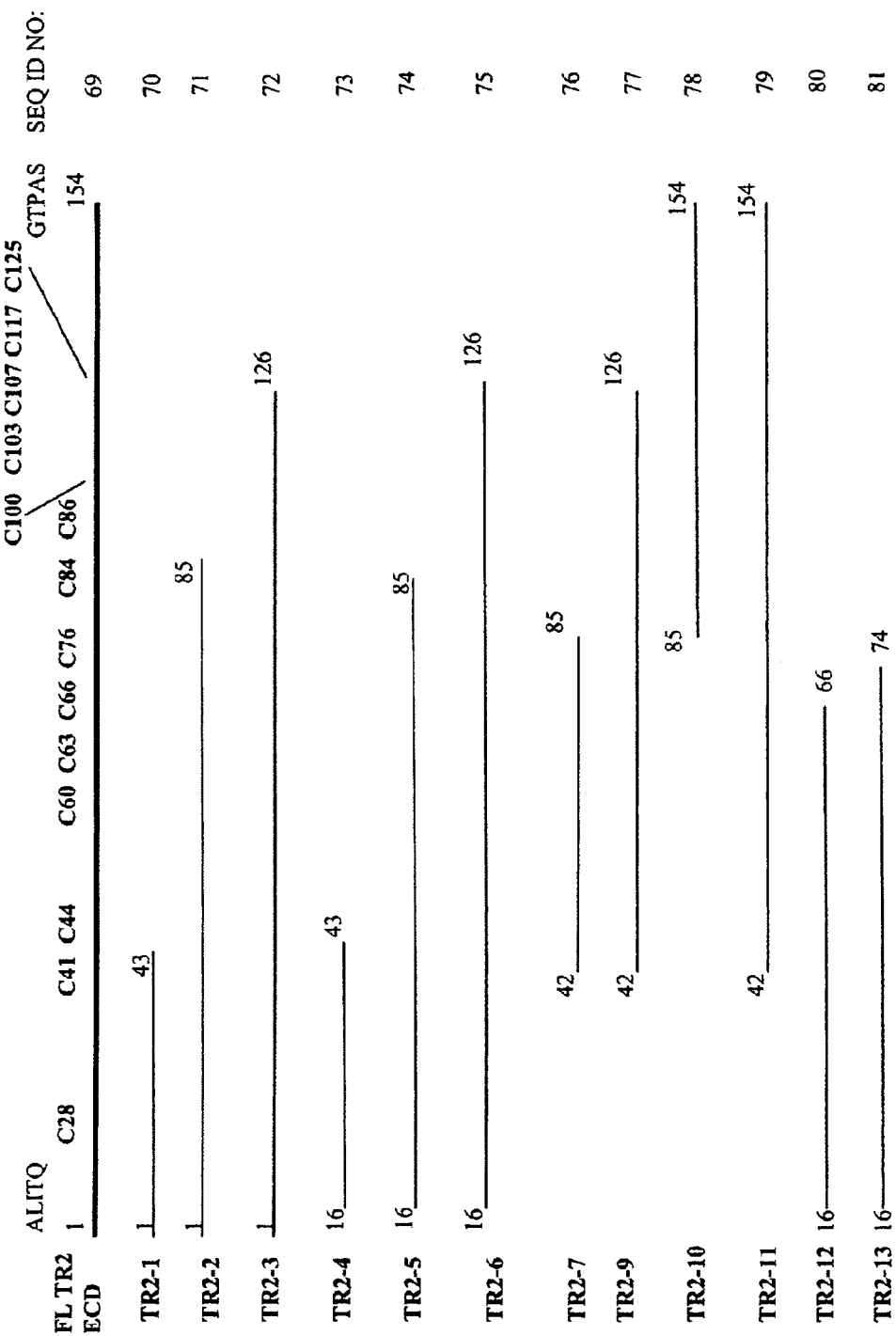

The section headings used herein are for organizational purposes only and are not to be construed as limiting the subject matter described. All documents or portions of documents cited in this application, including but not limited to patents, patent applications, articles, books, and treatises, are expressly incorporated by reference herein in their entirety for any purpose.

Definitions

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, delivery, and treatment of patients.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

The terms "polynucleotide" and "oligonucleotide" are used interchangeably, and as referred to herein mean a polymeric form of nucleotides of at least 10 bases in length. In certain embodiments, the bases may comprise at least one of ribonucleotides, deoxyribonucleotides, and a modified form of either type of nucleotide. The term includes single and double stranded forms of DNA. The term "polynucleotide" also encompasses sequences that comprise one or more of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, and 67. In certain embodiments, polynucleotides have nucleotide sequences that are about 90 percent, or about 95 percent, or about 96 percent, or about 97 percent, or about 98 percent, or about 99 percent identical to nucleotide sequences shown in FIGS. 3-19. In certain embodiments, polynucleotides complementary to specific polynucleotides that encode certain polypeptides described herein are provided.

In certain embodiments, a polynucleotide comprises a sequence encoding a polypeptide comprising at least one complementarity determining region (CDR) selected from CDR1a, CDR2a, and CDR3a, wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present; wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present; wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; and wherein the polypeptide, in association with an antibody light chain, binds TR-2.

In certain embodiments, a polynucleotide comprises a sequence encoding CDR2a, wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present.

In certain embodiments, a polynucleotide comprises a sequence encoding CDR3a comprising the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present.

In certain embodiments, a polynucleotide comprises a sequence encoding a polypeptide comprising at least two complementarity determining regions (CDR) selected from CDR1a, CDR2a, and CDR3a, wherein the polypeptide, in association with an antibody light chain, binds TR-2. In certain embodiments, a polynucleotide comprises a sequence encoding a polypeptide comprising CDR1a, CDR2a, and CDR3a, wherein the polypeptide, in association with an antibody light chain, binds TR-2.

In certain embodiments, a polynucleotide comprises a sequence encoding a polypeptide comprising an antibody heavy chain variable region. In certain embodiments, a polynucleotide comprises a sequence encoding a polypeptide comprising a human antibody heavy chain variable region. In certain embodiments, a polynucleotide comprises a sequence encoding a polypeptide comprising a heavy chain constant region. In certain embodiments, a polynucleotide comprises a sequence encoding a polypeptide comprising a human heavy chain constant region. In certain embodiments, a polynucleotide comprises a sequence encoding a polypeptide comprising an amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34. In certain embodiments, a polynucleotide comprises a sequence encoding a polypeptide comprising a non-human heavy chain constant region. In certain embodiments, a polynucleotide comprises a sequence encoding a polypeptide comprising a heavy chain constant region of a species other than human.

In certain embodiments, a polynucleotide comprises a sequence encoding a polypeptide comprising at least one complementarity determining region (CDR) selected from amino acids 26 to 35 of SEQ ID NO: 2; amino acids 50 to 66 of SEQ ID NO: 2; amino acids 99 to 110 of SEQ ID NO: 2; amino acids 26 to 37 of SEQ ID NO: 4; amino acids 52 to 67 of SEQ ID NO: 4; amino acids 100 to 109 of SEQ ID NO: 4; amino acids 26 to 37 of SEQ ID NO: 6; amino acids 52 to 67 of SEQ ID NO: 6; amino acids 100 to 109 of SEQ ID NO: 6; amino acids 26 to 37 of SEQ ID NO: 8; amino acids 52 to 67 of SEQ ID NO: 8; amino acids 100 to 109 of SEQ ID NO: 8; amino acids 26 to 35 of SEQ ID NO: 10; amino acids 50 to 66 of SEQ ID NO: 10; amino acids 99 to 110 of SEQ ID NO: 10; amino acids 26 to 35 of SEQ ID. NO: 12; amino acids 50 to 66 of SEQ ID NO: 12; amino acids 99 to 111 of SEQ ID NO: 12; amino acids 26 to 35 of SEQ ID. NO: 14; amino acids 50 to 65 of SEQ ID NO: 14; amino acids 98 to 111 of SEQ ID NO: 14; amino acids 26 to 37 of SEQ ID NO: 16; amino acids 52 to 67 of SEQ ID NO: 16; amino acids 100 to 109 of SEQ ID NO: 16; amino acids 26 to 35 of SEQ ID NO: 18; amino acids 50 to 66 of SEQ ID NO: 18; amino acids 99 to 105 of SEQ ID NO: 18; amino acids 26 to 35 of SEQ ID NO: 20; amino acids 50 to 66 of SEQ ID NO: 20; amino acids 99 to 118 of SEQ ID NO: 20; amino acids 26 to 35 of SEQ ID NO: 22; amino acids 50 to 66 of SEQ ID NO: 22; amino acids 99 to 118 of SEQ ID NO: 22; amino acids 26 to 35 of SEQ ID NO: 24; amino acids 50 to 65 of SEQ ID NO: 24; amino acids 98 to 108 of SEQ ID NO: 24; amino acids 26 to 35 of SEQ ID NO: 26; amino acids 50 to 66 of SEQ ID NO: 26; amino acids 99 to 110 of SEQ ID NO: 26; amino acids 26 to 35 of SEQ ID NO: 28; amino acids 50 to 66 of SEQ ID NO: 28; amino acids 99 to 117 of SEQ ID NO: 28; amino acids 26 to 37 of SEQ ID NO: 30; amino acids 52 to 67 of SEQ ID NO: 30; amino acids 100 to 111 of SEQ ID NO: 30; amino acids 26 to 37 of SEQ ID NO: 32; amino acids 52 to 67 of SEQ ID NO: 32; amino acids 100 to 111 of SEQ ID NO: 32; amino acids 26 to 37 of SEQ ID NO: 34; amino acids 52 to 67 of SEQ ID NO: 34; and amino acids 100 to 111 of SEQ ID NO: 34, wherein the polypeptide, in association with an antibody light chain, binds TR-2. In certain embodiments, a polynucleotide comprises a sequence encoding a polypeptide comprising at least two of the CDRs of SEQ ID NOS. 2, 4, 6, 8, 10, 12, 14, 16, 18, 20, 22, 24, 26, 28, 30, 32, or 34. In certain embodiments, a polynucleotide comprises a sequence encoding a polypeptide comprising three of the CDRs of SEQ ID NOS. 2, 4, 6, 8, 10, 12, 14, 16, 18, 20, 22, 24, 26, 28, 30, 32, or 34.

In certain embodiments, a polynucleotide comprises a sequence encoding a polypeptide comprising amino acids 26 to 35 of SEQ ID NO: 2, amino acids 50 to 66 of SEQ ID NO: 2, and amino acids 99 to 110 of SEQ ID NO: 2. In certain embodiments, a polynucleotide comprises a sequence encoding a polypeptide comprising amino acids 26 to 37 of SEQ ID NO: 4, amino acids 52 to 67 of SEQ ID NO: 4, and amino acids 100 to 109 of SEQ ID NO: 4. In certain embodiments, a polynucleotide comprises a sequence encoding a polypeptide comprising amino acids 26 to 37 of SEQ ID NO: 6, amino acids 52 to 67 of SEQ ID NO: 6, and amino acids 100 to 109 of SEQ ID NO: 6. In certain embodiments, a polynucleotide comprises a sequence encoding a polypeptide comprising amino acids 26 to 37 of SEQ ID NO: 8, amino acids 52 to 67 of SEQ ID NO: 8, and amino acids 100 to 109 of SEQ ID NO: 8. In certain embodiments, a polynucleotide comprises a sequence encoding a polypeptide comprising amino acids 26 to 35 of SEQ ID NO: 10, amino acids 50 to 66 of SEQ ID NO: 10, and amino acids 99-110 of SEQ ID NO: 10. In certain embodiments, a polynucleotide comprises a sequence encoding a polypeptide comprising amino acids 26 to 35 of SEQ ID NO: 12, amino acids 50 to 66 of SEQ ID NO: 12, and amino acids 99-111 of SEQ ID NO: 12. In certain embodiments, a polynucleotide comprises a sequence encoding a polypeptide comprising amino acids 26 to 35 of SEQ ID NO: 14, amino acids 50 to 65 of SEQ ID NO: 14, and amino acids 98 to 111 of SEQ ID NO: 14. In certain embodiments, a polynucleotide comprises a sequence encoding a polypeptide comprising amino acids 26 to 37 of SEQ ID NO: 16, amino acids 52 to 67 of SEQ ID NO: 16, and amino acids 100 to 109 of SEQ ID NO: 16. In certain embodiments, a polynucleotide comprises a sequence encoding a polypeptide comprising amino acids 26 to 35 of SEQ ID NO: 18, amino acids 50 to 66 of SEQ ID NO: 18, and amino acids 99 to 105 of SEQ ID NO: 18. In certain embodiments, a polynucleotide comprises a sequence encoding a polypeptide comprising amino acids 26 to 35 of SEQ ID NO: 20, amino acids 50 to 66 of SEQ ID NO: 20, and amino acids 99 to 118 of SEQ ID NO: 20. In certain embodiments, a polynucleotide comprises a sequence encoding a polypeptide comprising amino acids 26 to 35 of SEQ ID NO: 22, amino acids 50 to 66 of SEQ ID NO: 22, and amino acids 99 to 118 of SEQ ID NO: 22. In certain embodiments, a polynucleotide comprises a sequence encoding a polypeptide comprising amino acids 26 to 35 of SEQ ID NO: 24, amino acids 50 to 65 of SEQ ID NO: 24, and amino acids 98 to 108 of SEQ ID NO: 24. In certain embodiments, a polynucleotide comprises a sequence encoding a polypeptide comprising amino acids 26 to 35 of SEQ ID NO: 26, amino acids 50 to 66 of SEQ ID NO: 26, and amino acids 99 to 110 of SEQ ID NO: 26. In certain embodiments, a polynucleotide comprises a sequence encoding a polypeptide comprising amino acids 26 to 35 of SEQ ID NO: 28, amino acids 50 to 66 of SEQ ID NO: 28, and amino acids 99 to 117 of SEQ ID NO: 28. In certain embodiments, a polynucleotide comprises a sequence encoding a polypeptide comprising amino acids 26 to 37 of SEQ ID NO: 30, amino acids 52 to 67 of SEQ ID NO: 30, and amino acids 100 to 111 of SEQ ID NO: 30. In certain embodiments, a polynucleotide comprises a sequence encoding a polypeptide comprising amino acids 26 to 37 of SEQ ID NO: 32, amino acids 52 to 67 of SEQ ID NO: 32, and amino acids 100 to 111 of SEQ ID NO: 32. In certain embodiments, a polynucleotide comprises a sequence encoding a polypeptide comprising amino acids 26 to 37 of SEQ ID NO: 34, amino acids 52 to 67 of SEQ ID NO: 34, and amino acids 100 to 111 of SEQ ID NO: 34.

In certain embodiments, a polynucleotide comprises a sequence encoding a polypeptide comprising at least one complementarity determining region (CDR) selected from CDR1b, CDR2b, and CDR3b, wherein CDR1b comprises the amino acid sequence a1 b1 c1 d1 e1 f1 g1 h1 i1 j1 k1 l1 m1 n1 o1 p1 q1, wherein amino acid a1 is selected from arginine or lysine; amino acid b1 is selected from threonine, alanine, or serine; amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid l1 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present; wherein CDR2b comprises the amino acid sequence r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine; wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; and wherein the polypeptide, in association with an antibody heavy chain, binds TR-2.

In certain embodiments, a polynucleotide comprises a sequence encoding a polypeptide comprising at least two complementarity determining regions (CDR) selected from CDR1b, CDR2b, and CDR3b, wherein the polypeptide, in association with an antibody heavy chain, binds TR-2. In certain embodiments, a polynucleotide comprises a sequence encoding a polypeptide comprising CDR1b, CDR2b, and CDR3b, wherein the polypeptide, in association with an antibody heavy chain, binds TR-2.

In certain embodiments, a polynucleotide comprises a sequence encoding a polypeptide comprising an antibody light chain variable region. In certain embodiments, a polynucleotide comprises a sequence encoding a polypeptide comprising a human antibody light chain variable region. In certain embodiments, a polynucleotide comprises a sequence encoding a polypeptide comprising a light chain constant region. In certain embodiments, a polynucleotide comprises a sequence encoding a polypeptide comprising a human light chain constant region. In certain embodiments, a polynucleotide comprises a sequence encoding a polypeptide comprising an amino acid sequence as set forth in SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, or SEQ ID NO: 68. In certain embodiments, a polynucleotide comprises a sequence encoding a polypeptide comprising a non-human light chain constant region. In certain embodiments, a polynucleotide comprises a sequence encoding a polypeptide comprising a light chain constant region of a species other than human.

In certain embodiments, a polynucleotide comprises a sequence encoding a polypeptide comprising at least one complementarity determining region (CDR) selected from amino acids 24 to 34 of SEQ ID NO: 36; amino acids 50 to 56 of SEQ ID NO: 36; amino acids 89 to 97 of SEQ ID NO: 36; amino acids 24 to 34 of SEQ ID NO: 38; amino acids 50 to 56 of SEQ ID NO: 38; amino acids 89 to 97 of SEQ ID NO: 38; amino acids 24 to 34 of SEQ ID NO: 40; amino acids 50 to 56 of SEQ ID NO: 40; amino acids 89 to 97 of SEQ ID NO: 40; amino acids 24 to 34 of SEQ ID NO: 42; amino acids 50 to 56 of SEQ ID NO: 42; amino acids 89 to 97 of SEQ ID NO: 42; amino acids 24 to 34 of SEQ ID NO: 44; amino acids 50 to 56 of SEQ ID NO: 44; amino acids 89 to 97 of SEQ ID NO: 44; amino acids 24 to 34 of SEQ ID NO: 46; amino acids 50 to 56 of SEQ ID NO: 46; amino acids 89 to 97 of SEQ ID NO: 46; amino acids 24 to 40 of SEQ ID NO: 48; amino acids 56 to 62 of SEQ ID NO: 48; amino acids 95 to 103 of SEQ ID NO: 48; amino acids 24 to 39 of SEQ ID NO: 50; amino acids 55 to 61 of SEQ ID NO: 50; amino acids 94 to 102 of SEQ ID NO: 50; amino acids 24 to 40 of SEQ ID NO: 52; amino acids 56 to 62 of SEQ ID NO: 52; amino acids 95 to 103 of SEQ ID NO: 52; amino acids 24 to 34 of SEQ ID NO: 54; amino acids 50 to 56 of SEQ ID NO: 54; amino acids 89 to 97 of SEQ ID NO: 54; amino acids 24 to 34 of SEQ ID NO: 56; amino acids 50 to 56 of SEQ ID NO: 56; amino acids 89 to 97 of SEQ ID NO: 56; amino acids 24 to 40 of SEQ ID NO: 58; amino acids 56 to 62 of SEQ ID NO: 58; amino acids 95 to 103 of SEQ ID NO: 58; amino acids 24 to 34 of SEQ ID NO: 60; amino acids 50 to 56 of SEQ ID NO: 60; amino acids 89 to 97 of SEQ ID NO: 60; amino acids 24 to 34 of SEQ ID NO: 62; amino acids 50 to 56 of SEQ ID NO: 62; amino acids 89 to 97 of SEQ ID NO: 62; amino acids 24 to 35 of SEQ ID NO: 64; amino acids 51 to 57 of SEQ ID NO: 64; amino acids 90 to 88 of SEQ ID NO: 64; amino acids 24 to 34 of SEQ ID NO: 66; amino acids 50 to 57 of SEQ ID NO: 66; amino acids 89 to 97 of SEQ ID NO: 66; amino acids 24 to 34 of SEQ ID NO: 68; amino acids 50 to 56 of SEQ ID NO: 68; and amino acids 89 to 97 of SEQ ID NO: 68, wherein the polypeptide, in association with an antibody heavy chain, binds TR-2. In certain embodiments, a polynucleotide comprises a sequence encoding a polypeptide comprising at least two of the CDRs of SEQ ID NOS. 36, 38, 40, 42, 44, 46, 48, 50, 52, 54, 56, 58, 60, 62, 64, or 68. In certain embodiments, a polynucleotide comprises a sequence encoding a polypeptide comprising three of the CDRs of SEQ ID NOS. 36, 38, 40, 42, 44, 46, 48, 50, 52, 54, 56, 58, 60, 62, 64, or 68.

In certain embodiments, a polynucleotide comprises a sequence encoding a polypeptide comprising amino acids 24 to 34 of SEQ ID NO: 36, amino acids 50 to 56 of SEQ ID NO: 36, and amino acids 89-97 of SEQ ID NO: 36. In certain embodiments, a polynucleotide comprises a sequence encoding a polypeptide comprising amino acids 24 to 34 of SEQ ID NO: 38, amino acids 50 to 56 of SEQ ID NO: 38, and amino acids 89 to 97 of SEQ ID NO: 38. In certain embodiments, a polynucleotide comprises a sequence encoding a polypeptide comprising amino acids 24 to 34 of SEQ ID NO: 40, amino acids 50 to 56 of SEQ ID NO: 40, and amino acids 89 to 97 of SEQ ID NO: 40. In certain embodiments, a polynucleotide comprises a sequence encoding a polypeptide comprising amino acids 24 to 34 of SEQ ID NO: 42, amino acids 50 to 56 of SEQ ID NO: 42, and amino acids 89 to 97 of SEQ ID NO: 42. In certain embodiments, a polynucleotide comprises a sequence encoding a polypeptide comprising amino acids 24 to 34 of SEQ ID NO: 44, amino acids 50 to 56 of SEQ ID NO: 44, and amino acids 89-97 of SEQ ID NO: 44. In certain embodiments, a polynucleotide comprises a sequence encoding a polypeptide comprising amino acids 24 to 34 of SEQ ID NO: 46, amino acids 50 to 56 of SEQ ID NO: 46, and amino acids 89 to 97 of SEQ ID NO: 46. In certain embodiments, a polynucleotide comprises a sequence encoding a polypeptide comprising amino acids 24 to 40 of SEQ ID NO: 48, amino acids 56 to 62 of SEQ ID NO: 48, and amino acids 95 to 103 of SEQ ID NO: 48. In certain embodiments, a polynucleotide comprises a sequence encoding a polypeptide comprising amino acids 24 to 39 of SEQ ID NO: 50, amino acids 55 to 61 of SEQ ID NO: 50, and amino acids 94 to 102 of SEQ ID NO: 50. In certain embodiments, a polynucleotide comprises a sequence encoding a polypeptide comprising amino acids 24 to 40 of SEQ ID NO: 52, amino acids 56 to 62 of SEQ ID NO: 52, and amino acids 95 to 103 of SEQ ID NO: 52. In certain embodiments, a polynucleotide comprises a sequence encoding a polypeptide comprising 24 to 34 of SEQ ID NO: 54, amino acids 50 to 56 of SEQ ID NO: 54, and amino acids 89 to 97 of SEQ ID NO: 54. In certain embodiments, a polynucleotide comprises a sequence encoding a polypeptide comprising amino acids 24 to 34 of SEQ ID NO: 56, amino acids 50 to 56 of SEQ ID NO: 56, and amino acids 89 to 97 of SEQ ID NO: 56, In certain embodiments, a polynucleotide comprises a sequence encoding a polypeptide comprising amino acids 24 to 40 of SEQ ID NO: 58, amino acids 56 to 62 of SEQ ID NO: 58, and amino acids 95 to 103 of SEQ ID NO: 58. In certain embodiments, a polynucleotide comprises a sequence encoding a polypeptide comprising amino acids 24 to 34 of SEQ ID NO: 60, amino acids 50 to 56 of SEQ ID NO: 60, and amino acids 89-97 of SEQ ID NO: 60. In certain embodiments, a polynucleotide comprises a sequence encoding a polypeptide comprising amino acids 24 to 34 of SEQ ID NO: 62, amino acids 50 to 56 of SEQ ID NO: 62, and amino acids 89 to 97 of SEQ ID NO: 62. In certain embodiments, a polynucleotide comprises a sequence encoding a polypeptide comprising amino acids 24 to 35 of SEQ ID NO: 64, amino acids 51 to 57 of SEQ ID NO: 64, and amino acids 90 to 88 of SEQ ID NO: 64. In certain embodiments, a polynucleotide comprises a sequence encoding a polypeptide comprising amino acids 24 to 34 of SEQ ID NO: 66, amino acids 50 to 57 of SEQ ID NO: 66, and amino acids 89 to 97 of SEQ ID NO: 66. In certain embodiments, a polynucleotide comprises a sequence encoding a polypeptide comprising amino acids 24 to 34 of SEQ ID NO: 68, amino acids 50 to 56 of SEQ ID NO: 68, and amino acids 89 to 97 of SEQ ID NO: 68.

In certain embodiments, this application discusses certain polynucleotides encoding antibody heavy and light chains. In certain embodiments, this application discusses certain polynucleotides encoding an antibody heavy chain variable region. In certain embodiments, this application discusses certain polynucleotides encoding a human antibody heavy chain variable region. In certain embodiments, this application discusses certain polynucleotides encoding antibody light chain variable regions. In certain embodiments, this application discusses certain polynucleotides encoding a human antibody light chain variable region. In certain embodiments, this application discusses certain polynucleotides encoding an antibody heavy chain constant region. In certain embodiments, this application discusses certain polynucleotides encoding a human antibody heavy chain constant region. In certain embodiments, this application discusses certain polynucleotides encoding an antibody heavy chain constant region of a species other than human. In certain embodiments, this application discusses certain polynucleotides encoding antibody light chain constant regions. In certain embodiments, this application discusses certain polynucleotides encoding a human antibody light chain constant region. In certain embodiments, this application discusses certain polynucleotides encoding an antibody light chain constant region of a species other than human. In certain embodiments, this application discusses certain polynucleotides encoding a single-chain antibody.

In certain embodiments, these antibody heavy and light chain polynucleotides and polypeptides are human antibody heavy and light chain polynucleotides and polypeptides. In certain embodiments a polynucleotide comprises a nucleotide sequence as set forth in SEQ ID NOS. SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, or 67. In certain embodiments, a polynucleotide comprises a nucleotide sequence that has one or more deletions, additions, and/or substitutions of one or more nucleotides of those sequences. In certain embodiments, a polynucleotide comprises a nucleotide sequence encoding an amino acid sequence comprising an amino acid sequence as set forth in SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, or 68. In certain embodiments, variable region sequences comprising complementarity determining regions (CDRs), e.g., CDR1 through CDR3, are provided. In certain embodiments, variable region polynucleotides and polypeptides are human variable region polynucleotides and polypeptides.

The term "naturally occurring nucleotides" includes deoxyribonucleotides and ribonucleotides. Deoxyribonucleotides include, but are not limited to, adenosine, guanine, cytosine, and thymidine. Ribonucleotides include, but are not limited to, adenosine, cytosine, thymidine, and uracil. The term "modified nucleotides" includes, but is not limited to, nucleotides with modified or substituted sugar groups and the like. The term "polynucleotide linkages" includes, but is not limited to, polynucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990). In certain embodiments, a polynucleotide can include a label for detection.

The term "isolated polypeptide" refers to any polypeptide that (1) is free of at least some proteins with which it would normally be found, (2) is essentially free of other proteins from the same source, e.g., from the same species, (3) is expressed by a cell from a different species, or (4) does not occur in nature.

The terms "polypeptide," "peptide," and "protein" are used interchangeably herein and refer to a polymer of two or more amino acids joined to each other by peptide bonds or modified peptide bonds, i.e., peptide isosteres. The terms apply to amino acid polymers containing naturally occurring amino acids as well as amino acid polymers in which one or more amino acid residues is a non-naturally occurring amino acid or a chemical analogue of a naturally occurring amino acid. An amino acid polymer may contain one or more amino acid residues that has been modified by one or more natural processes, such as post-translational processing, and/or one or more amino acid residues that has been modified by one or more chemical modification techniques known in the art.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide. In certain embodiments, a variant of a reference polypeptide has an altered post-translational modification site (i.e., a glycosylation site). In certain embodiments, both a reference polypeptide and a variant of a reference polypeptide are specific binding agents. In certain embodiments, both a reference polypeptide and a variant of a reference polypeptide are antibodies.

Variants of a reference polypeptide include, but are not limited to, glycosylation variants. Glycosylation variants include variants in which the number and/or type of glycosylation sites have been altered as compared to the reference polypeptide. In certain embodiments, glycosylation variants of a reference polypeptide comprise a greater or a lesser number of N-linked glycosylation sites than the reference polypeptide. In certain embodiments, an N-linked glycosylation site is characterized by the sequence Asn-X-Ser or Asn-X-Thr, wherein the amino acid residue designated as X may be any amino acid residue except proline. In certain embodiments, glycosylation variants of a reference polypeptide comprise a rearrangement of N-linked carbohydrate chains wherein one or more N-linked glycosylation sites (typically those that are naturally occurring) are eliminated and one or more new N-linked sites are created.

Variants of a reference polypeptide include, but are not limited to, cysteine variants. In certain embodiments, cysteine variants include variants in which one or more cysteine residues of the reference polypeptide are replaced by one or more non-cysteine residues; and/or one or more non-cysteine residues of the reference polypeptide are replaced by one or more cysteine residues. Cysteine variants may be useful, in certain embodiments, when a particular polypeptide must be refolded into a biologically active conformation, e.g., after the isolation of insoluble inclusion bodies. In certain embodiments, cysteine variants of a reference polypeptide have fewer cysteine residues than the reference polypeptide. In certain embodiments, cysteine variants of a reference polypeptide have an even number of cysteines to minimize interactions resulting from unpaired cysteines. In certain embodiments, cysteine variants have more cysteine residues than the native protein.

A "derivative" of a reference polypeptide refers to: a polypeptide: (1) having one or more modifications of one or more amino acid residues of the reference polypeptide; and/or (2) in which one or more peptidyl linkages has been replaced with one or more non-peptidyl linkages; and/or (3) in which the N-terminus and/or the C-terminus has been modified. Certain exemplary modifications include, but are not limited to, acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. In certain embodiments, both a reference polypeptide and a derivative of a reference polypeptide are specific binding agents. In certain embodiments, both a reference polypeptide and a derivative of a reference polypeptide are antibodies.

Polypeptides include, but are not limited to, amino acid sequences modified either by natural processes, such as post-translational processing, or by chemical modification techniques that are well known in the art. In certain embodiments, modifications may occur anywhere in a polypeptide, including the peptide backbone, the amino acid side-chains and the amino or carboxyl termini. In certain such embodiments, the modifications may be present to the same or varying degrees at several sites in a given polypeptide. In certain embodiments, a given polypeptide contains many types of modifications such as deletions, additions, and/or substitutions of one or more amino acids of a native sequence. In certain embodiments, polypeptides may be branched and/or cyclic. Cyclic, branched and branched cyclic polypeptides may result from post-translational natural processes (including, but not limited to, ubiquitination) or may be made by synthetic methods. The term "polypeptide" also encompasses sequences that comprise the amino acid sequences of the heavy chain and/or light chain of an antibody selected from Ab A, Ab B, Ab C, Ab D, Ab E, Ab F, Ab G, Ab H, Ab I, Ab J, Ab K, Ab L, Ab M, Ab N, Ab O, Ab P, and Ab Q, as described below (see SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68). The term "polypeptide" also encompasses sequences that have one or more deletions, additions, and/or substitutions of one or more amino acids of those sequences. In certain embodiments, certain polypeptide sequences comprise at least one complementarity determining region (CDR).

In certain embodiments, a polypeptide comprises at least one complementarity determining region (CDR) selected from CDR1a, CDR2a, and CDR3a wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present; wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present; wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; and wherein the polypeptide, in association with an antibody light chain, binds TR-2.

In certain embodiments, a polypeptide comprises at least two complementarity determining regions (CDR) selected from CDR1a, CDR2a, and CDR3a, wherein the polypeptide, in association with an antibody light chain, binds TR-2. In certain embodiments, a polypeptide comprises CDR1a, CDR2a, and CDR3a, wherein the polypeptide, in association with an antibody light chain, binds TR-2.

In certain embodiments, a polypeptide comprises an antibody heavy chain variable region. In certain embodiments, a polypeptide comprises a human antibody heavy chain variable region. In certain embodiments, a polypeptide comprises a heavy chain constant region. In certain embodiments, a polypeptide comprises a human heavy chain constant region. In certain embodiments, a polypeptide comprises an amino acid sequence as set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, or SEQ ID NO: 34. In certain embodiments, a polypeptide comprises a non-human heavy chain constant region. In certain embodiments, a polypeptide comprises a heavy chain constant region of a species other than human.

In certain embodiments, a polypeptide comprises at least one complementarity determining region (CDR) selected from amino acids 26 to 35 of SEQ ID NO: 2; amino acids 50 to 66 of SEQ ID NO: 2; amino acids 99 to 110 of SEQ ID NO: 2; amino acids 26 to 37 of SEQ ID NO: 4; amino acids 52 to 67 of SEQ ID NO: 4; amino acids 100 to 109 of SEQ ID NO: 4; amino acids 26 to 37 of SEQ ID NO: 6; amino acids 52 to 67 of SEQ ID NO: 6; amino acids 100 to 109 of SEQ ID NO: 6; amino acids 26 to 37 of SEQ ID NO: 8; amino acids 52 to 67 of SEQ ID NO: 8; amino acids 100 to 109 of SEQ ID NO: 8; amino acids 26 to 35 of SEQ ID NO: 10, amino acids 50 to 66 of SEQ ID NO: 10; amino acids 99-110 of SEQ ID NO: 10; amino acids 26 to 35 of SEQ ID NO: 12; amino acids 50 to 66 of SEQ ID NO: 12; amino acids 99-111 of SEQ ID NO: 12; amino acids 26 to 35 of SEQ ID NO: 14; amino acids 50 to 65 of SEQ ID NO: 14; amino acids 98 to 111 of SEQ ID NO: 14; amino acids 26 to 37 of SEQ ID NO: 16; amino acids 52 to 67 of SEQ ID NO: 16; amino acids 100 to 109 of SEQ ID NO: 16; amino acids 26 to 35 of SEQ ID NO: 18; amino acids 50 to 66 of SEQ ID NO: 18; amino acids 99 to 105 of SEQ ID NO: 18; amino acids 26 to 35 of SEQ ID NO: 20; amino acids 50 to 66 of SEQ ID NO: 20; amino acids 99 to 118 of SEQ ID NO: 20; amino acids 26 to 35 of SEQ ID NO: 22; amino acids 50 to 66 of SEQ ID NO: 22; amino acids 99 to 118 of SEQ ID NO: 22; amino acids 26 to 35 of SEQ ID NO: 24; amino acids 50 to 65 of SEQ ID NO: 24; amino acids 98 to 108 of SEQ ID NO: 24; amino acids 26 to 35 of SEQ ID NO: 26; amino acids 50 to 66 of SEQ ID NO: 26; amino acids 99 to 110 of SEQ ID NO: 26; amino acids 26 to 35 of SEQ ID NO: 28; amino acids 50 to 66 of SEQ ID NO: 28; amino acids 99 to 117 of SEQ ID NO: 28; amino acids 26 to 37 of SEQ ID NO: 30; amino acids 52 to 67 of SEQ ID NO: 30; amino acids 100 to 111 of SEQ ID NO: 30; amino acids 26 to 37 of SEQ ID NO: 32; amino acids 52 to 67 of SEQ ID NO: 32; amino acids 100 to 111 of SEQ ID NO: 32; amino acids 26 to 37 of SEQ ID NO: 34; amino acids 52 to 67 of SEQ ID NO: 34; and amino acids 100 to 111 of SEQ ID NO: 34, wherein the polypeptide, in association with an antibody light chain, binds TR-2. In certain embodiments, a polypeptide comprises at least two of the CDRs of SEQ ID NOS. 2, 4, 6, 8, 10, 12, 14, 16, 18, 20, 22, 24, 26, 28, 30, 32, or 34. In certain embodiments, a polypeptide comprises at least three of the CDRs of SEQ ID NOS. 2, 4, 6, 8, 10, 12, 14, 16, 18, 20, 22, 24, 26, 28, 30, 32, or 34.

In certain embodiments, a polypeptide comprises amino acids 26 to 35 of SEQ ID NO: 2, amino acids 50 to 66 of SEQ ID NO: 2, and amino acids 99 to 110 of SEQ ID NO: 2. In certain embodiments, a polypeptide comprises amino acids 26 to 37 of SEQ ID NO: 4, amino acids 52 to 67 of SEQ ID NO: 4, and amino acids 100 to 109 of SEQ ID NO: 4. In certain embodiments, a polypeptide comprises amino acids 26 to 37 of SEQ ID NO: 6, amino acids 52 to 67 of SEQ ID NO: 6, and amino acids 100 to 109 of SEQ ID NO: 6. In certain embodiments, a polypeptide comprises amino acids 26 to 37 of SEQ ID NO: 8, amino acids 52 to 67 of SEQ ID NO: 8, and amino acids 100 to 109 of SEQ ID NO: 8. In certain embodiments, a polypeptide comprises amino acids 26 to 35 of SEQ ID NO: 10, amino acids 50 to 66 of SEQ ID NO: 10, and amino acids 99-110 of SEQ ID NO: 10. In certain embodiments, a polypeptide comprises amino acids 26 to 35 of SEQ ID NO: 12, amino acids 50 to 66 of SEQ ID NO: 12, and amino acids 99-111 of SEQ ID NO: 12. In certain embodiments, a polypeptide comprises amino acids 26 to 35 of SEQ ID NO: 14, amino acids 50 to 65 of SEQ ID NO: 14, and amino acids 98 to 111 of SEQ ID NO: 14. In certain embodiments, a polypeptide comprises amino acids 26 to 37 of SEQ ID NO: 16, amino acids 52 to 67 of SEQ ID NO: 16, and amino acids 100 to 109 of SEQ ID NO: 16. In certain embodiments, a polypeptide comprises amino acids 26 to 35 of SEQ ID NO: 18, amino acids 50 to 66 of SEQ ID NO: 18, and amino acids 99 to 105 of SEQ ID NO: 18. In certain embodiments, a polypeptide comprises amino acids 26 to 35 of SEQ ID NO: 20, amino acids 50 to 66 of SEQ ID NO: 20, and amino acids 99 to 118 of SEQ ID NO: 20. In certain embodiments, a polypeptide comprises amino acids 26 to 35 of SEQ ID NO: 22, amino acids 50 to 66 of SEQ ID NO: 22, and amino acids 99 to 118 of SEQ ID NO: 22. In certain embodiments, a polypeptide comprises amino acids 26 to 35 of SEQ ID NO: 24, amino acids 50 to 65 of SEQ ID NO: 24, and amino acids 98 to 108 of SEQ ID NO: 24. In certain embodiments, a polypeptide comprises amino acids 26 to 35 of SEQ ID NO: 26, amino acids 50 to 66 of SEQ ID NO: 26, and amino acids 99 to 110 of SEQ ID NO: 26. In certain embodiments, a polypeptide comprises amino acids 26 to 35 of SEQ ID NO: 28, amino acids 50 to 66 of SEQ ID NO: 28, and amino acids 99 to 117 of SEQ ID NO: 28. In certain embodiments, a polypeptide comprises amino acids 26 to 37 of SEQ ID NO: 30, amino acids 52 to 67 of SEQ ID NO: 30, and amino acids 100 to 111 of SEQ ID NO: 30. In certain embodiments, a polypeptide comprises amino acids 26 to 37 of SEQ ID NO: 32, amino acids 52 to 67 of SEQ ID NO: 32, and amino acids 100 to 111 of SEQ ID NO: 32. In certain embodiments, a polypeptide comprises amino acids 26 to 37 of SEQ ID NO: 34, amino acids 52 to 67 of SEQ ID NO: 34, and amino acids 100 to 111 of SEQ ID NO: 34.

In certain embodiments, a polypeptide comprises at least one complementarity determining region (CDR) selected from CDR1b, CDR2b, and CDR3b, wherein CDR1b comprises a1 b1 c1 d1 e1 f1 g1 h1 i1 j1 k1 l1 m1 n1 o1 p1 q1, wherein amino acid a1 is selected from arginine or lysine; amino acid b1 is selected from threonine, alanine, or serine; amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid 11 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present; wherein CDR2b comprises the amino acid r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine; wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; and wherein the polypeptide, in association with an antibody heavy chain, binds TR-2.

In certain embodiments, a polypeptide comprises at least two complementarity determining regions (CDR) selected from CDR1b, CDR2b, and CDR3b, wherein the polypeptide, in association with an antibody heavy chain, binds TR-2. In certain embodiments, a polypeptide comprises CDR1b, CDR2b, and CDR3b, wherein the polypeptide, in association with an antibody heavy chain, binds TR-2.

In certain embodiments, a polypeptide comprises an antibody light chain variable region. In certain embodiments, a polypeptide comprises a human antibody light chain variable region. In certain embodiments, a polypeptide comprises a light chain constant region. In certain embodiments, a polypeptide comprises a human light chain constant region. In certain embodiments, a polypeptide comprises an amino acid sequence as set forth in SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, or SEQ ID NO: 68. In certain embodiments, a polypeptide comprises a non-human light chain constant region. In certain embodiments, a polypeptide comprises a light chain constant region of a species other than human.

In certain embodiments, a polypeptide which comprises at least one complementarity determining region (CDR) selected from amino acids 24 to 34 of SEQ ID NO: 36; amino acids 50 to 56 of SEQ ID NO: 36; amino acids 89-97 of SEQ ID NO: 36; amino acids 24 to 34 of SEQ ID NO: 38; amino acids 50 to 56 of SEQ ID NO: 38; amino acids 89 to 97 of SEQ ID NO: 38; amino acids 24 to 34 of SEQ ID NO: 40; amino acids 50 to 56 of SEQ ID NO: 40; amino acids 89 to 97 of SEQ ID NO: 40; amino acids 24 to 34 of SEQ ID NO: 42; amino acids 50 to 56 of SEQ ID NO: 42; amino acids 89 to 97 of SEQ ID NO: 42; amino acids 24 to 34 of SEQ ID NO: 44; amino acids 50 to 56 of SEQ ID NO: 44; amino acids 89-97 of SEQ ID NO: 44; amino acids 24 to 34 of SEQ ID NO: 46; amino acids 50 to 56 of SEQ ID NO: 46; amino acids 89 to 97 of SEQ ID NO: 46; amino acids 24 to 40 of SEQ ID NO: 48; amino acids 56 to 62 of SEQ ID NO: 48; amino acids 95 to 103 of SEQ ID NO: 48; amino acids 24 to 39 of SEQ ID NO: 50; amino acids 55 to 61 of SEQ ID NO: 50; amino acids 94 to 102 of SEQ ID NO: 50; amino acids 24 to 40 of SEQ ID NO: 52; amino acids 56 to 62 of SEQ ID NO: 52; amino acids 95 to 103 of SEQ ID NO: 52; 24 to 34 of SEQ ID NO: 54; amino acids 50 to 56 of SEQ ID NO: 54; amino acids 89 to 97 of SEQ ID NO: 54; amino acids 24 to 34 of SEQ ID NO: 56, amino acids 50 to 56 of SEQ ID NO: 56; amino acids 89 to 97 of SEQ ID NO: 56; amino acids 24 to 40 of SEQ ID NO: 58; amino acids 56 to 62 of SEQ ID NO: 58; amino acids 95 to 103 of SEQ ID NO: 58; amino acids 24 to 34 of SEQ ID NO: 60; amino acids 50 to 56 of SEQ ID NO: 60; amino acids 89-97 of SEQ ID NO: 60; amino acids 24 to 34 of SEQ ID NO: 62; amino acids 50 to 56 of SEQ ID NO: 62; amino acids 89 to 97 of SEQ ID NO: 62; amino acids 24 to 35 of SEQ ID NO: 64; amino acids 51 to 57 of SEQ ID NO: 64; amino acids 90 to 88 of SEQ ID NO: 64; amino acids 24 to 34 of SEQ ID NO: 66; amino acids 50 to 57 of SEQ ID NO: 66; amino acids 89 to 97 of SEQ ID NO: 66; amino acids 24 to 34 of SEQ ID NO: 68; amino acids 50 to 56 of SEQ ID NO: 68; and amino acids 89 to 97 of SEQ ID NO: 68, wherein the polypeptide, in association with an antibody heavy chain, binds TR-2. In certain embodiments, a polypeptide comprises at least two of the CDRs of SEQ ID NOS. 36, 38, 40, 42, 44, 46, 48, 50, 52, 54, 56, 58, 60, 62, 64, 66, or 68. In certain embodiments, a polypeptide comprises at least three of the CDRs of SEQ ID NOS. 36, 38, 40, 42, 44, 46, 48, 50, 52, 54, 56, 58, 60, 62, 64, 66, or 68.

In certain embodiments, a polypeptide comprises amino acids 24 to 34 of SEQ ID NO: 36, amino acids 50 to 56 of SEQ ID NO: 36, and amino acids 89-97 of SEQ ID NO: 36. In certain embodiments, a polypeptide comprises amino acids 24 to 34 of SEQ ID NO: 38, amino acids 50 to 56 of SEQ ID NO: 38, and amino acids 89 to 97 of SEQ ID NO: 38. In certain embodiments, a polypeptide comprises amino acids 24 to 34 of SEQ ID NO: 40, amino acids 50 to 56 of SEQ ID NO: 40, and amino acids 89 to 97 of SEQ ID NO: 40. In certain embodiments, a polypeptide comprises amino acids 24 to 34 of SEQ ID NO: 42, amino acids 50 to 56 of SEQ ID NO: 42, and amino acids 89 to 97 of SEQ ID NO: 42. In certain embodiments, a polypeptide comprises amino acids 24 to 34 of SEQ ID NO: 44, amino acids 50 to 56 of SEQ ID NO: 44, and amino acids 89-97 of SEQ ID NO: 44. In certain embodiments, a polypeptide comprises amino acids 24 to 34 of SEQ ID NO: 46, amino acids 50 to 56 of SEQ ID NO: 46, and amino acids 89 to 97 of SEQ ID NO: 46. In certain embodiments, a polypeptide comprises amino acids 24 to 40 of SEQ ID NO: 48, amino acids 56 to 62 of SEQ ID NO: 48, and amino acids 95 to 103 of SEQ ID NO: 48. In certain embodiments, a polypeptide comprises amino acids 24 to 39 of SEQ ID NO: 50, amino acids 55 to 61 of SEQ ID NO: 50, and amino acids 94 to 102 of SEQ ID NO: 50. In certain embodiments, a polypeptide comprises amino acids 24 to 40 of SEQ ID NO: 52, amino acids 56 to 62 of SEQ ID NO: 52, and amino acids 95 to 103 of SEQ ID NO: 52. In certain embodiments, a polypeptide comprises amino acids 24 to 34 of SEQ ID NO: 54, amino acids 50 to 56 of SEQ ID NO: 54, and amino acids 89 to 97 of SEQ ID NO: 54. In certain embodiments, a polypeptide comprises amino acids 24 to 34 of SEQ ID NO: 56, amino acids 50 to 56 of SEQ ID NO: 56, and amino acids 89 to 97 of SEQ ID NO: 56, In certain embodiments, a polypeptide comprises amino acids 24 to 40 of SEQ ID NO: 58, amino acids 56 to 62 of SEQ ID NO: 58, and amino acids 95 to 103 of SEQ ID NO: 58. In certain embodiments, a polypeptide comprises amino acids 24 to 34 of SEQ ID NO: 60, amino acids 50 to 56 of SEQ ID NO: 60, and amino acids 89-97 of SEQ ID NO: 60. In certain embodiments, a polypeptide comprises amino acids 24 to 34 of SEQ ID NO: 62, amino acids 50 to 56 of SEQ ID NO: 62, and amino acids 89 to 97 of SEQ ID NO: 62. In certain embodiments, a polypeptide comprises amino acids 24 to 35 of SEQ ID NO: 64, amino acids 51 to 57 of SEQ ID NO: 64, and amino acids 90 to 88 of SEQ ID NO: 64. In certain embodiments, a polypeptide comprises amino acids 24 to 34 of SEQ ID NO: 66, amino acids 50 to 57 of SEQ ID NO: 66, and amino acids 89 to 97 of SEQ ID NO: 66. In certain embodiments, a polypeptide comprises amino acids 24 to 34 of SEQ ID NO: 68, amino acids 50 to 56 of SEQ ID NO: 68, and amino acids 89 to 97 of SEQ ID NO: 68.

The term "naturally-occurring" as applied to an object means that an object can be found in nature. For example, a polypeptide or polynucleotide that is present in an organism (including viruses) that can be isolated from a source in nature and which has not been intentionally modified by man in the laboratory or otherwise is naturally-occurring.

The term "operably linked" as used herein refers to components that are in a relationship permitting them to function in their intended manner. For example, in the context of a polynucleotide sequence, a control sequence may be "operably linked" to a coding sequence when the control sequence and coding sequence are in association with each other in such a way that expression of the coding sequence is achieved under conditions compatible with the functioning of the control sequence.

The term "control sequence" refers to polynucleotide sequences which may effect the expression and processing of coding sequences with which they are in association. The nature of such control sequences may differ depending upon the host organism. Certain exemplary control sequences for prokaryotes include, but are not limited to, promoters, ribosomal binding sites, and transcription termination sequences. Certain exemplary control sequences for eukaryotes include, but are not limited to, promoters, enhancers, and transcription termination sequences. In certain embodiments, "control sequences" can include leader sequences and/or fusion partner sequences.

In certain embodiments, a first polynucleotide coding sequence is operably linked to a second polynucleotide coding sequence when the first and second polynucleotide coding sequences are transcribed into a single contiguous mRNA that can be translated into a single contiguous polypeptide.

In the context of polypeptides, two or more polypeptides are "operably linked" if each linked polypeptide is able to function in its intended manner. A polypeptide that is able to function in its intended manner when operably linked to another polypeptide may or may not be able to function in its intended manner when not operably linked to another polypeptide. For example, in certain embodiments, a first polypeptide may be unable to function in its intended manner when unlinked, but may be stabilized by being linked to a second polypeptide such that it becomes able to function in its intended manner. Alternatively, in certain embodiments, a first polypeptide may be able to function in its intended manner when unlinked, and may retain that ability when operably linked to a second polypeptide.

As used herein, two or more polypeptides are "fused" when the two or more polypeptides are linked by translating them as a single contiguous polypeptide sequence or by synthesizing them as a single contiguous polypeptide sequence. In certain embodiments, two or more fused polypeptides may have been translated in vivo from two or more operably linked polynucleotide coding sequences. In certain embodiments, two or more fused polypeptides may have been translated in vitro from two or more operably linked polynucleotide coding sequences.

As used herein, two or more polypeptides are "operably fused" if each linked polypeptide is able to function in its intended manner.

In certain embodiments, a first polypeptide that contains two or more distinct polypeptide units is considered to be linked to a second polypeptide so long as at least one of the distinct polypeptide units of the first polypeptide is linked to the second polypeptide. As a non-limiting example, in certain embodiments, an antibody is considered linked to a second polypeptide in all of the following instances: (a) the second polypeptide is linked to one of the heavy chain polypeptides of the antibody; (b) the second polypeptide is linked to one of the light chain polypeptides of the antibody; (c) a first molecule of the second polypeptide is linked to one of the heavy chain polypeptides of the antibody and a second molecule of the second polypeptide is linked to one of the light chain polypeptides of the antibody; and (d) first and second molecules of the second polypeptide are linked to the first and second heavy chain polypeptides of the antibody and third and fourth molecules of the second polypeptide are linked to first and second light chain polypeptides of the antibody.

In certain embodiments, the language "a first polypeptide linked to a second polypeptide" encompasses situations where: (a) only one molecule of a first polypeptide is linked to only one molecule of a second polypeptide; (b) only one molecule of a first polypeptide is linked to more than one molecule of a second polypeptide; (c) more than one molecule of a first polypeptide is linked to only one molecule of a second polypeptide; and (d) more than one molecule of a first polypeptide is linked to more than one molecule of a second polypeptide. In certain embodiments, when a linked molecule comprises more than one molecule of a first polypeptide and only one molecule of a second polypeptide, all or fewer than all of the molecules of the first polypeptide may be covalently or noncovalently linked to the second polypeptide. In certain embodiments, when a linked molecule comprises more than one molecule of a first polypeptide, one or more molecules of the first polypeptide may be covalently or noncovalently linked to other molecules of the first polypeptide.

As used herein, a "flexible linker" refers to any linker that is not predicted, according to its chemical structure, to be fixed in three-dimensional space. One skilled in the art can predict whether a particular linker is flexible in its intended context. In certain embodiments, a peptide linker comprising 3 or more amino acids is a flexible linker.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)). In certain embodiments, one or more unconventional amino acids may be incorporated into a polypeptide. The term "unconventional amino acid" refers to any amino acid that is not one of the twenty conventional amino acids. The term "non-naturally occurring amino acids" refers to amino acids that are not found in nature. Non-naturally occurring amino acids are a subset of unconventional amino acids. Unconventional amino acids include, but are not limited to, stereoisomers (e.g., D-amino acids) of the twenty conventional amino acids, unnatural amino acids such as $\alpha$-,$\alpha$-disubstituted amino acids, N-alkyl amino acids, lactic acid, homoserine, homocysteine, 4-hydroxyproline, $\gamma$-carboxyglutamate, $\epsilon$-N, N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline) known in the art. In the polypeptide notation used herein, the left-hand direction is the amino terminal direction and the right-hand direction is the carboxy-terminal direction, in accordance with standard usage and convention.

In certain embodiments, conservative amino acid substitutions include substitution with one or more unconventional amino acid residues. In certain embodiments, unconventional amino acid residues are incorporated by chemical peptide synthesis rather than by synthesis in biological systems.

The term "acidic residue" refers to an amino acid residue in D- or L-form that comprises at least one acidic group when incorporated into a polypeptide between two other amino acid residues that are the same or different. In certain embodiments, an acidic residue comprises a sidechain that comprises at least one acidic group. Exemplary acidic residues include, but are not limited to, aspartic acid (D) and glutamic acid (E). In certain embodiments, an acidic residue may be an unconventional amino acid.

The term "aromatic residue" refers to an amino acid residue in D- or L-form that comprises at least one aromatic group. In certain embodiments, an aromatic residue comprises a sidechain that comprises at least one aromatic group. Exemplary aromatic residues include, but are not limited to, phenylalanine (F), tyrosine (Y), and tryptophan (W). In certain embodiments, an aromatic residue may be an unconventional amino acid.

The term "basic residue" refers to an amino acid residue in F- or L-form that may comprise at least one basic group when incorporated into a polypeptide next to one or more amino acid residues that are the same or different. In certain embodiments, a basic residue comprises a sidechain that comprises at least one basic group. Exemplary basic residues include, but are not limited to, histidine (H), lysine (K), and arginine (R). In certain embodiments, a basic residue may be an unconventional amino acid.

The term "neutral hydrophilic residue" refers to an amino acid residue in D- or L-form that comprises at least one hydrophilic and/or polar group, but does not comprise an acidic or basic group when incorporated into a polypeptide next to one or more amino acid residues that are the same or different. Exemplary neutral hydrophilic residues include, but are not limited to, alanine (A), cysteine (C), serine (S), threonine (T), asparagine (N), and glutamine (Q). In certain embodiments, a neutral hydrophilic residue may be an unconventional amino acid.

The terms "lipophilic residue" and "Laa" refer to an amino acid residue in D- or L-form having at least one uncharged, aliphatic and/or aromatic group. In certain embodiments, a lipophilic residue comprises a side chain that comprises at least one uncharged, aliphatic, and/or aromatic group. Exemplary lipophilic sidechains include, but are not limited to, alanine (A), phenylalanine (F), isoleucine (I), leucine (L), norleucine (Nle), methionine (M), valine (V), tryptophan (W), and tyrosine (Y). In certain embodiments, a lipophilic residue may be an unconventional amino acid.

The term "amphiphilic residue" refers to an amino acid residue in D- or L-form that is capable of being either a hydrophilic or lipophilic residue. An exemplary amphiphilic residue includes, but is not limited to, alanine (A). In certain embodiments, an amphiphilic residue may be an unconventional amino acid.

The term "nonfunctional residue" refers to an amino acid residue in D- or L-form that lacks acidic, basic, and aromatic groups when incorporated into a polypeptide next to one or more amino acid residues that are the same or different. Exemplary nonfunctional amino acid residues include, but are not limited to, methionine (M), glycine (G), alanine (A), valine (V), isoleucine (I), leucine (L), and norleucine (Nle). In certain embodiments, a nonfunctional residue may be an unconventional amino acid.

In certain embodiments, glycine (G) and proline (P) are considered amino acid residues that can influence polypeptide chain orientation.

In certain embodiments, a conservative substitution may involve replacing a member of one residue type with a member of the same residue type. As a non-limiting example, in certain embodiments, a conservative substitution may involve replacing an acidic residue, such as D, with a different acidic residue, such as E. In certain embodiments, a non-conservative substitution may involve replacing a member of one residue type with a member of a different residue type. As a non-limiting example, in certain embodiments, a non-conservative substitution may involve replacing an acidic residue, such as D, with a basic residue, such as K. In certain embodiments, a cysteine residue is substituted with another amino acid residue to prevent disulfide bond formation with that position in the polypeptide.

In making conservative or non-conservative substitutions, according to certain embodiments, the hydropathic index of amino acids may be considered. Each amino acid has been assigned a hydropathic index on the basis of its hydrophobicity and charge characteristics. The hydropathic indices of the 20 naturally-occurring amino acids are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131 (1982). It is known in certain instances that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the polypeptide.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. In certain instances, one may also identify epitopes from primary amino acid sequences on the basis of hydrophilicity. These regions are also referred to as "epitopic core regions."

Exemplary amino acid substitutions are set forth in Table 1.

TABLE 1

Amino Acid Substitutions

| Original Residues | Exemplary Substitutions | More specific exemplary Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Similarly, as used herein, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to herein as the transcription direction; sequence regions on the DNA strand having the same sequence as the RNA and which are 5' to the 5' end of the RNA transcript are referred to herein as "upstream sequences"; sequence regions on the DNA strand having the same sequence as the RNA and which are 3' to the 3' end of the RNA transcript are referred to herein as "downstream sequences."

In certain embodiments, conservative amino acid substitutions encompass non-naturally occurring amino acid residues, which are typically incorporated by chemical peptide synthesis rather than by synthesis in biological systems. Those non-naturally occurring amino acid residues include, but are not limited to, peptidomimetics and other reversed or inverted forms of amino acid moieties.

A skilled artisan will be able to determine suitable substitution variants of a reference polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity, including, but not limited to, the CDRs of an antibody, or that may be important for structure may be subject to conservative amino acid substitutions without destroying the biological activity or without adversely affecting the polypeptide structure.

Additionally, in certain embodiments, one skilled in the art can review structure-function studies identifying residues in similar polypeptides that are important for activity and/or structure. In view of such a comparison, in certain embodiments, one can predict the importance of amino acid residues in a polypeptide that correspond to amino acid residues which are important for activity or structure in similar polypeptides. In certain embodiments, one skilled in the art may opt for chemically similar amino acid substitutions for such predicted important amino acid residues.

In certain embodiments, one skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, in certain embodiments, one skilled in the art may generate test variants containing a single amino acid substitution at each desired amino acid residue. In certain embodiments, the variants can then be screened using activity assays known to those skilled in the art. For example, in certain embodiments, the variants can be screened for their ability to bind to TR-2. In certain embodiments, such variants could be used to gather information about suitable variants. For example, in certain embodiments, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided, either alone or in combination with other mutations.

A number of scientific publications have been devoted to the prediction of secondary structure. See Moult J., *Curr. Op. in Biotech.*, 7(4):422-427 (1996), Chou et al., *Biochemistry*, 13(2):222-245 (1974); Chou et al., *Biochemistry*, 113(2):211-222 (1974); Chou et al., *Adv. Enzymol. Relat. Areas Mol. Biol.*, 47:45-148 (1978); Chou et al., *Ann. Rev. Biochem.*, 47:251-276 and Chou et al., *Biophys. J.*, 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., *Nucl. Acid. Res.*, 27(1):244-247 (1999). It has been suggested that there are a limited number of folds in a given polypeptide or protein and that once a critical number of structures have been resolved, structural prediction will become dramatically more accurate. See, e.g., Brenner et al., *Curr. Op. Struct. Biol.*, 7(3):369-376 (1997).

Additional exemplary methods of predicting secondary structure include, but are not limited to, "threading" (Jones, D., *Curr. Opin. Struct. Biol.*, 7(3):377-87 (1997); Sippl et al., *Structure*, 4(1):15-19 (1996)), "profile analysis" (Bowie et al., *Science*, 253:164-170 (1991); Gribskov et al., *Meth. Enzym.*, 183:146-159 (1990); Gribskov et al., *Proc. Nat.*

Acad. Sci., 84(13):4355-4358 (1987)), and "evolutionary linkage" (See Holm, supra (1999), and Brenner, supra (1997).).

In certain embodiments, the identity and similarity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., *SIAMJ. Applied Math.*, 48:1073 (1988). In certain embodiments, polypeptides have amino acid sequences that are about 90 percent, or about 95 percent, or about 96 percent, or about 97 percent, or about 98 percent, or about 99 percent identical to amino acid sequences shown in FIGS. 3-19.

In certain embodiments, methods to determine identity are designed to give the largest match between the sequences tested. In certain embodiments, certain methods to determine identity are described in publicly available computer programs. Certain computer program methods to determine identity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (*BLAST Manual*, Altschul et al. NCB/NLM/NIH Bethesda, Md. 20894; Altschul et al., supra (1990)). In certain embodiments, the Smith Waterman algorithm, which is known in the art, may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix is also used by the algorithm. See, e.g., Dayhoff et al., *Atlas of Protein Sequence and Structure*, 5(3)(1978) for the PAM 250 comparison matrix; Henikoff et al., *Proc. Natl. Acad. Sci. USA*, 89:10915-10919 (1992) for the BLOSUM 62 comparison matrix.

In certain embodiments, the parameters for a polypeptide sequence comparison include the following:
Algorithm: Needleman et al., *J. Mol. Biol.*, 48:443-453 (1970);
Comparison matrix: BLOSUM 62 from Henikoff et al., supra (1992);
Gap Penalty: 12
Gap Length Penalty: 4
Threshold of Similarity: 0

In certain embodiments, the GAP program may be useful with the above parameters. In certain embodiments, the aforementioned parameters are the default parameters for polypeptide comparisons (along with no penalty for end gaps) using the GAP algorithm.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physicochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts).

In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described, e.g., in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino-terminal and/or carboxy-terminal deletion. In certain embodiments, fragments are at least 5 to 500 amino acids long. It will be appreciated that in certain embodiments, fragments are at least 5, 6, 8, 10, 14, 20, 50, 70, 100, 150, 200, 250, 300, 350, 400, 450, or 500 amino acids long.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.* 15:29 (1986); Veber and Freidinger TINS p. 392 (1985); and Evans et al. *J. Med. Chem.* 30:1229 (1987). Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as a human antibody, but have one or more peptide linkages optionally replaced by a linkage selected from: —$CH_2NH$—, —$CH_2S$—, —$CH_2$—$CH_2$—, —CH=CH-(cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992)); for example, and not limitation, by adding internal cysteine residues capable of forming intramolecular disulfide bridges which cyclize the peptide.

The term "specific binding agent" refers to a natural or non-natural molecule that specifically binds to a target. Examples of specific binding agents include, but are not limited to, proteins, peptides, nucleic acids, carbohydrates, lipids, and small molecule compounds. In certain embodiments, a specific binding agent is an antibody. In certain embodiments, a specific binding agent is an antigen binding region.

The term "specifically binds" refers to the ability of a specific binding agent to bind to a target with greater affinity than it binds to a non-target. In certain embodiments, specific binding refers to binding to a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore assay. In certain embodiments, affinity is determined by a kinetic method. In certain embodiments, affinity is determined by an equilibrium/solution method.

The term "specific binding agent to TR-2" refers to a specific binding agent that specifically binds any portion of TR-2. In certain embodiments, a specific binding agent to TR-2 is an antibody to TR-2. In certain embodiments, a specific binding agent is an antigen binding region.

"Antibody" or "antibody peptide(s)" both refer to an intact antibody, or a fragment thereof. In certain embodiments, the antibody fragment may be a binding fragment that competes with the intact antibody for specific binding. The term "antibody" also encompasses polyclonal antibodies and monoclonal antibodies. In certain embodiments, binding fragments are produced by recombinant DNA techniques. In certain embodiments, binding fragments are produced by enzymatic or chemical cleavage of intact antibodies. In certain embodiments, binding fragments are produced by recombinant DNA techniques. Binding fragments include, but are not limited to, Fab, Fab', F(ab')2, Fv, and single-chain antibodies. Non-antigen binding fragments include, but are not limited to, Fc fragments. In certain embodiments, an antibody specifically binds to an epitope that is specifically bound by at least one antibody selected from Ab A, Ab B, Ab C, Ab D, Ab E, Ab F, Ab G, Ab H, Ab I, Ab J, Ab K, Ab L, Ab M, Ab N, Ab O, Ab P, and Ab Q. The term "antibody" also encompasses anti-idiotypic antibodies that specifically bind to the variable region of another antibody. In certain embodiments, an anti-idiotypic antibody specifically binds to the variable region of an anti-TR-2 antibody. In certain embodiments, anti-idiotypic antibodies may be used to detect the presence of a particular anti-TR-2 antibody in a sample or to block the activity of an anti-TR-2 antibody.

The term "anti-TR-2 antibody" as used herein means an antibody that specifically binds to TR-2. In certain embodiments, an anti-TR-2 antibody binds to a TR-2 epitope to which at least one antibody selected from Ab A to Q binds. In various embodiments, TR-2 may be the TR-2 of any species, including, but not limited to, human, cynomolgus monkeys, mice, and rabbits. Certain assays for determining the specificity of an antibody are well known to the skilled artisan and include, but are not limited to, ELISA, ELISPOT, western blots, BIAcore assays, solution affinity binding assays, T cell costimulation assays, and T cell migration assays.

The term "isolated antibody" as used herein means an antibody which (1) is free of at least some proteins with which it would normally be found, (2) is essentially free of other proteins from the same source, e.g., from the same species, (3) is expressed by a cell from a different species, or (4) does not occur in nature.

The term "polyclonal antibody" refers to a heterogeneous mixture of antibodies that bind to different epitopes of the same antigen.

The term "monoclonal antibodies" refers to a collection of antibodies encoded by the same nucleic acid molecule. In certain embodiments, monoclonal antibodies are produced by a single hybridoma or other cell line, or by a transgenic mammal. Monoclonal antibodies typically recognize the same epitope. The term "monoclonal" is not limited to any particular method for making an antibody.

The term "CDR grafted antibody" refers to an antibody in which the CDR from one antibody is inserted into the framework of another antibody. In certain embodiments, the antibody from which the CDR is derived and the antibody from which the framework is derived are of different species. In certain embodiments, the antibody from which the CDR is derived and the antibody from which the framework is derived are of different isotypes.

The term "multi-specific antibody" refers to an antibody wherein two or more variable regions bind to different epitopes. The epitopes may be on the same or different targets. In certain embodiments, a multi-specific antibody is a "bi-specific antibody," which recognizes two different epitopes on the same or different antigens.

The term "catalytic antibody" refers to an antibody in which one or more catalytic moieties is attached. In certain embodiments, a catalytic antibody is a cytotoxic antibody, which comprises a cytotoxic moiety.

The term "humanized antibody" refers to an antibody in which all or part of an antibody framework region is derived from a human, but all or part of one or more CDR regions is derived from another species, for example a mouse.

The terms "human antibody" and "fully human antibody" are used interchangeably and refer to an antibody in which both the CDR and the framework comprise substantially human sequences. In certain embodiments, fully human antibodies are produced in non-human mammals, including, but not limited to, mice, rats, and lagomorphs. In certain embodiments, fully human antibodies are produced in hybridoma cells. In certain embodiments, fully human antibodies are produced recombinantly.

In certain embodiments, an anti-TR-2 antibody comprises:
(i) a first polypeptide comprising at least one complementarity determining region (CDR) selected from CDR1a, CDR2a, and CDR3a
wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present;
wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present;

wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; and wherein the first polypeptide, in association with an antibody light chain, binds TR-2; and (ii) a second polypeptide comprising at least one complementarity determining region (CDR) selected from CDR1b, CDR2b, and CDR3b wherein CDR1b comprises the amino acid sequence a1 b1 c1 d1 e1 f1 g1 h1 i1 j1 k1 l1 ml n1 o1 p1 q1, wherein amino acid a1 is selected from arginine or lysine; amino acid b1 is selected from threonine, alanine, or serine; amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid l1 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present;

wherein CDR2b comprises the amino acid sequence r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine;

wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; and wherein the second polypeptide, in association with an antibody heavy chain, binds TR-2.

In certain embodiments, an anti-TR-2 antibody comprises: a first polypeptide comprising complementarity determining regions (CDRs) as set forth in SEQ ID NO: 2 and a second polypeptide comprising CDRs as set forth in SEQ ID NO: 36. In certain embodiments, an anti-TR-2 antibody comprises: a first polypeptide comprising complementarity determining regions (CDRs) as set forth in SEQ ID NO: 4 and a second polypeptide comprising CDRs as set forth in SEQ ID NO: 38. In certain embodiments, an anti-TR-2 antibody comprises: a first polypeptide comprising complementarity determining regions (CDRs) as set forth in SEQ ID NO: 6 and a second polypeptide comprising CDRs as set forth in SEQ ID NO: 40. In certain embodiments, an anti-TR-2 antibody comprises: a first polypeptide comprising complementarity determining regions (CDRs) as set forth in SEQ ID NO: 8 and a second polypeptide comprising CDRs as set forth in SEQ ID NO: 42.

In certain embodiments, an anti-TR-2 antibody comprises: a first polypeptide comprising complementarity determining regions (CDRs) as set forth in SEQ ID NO: 10 and a second polypeptide comprising CDRs as set forth in SEQ ID NO: 44. In certain embodiments, an anti-TR-2 antibody comprises: a first polypeptide comprising complementarity determining regions (CDRs) as set forth in SEQ ID NO: 12 and a second polypeptide comprising CDRs as set forth in SEQ ID NO: 46. In certain embodiments, an anti-TR-2 antibody comprises: a first polypeptide comprising complementarity determining regions (CDRs) as set forth in SEQ ID NO: 14 and a second polypeptide comprising CDRs as set forth in SEQ ID NO: 48. In certain embodiments, an anti-TR-2 antibody comprises: a first polypeptide comprising complementarity determining regions (CDRs) as set forth in SEQ ID NO: 16 and a second polypeptide comprising CDRs as set forth in SEQ ID NO: 50. In certain embodiments, an anti-TR-2 antibody comprises: a first polypeptide comprising complementarity determining regions (CDRs) as set forth in SEQ ID NO: 18 and a second polypeptide comprising CDRs as set forth in SEQ ID NO: 52. In certain embodiments, an anti-TR-2 antibody comprises: a first polypeptide comprising complementarity determining regions (CDRs) as set forth in SEQ ID NO: 20 and a second polypeptide comprising CDRs as set forth in SEQ ID NO: 54. In certain embodiments, an anti-TR-2 antibody comprises: a first polypeptide comprising complementarity determining regions (CDRs) as set forth in SEQ ID NO: 22 and a second polypeptide comprising CDRs as set forth in SEQ ID NO: 56. In certain embodiments, an anti-TR-2 antibody comprises: a first polypeptide comprising complementarity determining regions (CDRs) as set forth in SEQ ID NO: 24 and a second polypeptide comprising CDRs as set forth in SEQ ID NO: 58. In certain embodiments, an anti-TR-2 antibody comprises: a first polypeptide comprising complementarity determining regions (CDRs) as set forth in SEQ ID NO: 26 and a second polypeptide comprising CDRs as set forth in SEQ ID NO: 60. In certain embodiments, an anti-TR-2 antibody comprises: a first polypeptide comprising complementarity determining regions (CDRs) as set forth in SEQ ID NO: 28 and a second polypeptide comprising CDRs as set forth in SEQ ID NO: 62. In certain embodiments, an anti-TR-2 antibody comprises: a first polypeptide comprising complementarity determining regions (CDRs) as set forth in SEQ ID NO: 30 and a second polypeptide comprising CDRs as set forth in SEQ ID NO: 64. In certain embodiments, an anti-TR-2 antibody comprises: a first polypeptide comprising complementarity determining regions (CDRs) as set forth in SEQ ID NO: 32 and a second polypeptide comprising CDRs as set forth in SEQ ID NO: 66. In certain embodiments, an anti-TR-2 antibody comprises: a first polypeptide comprising complementarity determining regions (CDRs) as set forth in SEQ ID NO: 34 and a second polypeptide comprising CDRs as set forth in SEQ ID NO: 68. In certain embodiments, an anti-TR-2 antibody comprises a first polypeptide as set forth in paragraph [079] above and a second polypeptide as set forth in paragraph [084] above. In certain embodiments, an anti-TR-2 antibody comprises a first polypeptide as set forth in paragraph [080] above and a second polypeptide as set forth in paragraph [085] above. In certain embodiments, an anti-TR-2 antibody is a human antibody. In certain embodiments, an anti-TR-2 antibody comprises a detectable label. In certain embodiments, an anti-TR-2 antibody is a chimeric antibody.

"Chimeric antibody" refers to an antibody that has an antibody variable region of a first species fused to another molecule, for example, an antibody constant region of another second species. See, e.g., U.S. Pat. No. 4,816,567 and Morrison et al., *Proc Natl Acad Sci (USA)*, 81:6851-6855 (1985). In certain embodiments, the first species may be different from the second species. In certain embodiments, the first species may be the same as the second species. In certain embodiments, chimeric antibodies may be made through mutagenesis or CDR grafting to match a portion of the known sequence of anti-TR-2 antibody variable regions. CDR grafting typically involves grafting the CDRs from an antibody with desired specificity onto the framework regions (FRs) of another antibody.

A bivalent antibody other than a "multispecific" or "multifunctional" antibody, in certain embodiments, typically is understood to have each of its binding sites be identical.

An antibody substantially inhibits adhesion of a ligand to a receptor when an excess of antibody reduces the quantity of receptor bound to the ligand by at least about 20%, 40%, 60%, 80%, 85%, or more (as measured in an in vitro competitive binding assay).

The term "epitope" refers to a portion of a molecule capable of being bound by a specific binding agent. Exemplary epitopes may comprise any polypeptide determinant capable of specific binding to an immunoglobulin and/or T-cell receptor. Exemplary epitope determinants include, but are not limited to, chemically active surface groupings of molecules, for example, but not limited to, amino acids, sugar side chains, phosphoryl groups, and sulfonyl groups. In certain embodiments, epitope determinants may have specific three dimensional structural characteristics, and/or specific charge characteristics. In certain embodiments, an epitope is a region of an antigen that is bound by an antibody. Epitopes may be contiguous or non-contiguous. In certain embodiments, epitopes may be mimetic in that they comprise a three dimensional structure that is similar to an epitope used to generate the antibody, yet comprise none or only some of the amino acid residues found in that epitope used to generate the antibody.

The term "inhibiting and/or neutralizing epitope" refers to an epitope, which when bound by a specific binding agent results in a decrease in a biological activity in vivo, in vitro, and/or in situ. In certain embodiments, a neutralizing epitope is located on or is associated with a biologically active region of a target.

The term "activating epitope" refers to an epitope, which when bound by a specific binding agent results in activation or maintenance of a biological activity in vivo, in vitro, and/or in situ. In certain embodiments, an activating epitope is located on or is associated with a biologically active region of a target.

In certain embodiments, an epitope is specifically bound by at least one antibody selected from Ab A, Ab B, Ab C, Ab D, Ab E, Ab F, Ab G, Ab H, Ab I, Ab J, Ab K, Ab L, Ab M, Ab N, Ab O, Ab P, and Ab Q. In certain such embodiments, the epitope is substantially pure. In certain such embodiments, the epitope is at a concentration of at least 1 nM. In certain such embodiments, the epitope is at a concentration of between 1 nM and 5 nM. In certain such embodiments, the epitope is at a concentration of between 5 nM and 10 nM. In certain such embodiments, the epitope is at a concentration of between 10 nM and 15 nM.

In certain embodiments, an antibody specifically binds to an epitope that is specifically bound by at least one antibody selected from Ab A, Ab B, Ab C, Ab D, Ab E, Ab F, Ab G, Ab H, Ab I, Ab J, Ab K, Ab L, Ab M, Ab N, Ab O, Ab P, and Ab Q, and is substantially pure. In certain such embodiments, the antibody is at a concentration of at least 1 nM. In certain such embodiments, the antibody is at a concentration of between 1 nM and 5 nM. In certain such embodiments, the antibody is at a concentration of between 5 nM and 10 nM. In certain such embodiments, the antibody is at a concentration of between 10 nM and 15 nM.

In certain embodiments, an antibody specifically binds to amino acids 1 to 85 of mature human TR-2, and is substantially pure. In certain such embodiments, the antibody is at a concentration of at least 1 nM. In certain such embodiments, the antibody is at a concentration of between 1 nM and 5 nM. In certain such embodiments, the antibody is at a concentration of between 5 nM and 10 nM. In certain such embodiments, the antibody is at a concentration of between 10 nM and 15 nM.

In certain embodiments, an antibody competes for binding to an epitope with at least one antibody selected from Ab A, Ab B, Ab C, Ab D, Ab E, Ab F, Ab G, Ab H, Ab I, Ab J, Ab K, Ab L, Ab M, Ab N, Ab O, Ab P, and Ab Q. In certain such embodiments, the antibody is substantially pure. In certain such embodiments, the antibody is at a concentration of at least 1 nM. In certain such embodiments, the antibody is at a concentration of between 1 nM and 5 nM. In certain such embodiments, the antibody is at a concentration of between 5 nM and 10 nM. In certain such embodiments, the antibody is at a concentration of between 10 nM and 15 nM.

In certain embodiments, an antibody competes for binding to amino acids 1 to 85 of mature human TR-2 with at least one antibody selected from Ab A, Ab B, Ab C, Ab D, Ab E, Ab F, Ab G, Ab H, Ab I, Ab J, Ab K, Ab L, Ab M, Ab N, Ab O, Ab P, and Ab Q. In certain such embodiments, the antibody is substantially pure. In certain such embodiments, the antibody is at a concentration of at least 1 nM. In certain such embodiments, the antibody is at a concentration of between 1 nM and 5 nM. In certain such embodiments, the antibody is at a concentration of between 5 nM and 10 nM. In certain such embodiments, the antibody is at a concentration of between 10 nM and 15 nM.

The term "agent" is used herein to denote a chemical compound, a mixture of chemical compounds, a biological macromolecule, or an extract made from biological materials.

As used herein, the term "label" refers to any molecule that can be detected. In a certain embodiment, an antibody may be labeled by incorporation of a radiolabeled amino acid. In a certain embodiment, biotin moieties that can be detected by marked avidin (e.g., streptavidin containing a fluorescent marker or enzymatic activity that can be detected by optical or colorimetric methods) may be attached to the antibody. In certain embodiments, a label may be incorporated into or attached to another reagent which in turn binds to the antibody of interest. In certain embodiments, a label may be incorporated into or attached to an antibody that in turn specifically binds the antibody of interest. In certain embodiments, the label or marker can also be therapeutic. Various methods of labeling polypeptides and glycoproteins are known in the art and may be used. Certain general classes of labels include, but are not limited to, enzymatic, fluorescent, chemiluminescent, and radioactive labels. Certain examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I), fluorescent labels (e.g., fluorescein isothiocyanate (FITC), rhodamine, lanthanide phosphors, phycoerythrin (PE)), enzymatic labels (e.g., horseradish peroxidase, β-galactosidase, luciferase, alkaline phosphatase, glucose oxidase, glucose-6-phosphate dehydrogenase, alcohol dehydrogenase, malate dehydrogenase, penicillinase, luciferase), chemiluminescent labels, biotinyl groups, and predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths to reduce potential steric hindrance.

The term "sample", as used herein, includes, but is not limited to, any quantity of a substance from a living thing or formerly living thing. Such living things include, but are not limited to, humans, mice, monkeys, rats, rabbits, and other animals. Such substances include, but are not limited to, blood, serum, urine, cells, organs, tissues, bone, bone marrow, lymph nodes, and skin.

The term "pharmaceutical agent or drug" as used herein refers to a chemical compound or composition capable of inducing a desired therapeutic effect when properly administered to a patient.

The term "modulator," as used herein, is a compound that changes or alters the activity or function of a molecule. For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Certain exemplary activities and functions of a molecule include, but are not limited to, binding affinity, enzymatic activity, and signal transduction. Certain exemplary inhibitors include, but are not limited to, proteins, peptides, antibodies, peptibodies, carbohydrates, and small organic molecules. Exemplary peptibodies are described, e.g., in WO 01/83525.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (contaminant species cannot be detected in the composition by conventional detection methods) wherein the composition consists essentially of a single macromolecular species.

The term "patient" includes human and animal subjects.

According to certain embodiments, a cell line expressing anti-TR-2 antibodies is provided.

In certain embodiments, chimeric antibodies that comprise at least a portion of a human sequence and another species' sequence are provided. In certain embodiments, such a chimeric antibody may result in a reduced immune response in a host than an antibody without that host's antibody sequences. For example, in certain instances, an animal of interest may be used as a model for a particular human disease. To study the effect of an antibody on that disease in the animal host, one could use an antibody from a different species. But, in certain instances, such antibodies from another species, may elicit an immune response to the antibodies themselves in the host animal, thus impeding evaluation of these antibodies. In certain embodiments, replacing part of the amino acid sequence of an anti-TR-2 antibody with antibody amino acid sequence from the host animal may decrease the magnitude of the host animal's anti-antibody response.

In certain embodiments, a chimeric antibody comprises a heavy chain and a light chain, wherein the variable regions of the light chain and the heavy chain are from a first species and the constant regions of the light chain and the heavy chain are from a second species. In certain embodiments, the antibody heavy chain constant region is an antibody heavy chain constant region of a species other than human. In certain embodiments, the antibody light chain constant region is an antibody light chain constant region of a species other than human. In certain embodiments, the antibody heavy chain constant region is a human antibody heavy chain constant region, and the antibody heavy chain variable region is an antibody heavy chain variable region of a species other than human. In certain embodiments, the antibody light chain constant region is a human antibody light chain constant region, and the antibody light chain variable region is an antibody light chain variable region of a species other than human. Exemplary antibody constant regions include, but are not limited to, a human antibody constant region, a cynomolgus monkey antibody constant region, a mouse antibody constant region, and a rabbit antibody constant region. Exemplary antibody variable regions include, but are not limited to, a human antibody variable region, a mouse antibody variable region, a pig antibody variable region, a guinea pig antibody variable region, a cynomolgus monkey antibody variable region, and a rabbit antibody variable region. In certain embodiments, the framework regions of the variable region in the heavy chain and light chain may be replaced with framework regions derived from other antibody sequences.

Certain exemplary chimeric antibodies may be produced by methods well known to those of ordinary skill in the art. In certain embodiments, the polynucleotide of the first species encoding the heavy chain variable region and the polynucleotide of the second species encoding the heavy chain constant region can be fused. In certain embodiments, the polynucleotide of the first species encoding the light chain variable region and the nucleotide sequence of the second species encoding the light chain constant region can be fused. In certain embodiments, these fused nucleotide sequences can be introduced into a cell either in a single expression vector (e.g., a plasmid) or in multiple expression vectors. In certain embodiments, a cell comprising at least one expression vector may be used to make polypeptide. In certain embodiments, these fused nucleotide sequences can be introduced into a cell either in separate expression vectors or in a single expression vector. In certain embodiments, the host cell expresses both the heavy chain and the light chain, which combine to produce an antibody. In certain embodiments, a cell comprising at least one expression vector may be used to make an antibody. Exemplary methods for producing and expressing antibodies are discussed below.

In certain embodiments, conservative modifications to the heavy and light chains of an anti-TR-2 antibody (and corresponding modifications to the encoding nucleotides) will produce antibodies having functional and chemical characteristics similar to those of the original antibody. In contrast, in certain embodiments, substantial modifications in the functional and/or chemical characteristics of an anti-TR-2 antibody may be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

Certain desired amino acid substitutions (whether conservative or non-conservative) can be determined by those skilled in the art at the time such substitutions are desired. In certain embodiments, amino acid substitutions can be used to identify important residues of the anti-TR-2 antibodies, such as those which may increase or decrease the affinity of the antibodies to TR-2 or the effector function of the antibodies.

In certain embodiments, the effects of an anti-TR-2 antibody may be evaluated by measuring a reduction in the amount of symptoms of the disease. In certain embodiments, the disease of interest may be caused by a pathogen. In certain embodiments, a disease may be established in an animal host by other methods including introduction of a substance (such as a carcinogen) and genetic manipulation. In certain embodiments, effects may be evaluated by detecting one or more adverse events in the animal host. The term "adverse event" includes, but is not limited to, an adverse reaction in an animal host that receives an antibody that is not present in an animal host that does not receive the antibody. In certain embodiments, adverse events include, but are not limited to, a fever, an immune response to an antibody, inflammation, and/or death of the animal host.

Various antibodies specific to an antigen may be produced in a number of ways. In certain embodiments, an antigen containing an epitope of interest may be introduced into an animal host (e.g., a mouse), thus producing antibodies specific to that epitope. In certain instances, antibodies specific to an epitope of interest may be obtained from biological samples taken from hosts that were naturally exposed to the epitope. In certain instances, introduction of human immunoglobulin (Ig) loci into mice in which the endogenous Ig genes have been inactivated offers the opportunity to obtain human monoclonal antibodies (MAbs).

Naturally Occurring Antibody Structure

Naturally occurring antibody structural units typically comprise a tetramer. Each such tetramer typically is composed of two identical pairs of polypeptide chains, each pair having one full-length "light" chain (in certain embodiments, about 25 kDa) and one full-length "heavy" chain (in certain embodiments, about 50-70 kDa). The term "heavy chain" includes any polypeptide having sufficient variable region sequence to confer specificity for a particular antigen. A full-length heavy chain includes a variable region domain, $V_H$, and three constant region domains, $C_H1$, $C_H2$, and $C_H3$. The $V_H$ domain is at the amino-terminus of the polypeptide, and the $C_H3$ domain is at the carboxy-terminus. The term "heavy chain", as used herein, encompasses a full-length antibody heavy chain and fragments thereof.

The term "light chain" includes any polypeptide having sufficient variable region sequence to confer specificity for a particular antigen. A full-length light chain includes a variable region domain, $V_L$, and a constant region domain, $C_L$. Like the heavy chain, the variable region domain of the light chain is at the amino-terminus of the polypeptide. The term "light chain", as used herein, encompasses a full-length light chain and fragments thereof.

The amino-terminal portion of each chain typically includes a variable region ($V_H$ in the heavy chain and $V_L$ in the light chain) of about 100 to 110 or more amino acids that typically is responsible for antigen recognition. The carboxy-terminal portion of each chain typically defines a constant region ($C_H$ domains in the heavy chain and $C_L$ in the light chain) that may be responsible for effector function. Antibody effector functions include activation of complement and stimulation of opsonophagocytosis. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, typically, the variable and constant regions are joined by a "J" region of about 12 or more amino acids, with the heavy chain also including a "D" region of about 10 more amino acids. See, e.g., Fundamental Immunology Ch. 7 (Paul, W., ed., 2nd ed. Raven Press, N.Y. (1989)). The variable regions of each light/heavy chain pair typically form the antigen binding site.

The variable regions typically exhibit the same general structure of relatively conserved framework regions (FR) joined by three hypervariable regions, also called complementarity determining regions or CDRs. The CDRs from the heavy and light chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3, and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

As discussed above, there are several types of antibody fragments. A Fab fragment is comprised of one light chain and the $C_H1$ and variable regions of one heavy chain. The heavy chain of a Fab molecule cannot form a disulfide bond with another heavy chain molecule. A Fab' fragment contains one light chain and one heavy chain that contains more of the constant region, between the $C_H1$ and $C_H2$ domains, such that an interchain disulfide bond can be formed between two heavy chains to form a F(ab')2 molecule. A Fab fragment is similar to a F(ab')2 molecule, except the constant region in the heavy chains of the molecule extends to the end of the $C_H2$ domain. The Fv region comprises the variable regions from both the heavy and light chains, but lacks the constant regions. Single-chain antibodies are Fv molecules in which the heavy and light chain variable regions have been connected by a flexible linker to form a single polypeptide chain which forms an antigen-binding region. Exemplary single chain antibodies are discussed in detail, e.g., in WO 88/01649 and U.S. Pat. Nos. 4,946,778 and 5,260,203. A Fc fragment contains the $C_H2$ and $C_H3$ domains of the heavy chain and contains more of the constant region, between the $C_H1$ and $C_H2$ domains, such that an interchain disulfide bond can be formed between two heavy chains.

In certain embodiments, functional domains, $C_H1$, $C_H2$, $C_H3$, and intervening sequences can be shuffled to create a different antibody constant region. For example, in certain embodiments, such hybrid constant regions can be optimized for half-life in serum, for assembly and folding of the antibody tetramer, and/or for improved effector function. In certain embodiments, modified antibody constant regions may be produced by introducing single point mutations into the amino acid sequence of the constant region and testing the resulting antibody for improved qualities, e.g., one or more of those listed above.

In certain embodiments, an antibody of one isotype is converted to a different isotype by isotype switching without losing its specificity for a particular target molecule. Methods of isotype switching include, but are not limited to, direct recombinant techniques (see e.g., U.S. Pat. No. 4,816,397) and cell-cell fusion techniques (see e.g., U.S. Pat. No. 5,916, 771), among others. In certain embodiments, an antibody can be converted from one subclass to another subclass using techniques described above or otherwise known in the art without losing its specificity for a particular target molecule, including, but not limited to, conversion from an IgG2 subclass to an IgG1, IgG3, or IgG4 subclass.

Bispecific or Bifunctional Antibodies

A bispecific or bifunctional antibody typically is an artificial hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann Clin. Exp. Immunol. 79: 315-321 (1990), Kostelny et al. J. Immunol. 148:1547-1553 (1992).

Certain Preparation of Antibodies

In certain embodiments, antibodies can be expressed in cell lines other than hybridoma cell lines. In certain embodiments, sequences encoding particular antibodies, including chimeric antibodies, can be used for transformation of a suitable mammalian host cell. According to certain embodiments, transformation can be by any known method for introducing polynucleotides into a host cell, including, for example packaging the polynucleotide in a virus (or into a viral vector) and transducing a host cell with the virus or by transfecting a vector using procedures known in the art, as exemplified by U.S. Pat. Nos. 4,399,216; 4,912,040; 4,740,461; and 4,959, 455.

In certain embodiments, an expression vector comprises any of the polynucleotide sequences discussed herein. In certain embodiments, a method of making a polypeptide comprising producing the polypeptide in a cell comprising any of the above expression vectors in conditions suitable to express the polynucleotide contained therein to produce the polypeptide is provided.

In certain embodiments, an expression vector comprises a polynucleotide comprising a sequence encoding a polypeptide comprising at least one complementarity determining region (CDR) selected from CDR1a, CDR2a, and CDR3a, wherein CDR1a comprises the amino acid sequence a b c d e f g h i j k l, wherein amino acid a is glycine, amino acid b is selected from glycine, tyrosine, or phenylalanine; amino acid c is selected from serine or threonine; amino acid d is selected from isoleucine or phenylalanine; amino acid e is selected from serine, threonine, or asparagine; amino acid f is selected from serine, aspartic acid, tyrosine, asparagine, threonine, or glycine; amino acid g is selected from glycine, aspartic acid, or tyrosine; amino acid h is selected from glycine, aspartic acid, tyrosine, asparagine, or serine; amino acid i is selected from tyrosine, isoleucine, histidine, methionine, or tryptophan; amino acid j is selected from asparagine, tyrosine, histidine, serine, or phenylalanine; amino acid k is tryptophan or is not present; and amino acid l is serine or is not present; wherein CDR2a comprises the amino acid sequence m n o p q r s t u v w x y z a' b' c', wherein amino acid m is selected from tryptophan, tyrosine, histidine, valine, glutamic acid, or serine; amino acid n is selected from methionine or isoleucine; amino acid o is selected from asparagine, tyrosine, serine, tryptophan, or histidine; amino acid p is selected from proline, tyrosine, serine, arginine, histidine, or asparagine; amino acid q is selected from asparagine, serine, or aspartic acid; amino acid r is selected from serine or glycine; amino acid s is selected from aspartic acid, serine, threonine, or arginine; amino acid t is selected from asparagine, threonine, alanine, isoleucine, or tyrosine; amino acid u is selected from threonine, tyrosine, leucine, lysine, asparagine, or isoleucine; amino acid v is selected from glycine, tyrosine, aspartic acid, or cysteine; amino acid w is selected from tyrosine or asparagine; amino acid x is selected from alanine or proline; amino acid y is selected from glutamine, serine, or aspartic acid; amino acid z is selected from lysine, leucine, or serine; amino acid a' is selected from phenylalanine, lysine, or valine; amino acid b' is selected from glutamine, serine, or lysine; and amino acid c' is glycine or is not present; wherein CDR3a comprises the amino acid sequence d' e' f' g' h' i' j' k' l' m' n' o' p' q' r' s' t' u' v' w', wherein amino acid d' is selected from tryptophan, aspartic acid, glycine, serine, or glutamic acid; amino acid e' is selected from asparagine, aspartic acid, glycine, arginine, serine, valine, or leucine; amino acid f' is selected from histidine, serine, alanine, tyrosine, proline, asparagine, glycine or threonine; amino acid g' is selected from tyrosine, serine, alanine, arginine, tryptophan, glycine or valine; amino acid h' is selected from glycine, alanine, serine, asparagine, methionine, tyrosine, tryptophan, cysteine, or aspartic acid; amino acid i' is selected from serine, tryptophan, glycine, phenylalanine, aspartic acid, tyrosine, or threonine; amino acid j' is selected from glycine, threonine, serine, leucine, valine, asparagine, tryptophan, or tyrosine; amino acid k' is selected from serine, phenylalanine, aspartic acid, tryptophan, glycine, or tyrosine, or is not present; amino acid l' is selected from histidine, aspartic acid, alanine, tryptophan, tyrosine, serine, phenylalanine, valine, or glycine, or is not present; amino acid m' is selected from phenylalanine, tyrosine, glutamic acid, proline, aspartic acid, cysteine, isoleucine, or methionine, or is not present; amino acid n' is selected from aspartic acid, phenylalanine, alanine, leucine, or serine, or is not present; amino acid o' is selected from tyrosine, leucine, aspartic acid, phenylalanine, proline, or valine, or is not present; amino acid p' is selected from leucine, aspartic acid, or tyrosine, or is not present; amino acid q' is selected from serine or tyrosine, or is not present; amino acid r' is tyrosine or is not present; amino acid s' is selected from glycine or tyrosine, or is not present; amino acid t' is selected from glycine or methionine, or is not present; amino acid u' is selected from methionine or aspartic acid, or is not present; amino acid v' is selected from aspartic acid or valine, or is not present; and amino acid w' is valine or is not present; and wherein the polypeptide, in association with an antibody light chain, binds TR-2. In certain embodiments, a method of making a polypeptide comprising producing the polypeptide in a cell comprising the above expression vector in conditions suitable to express the polynucleotide contained therein to produce the polypeptide is provided.

In certain embodiments, an expression vector comprises a polynucleotide comprising a sequence encoding a polypeptide comprising at least one complementarity determining region (CDR) selected from CDR1b, CDR2b, and CDR3b, wherein CDR1b comprises the amino acid sequence a1 b1 c1 d1 e1 f1 g1 h1 i1 j1 k1 l1 m1 n1 o1 p1 q1, wherein amino acid a1 is selected from arginine or lysine; amino acid b1 is selected from threonine, alanine, or serine; amino acid c1 is serine; amino acid d1 is glutamine; amino acid e1 is selected from serine or glycine; amino acid f1 is selected from isoleucine, leucine, or valine; amino acid g1 is selected from serine, leucine, or arginine; amino acid h1 is selected from threonine, serine, isoleucine, asparagine, arginine, histidine, or tyrosine; amino acid i1 is selected from tyrosine, arginine, tryptophan, aspartic acid, or serine; j1 is selected from leucine, isoleucine, asparagine, tyrosine, or serine; amino acid k1 is selected from asparagine, glycine, valine, alanine, or leucine; amino acid l1 is selected from tyrosine, alanine, or asparagine, or is not present; amino acid m1 is selected from asparagine or lysine, or is not present; amino acid n1 is selected from tyrosine, asparagine, or isoleucine, or is not present; amino acid o1 is selected from leucine or tyrosine, or is not present; amino acid p1 is selected from aspartic acid or leucine, or is not present; and amino acid q1 is selected from valine, alanine, or threonine, or is not present; wherein CDR2b comprises the amino acid sequence r1 s1 t1 u1 v1 w1 x1, wherein amino acid r1 is selected from alanine, aspartic acid, leucine, tryptophan, glycine, or valine; amino acid s1 is selected from threonine, valine, glycine, or alanine; amino acid t1 is serine; amino acid u1 is selected from serine, asparagine, or threonine; amino acid v1 is selected from leucine, phenylalanine, or arginine; amino acid w1 is selected from glutamine, alanine, or glutamic acid; and amino acid x1 is selected from serine, arginine, or threonine; wherein CDR3b comprises the amino acid sequence y1 z1 a1' b1' c1' d1' e1' f1' g1', wherein amino acid y1 is selected from glutamine, methionine, leucine, or histidine; amino acid z1 is selected from glutamine or lysine; amino acid a1' is selected from serine, threonine, alanine, histidine, tyrosine, or phenylalanine; amino acid b1' is selected from tyrosine, leucine, asparagine, or glycine; amino acid c1' is selected from serine, glutamine, isoleucine, or lysine; amino acid d1' is selected from threonine, phenylalanine, tyrosine, alanine, or serine; amino acid e1' is proline; amino acid f1' is selected from leucine, phenylalanine, tryptophan, serine, or arginine; and amino acid g1' is selected from threonine or serine; and wherein the polypeptide, in association with an antibody heavy chain, binds TR-2. In certain embodiments, a method of making a polypeptide comprising producing the polypeptide in a cell comprising the above expression vector in conditions suitable to express the polynucleotide contained therein to produce the polypeptide is provided. In certain embodiments, a cell comprising at least one of the above expression vectors is provided. In certain embodiments, a method of making an polypeptide comprising producing the polypeptide in a cell comprising the above expression vector in conditions suitable to express the polynucleotide contained therein to produce the polypeptide is provided.

In certain embodiments, an expression vector expresses an anti-TR-2 antibody heavy chain. In certain embodiments, an expression vector expresses an anti-TR-2 antibody light chain. In certain embodiments, an expression vector expresses both an anti-TR-2 antibody heavy chain and an anti-TR-2 antibody light chain. In certain embodiments, a method of making an anti-TR-2 antibody comprising producing the antibody in a cell comprising at least one of the expression vectors described herein in conditions suitable to express the polynucleotides contained therein to produce the antibody is provided.

In certain embodiments, the transfection procedure used may depend upon the host to be transformed. Certain methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain mammalian cell lines available as hosts for expression are known in the art and include, but are not limited to, many immortalized cell lines available from the American Type Culture Collection (ATCC), including but not limited to Chinese hamster ovary (CHO) cells, E5 cells, HeLa cells, baby hamster kidney (BHK) cells, monkey kidney cells (COS), human hepatocellular carcinoma cells (e.g., Hep G2), NSO cells, SP20 cells, Per C6 cells, 293 cells, and a number of other cell lines. In certain embodiments, cell lines may be selected through determining which cell lines have high expression levels and produce antibodies with constitutive antigen binding properties.

In certain embodiments, the vectors that may be transfected into a host cell comprise control sequences that are operably linked to a polynucleotide encoding an anti-TR-2 antibody. In certain embodiments, control sequences facilitate expression of the linked polynucleotide, thus resulting in the production of the polypeptide encoded by the linked polynucleotide. In certain embodiments, the vector also comprises polynucleotide sequences that allow chromosome-independent replication in the host cell. Exemplary vectors include, but are not limited to, plasmids (e.g., BlueScript, puc, etc.), cosmids, and YACS.

Certain Antibody Uses

According to certain embodiments, antibodies are useful for detecting a particular antigen in a sample. In certain embodiments, this allows the identification of cells or tissues which produce the protein. For example, in certain embodiments, anti-TR-2 antibodies may be used to detect the presence of TR-2 in a sample. In certain embodiments, a method for detecting the presence or absence of TR-2 in a sample comprises (a) combining an anti-TR-2 antibody and the sample; (b) separating antibodies bound to an antigen from unbound antibodies; and (c) detecting the presence or absence of antibodies bound to the antigen.

Assays in which an antibody may be used to detect the presence or absence of an antigen include, but are not limited to, an ELISA and a western blot. In certain embodiments, an anti-TR-2 antibody may be labeled. In certain embodiments, an anti-TR-2 antibody may be detected by a labeled antibody that binds to the anti-TR-2 antibody. In certain embodiments, a kit for detecting the presence or absence of TR-2 in a sample is provided. In certain embodiments, the kit comprises an anti-TR-2 antibody and reagents for detecting the antibody.

In certain embodiments, antibodies may be used to substantially isolate a chemical moiety such as, but not limited to, a protein. In certain embodiments, the antibody is attached to a "substrate," which is a supporting material used for immobilizing the antibody. Substrates include, but are not limited to, tubes, plates (i.e., multi-well plates), beads such as microbeads, filters, balls, and membranes. In certain embodiments, a substrate can be made of water-insoluble materials such as, but not limited to, polycarbonate resin, silicone resin, or nylon resin. Exemplary substrates for use in affinity chromatography include, but are not limited to, cellulose, agarose, polyacrylamide, dextran, polystyrene, polyvinyl alcohol, and porous silica. There are many commercially available chromatography substrates that include, but are not limited to, Sepharose 2B, Sepharose 4B, Sepharose 6B and other forms of Sepharose (Pharmacia); Bio-Gel (and various forms of Bio-Gel such as Biogel A, P, or CM), Cellex (and various forms of Cellex such as Cellex AE or Cellex-CM), Chromagel A, Chromagel P and Enzafix (Wako Chemical Indus.). The use of antibody affinity columns is known to a person of ordinary skill in the art. In certain embodiments, a method for isolating TR-2 comprises (a) attaching a TR-2 antibody to a substrate; (b) exposing a sample containing TR-2 to the antibody of part (a); and (c) isolating TR-2. In certain embodiments, a kit for isolating TR-2 is provided. In certain embodiments, the kit comprises an anti-TR-2 antibody attached to a substrate and reagents for isolating TR-2.

The term "affinity chromatography" as used herein means a method of separating or purifying the materials of interest in a sample by utilizing the interaction (e.g., the affinity) between a pair of materials, such as an antigen and an antibody, an enzyme and a substrate, or a receptor and a ligand.

In certain embodiments, antibodies which bind to a particular protein and block interaction with other binding compounds may have therapeutic use. In this application, when discussing the use of anti-TR-2 antibodies to treat diseases or conditions, such use may include use of the anti-TR-2 antibodies themselves; compositions comprising anti-TR-2 antibodies; and/or combination therapies comprising anti-TR-2 antibodies and one or more additional active ingredients. When anti-TR-2 antibodies are used to "treat" a disease or condition, such treatment may or may not include prevention of the disease or condition. In certain embodiments, anti-TR-2 antibodies can block the interaction of the TR-2 receptor with its ligand, TRAIL. In certain embodiments, anti-TR-2 antibodies can activate the TR-2 receptor. In certain embodiments, anti-TR-2 antibodies can constitutively activate the TR-2 receptor. Because TR-2 is associated with apoptosis, in certain embodiments, anti-TR-2 antibodies may have therapeutic use in treating diseases in which cell death or prevention of cell death is desired. Such diseases include, but are not limited to, cancer associated with any tissue expressing TR-2, inflammation, and viral infections.

In certain embodiments, an anti-TR-2 antibody is administered alone. In certain embodiments, an anti-TR-2 antibody is administered prior to the administration of at least one other therapeutic agent. In certain embodiments, an anti-TR-2 antibody is administered concurrent with the administration of at least one other therapeutic agent. In certain embodiments, an anti-TR-2 antibody is administered subsequent to the administration of at least one other therapeutic agent. Exemplary therapeutic agents, include, but are not limited to, at least one other cancer therapy agent. Exemplary cancer therapy agents include, but are not limited to, radiation therapy and chemotherapy.

In certain embodiments, anti-TR-2 antibody pharmaceutical compositions can be administered in combination therapy, i.e., combined with other agents. In certain embodiments, the combination therapy comprises an anti-TR-2 antibody, in combination with at least one anti-angiogenic agent. Exemplary agents include, but are not limited to, in vitro synthetically prepared chemical compositions, antibodies, antigen binding regions, radionuclides, and combinations and conjugates thereof. In certain embodiments, an agent may act as an agonist, antagonist, allosteric modulator, or toxin. In certain embodiments, an agent may act to inhibit or stimulate its target (e.g., receptor or enzyme activation or inhibition), and thereby promote cell death or arrest cell growth.

Exemplary chemotherapy treatments include, but are not limited to anti-neoplastic agents including, but not limited to, alkylating agents including, but not limited to: nitrogen mustards, including, but not limited to, mechlorethamine, cyclophosphamide, ifosfamide, melphalan and chlorambucil; nitrosoureas, including, but not limited to, carmustine BCNU, lomustine, CCNU, and semustine, methyl-CCNU; TEMODAL™, temozolomide; ethylenimines/methylmelamine, including, but not limited to, thriethylenemelamine (TEM), triethylene, thiophosphoramide, thiotepa, hexamethylmelamine (HMM), and altretamine; alkyl sulfonates, including, but not limited to, busulfan; triazines, including, but not limited to, dacarbazine (DTIC); antimetabolites, including, but not limited to, folic acid analogs such as methotrexate and trimetrexate; pyrimidine analogs, including, but not limited to, 5-fluorouracil (5FU), fluorodeoxyuridine, gemcitabine, cytosine arabinoside (AraC, cytarabine), 5-azacytidine, and 2,2'-difluorodeoxycytidine; purine analogs, including, but not limited to, 6-mercaptopurine, 6-thioguanine, azathioprine, 2'-deoxycoformycin (pentostatin), erythrohydroxynonyladenine (EHNA), fludarabine phosphate, cladribine, and 2-chlorodeoxyadenosine (2-CdA); natural products, including, but not limited to, antimitotic drugs such as paclitaxel; ymca alkaloids, including, but not limited to, vinblastine (VLB), vincristine, and vinorelbine; taxotere; estramustine and estramustine phosphate; ppipodophylotoxins, including, but not limited to, etoposide and teniposide; antibiotics, including, but not limited to, actinomycin D, daunomycin, rubidomycin, doxorubicin, mitoxantrone, idarubicin, bleomycins, plicamycin, mithramycin, mitomycin C, and actinomycin; enzymes, including, but not limited to, L-asparaginase; biological response modifiers, including, but not limited to, interferon-alpha, IL-2, G-CSF, and GM-CSF; doxycyckine; irinotecan hydrochloride; miscellaneous agents, including, but not limited to, platinium coordination complexes such as cisplatin and carboplatin; anthracenediones, including, but not limited to, mitoxantrone; substituted urea, including, but not limited to, hydroxyurea; methyihydrazine derivatives, including, but not limited to, N-methylhydrazine (MIH) and procarbazine; ad renocortical suppressants, including, but not limited to, mitotane (o,p'-DDD) and aminoglutethimide; hormones and antagonists, including, but not limited to, adrenocorticosteroid antagonists such as prednisone and equivalents, dexamethasone and aminoglutethimide; GEMZAR™, gemcitabine; progestin, including, but not limited to, hydroxyprogesterone caproate, medroxyprogesterone acetate and megestrol acetate; estrogen, including, but not limited to, diethylstilbestrol and ethinyl estradiol equivalents; antiestrogen, including, but not limited to, tamoxifen; androgens, including, but not limited to, testosterone propionate and fluoxymesterone/equivalents; antiandrogens, including, but not limited to, flutamide, gonadotropin-releasing hormone analogs and leuprolide; and non- steroidal antiandrogens, including, but not limited to, flutamide.

Exemplary cancer therapies, which may be administered with an anti-TR-2 antibody, include, but are not limited to, targeted therapies. Examples of targeted therapies include, but are not limited to, use of therapeutic antibodies. Exemplary therapeutic antibodies, include, but are not limited to, mouse, mouse-human chimeric, CDR-grafted, humanized, and human antibodies, and synthetic antibodies, including, but not limited to, those selected by screening antibody libraries. Exemplary antibodies include, but are not limited to, those which bind to cell surface proteins Her2CDC20, CD33, mucin-like glycoprotein, and epidermal growth factor receptor (EGFr) present on tumor cells, and optionally induce a cytostatic and/or cytotoxic effect on tumor cells displaying these proteins. Exemplary antibodies also include, but are not limited to, HERCEPTIN™, trastuzumab, which may be used to treat breast cancer and other forms of cancer; RITUXAN™, rituximab, ZEVALIN™, ibritumomab tiuxetan, and LYMPHOCIDE™, epratuzumab, which may be used to treat non-Hodgkin's lymphoma and other forms of cancer; GLEEVEC™, imatinib mesylate, which may be used to treat chronic myeloid leukemia and gastrointestinal stromal tumors; and BEXXAR™, tositumomab and iodine 131 tositumomab, which may be used for treatment of non-Hodgkin's lymphoma.Certain exemplary antibodies also include ERBITUX™, cetuximab, IMC-C225; lressa™; gefitinib; TARCEVA™, erlotinib; KDR (kinase domain receptor) inhibitors; anti VEGF antibodies and antagonists (e.g., AVASTIN™, bevacizumab; and VEGF-TRAP™. aflibercept); anti VEGF receptor antibodies and antigen binding regions; anti-Ang-1 and Ang-2 antibodies and antigen binding regions; antibodies to Tie-2 and other Ang-1 and Ang-2 receptors; Tie-2 ligands; antibodies against Tie-2 kinase inhibitors; and CAMPATH®, alemtuzumab. In certain embodiments, cancer therapy agents are other polypeptides which selectively induce apoptosis in tumor cells, including, but not limited to, TNF- related polypeptides such as TRAIL.

In certain embodiments, specific binding agents (including, but not limited to, anti-IGF-R1 antibodies) that antagonize the binding of the ligands IGF-1 and/or IGF-2 to insulin-like growth factor-1 receptor ("IGF-1R") and promote apoptosis of cells expressing IGF-1R are formulated or administered in combination with specific binding agents (including, but not limited to, TRAIL and anti-TR2 antibodies) that agonize and thereby promote apoptosis of cells expressing TRAIL-R2. Exemplary anti-IGF-1 R antibodies are known in the art and are disclosed, for example, in WO 2006/069202, filed Dec. 20, 2005, which is incorporated by reference herein for any purpose.

In certain embodiments, cancer therapy agents are anti-angiogenic agents which decrease angiogenesis. Certain such agents include, but are not limited to, ERBITUX™, cetuximab, IMC-C225; KDR (kinase domain receptor) inhibitory agents (e.g., antibodies and antigen binding regions that specifically bind to the kinase domain receptor); anti-VEGF agents (e.g., antibodies or antigen binding regions that specifically bind VEGF, or soluble VEGF receptors or a ligand binding region thereof) such as AVASTIN™, bevacizumab, or VEGF-TRAP™, aflibercept; anti-VEGF receptor agents (e.g., antibodies or antigen binding regions that specifically bind thereto); EGFR inhibitory agents (e.g., antibodies or antigen binding regions that specifically bind thereto) such as ABX-EGF, panitumumab, IRESSA™, gefitinib, TARCEVA™, erlotinib, anti-Ang1 and anti-Ang2 agents (e.g., antibodies or antigen binding regions specifically binding thereto or to their receptors, e.g., Tie2/Tek); and anti-Tie-2 kinase inhibitory agents (e.g., antibodies or antigen binding regions that specifically bind thereto). In certain embodiments, the pharmaceutical compositions may also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met."

Exemplary anti-angiogenic agents include, but are not limited to, Campath, IL-8, B-FGF, Tek antagonists (Ceretti et al., U.S. Patent Application Publication No. 2003/0162712; U.S. Pat. No. 6,413,932); anti-TWEAK agents (e.g., specifically binding antibodies or antigen binding regions, or soluble TWEAK receptor antagonists; see, e.g., Wiley, U.S. Pat. No. 6,727,225); ADAM disintegrin domain to antagonize the binding of integrin to its ligands (Fanslow et al., U.S. Patent Application Publication No. 2002/0042368); specifically binding anti-eph receptor and/or anti-ephrin antibodies or antigen binding regions (U.S. Pat. Nos. 5,981,245; 5,728, 813; 5,969,110; 6,596,852; 6,232,447; 6,057,124; and patent family members thereof); anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Exemplary anti-angiogenic/anti-tumor agents include, but are not limited to, SF-7784 (Pfizer, USA); cilengitide (Merck KgaA, Germany, EPO 770622); pegaptanib octasodium (Gilead Sciences, USA); Alphastatin (BioActa, UK); M-PGA (Celgene, USA, U.S. Pat. No. 5,712,291); ilomastat (Arriva, USA, U.S. Pat. No. 5,892,112); emaxanib (Pfizer, USA, U.S. Pat. No. 5,792,783); vatalanib (Novartis, Switzerland); 2-methoxyestradiol (EntreMed, USA); TLC ELL-12 (Elan, Ireland); anecortave acetate (Alcon, USA); alpha-D148 Mab (Amgen, USA); CEP-7055 (Cephalon, USA); anti-Vn Mab (Crucell, Netherlands); DAC:antiangiogenic (ConjuChem, Canada); Angiocidin (InKine Pharmaceutical, USA); KM-2550 (Kyowa Hakko, Japan); SU-0879 (Pfizer, USA); CGP-79787 (Novartis, Switzerland, EP 970070); ARGENT technology (Ariad, USA); YIGSR-Strealth (Johnson & Johnson, USA); fibrinogen-E fragment (BioActa, UK); angiogenesis inhibitor (Trigen, UK); TBC-1635 (Encysive Pharmaceuticals, USA); SC-236 (Pfizer, USA); ABT-567 (Abbott, USA); Metastatin (EntreMed, USA); angiogenesis inhibitor (Tripep, Sweden); maspin (Sosei, Japan); 2-methoxyestradiol (Oncology Sciences Corporation, USA); ER-68203-00 (IVAX, USA); Benefin (Lane Labs, USA); Tz-93 (Tsumura, Japan); TAN-1120 (Takeda, Japan); FR-111142 (Fujisawa, Japan, JP 02233610); platelet factor 4 (RepliGen, USA, EP 407122); vascular endothelial growth factor antagonist (Borean, Denmark); temsirolimus (CCI-779) (University of South Carolina, USA); bevacizumab (pINN) (Genentech, USA); angiogenesis inhibitors (SUGEN, USA); XL 784 (Exelixis, USA); XL 647 (Exelixis, USA); Mab, alpha5beta3 integrin, Vitaxin and second generation Vitaxin (Applied Molecular Evolution, USA and MedImmune USA); Retinostat® gene therapy (Oxford BioMedica, UK); enzastaurin hydrochloride (USAN) (Lilly, USA); CEP 7055 (Cephalon, USA and Sanofi-Synthelabo, France); BC 1 (Genoa Institute of Cancer Research, Italy); angiogenesis inhibitor (Alchemia, Australia); VEGF antagonist (Regeneron, USA); rBPI 21 and BPI-derived antiangiogenic (XOMA, USA); PI 88 (Progen, Australia); cilengitide (pINN) (Merck KgaA, Germany; Munich Technical University, Germany; Scripps Clinic and Research Foundation, USA); cetuximab (INN) (Aventis, France); AVE 8062 (Ajinomoto, Japan); AS 1404 (Cancer Research Laboratory, New Zealand); SG 292 (Telios, USA); Endostatin (Boston Children's Hospital, USA); 2-methoxyestradiol (Boston Childrens Hospital, USA); ZD 6474 (AstraZeneca, UK); ZD 6126 (Angiogene Pharmaceuticals, UK); PPI 2458 (Praecis, USA); AZD 9935 (AstraZeneca, UK); AZD 2171 (AstraZeneca, UK); vatalanib (pINN) (Novartis, Switzerland and Schering AG, Germany); tissue factor pathway inhibitors (EntraMed, USA); pegaptanib (Pinn) (Gilead Sciences, USA); xanthorrhizol (Yonsei University, South Korea); vaccine, genebased, VEGF-2 (Scripps Clinic and Research Foundation, USA); SPV5.2 (Supratek, Canada); SDX 103 (University of California at San Diego, USA); PX 478 (Pro1X, USA); Metastatin (EntreMed, USA); troponin I (Harvard University, USA); SU 6668 (SUGEN, USA); OXI 4503 (OXiGENE, USA); o-guanidines (Dimensional Pharmaceuticals, USA); motuporamine C (British Columbia University, Canada); CDP 791 (Celltech Group, UK); atiprimod (pINN) (GlaxoSmithKline, UK); E 7820 (Eisai, Japan); CYC 381 (Harvard University, USA); AE 941 (Aeterna, Canada); FGF2 cancer vaccine (EntreMed, USA); urokinase plasminogen activator inhibitor (Dendreon, USA); oglufanide (pINN) (Melmotte, USA); HIF-1alfa inhibitors (Xenova, UK); CEP 5214 (Cephalon, USA); BAY RES 2622 (Bayer, Germany); Angiocidin (InKine, USA); A6 (Angstrom, USA); KR 31372 (Korean Research Institute of Chemical Technology, South Korea); GW 2286 (GlaxoSmithKline, UK); EHT 0101 (ExonHit, France); CP 868596 (Pfizer, USA); CP 564959 (OSI, USA); CP 547632 (Pfizer, USA); 786034 (GlaxoSmithKline, UK); KRN 633 (Kirin Brewery, Japan); drug delivery system, intraocular, 2-methoxyestradiol (EntreMed, USA); anginex (Maastricht University, Netherlands, and Minnesota University, USA); ABT 510 (Abbott, USA); AAL 993 (Novartis, Switzerland); VEGI (ProteomTech, USA); tumor necrosis factor-alpha inhibitors (National Institute on Aging, USA); SU 11248 (Pfizer, USA and SUGEN USA); ABT 518 (Abbott, USA); YH16 (Yantai Rongchang, China); S-3APG (Boston Childrens Hospital, USA and EntreMed, USA); Mab, KDR (ImClone Systems, USA); Mab, alpha5 beta1 (Protein Design, USA); KDR kinase inhibitor (Celltech Group, UK, and Johnson & Johnson, USA); GFB 116 (South Florida University, USA and Yale University, USA); CS 706 (Sankyo, Japan); combretastatin A4 prodrug (Arizona State University, USA); chondroitinase AC (IBEX, Canada); BAY RES 2690 (Bayer, Germany); AGM 1470 (Harvard University, USA, Takeda, Japan, and TAP, USA); AG 13925 (Agouron, USA); Tetrathiomolybdate (University of Michigan, USA); GCS 100 (Wayne State University, USA); CV 247 (Ivy Medical, UK); CKD 732 (Chong Kun Dang, South Korea); Mab, vascular endothelium growth factor (Xenova, UK); irsogladine (INN) (Nippon Shinyaku, Japan); RG 13577 (Aventis, France); WX 360 (Wilex, Germany); squalamine (pINN) (Genaera, USA); RPI 4610 (Sirna, USA); galacto fucan sulphate (Marinova, Australia); heparanase inhibitors (InSight, Israel); KL 3106 (Kolon, South Korea); Honokiol (Emory University, USA); ZK CDK (Shering AG, Germany); ZK Angio (Schering AG, Germany); ZK 229561 (Novartis, Switzerland, and Schering AG, Germany); XMP 300 (XOMA, USA); VGA 1102 (Taisho, Japan); VEGF receptor modulators (Pharmacopeia, USA); VE-cadherin-2 antagonists (ImClone Systems, USA); Vasostatin (National Institutes of Health, USA); vaccine, Flk-1 (ImClone Systems, USA); TZ 93 (Tsumura, Japan); TumStatin (Beth Israel Hospital, USA); truncated soluble FLT 1 (vascular endothelial growth factor receptor 1) (Merck & Co, USA); Tie-2 ligands (Regeneron, USA); and thrombospondin 1 inhibitor (Allegheny Health, Education and Research Foundation, USA).

Certain cancer therapy agents include, but are not limited to: thalidomide and thalidomide analogues (N-(2,6-dioxo-3-piperidyl)phthalimide); tecogalan sodium (sulfated polysaccharide peptidoglycan); VELCADE®, bortezomib; rapamycin; TAN 1120 (8-acetyl-7,8,9,10-tetrahydro-6,8,11-trihydroxy-1 -methoxy- 10-[[octahydro-5-hydroxy-2-(2-hydroxypropyl)-4,10-dimethylpyrano[3,4-d]-1,3,6-dioxazocin-8-yl]oxy]-5,12-naphthacenedione); suradista (7,7'-[carbonylbis[imino(1 -methyl-1H-pyrrole-4,2-diyl)carbonylimino(1 -methyl-1H- pyrrole-4,2-diyl)carbonylimino]] bis-1,3-naphthalenedisulfonic acid tetrasodium salt); SU 302; SU 301; SU 1498 ((E)-2-cyano-3-[4-hydroxy-3,5-bis( 1 -methylethyl)phenyl]-N-(3-phenylpropyl)-2-pro penamide); SU 1433 (4-(6,7-dimethyl-2-quinoxalinyl)- 1,2-benzenediol); ST 1514; SR 25989; soluble Tie-2; SERM derivatives; Pharmos; semaxanib (pINN)(3-[(3,5-dimethyl-1H-pyrrol-2-yl)methylene]-1,3-dihydro-2H-indol-2-one); S 836; RG 8803; RESTIN; R 440 (3-(1-methyl-1H-indol-3-yl)-4-(1-methyl-6-nitro-1H-indol-3-yl)-1H-pyrrole-2,5-dione); R 123942 (1 -[6-(1,2,4-thiadiazol-5-yl)-3-Pyridazinyl]-N-[3-(trifluoromethyl)phenyl]-4-piperidinamine); prolyl hydroxylase inhibitor; progression elevated genes; prinomastat (INN) ((S)-2,2-dimethyl-4-[[p-(4-pyridyloxy)phenyl]sulphonyl]-3-thiomorpholinecarbohyd roxamic acid); NV 1030; NM 3 (8-hydroxy-6-methoxy-alpha-methyl-1-oxo-1H-2-benzopyran-3-acetic acid); NE 681; NF 050; MIG; METH2; METH1; manassantin B (alpha-[1-[4-[5-[4-[2-(3,4-dimethoxyphenyl)-2-hydroxy-1-methylethoxy]-3-methoxyphenyl]tetrahydro-3,4-dimethyl-2-furanyl]-2-methoxyphenoxy] ethyl]- 1,3-benzodioxole-5-methanol); KDR monoclonal antibody; alpha5beta3 integrin monoclonal antibody; LY 290293 (2-amino-4-(3-pyridinyl)-4H-naphtho[1,2-b]pyran-3-carbonitrile); KP 0201448; KM 2550; integrin- specific peptides; INGN 401; GYKI 66475; GYKI 66462; greenstatin (101-354-plasminogen (human)); gene therapy for rheumatoid arthritis, prostate cancer, ovarian cancer, glioma, endostatin, colorectal cancer, ATF BTPI, antiangiogenesis genes, angiogenesis inhibitor, or angiogenesis; gelatinase inhibitor, FR 111142 (4,5-dihydroxy-2-hexenoic acid 5-methoxy-4-[2-methyl-3-(3-methyl-2-butenyl)oxi ranyl]-1-oxaspiro[2.5]oct-6-yl ester); forfenimex (pINN)(S)-alpha-amino-3-hydroxy-4-(hyd roxymethyl)benzeneacetic acid); fibronectin antagonist (1-acetyl-L-prolyl-L-histidyl-L-seryl-L-cysteinyl-L-aspartamide); fibroblast growth factor receptor inhibitor; fibroblast growth factor antagonist; FCE 27164 (7,7'-[carbonylbis[imino(1-methyl-1H-pyrrole-4,2-diyl)carbonylimino( 1-methyl-1H- pyrrole-4,2-diyl)carbonylimino]] bis-1,3,5-naphthalenetrisulfonic acid hexasodium salt); FCE 26752 (8,8'-[carbonylbis[imino(1-methyl-1H-pyrrole-4,2-diyl)carbonylimino(1-methyl-1H-pyrrole-4,2-diyl)carbonylimino]]bis- 1,3,6-naphthalenetrisulfonic acid); endothelial monocyte activating polypeptide II; VEGFR antisense oligonucleotide; anti-angiogenic and trophic factors; ANCHOR angiostatic agent; endostatin; Del-1 angiogenic protein; CT 3577; contortrostatin; CM 101; chondroitinase AC; CDP 845; CanStatin; BST 2002; BST 2001; BLS 0597; BIBF 1000; ARRESTIN; apomigren (1304-1388-type XV collagen (human gene COL15A1 alpha1-chain precursor)); angioinhibin; aaATIII; A 36; 9alpha-fluoromedroxyprogesterone acetate ((6-alpha)- 17-(acetyloxy)-9-fluoro-6-methyl-pregn-4-ene-3,20-dione); 2-methyl-2-phthalimidino-glutaric acid (2-(1,3-dihydro-1-oxo-2H-isoindol-2-yl)-2-methylpentanedioic acid); Yttrium 90 labelled monoclonal antibody BC-1; Semaxanib (3-(4,5-Dimethylpyrrol-2-ylmethylene)indolin-2-one)(C15 H14 N2 O); PI 88 (phosphomannopentaose sulfate); Alvocidib (4H-1-Benzopyran-4-one, 2-(2-chlorophenyl)-5,7-dihydroxy-8-(3-hydroxy-1-methyl-4-piperidinyl)-cis-(-)-) (C21 H20 Cl N O5); E 7820; SU 11248 (5-[3-Fluoro-2-oxo-1,2-dihydroindol-(3Z)-ylidenemethyl]-2,4-dimethyl-1H- pyrrole-3-carboxylic acid (2-diethylaminoethyl)amide) (C22 H27 F N4 O2); Squalamine (Cholestane-7,24-diol, 3-[[3-[(4-aminobutyl)aminopropyl]amino]-, 24-(hydrogen sulfate), (3.beta.,5.alpha.,7.alpha.)-) (C34 H65 N3 O5 S); Eriochrome Black T; AGM 1470 (Carbamic acid, (chloroacetyl)-, 5-methoxy-4-[2-methyl-3-(3-methyl-2-butenyl)oxiranyl]-1-oxaspiro[2,5] oct-6-yl ester, [3R-[3alpha, 4alpha (2R, 3R),5beta, 6beta]]) (C19 H28 Cl N O6); AZD 9935; BIBF 1000; AZD 2171; ABT 828; KS-interleukin-2; Uteroglobin; A 6; NSC 639366 (1-[3-(Diethylamino)-2-hydroxypropylamino]-4-(oxyran-2-ylmethylamino)anthraquinone fumerate)(C24 H29 N3 O4. C4 H4 O4); ISV 616; anti-ED-B fusion proteins; HUI 77; Troponin I; BC-1 monoclonal antibody; SPV 5.2; ER 68203; CKD 731 (3-(3,4,5-Trimethoxyphenyl)-2(E)-propenoic acid (3R,4S,5S,6R)-4-[2(R)-methyl-3(R)-3(R)-(3-methyl-2-butenyl)oxiran-2-yl]-5-methoxy-1-oxaspiro[2.5]oct-6-yl ester) (C28 H38 O8); IMC-1C11; aaATIII; SC 7; CM 101; Angiocol; Kringle 5; CKD 732 (3-[4-2-(Dimethylamino)ethoxy]phenyl]-2(E)-propenoic acid)(C29 H41 N O6); U 995; Canstatin; SQ 885; CT 2584 (1-[11-(Dodecylamino)-10 -hydroxyundecyl]-3,7-dimethylxanthine)(C30 H55 N5 O3); Salmosin; EMAP II; TX 1920 (1-(4-Methylpiperazino)-2-(2-nitro-1H-1-imidazoyl)-1-ethanone) (C10 H15 N5 O3); Alpha-v Beta-x inhibitor; CHIR 11509 (N-(1-Propynyl)glycyl-[N-(2-naphthyt)]glycyl-[N-(carbamoylmethyl)]glycine bis(4-methoxyphenyl)methylamide) (C36 H37 N5 O6); BST 2002; BST 2001; B 0829; FR 111142; 4,5-Dihydroxy-2(E)-hexenoic acid (3R,4S,5S,6R)-4-[1(R),2(R)-epoxy-1,5-dimethyl-4-hexenyl]-5-methoxy-1-oxaspiro[2.5]octan-6-yl ester (C22 H34 O7); and kinase inhibitors including, but not limited to, N-(4-chlorophenyl)-4-(4-pyridinylmethyl)-1-phthalazinamine; 4-[4-[[[[4-chloro-3-(trifluoromethyl)phenyl]amino]carbonyl] amino]phenoxy]-N-methyl-2-pyridinecarboxamide; N-[2-(diethylamino)ethyl]-5-[(5-fluoro-1,2-dihydro-2-oxo-3H-indol-3-ylidene)methyl]-2,4-dimethyl-1H-pyrrole-3-carboxamide; 3-[(4-bromo-2,6-difluorophenyl)methoxy]-5-[[[[4-(1-pyrrolidinyl)butyl]amino]carbonyl]amino]-4-isothiazolecarboxamide; N-(4-bromo-2-fluorophenyl)-6-methoxy-7-[(1-methyl-4-piperidinyl)methoxy]-4-quinazolinamine; 3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine; N-[5-[[[5-(1,1-dimethylethyl)-2-oxazolyl]methyl]thio]-2-thiazolyl]-4-piperidinecarboxamide; N-[3-chloro-4-[(3-fluorophenyl)methoxy]phenyl]-6-[5-[[[2-(methylsulfonyl) ethyl]amino]methyl]-2-furanyl]-4-quinazolinamine; 4-[(4-Methyl-1-piperazinyl)methyl]-N-[4-methyl-3-[[4-(3-pyridinyl)-2-pyrimidinyl]amino]-phenyl]benzamide;N-(3-chloro-4-fluorophenyl)-7-methoxy-6-[3-(4-morpholinyl) propoxy]-4-quinazolinamine; N-(3-ethynylphenyl)-6,7-bis (2-methoxyethoxy)-4-quinazolinamine; N-(3-((((2R)-1-methyl-2-pyrrolidinyl)methyl)oxy)-5-(trifluoromethyl) phenyl)-2-((3-(1,3-oxazol-5-yl)phenyl)amino)-3-pyridinecarboxamide; 2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide; N-[3-(Azetidin-3-ylmethoxy)-5-trifluoromethyl-phenyl]-2-(4-fluoro-benzylamino)-nicotinamide; 6-fluoro-N-(4-(1-methylethyl)phenyl)-2-((4-pyridinylmethyl)amino)-3-pyridinecarboxamide; 2-((4-pyridinylmethyl)amino)-N-(3-(((2S)-2-pyrrolidinylmethyl)oxy)-5-(trifluoromethyl) phenyl)-3-pyridinecarboxamide; N-(3-(1,1-dimethylethyl)-1H-pyrazol-5-yl)-2-((4-pyridinylmethyl)amino)-3-pyridinecarboxamide; N-(3,3-dimethyl-2,3-dihydro-1-benzofuran-6-yl)-2-((4-pyridinylmethyl)amino)-3-pyridinecarboxamide; N-(3-((((2S)-1-methyl-2-pyrrolidinyl)methyl)oxy)-5-(trifluoromethyl)phenyl)-2-((4-pyridinylmethyl)amino)-3-pyridinecarboxamide; 2-((4-pyridinylmethyl)amino)-N-(3-((2-(1-pyrrolidinyl)ethyl) oxy)-4-(trifluoromethyl)phenyl)-3-pyridinecarboxamide; N-(3,3-dimethyl-2,3-dihydro-1H-indol-6-yl)-2-((4-pyridinylmethyl)amino)-3-pyridinecarboxamide; N-(4-(pentafluoroethyl)-3-(((2S)-2-pyrrolidinylmethyl)oxy)phenyl)-2-((4-pyridinylmethyl)amino)-3-pyridinecarboxamide; N-(3-((3-azetidinylmethyl)oxy)-5-(trifluoromethyl)phenyl)-2-((4-pyridinylmethyl)amino)-3-pyridinecarboxamide; N-(3-(4-piperidinyloxy)-5-(trifluoromethyl)phenyl)-2-((2-(3-pyridinyl)ethyl)amino)-3-pyridinecarboxamide; N-(4,4-dimethyl-1,2,3,4-tetrahydro-isoquinolin-7-yl)-2-(1H-indazol-6-ylamino)-nicotinamide; 2-(1H-indazol-6-ylamino)-N-[3-(1-methylpyrrolidin-2-ylmethoxy)-5-trifluoromethyl-phenyl]-nicotinamide; N-[1-(2-dimethylamino-acetyl)-3,3-dimethyl-2,3-dihydro-1H-indol-6-yl]-2-(1H-indazol-6-ylamino)-nicotinamide; 2-(1H-indazol-6-ylamino)-N-[3-(pyrrolidin-2-ylmethoxy)-5-trifluoromethyl-phenyl]-nicotinamide; N-(1-acetyl-3,3-dimethyl-2,3-dihydro-1H-indol-6-yl)-2-(1H-indazol-6-ylamino)-nicotinamide; N-(4,4-dimethyl-1-oxo-1,2,3,4-tetrahydro-isoquinolin-7-yl)-2-(1H-indazol-6-ylamino)-nicotinamide; N-[4-(tert-butyl)-3-(3-piperidylpropyl) phenyl][2-(1 H-indazol-6-ylamino)(3-pyridyl)] carboxamide; N-[5-(tert-butyl)isoxazol-3-yl][2-(1H-indazol-6-ylamino)(3-pyridyl)]carboxamide; and N-[4-(tert-butyl)phenyl][2-(1H-indazol-6-ylamino)(3-pyridyl)] carboxamide, and kinase inhibitors disclosed in U.S. Pat. Nos. 6,258,812; 6,235,764; 6,630,500; 6,515,004; 6,713,485; 5,521,184; 5,770,599; 5,747,498; 5,990,141; U.S. Patent Application Publication No. US2003/0105091; and Patent Cooperation Treaty publication nos. WO01/37820; WO01/32651; WO02/68406; WO02/66470; WO02/55501; WO04/05279; WO04/07481; WO04/07458; WO04/09784; WO02/59110; WO99/45009; WO98/35958; WO00/59509; WO99/

61422; WO00/12089; and WO00/02871, each of which publications are hereby incorporated by reference for any purpose.

TR-2 is expressed in a variety of cells, including liver, brain, kidney, colon, breast, lung, spleen, thymus, peripheral blood lymphocytes, pancreas, prostate, testis, ovary, uterus, and various tissues along the gastro-intestinal tract. Exemplary TR-2 related cancers include, but are not limited to, liver cancer, brain cancer, renal cancer, breast cancer, pancreatic cancer, colorectal cancer, lung cancer (small cell lung cancer and non-small-cell lung cancer), spleen cancer, cancer of the thymus or blood cells (i.e., leukemia), prostate cancer, testicular cancer, ovarian cancer, uterine cancer, gastric carcinoma, head and neck squamous cell carcinoma, melanoma, and lymphoma.

In certain embodiments, an anti-TR-2 antibody may be used alone or with at least one additional therapeutic agent for the treatment of cancer. In certain embodiments, an anti-TR-2 antibody is used in conjunction with a therapeutically effective amount of an additional therapeutic agent. Exemplary therapeutic agents that may be administered with an anti-TR-2 antibody include, but are not limited to, a member of the geldanamycin family of anisamycin antibiotics; a Pro-HGF; NK2; a c-Met peptide inhibitor; an antagonist of Grb2 Src homology 2; a Gab1 modulator; dominant-negative Src; a von-Hippel-Landau inhibitor, including, but not limited to, wortmannin; P13 kinase inhibitors, other anti-receptor therapies, anti EGFr, a COX-2 inhibitor, CELEBREX™, celecoxib, VIOXX™, rofecoxib; a vascular endothelial growth factor (VEGF), a VEGF modulator, a fibroblast growth factor (FGF), an FGF modulator, an epidermal growth factor (EGF); an EGF modulator; a keratinocyte growth factor (KGF), a KGF-related molecule, a KGF modulator; and a matrix metalloproteinase (MMP) modulator.

In certain embodiments, anti-TR-2 antibody is used with particular therapeutic agents to treat various cancers. In certain embodiments, in view of the condition and the desired level of treatment, two, three, or more agents may be administered. Where the compounds are used together with one or more other components, the compound and the one or more other components may be administered together, separately, or sequentially (e.g., in a pharmaceutical format). In certain embodiments, such agents may be provided together by inclusion in the same formulation. In certain embodiments, such agents and an anti-TR-2 antibody may be provided together by inclusion in the same formulation. In certain embodiments, such agents may be formulated separately and provided together by inclusion in a treatment kit. In certain embodiments, such agents and an anti-TR-2 antibody may be formulated separately and provided together by inclusion in a treatment kit. In certain embodiments, such agents may be provided separately.

In certain embodiments, when administered by gene therapy, the genes encoding protein agents and/or an anti-TR-2 antibody may be included in the same vector. In certain embodiments, the genes encoding protein agents and/or an anti-TR-2 antibody may be under the control of the same promoter region. In certain embodiments, the genes encoding protein agents and/or an anti-TR-2 antibody may be in separate vectors.

In certain embodiments, anti-TR-2 antibodies may be used to treat non-human animals, such as pets (dogs, cats, birds, primates, etc.), and domestic farm animals (horses cattle, sheep, pigs, birds, etc.). In certain such instances, an appropriate dose may be determined according to the animal's body weight. For example, in certain embodiments, a dose of 0.2-1 mg/kg may be used. In certain embodiments, the dose may be determined according to the animal's surface area, an exemplary dose ranging from 0.1 to 20 mg/in$^2$, or from 5 to 12 mg/m$^2$. For small animals, such as dogs or cats, in certain embodiments, a suitable dose is 0.4 mg/kg. In certain embodiments, anti-TR-2 antibodies are administered by injection or other suitable route one or more times per week until the animal's condition is improved, or it may be administered indefinitely.

It is understood that the response by individual patients to the aforementioned medications or combination therapies may vary, and an appropriate efficacious combination of drugs for each patient may be determined by his or her physician.

The cynomolgus monkey provides a useful model for certain diseases. Exemplary diseases include, but are not limited to, transplantation rejection syndrome and inflammatory bowel disease-like disease. When testing the efficacy of a human MAb in cynomolgus monkey human disease model, in certain embodiments, it is useful to determine whether the anti-TR-2 MAb binds to TR-2 in humans and cynomolgus monkeys at a comparable level.

In certain embodiments, an anti-TR-2 antibody may be part of a conjugate molecule comprising all or part of the anti-TR-2 antibody and a cytotoxic agent. The term "cytotoxic agent" refers to a substance that inhibits or prevents the function of cells and/or causes the death or destruction of cells. The term includes, but is not limited to, radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof. Exemplary cytotoxic agents include, but are not limited to, Adriamycin, Doxorubicin, 5-Fluorouracil, Cytosine arabinoside ("Ara-C"), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins, Melphalan and other related nitrogen mustards.

In certain embodiments, an anti-TR-2 antibody may be part of a conjugate molecule comprising all or part of the anti-TR-2 antibody and a prodrug. In certain embodiments, the term "prodrug" refers to a precursor or derivative form of a pharmaceutically active substance. In certain embodiments, a prodrug is less cytotoxic to cells compared to the parent drug and is capable of being enzymatically activated or converted into the more active cytotoxic parent form. Exemplary prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs and optionally substituted phenylacetamide-containing prodrugs, 5-fluorocytosine and other 5-fluorouridine prodrugs which can be converted into a more active cytotoxic free drug. Examples of cytotoxic drugs that can be derivatized into a prodrug form include, but are not limited to, those cytotoxic agents described above. See, e.g., U.S. Pat. No. 6,702,705.

In certain embodiments, antibody conjugates function by having the antibody portion of the molecule target the cytotoxic portion or prodrug portion of the molecule to a specific population of cells in the patient. In the case of anti-TR-2 antibodies, such conjugate molecules may be used, for example, in certain embodiments, to destroy abnormally proliferating cells, such as cancer cells.

In certain embodiments, methods of treating a patient comprising administering a therapeutically effective amount of an anti-TR-2 antibody are provided. In certain embodiments, methods of treating a patient comprising administering a therapeutically effective amount of an antibody conjugate are provided. In certain embodiments, an antibody is used in conjunction with a therapeutically effective amount of at least one additional therapeutic agent, as discussed above.

As discussed above, in certain embodiments, anti-TR-2 antibodies may be administered concurrently with one or more other drugs that are administered to the same patient, each drug being administered according to a regimen suitable for that medicament. Such treatment encompasses pre-treatment, simultaneous treatment, sequential treatment, and alternating regimens. Additional examples of such drugs include, but are not limited to, antivirals, antibiotics, analgesics, corticosteroids, antagonists of inflammatory cytokines, DMARDs, nonsteroidal anti-inflammatories, chemotherapeutics, inhibitors of angiogenesis, and stimulators of angiogenesis.

In certain embodiments, various medical disorders are treated with anti-TR-2 antibodies in combination with another stimulator of apoptosis. For example, in certain embodiments, anti-TR-2 antibodies may be administered in a composition that also contains a compound that stimulates apoptosis of one or more cells. In certain embodiments, the anti-TR-2 antibody and stimulators of apoptosis may be administered as separate compositions, and these may be administered by the same or different routes.

In certain embodiments, pharmaceutical compositions are provided comprising a therapeutically effective amount of an antibody together with a pharmaceutically acceptable diluent, carrier, solubilizer, emulsifier, preservative and/or adjuvant.

In certain embodiments, pharmaceutical compositions are provided comprising a therapeutically effective amount of an antibody and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In certain embodiments, antibodies of the present invention are provided in a bufferless formulation as disclosed in PCT/US06/22599 filed Jun. 8, 2006, which is incorporated by reference herein for any purpose.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (*Remington's Pharmaceutical Sciences,* 18$^{th}$ Edition, A. R. Gennaro, ed., Mack Publishing Company (1990).

In certain embodiments, an antibody and/or an additional therapeutic molecule is linked to a half-life extending vehicle known in the art. Such vehicles include, but are not limited to, the Fc domain, polyethylene glycol, and dextran. Such vehicles are described, e.g., in U.S. Pat. No. 6,660,843 and published PCT Application No. WO 99/25044.

In certain embodiments, the optimal pharmaceutical composition will be determined by one skilled in the art depending upon, for example, the intended route of administration, delivery format and desired dosage. See, for example, *Remington's Pharmaceutical Sciences,* supra. In certain embodiments, such compositions may influence the physical state, stability, rate of in vivo release and rate of in vivo clearance of the antibodies.

In certain embodiments, the primary vehicle or carrier in a pharmaceutical composition may be either aqueous or non-aqueous in nature. For example, in certain embodiments, a suitable vehicle or carrier may be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which may further include sorbitol or a suitable substitute therefor. In certain embodiments, a pharmaceutical composition is an aqueous or liquid formulation comprising an acetate buffer of about pH 4.0-5.5, a polyol (polyalcohol), and optionally, a surfactant, wherein the composition does not comprise a salt, e.g., sodium chloride, and wherein the composition is isotonic for the patient. Exemplary polyols include, but are not limited to, sucrose, glucose, sorbitol, and mannitol. An exemplary surfactant includes, but is not limited to, polysorbate. In certain embodiments, a pharmaceutical composition is an aqueous or liquid formulation comprising an acetate buffer of about pH 5.0, sorbitol, and a polysorbate, wherein the composition does not comprise a salt, e.g., sodium chloride, and wherein the composition is isotonic for the patient. Certain exemplary compositions are found, for example, in U.S. Pat. No. 6,171,586. Additional pharmaceutical carriers include, but are not limited to, oils, including petroleum oil, animal oil, vegetable oil, peanut oil, soybean oil, mineral oil, sesame oil, and the like. In certain embodiments, aqueous dextrose and glycerol solutions can also be employed as liquid carriers, particularly for injectable solutions. In certain embodiments, a composition comprising an antibody, with or without at least one additional therapeutic agent, may be prepared for storage by mixing the selected composition having the desired degree of purity with optional formulation agents (*Remington's Pharmaceutical Sciences,* supra) in the form of a lyophilized cake or an aqueous solution. Further, in certain embodiments, a composition comprising an antibody, with or without at least one additional therapeutic agent, may be formulated as a lyophilizate using appropriate excipient solutions (e.g., sucrose) as diluents.

In certain embodiments, anti-TR-2 antibodies are administered in the form of a physiologically acceptable composition comprising purified recombinant protein in conjunction with physiologically acceptable carriers, excipients or diluents. In certain embodiments, such carriers are nontoxic to recipients at the dosages and concentrations employed. In certain embodiments, preparing such compositions may involve combining the anti-TR-2 antibodies with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and/or other stabilizers, and excipients. In certain embodiments, appropriate dosages are determined in standard dosing trials, and may vary according to the chosen route of administration. In certain embodiments, in accordance with appropriate industry standards, preservatives may also be added, which include, but are not limited to, benzyl alcohol. In certain embodiments, the amount and frequency of administration may be determined based on such factors as the nature and severity of the disease being treated, the desired response, the age and condition of the patient, and so forth.

In certain embodiments, pharmaceutical compositions can be selected for parenteral delivery. The preparation of certain such pharmaceutically acceptable compositions is within the skill of the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition may be in the form of a pyrogen-free, parenterally acceptable aqueous solution comprising the desired antibody, with or without additional therapeutic agents, in a pharmaceutically acceptable vehicle. In certain embodiments, a vehicle for parenteral injection is sterile distilled water in which the antibody, with or without at least one additional therapeutic agent, is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads, or liposomes, that may provide for the controlled or sustained release of the product which may then be delivered via a depot injection. In certain embodiments, hyaluronic acid may also be used, and may have the effect of promoting sustained duration in the circulation. In certain embodiments, implantable drug delivery devices may be used to introduce the desired molecule.

In certain embodiments, a pharmaceutical composition may be formulated for inhalation. In certain embodiments, an antibody, with or without at least one additional therapeutic agent, may be formulated as a dry powder for inhalation. In certain embodiments, an inhalation solution comprising an antibody, with or without at least one additional therapeutic agent, may be formulated with a propellant for aerosol delivery. In certain embodiments, solutions may be nebulized. Pulmonary administration is further described in PCT publication no. WO94/20069, which describes pulmonary delivery of chemically modified proteins.

In certain embodiments, it is contemplated that formulations may be administered orally. In certain embodiments, an antibody, with or without at least one additional therapeutic agent, that is administered in this fashion may be formulated with or without those carriers customarily used in the compounding of solid dosage forms such as tablets and capsules. In certain embodiments, a capsule may be designed to release the active portion of the formulation at the point in the gastrointestinal tract when bioavailability is maximized and pre-systemic degradation is minimized. In certain embodiments, at least one additional agent can be included to facilitate absorption of the antibody and/or any additional therapeutic agents. In certain embodiments, diluents, flavorings, low melting point waxes, vegetable oils, lubricants, suspending agents, tablet disintegrating agents, and/or binders may also be employed.

In certain embodiments, a pharmaceutical composition may involve an effective quantity of antibodies, with or without at least one additional therapeutic agent, in a mixture with non-toxic excipients which are suitable for the manufacture of tablets. In certain embodiments, by dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; and binding agents, such as starch, gelatin, and acacia; and lubricating agents such as magnesium stearate, stearic acid, and talc.

Additional pharmaceutical compositions will be evident to those skilled in the art, including formulations involving antibodies, with or without at least one additional therapeutic agent, in sustained- or controlled-delivery formulations. In certain exemplary sustained- or controlled-delivery formulations include, but are not limited to, liposome carriers, bio-erodible microparticles, porous beads, and depot injections. Certain exemplary techniques for preparing certain formulations are known to those skilled in the art. See for example, PCT publication no. WO93/15722, which describes the controlled release of porous polymeric microparticles for the delivery of pharmaceutical compositions. In certain embodiments, sustained-release preparations may include semipermeable polymer matrices in the form of shaped articles, e.g. films, or microcapsules. Sustained release matrices include, but are not limited to, polyesters, hydrogels, polylactides (U.S. Pat. No. 3,773,919 and EP 058,481), copolymers of L-glutamic acid and gamma ethyl-L-glutamate (Sidman et al., *Biopolymers,* 22:547-556 (1983)), poly (2-hydroxyethyl-methacrylate) (Langer et al., *J. Biomed. Mater. Res.,* 15:167-277 (1981) and Langer, *Chem. Tech.,* 12:98-105 (1982)), ethylene vinyl acetate (Langer et al., supra), and poly-D(-)-3-hydroxybutyric acid (EP 133,988). In certain embodiments, sustained release compositions may also include liposomes, which can be prepared, in certain embodiments, by any of several methods known in the art. See e.g., Eppstein et al., *Proc. Natl. Acad. Sci. USA,* 82:3688-3692 (1985); EP 036,676; EP 088,046 and EP 143,949.

In certain embodiments, the pharmaceutical composition to be used for in vivo administration is sterile. In certain embodiments, the pharmaceutical composition to be used for in vivo administration is made sterile by filtration through sterile filtration membranes. In certain embodiments, where the composition is lyophilized, sterilization using sterile filtration membranes may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, after the pharmaceutical composition has been formulated, it may be stored in sterile vials as a solution, suspension, gel, emulsion, solid, or as a dehydrated or lyophilized powder. In certain embodiments, such formulations may be stored either in a ready-to-use form or in a form (e.g., a lyophilized form) that is reconstituted prior to administration.

In certain embodiments, kits for producing a single-dose administration unit are provided. In certain embodiments, the kits may each contain both a first container having a dried protein and a second container having an aqueous formulation. In certain embodiments, kits containing single and/or multi-chambered pre-filled syringes (e.g., liquid syringes and lyosyringes) are included.

In certain embodiments, the effective amount of a pharmaceutical composition comprising an antibody, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the antibody, with or without at least one additional therapeutic agent, is being used, the route of administration, and the size (body weight, body surface or organ size) and/or condition (the age and general health) of the patient. In certain embodiments, the clinician may titer the dosage and modify the route of administration to obtain the optimal therapeutic effect. In certain embodiments, a typical dosage may range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg; or 0.1 mg/kg up to about 100 mg/kg.

In certain embodiments, the frequency of dosing will take into account the pharmacokinetic parameters of the antibody and/or any additional therapeutic agents in the formulation used. In certain embodiments, a clinician will administer the composition until a dosage is reached that achieves the desired effect. In certain embodiments, the composition may therefore be administered as a single dose, or as two or more doses (which may or may not contain the same amount of the desired molecule) over time, or as a continuous infusion via an implantation device or catheter. Certain methods of further refining the appropriate dosage are within the skill in the art. In certain embodiments, appropriate dosages may be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

As discussed above, in various embodiments, any efficacious route of administration may be used to administer anti-TR-2 antibodies. If injected, in certain embodiments, anti-TR-2 antibodies may be administered, for example, via intra-articular, intravenous, intramuscular, intralesional, intraperitoneal, intracranial, intranasal, inhalation or subcutaneous routes by bolus injection or by continuous infusion. Exemplary methods of administration include, but are not limited to, sustained release from implants, aerosol inhalation, eyedrops, oral preparations, including pills, syrups, lozenges, and chewing gum, and topical preparations such as lotions, gels, sprays, ointments, and other suitable techniques.

In certain embodiments, administration by inhalation is beneficial when treating diseases associated with pulmonary disorders. In certain embodiments, anti-TR-2 antibodies may be administered by implanting cultured cells that express the antibodies. In certain embodiments, the patient's own cells are induced to produce by transfection in vivo or ex vivo with one or more vectors that encode an anti-TR-2 antibody. In certain embodiments, this vector can be introduced into the patient's cells, for example, by injecting naked DNA or liposome-encapsulated DNA that encodes an anti-TR-2 antibody, or by other methods of transfection. When anti-TR-2 antibodies are administered in combination with one or more other biologically active compounds, in certain embodiments, these may be administered by the same or by different routes, and may be administered together, separately, or sequentially.

In certain embodiments, the composition may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

In certain embodiments, it may be desirable to use a pharmaceutical composition comprising an antibody, with or without at least one additional therapeutic agent, in an ex vivo manner. In such embodiments, cells, tissues and/or organs that have been removed from the patient are exposed to a pharmaceutical composition comprising an antibody, with or without at least one additional therapeutic agent, after which the cells, tissues and/or organs are subsequently implanted back into the patient.

In certain embodiments, an antibody and any additional therapeutic agents can be delivered by implanting certain cells that have been genetically engineered, using methods such as those described herein, to express and secrete the polypeptides. In certain embodiments, such cells may be animal or human cells, and may be autologous, heterologous, or xenogeneic. In certain embodiments, the cells may be immortalized. In certain embodiments, in order to decrease the chance of an immunological response, the cells may be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

EXAMPLES

Example 1

Production of Certain Human Monoclonal Antibodies

Human anti-TR-2 antibodies were produced in one of two ways. Transgenic mice expressing human immunoglobulin genes (Xenomouse®) were exposed to human TR-2. Certain human anti-TR-2 monoclonal antibodies were produced from those mice using hybridoma-techniques. Certain other human anti-TR-2 monoclonal antibodies were produced from those mice using XenoMax technology, which incorporates the selected lymphocyte antibody method ("SLAM") technique (see, e.g., U.S. Pat. No. 5,627,052; and Babcook et al., Proc. Natl. Acad. Sci. USA 93:7843-7848 (1996)).

Figure 1:
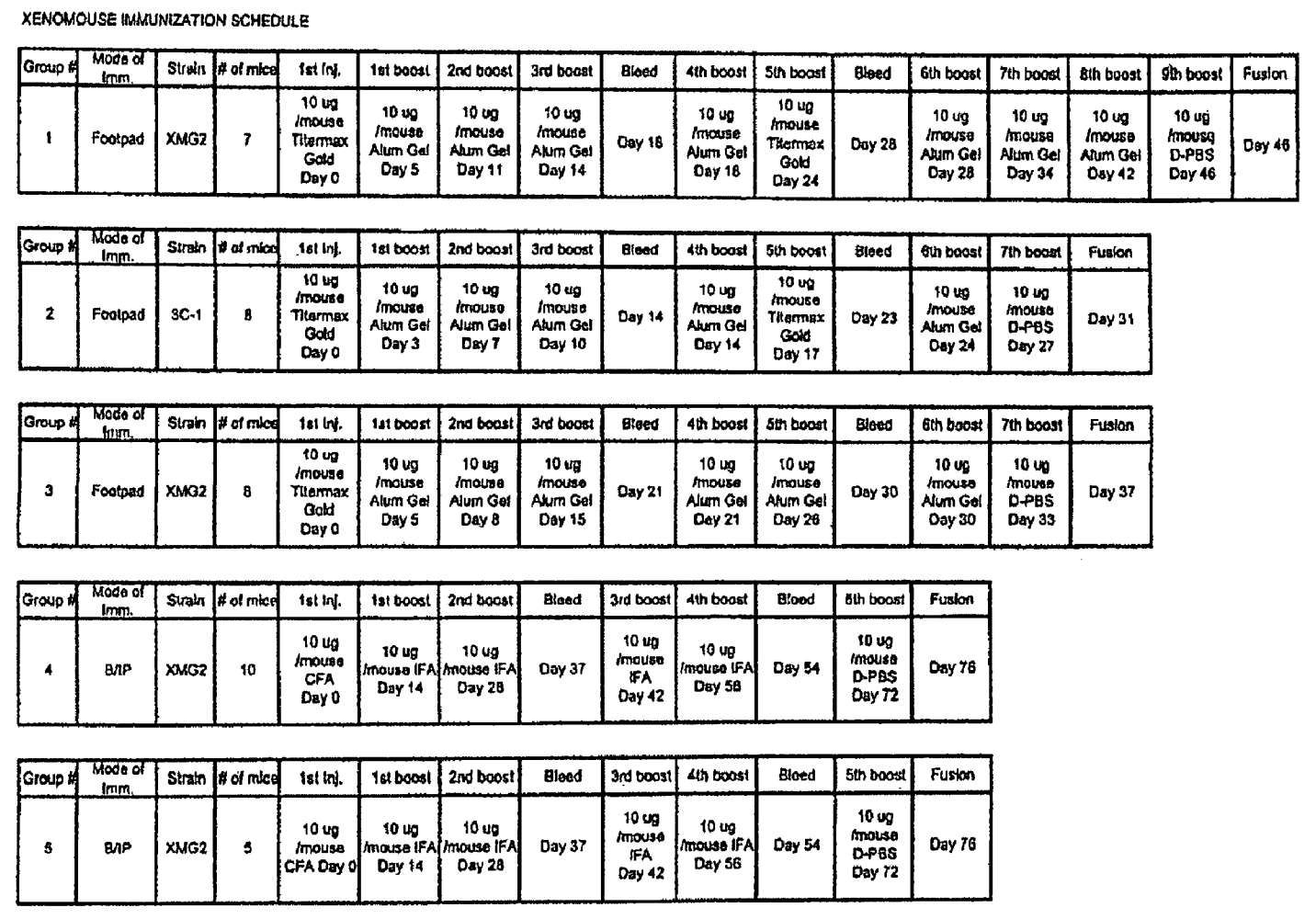

The methodology used to produce human anti-TR-2 monoclonal antibodies in transgenic mice expressing human immunoglobulin genes was as follows. Five groups of mice were immunized with recombinant human TR-2 with a C-terminal hexahistidine tag (TR-2-His) (mature amino acid sequence ALITQQDLAPQQRAAPQQKRSSPSEG-LCPPGHHISEDGRDCISCKY GQDYSTHWNDLLFCL-RCTRCDSGEVELSPCTTTRNTVCQCEEGTFREEDS PEMCRKCRTGCPRGMVKVGDCTPWS-DIECVHKESGTKHSGEAPAVEETVT SSPGT-PASRSGSSHHHHHH (SEQ ID NO: 140)) (Genbank Reference Number NM-003842), as shown in FIG. 1. The mice in group one, group three, group four, and group five were engineered to produce antibodies of the IgG2 isotype (FIG. 2). The mice in group two were engineered to produce antibodies of the IgG4 isotype (FIG. 2). Group one included 7 mice, group two included 8 mice, group three included 8 mice, group four included 10 mice, and group five included 5 mice. The mice in group one, group two, and group three were immunized by injection of TR-2-His into the footpad (10 µg per injection), while the mice in group four and group five were immunized intraperitoneally (10 µg per injection) with TR-2-His. On day 0, 10 µg antigen was administered by the described route. At specified intervals, booster injections were administered to the mice. Group one mice had nine booster injections, at days 5, 11, 14, 18, 24, 28, 34, 42, and 46. Group two and group three mice had 7 booster injections; those for group 2 were at days 3, 7, 10, 14, 17, 24, and 27, and those for group three were at days 5, 8, 15, 21, 26, 30, and 33. Group four and group five mice had 5 booster injections, at days 14, 28, 42, 56, and 72. Each first injection and each booster injection contained 10 µg TR-2-His with an adjuvant, either Titermax Gold (Groups one, two, and three), alum gel (groups one, two, and three), Complete Freund's Adjuvant (CFA) (groups four and five), Incomplete Freund's Adjuvant (IFA) (groups four and five), or Dulbecco's phosphate-buffered saline (D-PBS) (groups one, two, three, four, and five) (see FIG. 1). Mice were bled after three injections (groups four and five), after four injections (groups one, two, and three), after six injections (groups one and two), and after ten injections (group one). The reactivity of each bleed to TR-2-His was assessed by ELISA, as shown in FIG. 2.

The ELISA assay was performed as follows. Multiwell plates were coated with soluble TR-2-His (0.5 µg/mL) by passive adsorption overnight at 4° C. The coated wells were washed and blocked for 30 minutes with milk. Ten µL of each mouse serum was combined with 40 µL milk and incubated in the wells of different plates for 1 hour, 1.25 hours, or 2 hours. The plates were washed five times with water. The plates were then incubated with a goat anti-human IgG Fc-specific horseradish peroxidase-conjugated antibody (Pierce) at a final concentration of 1 µg/mL for 1 hour at room temperature. The plates were washed five times with water. The plates were incubated with K blue substrate (Neogen) for 30 minutes. Negative controls included blank wells lacking TR-2-His and wells including TR-2-His but incubated with naive G2 sera expected to lack anti-TR-2 antibodies.

The methodologies used to produce human anti-TR-2 monoclonal antibodies were as follows. For XenoMax technology, CD19+ B cells were isolated from the hyperimmune transgenic mice that were harvested on day 37 (mouse M712-7 from group three), or day 76 (mouse M564-1 from group four, and mice M564-3, M564-5, and M563-5 from group five after the initiation of immunization. The B cells were cultured for 1 week to allow their expansion and consequent differentiation into plasma cells. The supernatants containing the secreted antibody was saved for further analysis and the plasma cells in each well were frozen at −80 degrees celcius in media containing 10% DMSO and 90% FCS. For hybridoma technology, the cells from the remaining hyperimmune transgenic mice were harvested on day 31, 37 or 46 for further analysis as shown in FIG. 1.

For XenoMax technology, supernates from the B cell cultures were screened by ELISA for the presence of antibodies to TR-2. Anti-TR-2 antibodies were detected by assessing binding to immobilized TR-2-His using an anti-human IgG antibody detection reagent as follows. Plates were coated with soluble TR-2-His (0.5 µg/ml) by passive adsorption overnight at 4° C. After washing the plates five times with water and blocking the wells in the plates with milk for 30 minutes, 10 µL cell culture supernate from each individual hybridoma was combined with 40 µL milk and incubated in the wells of different plates for 1 hour, 1.25 hours, or 2 hours. The plates were washed five times with water, and incubated with a goat anti-human IgG Fc-specific horseradish peroxidase (Pierce)-conjugated antibody at a final concentration of 1 µg/mL for 1 hour at room temperature. After washing the plates five times with water, the plates were incubated with K blue substrate (Neogen) for 30 minutes. Negative controls included blank wells lacking TR-2-His and wells using naive G2 sera expected to lack anti-TR-2 antibodies. Positive samples were screened by ELISA a second time against TR-2-His to confirm the identity of cells producing antibodies specific for TR-2.

The antibodies reactive with TR-2, identified above, were screened for their ability to induce apoptosis of WM-266 melanoma cells (ATCC Cat. No. CRL-1676) using an apoptosis assay. WM-266 cells were cultured in a microtiter plate at a density of 4500 cells/well in normal culture medium as recommended by ATCC overnight. For B cell cultures, 20 µL of antigen-specific B cell culture supernatant or control B cell culture supernatant was added to 180 µL of apoptosis medium mixture (cell culture medium containing 1 µg/mL cycloheximide (CHX) and 0.5% fetal calf serum ("FCS")). The culture media from the WM-266 cells was removed and the antibody-apoptosis medium mixture was added to the cells one row at a time. The cells were incubated with the antibody-apoptosis medium for 20 hours to allow apoptosis to occur. The DNA-binding fluorescent dyes propidium iodide (Sigma) and Hoechst 33342 (Molecular Probes) were added to each well at a final concentration of 0.5 µg/mL and 2.5 µg/mL, respectively. Hoechst 33342 is membrane-permeable, and thus labels both live and dead cells; propidium iodide is not membrane-permeable, and thus labels only dead cells. After one hour at 37° C., images of each well were captured and analyzed for total number of cells (by assessing the amount of Hoechst label) and total number of dead cells (by assessing the amount of propidium iodide label). The percent apoptosis was determined as (propidium iodide-positive cells/Hoechst-positive cells)×100.

For XenoMax technology, the antibodies from several wells that displayed the best induction of apoptosis were selected for rescue using the haemolytic plaque assay. TR-2-His was biotinylated and coated onto streptavidin-coated sheep red blood cells. Plasma cells corresponding to antigen-specific wells were thawed and incubated with the antigen-coated red blood cells in the presence of complement and guinea pig anti-human IgG enhancing serum. Plasma cells producing antibodies against TR-2-His caused the sheep red blood cells around them to lyse and thus allowed the identification of antigen-specific plasma cells in the mixture. Those plasma cells were isolated by micromanipulation of single cells from the mixture.

After isolation of the desired single plasma cells, mRNA was extracted from those cells. The mRNAs encoding the heavy and light chain variable sequences were converted to cDNA and amplified by reverse transcriptase PCR using degenerate antisense primers specific for the leader sequences and the constant regions of human IgG2 and human kappa mRNA The primer sequences are provided in Table 2 below:

TABLE 2

| Primer Name | Primer seq |
|---|---|
| AS-Ck RT | 5' GTA GGT GCT GTC CT 3'<br>(SEQ ID NO: 97) |
| AS-γCH1 RT | 5' TGA GTT CCA CGA CA 3'<br>(SEQ ID NO: 98) |
| AS-C Lambda RT | 5' CTT CCA AGC CAC T 3'<br>(SEQ ID NO: 99) |
| AS-C Lambda RT | 5' CA (GA) GC ACT GTC A 3'<br>(SEQ ID NO: 100) |
| AS-Ck outer | 5' GTA GGT GCT GTC CTT GCT 3'<br>(SEQ ID NO: 101) |
| AS-Ck middle | 5' CTC TGT GAC ACT CTC CTG GGA 3'<br>(SEQ ID NO: 102) |
| AS-Ck inner with Xba I | 5' GCT CTA GAT TGG AGG GCG TTA TCC ACC TTC CAC T 3'<br>(SEQ ID NO: 103) |
| AS-Ck inner with Nhe I | 5' AAC TAG CTA GCA GTT CCA GAT TTC AAC TGC TCA TCA GAT 3'<br>(SEQ ID NO: 104) |
| AS-CL outer | 5' GCT CCC GGG TAG AAG TCA 3'<br>(SEQ ID NO: 105) |
| AS-CL middle | 5' AC(CT) AGT GTG GCC TTG TTG GCT T 3'<br>(SEQ ID NO: 106) |
| AS-CL inner | 5' GCT CTA GAG GG(CT) GGG AAC AGA GTG AC 3'<br>(SEQ ID NO: 107) |
| ASγ-CH1 outer | 5' ACG ACA CCG TCA CCG GTT 3'<br>(SEQ ID NO: 108) |
| ASγ-CH1 middle | 5' AAG TAG TCC TTG ACC AGG CAG CCC A 3'<br>(SEQ ID NO: 109) |
| ASγ-CH1 inner with Xba I (G1 specific) | 5' GCT CTA GAG GGT GCC AGG GGG AAG ACC GAT 3'<br>(SEQ ID NO: 110) |
| ASγ-CH1 inner with Xba I (G2, G3 &G4 specific) | 5' GCT CTA GAG CAG GGC GCC AGG GGG AAG A 3'<br>(SEQ ID NO: 111) |
| S-Vk1&2 Leader outer | 5' ATG AGG (CG)TC CC(CT) GCT CAG CT 3'<br>(SEQ ID NO: 112) |
| S-Vk3 Leader outer | 5' ATG GAA (AG)CC CCA GC(GT) CAG CTT 3'<br>(SEQ ID NO: 113) |
| S-Vk4 Leader outer | 5' ATG GTG TTG CAG ACC CAG GTC T 3'<br>(SEQ ID NO: 114) |
| S-Vk1&2 Leader inner with Bgl II | 5' GAA GAT CTC ACC ATG AGG (CG)TC CC(CT) GCT CAG CT(CT) CT 3'<br>(SEQ ID NO: 115) |
| S-Vk3 Leader inner with Bgl II | 5' GAA GAT CTC ACC ATG GAA (AG)CC CCA GC(GT) CAG CTT CTC TT 3'<br>(SEQ ID NO: 116) |
| S-Vk4 Leader inner with Bgl II | 5' GAA GAT CTC ACC ATG GTG TTG CAG ACC CAG GTC TTC AT 3'<br>(SEQ ID NO: 117) |
| S-VL1-4 Leader outer | 5' C(GA)T C(AT)C CAC CAT G(GA)C (CA)(TA)G 3'<br>(SEQ ID NO: 118) |
| S-VL1 Leader outer | 5' CAC CAT G(GA)C C(TA)G (GC)T(CT) CCC T 3'<br>(SEQ ID NO: 119) |

TABLE 2-continued

| Primer Name | Primer seq |
|---|---|
| S-VL2 Leader outer | 5' ACC ATG GCC TGG (GA)CT C(TC)(GT) CT 3'<br>(SEQ ID NO: 120) |
| S-VL3 Leader outer | 5' CAC CAT GGC (CA)TG G(GA)(TC) C(CGA)(CT) T 3'<br>(SEQ ID NO: 121) |
| S-VL4 Leader outer | 5' CAC CAT GGC (CT)TG G(GA)(TC) CC(CA) A(CT)T 3'<br>(SEQ ID NO: 122) |
| S-VL1 Leader inner with Bgl II | 5' GAA GAT CTC ACC ATG (GA)CC (TA)G(GC) T(CT)C CCT CT 3'<br>(SEQ ID NO: 123) |
| S-VL2 Leader inner with Bgl II<br>(Also amplifies VL5-7, 9, 10) | 5' GAA GAT CTC ACC ATG GCC TGG (GA)CT C(TC) (GT) CT(CG) (TC)T 3'<br>(SEQ ID NO: 124) |
| S-VL3 Leader inner with Bgl II | 5' GAA GAT CTC ACC ATG GC(CA) TGG (GA)(TC)C (CGA)(CT)T CTC 3'<br>(SEQ ID NO: 125) |
| S-VL4 Leader inner with Bgl II | 5' GAA GAT CTC ACC ATG GC(CT) TGG (GA)(TC)C C(CA)A (CT)TC 3'<br>(SEQ ID NO: 126) |
| S-VH1 Leader outer | 5' CAC CAT GGA (GC)TG GAC CTG GAG (GCA)(AGTC)T C 3'<br>(SEQ ID NO: 127) |
| S-VH2 Leader outer | 5' CAC CAT GGA CAT ACT TTG (CT)TC CAC GCT C 3'<br>(SEQ ID NO: 128) |
| S-VH3 Leader outer | 5' CAC CAT GGA [AG]TT [TG]GG [AG]CT [GCT][ACT]G CT 3'<br>(SEQ ID NO: 129) |
| S-VH4 Leader outer | 5' CAC CAT GAA [AG]CA [TC]CT GTG GTT CTT CCT [TC]CT 3'<br>(SEQ ID NO: 130) |
| S-VH5 Leader outer | 5' CAC CAT GGG GTC AAC CG[CT] CAT CCT 3'<br>(SEQ ID NO: 131) |
| S-VH6 Leader outer | 5' CAC CAT GTC TGT CTC CTT CCT CAT CTT C 3'<br>(SEQ ID NO: 132) |
| S-VH1 Leader inner with Bgl II | 5' GAA GAT CTC ACC ATG GA[GC] TGG ACC TGG AG[GCA] [AGTC]TC C 3'<br>(SEQ ID NO: 133) |
| S-VH2 Leader inner with Bgl II | 5' GAA GAT CTC ACC ATG GAC ATA CTT TG[CT] TCC ACG CTC C 3'<br>(SEQ ID NO: 134) |
| S-VH3 Leader inner with Bgl II | 5' GAA GAT CTC ACC ATG GA[AG] TT[TG] GG[AG] CT[GCT] [ACT]GC TGG (GAC)TT TT(TC) CT 3'<br>(SEQ ID NO: 135) |
| S-VH4 Leader inner with Bgl II | 5' GAA GAT CT C ACC ATG AA[AG] CA[TC] CTG TGG TTC TTC CT[TC] CTC 3'<br>(SEQ ID NO: 136) |
| S-VH5 Leader inner with Bgl II | 5' GAA GAT CTC ACC ATG GGG TCA ACC G[CT]C ATC CT 3'<br>(SEQ ID NO: 137) |
| S-VH6 Leader inner with Bgl II | 5' GAA GAT CTC ACC ATG TCT GTC TCC TTC CTC ATC TTC T 3'<br>(SEQ ID NO: 138) |
| S-VH7 Leader inner with Bgl II | 5' GAA GAT CTC ACC ATG GAC TGG ACC TGG AGG ATC CTC TTC TTG GT 3'<br>(SEQ ID NO: 139) |

The primers introduced the following restriction sites at the 5' end (BgIII) and the 3' end (Xba1) of the heavy chain cDNA. Similarly, the primers introduced the following restriction sites at the 5' end (BgIII) and the 3' end (NheI) of the kappa chain cDNA.

The variable heavy chain cDNA amplicon was digested with appropriate restriction enzymes for the restriction enzyme sites that were added during the PCR reaction. The products of that digestion were cloned into each of an IgG1, IgG2, and IgG4 expression vector with compatible overhangs for cloning. The IgG2 and IgG4 expression vectors were digested with BamHI and XbaI to generate compatible overhangs for sub-cloning. The IgG1 expression construct was digested with BamHI and NheI to generate compatible overhangs for sub-cloning. These vectors were generated by cloning the constant domain of human IgG1, IgG2 or IgG4 into the multiple cloning site of the vector pcDNA3.1+/Hygro (Invitrogen).

The variable light chain cDNA amplicon was also digested with appropriate restriction enzymes for the restriction enzyme sites that were added during the PCR reaction. The products of that digestion were cloned into an IgK expression vector that had been digested with BamHI and NheI to provide compatible overhangs for sub-cloning. That vector was generated by cloning the constant domain of the human IgK gene into the multiple cloning site of the vector pcDNA4.1+/Neo (Invitrogen).

The heavy chain and the light chain expression vectors were then co-lipofected into a 60 mm dish of 70 % confluent human embryonal kidney 293 cells (ATCC, Cat. No. CRL-1573). For 24 hours, the transfected cells were allowed to secrete a recombinant antibody with the identical specificity as the original plasma cell. The supernatant (3 mL) was harvested from the HEK 293 cells and the secretion of an intact antibody was demonstrated with a sandwich ELISA to specifically detect human IgG. Control plates were coated with 2 mg/mL Goat anti-human IgG H+L O/N as for binding plates. The plates were washed five times with water. Recombinant antibodies were titrated 1:2 for 7 wells from the undiluted lipofection supernatant. The plates were washed five times with dH2O. A goat anti-human IgG Fc-specific HRP-conjugated antibody was added at a final concentration of 1 µg/mL for 1 hour at room temperature for the secretion and the two binding assays. The plates were washed five times with dH2O. The plates were developed with the addition of tetramethylbenzidine (TMB) for 30 minutes and the ELISA was stopped by the addition of 1 M phosphoric acid.

In addition to the XenoMax methodology described above, certain antibodies were obtained using hybridoma technology. Immunized mice were sacrificed by cervical dislocation, and the draining lymph nodes were harvested and pooled from each cohort. The lymphoid cells were dissociated by grinding in Dulbecco's Modified Eagle's Medium ("DMEM") to release the cells from the tissues. Recovered cells were suspended in DMEM. The cells were counted, and 0.9 mL DMEM per 100 million lymphocytes was added to the cell pellet to resuspend the cells gently but completely. The resuspended cells were incubated with 100 µL of CD90$^+$ magnetic beads per 100 million cells at 4° C. for 15 minutes. The magnetically-labeled cell suspension (containing up to $10^8$ positive cells (or up to $2 \times 10^9$ total cells)) was loaded onto an LS$^+$ column. The column was washed with DMEM. The total effluent was collected as the CD90$^-$negative fraction, which was expected to contain mostly B cells.

The fusion was performed by mixing washed enriched B cells from above and nonsecretory myeloma P3X63Ag*.653 cells (ATCC (CRL 1580, see, e.g., Kearney et al., J. Immunol. 123, 1979, 1548-1550)) at a ratio of 1:1. The cell mixture was gently pelleted by centrifugation at 800 ×g. After complete removal of the supernatant from the cells, the cells were treated with 2 to 4 ml of Pronase solution (CalBiochem; 0.5 mg/ml in phosphate-buffered saline ("PBS")) for no more than 2 minutes. Three to five mL of fetal bovine serum ("FBS") was added to stop the enzyme activity and the suspension was adjusted to a 40 mL total volume using electro cell fusion solution ("ECFS") (0.3 M sucrose, 0.1 mM magnesium acetate, 0.1 mM calcium acetate). The supernatant was removed after centrifugation and the cells were resuspended in 40 mL ECFS. This wash step was repeated and the cells again were resuspended in 40 mL ECFS to a concentration of $2 \times 10^6$ cells/mL.

Electro-cell fusion was performed using a fusion generator (model ECM2001, Genetronic, Inc.). The fusion chamber size used was 2.0 mL, using the following instrument settings: alignment condition: 50 V, 50 seconds; membrane breaking at 3000 V, 30 microseconds; post-fusion holding time: 3 seconds.

After electro-cell fusion took place, the cell suspensions were carefully removed from the fusion chamber under sterile conditions and transferred into a sterile tube containing the same volume of hybridoma culture medium, containing DMEM, (JRH Biosciences), 15 % FBS (Hyclone), supplemented with L-glutamine, penicillin/streptomycin, OPI (oxaloacetate, pyruvate, bovine insulin), and IL-6 (Boehringer Mannheim). The cells were incubated for 15 to 30 minutes at 37° C., and then centrifuged at 400 ×g (1000 rpm) for 5 minutes. The cells were gently resuspended in a small volume of hybridoma selection medium (hybridoma culture medium supplemented with 0.5 × hyaluronic acid (Sigma)). The total volume was adjusted appropriately with more hybridoma selection medium based on a final plating volume of $5 \times 10^6$ B cells total per 96-well plate and 200 µL per well. The cells were mixed gently, pipetted into 96-well plates, and allowed to grow. On day 7 or 10, one-half the medium was removed, and the cells were re-fed with fresh hybridoma selection medium.

After 14 days of culture, hybridoma supernatants were screened for TR2-specific monoclonal antibodies by ELISA. In the Primary screen, the ELISA plates (Fisher, Cat. No. 12-565-136) were coated with 50 µL/well of TR2 protein (2 µg/mL) in Coating Buffer (0.1 M Carbonate Buffer, pH 9.6, NaHCO$_3$ 8.4 g/L), then incubated at 4° C. overnight. After incubation, the plates were washed with Washing Buffer (0.05 % Tween 20 in PBS) one time. 200 µL/well Blocking Buffer (0.5 % BSA, 0.1 % Tween 20, 0.01 % Thimerosal in 1 × PBS) were added and the plates were incubated at room temperature for 1 hour. After incubation, the plates were washed with Washing Buffer one time. Aliquots (50 µL/well) of hybridoma supernatants and positive and negative controls were added, and the plates were incubated at room temperature for 2 hours. The positive control used throughout was serum from a hyperimmune XenoMouse animal and the negative control was serum from the KLH-immunized XenoMouse animal. After incubation, the plates were washed three times with Washing Buffer. 100 µL/well of detection antibody goat anti-huIgGFc-HRP (Caltag Inc., Cat. No. H10507, using concentration was 1:2000 dilution) was added and the plates were incubated at room temperature for 1 hour. After incubation, the plates were washed three times with Washing Buffer. 100 µl/well of TMB (BioFX Lab. Cat. No. TMSK-0100-01) was added, and the plates were allowed to develop for about 10 minutes (until negative control wells barely started to show color). 50 µl/well stop solution (TMB Stop Solution (BioFX Lab. Cat. No. STPR-0100-01) was then added and the plates were read on an ELISA plate reader at a wavelength of 450 nm.

The antibodies produced by the hybridomas were analyzed using the same apoptosis assay described above. WM-266 cells were cultured at a density of 4500 cells/well in normal culture medium overnight in a microtiter plate. A 2× apoptosis medium mixture was prepared using cell culture medium without FCS and additionally including 1.8 µg/mL cycloheximide and 0.9 % FCS. Separate microtiter plates were used to titrate hybridoma supernatant 1:2 (in the 2× apoptosis medium mixture) in parallel with an isotype-matched negative control anti-KLH antibody. The culture media was removed from the WM-266 cells and 100 µL of the antibody-apoptosis medium mixture was added to each cell-containing well, one row at a time. The microtiter plates were incubated for 20 hours to allow apoptosis to occur. The DNA-binding fluorescent dyes propidium iodide (Sigma) and Hoechst 33342 (Molecular Probes) were added to each well at a final concentration of 0.5 µg/mL and 2.5 µg/mL respectively. After 1 hour at 37° C., fluorescent images of each well were captured and analyzed for total number of dead cells (PI) and total number of cells (Hoechst). The percent apoptosis was determined as (PI-positive cells/Hoechst-positive cells)×100.

Seventeen different anti-TR-2 antibodies were obtained (Antibodies A-Q) using either the XenoMax or hybridoma methodologies. All of the antibodies were sequenced, and the sequences of the heavy and light chain variable regions identified (see FIGS. 3-19). Alignments of the heavy chains and the light chains of the seventeen antibodies are shown in FIGS. 20 and 21.

Certain antibodies were examined for their ability to induce apoptosis in cells, using a similar apoptosis assay to the one described above. WM-266 melanoma cells were cultured in a microtiter plate at a density of 4500 cells/well in normal culture medium overnight. In a separate microtiter plate, the recombinant antibodies to be tested, an appropriate positive control (M413, a mouse IgG1 anti-TR-2 antibody having a heavy chain variable sequence: MEVQLVESGGGLVQPGGSLKLSCAASG-FTFSTYGMSWVRQTPDKRLELVA LINSQGGSTYNS-DSVKGRFTISRDNARNTLYLQMSSLK-SEDTAMYYCARRD YESLDSWGQGTSVTVSSG (SEQ ID NO: 141) and a light chain variable sequence: DIVLTQS-PASLPVSLGQRATISCRASESVEY-SGTSLIQWYRQKPGQPPKLLIY AASNVDSEVPARFSG SGSGTDFSLYIHPVEEDDIAMYFCQQSRKVPWTFGG GTKLEIKRTDAAPGLEAA (SEQ ID NO: 142)), and isotype-matched negative control antibodies (a potential anti-TR2 antibody that failed to show activity) were titrated such that the final concentration of antibody would cover a range of 0.0001 µg/mL to 5 µg/mL. The antibodies were mixed in apoptosis medium containing a final concentration of 0.9 µg/mL CHX and 0.45 % FCS. The culture media was removed from the WM-266 cells and the antibody-apoptosis medium mixture was added to the cells. After 20 hours of culture, the cells were stained with propidium iodide (Sigma) and Hoechst 33342 (Molecular Probes). After 1 hour at 37° C., an image of each well was captured and analyzed for total number of dead cells (PI) and total number of cells (Hoechst). The percent apoptosis was determined as (PI-positive cells/Hoechst-positive cells)×100. Significant cell death was observed in cells treated with M413 or with certain anti-TR-2 antibodies described above.

Example 2

Kinetic Analyses of Anti-TR-2 Antibody Binding to TR-2

The kinetics of the binding of anti-TR-2 antibodies A to Q to TR-2 was analyzed using a Biacore® 2000 instrument. High-density goat anti-human antibody surfaces were prepared on CM-5 Biacore® chips using routine amine coupling. Each purified anti-TR-2 antibody was diluted to approximately 1 µg/ml in HBS-P running buffer containing 100 µg/ml BSA. Each anti-TR-2 antibody was captured on a separate surface using a two minute contact time and a five minute wash to stabilize the anti-TR-2 antibody surface on the chip.

To analyze the kinetics of TR-2 binding to each individual anti-TR-2 antibody, 226 nM recombinant human TR-2-His (described in Example 1) was kinetically injected over each anti-TR-2 surface for one minute (using kinject) at 25° C., followed by a five minute dissociation period. The baseline drift resulting from a buffer injection lacking TR-2 over the anti-TR-2 antibody surface was subtracted from the observed binding on each of the other surfaces. Additionally, the data for TR-2 binding to anti-TR-2 antibody were normalized for the amount of monoclonal antibody captured on each surface. Each data set was fit globally to a 1:1 interaction model to determine binding kinetics. The $k_a$, $k_d$, and $K_d$ values obtained for each antibody are shown in Table 3.

TABLE 3

| Kinetics of TR-2 binding to anti-TR-2 antibody at 25° C. | | | |
|---|---|---|---|
| Antibody | $k_a$ (M$^{-1}$s$^{-1}$) | $k_d$ (s$^{-1}$) | $K_d$ (nM) |
| A | 5.3 × 10$^5$ | 3.7 × 10$^{-3}$ | 6.9 |
| B | 5.7 × 10$^5$ | 1.1 × 10$^{-2}$ | 19 |
| C | 6.8 × 10$^5$ | 2.6 × 10$^{-3}$ | 3.9 |
| D | 6.2 × 10$^5$ | 2.7 × 10$^{-3}$ | 4.5 |
| E | 8.7 × 10$^5$ | 1.8 × 10$^{-3}$ | 2.1 |
| F | 3.8 × 10$^5$ | 5.0 × 10$^{-3}$ | 13 |
| G | 6.0 × 10$^5$ | 1.9 × 10$^{-2}$ | 31 |
| H | 8.6 × 10$^5$ | 8.4 × 10$^{-3}$ | 9.8 |
| I | 2.9 × 10$^5$ | 1.3 × 10$^{-3}$ | 4.4 |
| J | 5.7 × 10$^5$ | 7.1 × 10$^{-3}$ | 12 |
| K | 6.8 × 10$^5$ | 1.2 × 10$^{-2}$ | 18 |
| L | 6.0 × 10$^5$ | 1.1 × 10$^{-2}$ | 18 |
| M | 3.4 × 10$^5$ | 1.2 × 10$^{-2}$ | 37 |
| N | 8.1 × 10$^5$ | 5.5 × 10$^{-2}$ | 68* |
| O | 4.4 × 10$^5$ | 8.4 × 10$^{-3}$ | 19 |
| P | 8.1 × 10$^5$ | 2.7 × 10$^{-2}$ | 33* |
| Q | 1.2 × 10$^6$ | 1.6 × 10$^{-2}$ | 13* |

*Data for that sample exhibited heterogeneity and fit poorly to a 1:1 model.

Example 3

Cell Killing Assays

Cell killing assays were performed with certain human anti-TR-2 antibodies described in Example 2 to determine the degree to which each antibody triggered apoptosis and cell death. Certain human anti-TR-2 antibodies, as well as mouse anti-TR-2 antibodies M412 and M413, were immobilized in separate wells of 96-well Protein G-coated plates (reactin-bind Protein G coated plates, Pierce Cat. No. 15131). M412 is a mouse IgG1 anti-TR-2 antibody having a heavy chain variable sequence: KVQLQQSGTELVKPGASVKLSCKAS-GYTFTEYIIHWVKQRSGQGLEWIGWF YPGSGY-IKYNEKFKDKATMTADKSSSTVYMELSRLTSEDSAV YFCTRHEED GYYAAYWGQGTLVTVSA (SEQ ID NO: 143) and a light chain variable sequence: DIVMTQSHK-FMSTSVGDRVSITCKASQDVSSAVAW-YQQKPGQSPKLLIYWA STRHTGVPDRFTGSGSGT-DYTLTISSVQAEDLALYYCQQHYSTPYTFGGGT KLEIKR (SEQ ID NO: 144). M413 is a mouse IgG1 anti-TR-2 antibody as described above in Example 1. Each antibody was added at a concentration of 50 µg/ml to a first well, and serially diluted 1:3× in each of seven additional wells. Each antibody dilution was performed in triplicate. Plates were incubated for 24 hours at 4° C. prior to use. Following the washing of each well with culture media (RPMI plus 10 % FBS), one of four different cell lines was plated onto each immobilized antibody, at a density of 50,000 cells per well in a total volume of 200 µL. The cell lines tested were COLO 205 cells (human colon adenocarcinoma), MDA-231 cells (human breast cancer), WM35 cells (human melanoma), and WM793 cells (human melanoma). Cells were incubated at 37° C./6 % $CO_2$ for 24 hours, followed by a 6 hour incubation with $^3$H-thymidine. The percentage of viable cells was assessed by determining the level of $^3$H-thymidine incorporation in the treated cells relative to the level of $^3$H-thymidine incorporation into the untreated cells. The $ED_{50}$ of each antibody was derived from the cell viability titration curve by determining the concentration of antibody that reduced the viability of treated cells by 50 % relative to untreated cells. The $ED_{50}$ of the human antibodies for COLO 205 cells ranged from 0 μg/ml to 3.25 μg/ml. The mouse antibodies M412 and M413 had $ED_{50}$s of 1.85 μg/ml and 0.07 μg/ml, respectively, for those cells. The $ED_{50}$ of the human antibodies for MDA-231 cells ranged from 0.05 μg/ml to 0.5 μg/ml. The mouse antibodies M412 and M413 had $ED_{50}$s of 0.6 μg/ml and 0.07 μg/ml, respectively, for those cells. The $ED_{50}$ of the human antibodies for WM35 cells ranged from 0.1 μg/ml to 0.6 μg/ml. The mouse antibodies M412 and M413 had $ED_{50}$s of 1.85 μg/ml and 0.07 μg/ml, respectively, for those cells. The $ED_{50}$ of the human antibodies for WM793 cells ranged from 0.02 μg/ml to 0.2 μg/ml. The mouse antibodies M412 and M413 had $ED_{50}$s of 1.85 μg/ml and 0.05 μg/ml, respectively, for those cells.

Example 4

Human TR-2 Expression in Tumor Cell Lines

Human tumor cell lines were screened for expression of TR-2. Cell lines used included those from breast, central nervous system, colon, liver, lung, cervix, uterine, ovarian, pancreatic, prostate, and renal cancers, as well as leukemia and melanoma.

The expression of TR-2 on human tumor cells was determined using a cell-based array. Briefly, $4\times10^5$ cells in 100 MI CBA buffer (PBS, 3 % FBS, 0.02 % Azide) were distributed into each of the wells of 20 V-bottom 96-well plates. CBA buffer (150 μL) was added to each well and the plates were centrifuged to spin down the cells. The medium was discarded and 100 μL of antibody solution (one of the antibodies A to Q) at 10 μg/ml was added to the cell pellet resuspended in PBS containing 2 % PBS ("assay buffer"). After a 25 minute incubation on ice, the cells were washed once in assay buffer. 100 μL of a secondary goat anti-human IgG Fc-specific horseradish peroxidase (HRP, Pierce) was added to the wells, and the plates were incubated on ice for 20 minutes. The plates were washed twice with assay buffer, and 100 μL of the TMB substrate (ZYMED) was added for 10 minutes at room temperature. The plates were centrifuged and 50 μL of each supernate was transferred into a clean plate containing 50 μL stop solution (BioFX Laboratories). Optical density readings were performed at 450 nm using the SpectraMax/plus reader (Molecular Devices). The data were normalized by subtracting the optical density values obtained from an isotype control antibody.

Several cell lines had an $OD_{450}$ greater than 0.1 in the assay, including breast cancer cell lines HS 578.T (OD of 0.122) and T-47 D (OD of 0.112), colon cancer cell lines TE 671 (u) (OD of 0.109), HT-29 (OD of 0.193), SW-948 (OD of 0.122), KM-12 (OD of 0.354), and HCC-2998 (OD of 0.133), liver cancer cell lines NCI-N87 (OD of 0.154) and NCI-SNU-5 (OD of 0.137), leukemia cell lines HL-60 (OD of 0.233) and hPBMC (OD of 0.131), non-small-cell lung cancer cell line JY (OD of 0.118), CCRF-CEM (OD of 0.106), NCI-H2126 (OD of 0.108) and NCI-H460 (OD of 0.122), melanoma cell lines SK-mel-5 (OD of 0.131), LOX IMVI (OD of 0.102), RPMI 7951 (OD of 0.101), and UACC-62 (OD of 0.127), pancreas cancer cell lines HPAF II (OD of 0.117) and CAPAN-1 (OD of 0.101), prostate cancer cell line LNCaP (OD of 0.174), and renal carcinoma cell lines Caki-1 (OD of 0.148) and UO-31 (OD of 0.104). The greatest expression of TR-2 among the tumor cell lines studied was found in colon cancer cell lines KM-12 and HT-29, and in leukemia cell line HL-60. None of the central nervous system, small-cell liver, cervical, uterine, or ovarian cancer cell lines studied had an OD450 greater than background.

To determine TR-2 expression profile on human tumor cell lines, the above human tumor cell lines were assayed with the mouse anti-TR-2 antibody M412. The expression of TR-2 on human tumor cells was determined using a cell-based array. Briefly, $4\times10^5$ cells in 100 MI CBA buffer (PBS, 3 % FBS, 0.02 % Azide) were distributed into each of the wells of 20 V-bottom 96-well plates. CBA buffer (150 μL) was added to each well and the plates were centrifuged to spin down the cells. The medium was discarded and 100 μL of mouse anti-TR-2 monoclonal antibody M412 at 10 μg/ml was added to the cell pellet resuspended in PBS containing 2 % PBS ("assay buffer"). After a 25 minute incubation on ice, the cells were washed once in assay buffer. 100 μL of a secondary goat anti-mouse IgG Fc-specific horseradish peroxidase (HRP, Pierce) was added to the wells, and the plates were incubated on ice for 20 minutes. The plates were washed twice with assay buffer, and 100 μL of the TMB substrate (ZYMED) was added for 10 minutes at room temperature. The plates were centrifuged and 50 μL of each supernate was transferred into a clean plate containing 50 μL stop solution (BioFX Laboratories). Optical density readings were performed at 450 nm using the SpectraMax/plus reader (Molecular Devices). The data were normalized by subtracting the optical density values obtained from an isotype control antibody.

Many of the cell lines had TR-2 expression. The highest expressors (those with an OD450 nm greater than 0.3) included breast cancer cell lines HS 578.T (OD of 0.403), MDA-MB-231 (OD of 0.408), and T-47 D (OD of 0.366), CNS cancer cell lines SF-295 (OD of 0.354) and U251 (OD of 0.323), colon cancer cell lines HCT-116 (OD of 0.41), HT-29 (OD of 0.869), SW-707 (OD of 0.323), SW-948 (OD of 0.423), KM-12 (OD of 0.77), and HCC-2998 (OD of 0.635), liver cancer cell line NCI-SNU-1 (OD of 0.354), leukemia cell line A 673 (OD of 0.347), non-small-cell lung cancer cell lines HOP-62 (OD of 0.313), HOP-62 (OD of 0.47), NCI-H2126 (OD of 0.501), NCI-H460 (OD of 0.326), small cell lung cancer line A549 (OD of 0.381), melanoma cell lines LOX IMVI (OD of 0.573), RPMI 7951 (OD of 0.322), and UACC-62 (OD of 0.319), ovarian cancer cell line IGROV1 (OD of 0.312), prostate cancer cell lines DU 145 (OD of 0.372), 22 Rv1 (OD of 0.301), and LNCaP (OD of 0.63), and renal carcinoma cell lines Caki-1 (OD of 0.93), Caki-2 (OD of 0.443), SN12 C (OD of 0.313), and UO-31 (OD of 0.331). The greatest expression of TR-2 among the tumor cell lines treated with mouse anti-TR-2 antibody was found in renal carcinoma cell line Caki-1, and in colon cancer cell lines HT-29 and KM-12.

Example 5

Antibody Cross-Reactivity

The ability of certain of the human anti-TR-2 antibodies to block the binding of the others to TR-2 was assessed, as described in Jia et al., J. Immunol. Methods 288: 91-98 (2004). The beads were conjugated with anti-human IgG antibodies using the coupling procedure taken directly from the Luminex 100 User's Manual, Version 1.7. After the beads were activated, they were coupled to a Pharmingen mouse anti-hIgG mAb, following the manufacturer's instructions.

Two experiments were performed. In a first experiment, the coated beads were incubated for two hours at room temperature. In a second experiment, the coated beads were incubated overnight at 4° C. At the end of the incubation, the coated beads were blocked and then counted using a Coulter cell counter. Conjugated beads were either used immediately or were stored at 4° C. in the dark for future use.

The categorization of the anti-TR-2 antibodies based on epitope cross-reactivity was performed by the following steps. First, each set of bead-mouse anti-hIgG complexes from above were separately incubated with a reference antibody ("reference antibody") on a rotator overnight at 4° C. The reference antibody was selected from anti-TR-2 antibodies A-Q, described above. After antibody capture, 2000 of each bead-mouse anti-hIgG-reference Ab complexes were pooled together in one tube, and then immediately added to each well of a 96-well plate and aspirated. TR-2 (50 ng) was added to each well and incubated for 1 hour at room temperature. After washing the wells, 100-500 ng/mL of another of the human anti-TR-2 antibodies (the "probe antibody") was added to each well and incubated for 2 hours at room temperature. After washing the wells, bound probe antibody was detected using 1 µg/ml of a biotinylated version of the same monoclonal mouse anti-hIgG used for capturing the reference antibody. Following incubation and washing of the wells, 0.5 µg/ml streptavidin-phycoerythrin was added. The mixture was incubated for 30 minutes at room temperature and then the phycoerythrin signal was detected using the Luminex 100. An additional set of wells lacking antigen was used as a negative control to aid in data analysis.

The data was analyzed in a two-step process. First, the data was normalized using the negative control values. Second, the anti-TR-2 antibodies were clustered according to their ability to impede binding of one or more other anti-TR-2 antibodies. For the clustering analysis, a dissimilarity matrix was generated from the normalized intensity matrix. Antibodies were clustered based on the values in the average dissimilarity matrix using the SPLUS 2000 agglomerative nesting hierarchical clustering subroutine with the Manhattan metric, using an input dissimilarity matrix of the actual average dissimilarity matrix.

Based on the findings, the antibodies were placed into four different epitope groups. Within any one group, the binding of one of the group members to TR-2 blocks the binding of another member of the same group to TR-2. However, the binding of one of the members of group 1 to TR-2, for example, does not block the binding of one of the members of groups 2, 3, or 4 to TR-2. Those groups are shown in FIG. 22.

Example 6

Epitope Mapping

To identify the specific region of TR-2 important for binding to certain described anti-TR-2 antibodies, an epitope mapping study was performed. An N-avidin-TR-2 construct was made by PCR-amplifying the coding sequence for mature TR-2 (MacFarlane, 1997) from a template source and cloning it into a pCEP4 vector (Invitrogen) containing the chicken avidin sequence in an orientation such that upon insertion at a HindIII site, the TR-2 sequence was joined at the C-terminus of the avidin sequence. The forward primer for the mature TR-2 coding sequence was GTAAGCAAGCTTGGCTCTGATCACCCAACAAGA (SEQ ID NO: 145), and the reverse primer was GATTAGGGATCCAGAGGCAGGAGTCCCTGG (SEQ ID NO: 146). The amino acid sequence of the resulting avidin-TR-2 fusion protein was MVHATSPLLLLLL LSLALVAPGLSARKCSLTGKWTNDLGSNMTIGAVNSKGEFTGTYTTAVTATS NEIKESPLHGTQNTINKRTQPTFGFTVNWKFSESTTVFTGQCFIDRNGKEVL KTMWLLRSSVNDIGDDWKATRVGINIFTRLRTQKEQLLASLALITQQDLAPQ QRAAPQQKRSSPSEGLCPPGHHISEDGRDCISCKYGQDYSTHWNDLLFCL RCTRCDSGEVELSPCTTTRNTVCQCEEGTFREEDSPEMCRKCRTGCPRG MVKVGDCTPWSDIECVHKESGTKHSGEAPAVEETVTSSPGTPAS (SEQ ID NO: 69).

Twelve molecules comprising N-avidin and truncations of human TR-2 were synthesized as described below. Three molecules had only C-terminal truncations of human TR-2 (TR-2-1 through TR-2-3), and nine molecules had truncations at both the N- and the C-terminus of human TR-2 (TR-2-4 through TR-2-13) (shown schematically in FIG. 23). Polynucleotides encoding human TR-2 truncations were prepared by PCR amplification using the primers described below. To form each of the twelve molecules, the truncated human TR-2 resulting from the amplification was inserted into the pCEP4 vector (Invitrogen) containing the chicken avidin sequence that is described above. The polynucleotide encoding amino acids 1-43 of mature TR-2 was amplified using the forward primer GTAAGCAAGCTTGGCTCTGATCACCCAACAAGA (SEQ ID NO: 145) and the reverse primer TAGTTGGGATCCTCAGGAGATGCAATCTCT ACCGT (SEQ ID NO: 147). The amino acid sequence of TR-2-1 was MVHATSPLLLLLLLSLALVAPGLSARKCSLTGKWTNDLGSNMTIGAVNS KGEFTGTYTTAVTATSNEIKESPLH-GTQNTINKRTQPTFGFTVNWKFSESTT VFTGQCFIDRNGKEVLKTMWLLRSSVNDIGDDWKATRVGINIFTRLRTQKEQ LLASLALITQQDLAPQQRAAPQQKRSSPSEGLCPPGHHISEDGRDCIS (SEQ ID NO: 70).

The polynucleotide encoding amino acids 1-85 of mature TR-2 was amplified using the forward primer GTAAGCAAGCTTGGCTCTGATCACCCAACAAGA (SEQ ID NO: 145) and the reverse primer GGTAGTGGATCCTCACTGACACACTGTGTTTCTGG (SEQ ID NO: 148). The amino acid sequence of TR-2-2 was MVHATSPLLLLLLLSLALVAPGLSARKCSLTGKWTNDLGSNMTIGAVNSKG EFTGTYTTAVTATSNEIKESPLHGTQNTINKRTQPTFGFTVNWKFSESTTVFT GQCFIDRNGKEVLKTMWLLRSSVNDIGDDWKATRVGINIFTRLRTQKEQLLA SLALITQQDLAPQQRAAPQQKRSSPSEGLCPPGHHISEDGRDCISCKYGQD YSTHWNDLLFCLRCTRCDSGEVELSPCTTTRNTVCQ (SEQ ID NO: 71).

The polynucleotide encoding amino acids 1-126 of mature TR-2 was amplified using the forward primer GTAAGCAAGCTTGGCTCTGATC ACCCAACAAGA (SEQ ID NO: 145) and the reverse primer GTAATGGGATCCTC AGACACATTCGATGTCACTCC (SEQ ID NO: 149). The amino acid sequence of TR-2-3 was MVHATSPLLLLLLLSLALVAPGLSARKCSLTGKWTNDLGSNMTIGA VNSKGEFTGTYTTAVTATSNEIKESPLHGTQNTINKRTQPTFGFTVNWKFSE STTVFTGQCFIDRNGKEVLKTMWLLRSSVNDIGDDWKATRVGINIFTRLRTQ KEQLLASLALITQQDLAPQQRAAPQQKRSSPSEGLCPPGHHISEDGRDCISC KYGQDYSTHWNDLLFCLRCTRCDSGEVELSPCTTTRNTVCQCEEGTFREE DSPEMCRKCRTGCPRGMVKVGDCTPWSDIECV (SEQ ID NO: 72).

The polynucleotide encoding amino acids 16-43 of mature TR-2 was amplified using the forward primer GTAATGAAGCTTGCCACAACA AAAGAGGTCCAG (SEQ ID NO: 150) and the reverse primer TAGTTGGGAT CCTCAGGAGATGCAATCTCTACCGT (SEQ ID NO: 147). The amino acid sequence of TR-2-4 was MVHATSPLLLLLLLSLALVAPGLSARKCSLTGKWTNDLGSNMTIGAVNSKGE FTGTYTTAVTATSNEIKESPLHGTQNTINKRTQPTFGFTVNWKFSESTTVFT GQCFIDRNGKEVLKTMWLLRSSVNDIGDDWKATRVGINIFTRLRTQKEQLLA SLPQQKRSSPSEGLCPPGHHISEDGRDCIS (SEQ ID NO: 73).

The polynucleotide encoding amino acids 16-85 of mature TR-2 was amplified using the forward primer GTAATGAAGCTTGCCACAACAAA AGAGGTCCAG (SEQ ID NO: 150) and the reverse primer GGTAGTGGA TCCTCACTGACACACTGTGTTTCTGG (SEQ ID NO: 148). The amino acid sequence of TR-2-5 was MVHATSPLLLLLLLSLALVAPGLSARKCSLTGKWTNDL GSNMTIGAVNSKGEFTGTYTTAVTATSNEIKESPLHGTQNTINKRTQPTFGF TVNWKFSESTTVFTGQCFIDRNGKEVLKTMWLLRSSVN DIGDDWKATRVGI NIFTRLRTQKEQLLASLPQQKRSSPSEGLCPPGHHISEDGRDCISCKYGQDY STHWNDLLFCLRCTRCDSGEVELSPCTTTRNTVCQ (SEQ ID NO: 74).

The polynucleotide encoding amino acids 16-126 of mature TR-2 was amplified using the forward primer GTAATGAAGCTTGCCACAACAAA AGAGGTCCAG (SEQ ID NO: 150) and the reverse primer GTAATGGGATCCTCA GACACATTCGATGTCACTCC (SEQ ID NO: 149). The amino acid sequence of TR-2-6 was MVHATSPLLLLLLLSLALVAPGLSARKCSLTGKWTNDLGSNMTIGA VNSKGEFTGTYTTAVTATSNEIKESPLHGTQNTINKRTQPTFGFTVNWKFSE STTVFTGQCFIDRNGKEVLKTMWLLRSSVNDIGDDWKATRVGINIFTRLRTQ KEQLLASLPQQKRSSPSEGLCPPGHHISEDGRDCISCKYGQDYSTHWNDLL FCLRCTRCDSGEVELSPCTTTRNTVCQCEEGTFREEDSPEMCRKCRTGCP RGMVKVGDCTPWSDIECV (SEQ ID NO: 75).

The polynucleotide encoding amino acids 42-85 of mature TR-2 was amplified using the forward primer GATTGAAAGCTTGATCTCCTGCAAATATGGACAG (SEQ ID NO: 151) and the reverse primer GGTAGTGGATCCTCACTGACACACTGTGTTTCTGG (SEQ ID NO: 148). The amino acid sequence of TR-2-7 was MVHATSPLLLLLLLSLALVAPGLSARKCSLTGKWTNDLGSNMTIGAVNS KGEFTGTYTTAVTATSNEIKESPLHGTQNTINKRTQPTFGFTVNWKFSESTT VFTGQCFIDRNGKEVLKTMWLLRSSVNDIGDDWKATRVGINIFTRLRTQKEQ LLASLISCKYGQDYSTHWNDLLFCLRCTRCDSGEVELSPCTTTRNTVCQ (SEQ ID NO: 76).

The polynucleotide encoding amino acids 42-126 of mature TR-2 was amplified using the forward primer GATTGAAAGCTTGATCTCCTGCAAATATGGACAG (SEQ ID NO: 151) and the reverse primer GTAATGGGATCCTCAGACACATTCGATGTCACTCC (SEQ ID NO: 149). The amino acid sequence of TR-2-9 was MVHATSPLLLLLLLSLALVAPGLSARKCSLTGKWTNDLGSNMTIGA VNSKGEFTGTYTTAVTATSNEIKESPLHGTQNTINKRTQPTFGFTVNWKFSE STTVFTGQCFIDRNGKEVLKTMWLLRSSVNDIGDDWKATRVGINIFTRLRTQ KEQLLASLISCKYGQDYSTHWNDLLFCLRCTRCDSGEVELSPCTTTRNTVC QCEEGTFREEDSPEMCRKCRTGCPRGMVKVGDCTPWSDIECV (SEQ ID NO: 77).

The polynucleotide encoding amino acids 85-154 of mature TR-2 was amplified using the forward primer GTAATGAAGCTTGCAGTGCGAAGAAGGCACCT (SEQ ID NO: 152) and the reverse primer GATTAGGGATCCAGAGGCAGGAGTCCCTGG (SEQ ID NO: 146). The amino acid sequence of TR-2-10 was MVHATSPLLLLLLLSLALVAPGLSARKCSLTGKWTNDLGSNMTIGAVNSKG EFTGTYTTAVTATSNEIKESPLHGTQNTINKRTQPTFGFTVNWKFSESTTVFT GQCFIDRNGKEVLKTMWLLRSSVNDIGDDWKATRVGINIFTRLRTQKEQLLA SLQCEEGTFREEDSPEMCRKCRTGCPRGMVKVGDCTPWSDIECVHKESGT KHSGEAPAVEETVTSSPGTPAS (SEQ ID NO: 78).

The polynucleotide encoding amino acids 42-154 of mature TR-2 was amplified using the forward primer GATTGAAAGCTTGATCTCCTGC AAATATGGACAG (SEQ ID NO: 151) and the reverse primer GATTAGGGATCCA GAGGCAGGAGTCCCTGG (SEQ ID NO: 146). The amino acid sequence of TR-2-11 was MVHATSPLLLLLLLSLALVAPGLSARKCSLTGKWTNDLGSNMTIGAVN SKGEFTGTYTTAVTATSNEIKESPLHGTQNTINKRTQPTFGFTVNWKFSEST TVFTGQCFIDRNGKEVLKTMWLLRSSVNDIGDDWKATRVGINIFTRLRTQKE QLLASLISCKYGQDYSTHWNDLLFCLRCTRCDSGEVELSPCTTTRNTVCQC EEGTFREEDSPEMCRKCRTGCPRGMVKVGDCTPWSDIECVHKESGTKHS GEAPAVEETVTSSPGTPAS (SEQ ID NO: 79).

The polynucleotide encoding amino acids 16-66 of mature TR-2 was amplified using the forward primer TGATTGAAGCTTGCCACAACAA AAGAGGTCCAG (SEQ ID NO: 150) and the reverse primer GATGGAGGATCCT CAACACCTGGTGCAGCGCAAG (SEQ ID NO: 153). The amino acid sequence of TR-2-12 was MVHATSPLLLLLLLSLALVAPGLSARKCSLTGKWTNDLGSNMTI GAVNSKGEFTGTYTTAVTATSNEIKESPLHGTQNTINKRTQPTFGFTVNWKF SESTTVFTGQCFIDRNGKEVLKTMWLLRSSVNDIGDDWKATRVGINIFTRLR TQKEQLLASLPQQKRSSPSEGLCPPGHHISEDGRDCISYKYGQDYSTHWND LLFCLRCTRC (SEQ ID NO: 80).

The polynucleotide encoding amino acids 16-74 of mature TR-2 was amplified using the forward primer TGATTGAAGCTTGCCACAACA AAAGAGGTCCAG (SEQ ID NO: 150) and the reverse primer GTAAGTGGATCC TCAGCAGGGACTTAGCTCCACT (SEQ ID NO: 154). The amino acid sequence of TR-2-13 was MVHATSPLLLLLLLSLALVAPGLSARKCSLTGKWTNDLGSNMT IGAVNSKGEFTGTYTTAVTATSNEIKESPLHGTQNTINKRTQPTFGFTVNWK FSESTTVFTGQCFIDRNGKEVLKTMWLLRSSVNDIGDDWKATRVGINIFTRL RTQKEQLLASLPQQKRSSPSEGLCPPGH- HISEDGRDCISCKYGQDYSTHW NDLLFCLRCTRCDSGEVELS (SEQ ID NO: 81). Four molecules comprising N-avidin and truncations of TR-2 from cynomolgus monkey were synthesized as described below. The polynucleotide encoding amino acids 1 to 132 of mature cyno TR-2 was amplified using the forward primer GTTAGTAAGCTTGGCTCCAATCACCCGAC (SEQ ID NO: 155) and the reverse primer GTTGATGGATCCTTCTTTGTGGACACTCGAT (SEQ ID NO: 156). The amino acid sequence of cyno TR-2 (short) was MVHATSPLLLLLLLSLALVAPGLSARKCSLTGK-WTNDLGSNMTIGAVNSKGEFTGTYT TAVTATSNEIKESPLHGTQNTINKRTQPTFGFTVN-WKFSESTTVFTGQCFIDR NGKEVLKTMWLLRSSVNDIGDDWKATRV-GINIFTRLRTQKEQLLASLAPITR QSLDPQR-RAAPQQKRSSPTEGLCPPGHHISEDSRD-CISCKYGQDYSTHWN DFLFCLRCTKCDSGEVEVSSCTIIRN-TVCQCEEGTFREEDSPEICRKCRTG CPRGM-VKVKDCTPWSDIECPQRRIQT (SEQ ID NO: 82).

The polynucleotide encoding amino acids 1 to 154 of mature cyno TR-2 was amplified using the forward primer GTTAGTAAGCTTGGCTCCA ATCACCCGAC (SEQ ID NO: 155) and the reverse primer GTAGTTGGATCCTC AAGAAGCAGGAGTCCCAGGG (SEQ ID NO: 157). The amino acid sequence of cyno TR-2 (long) was MVHATSPLLLLLLLSLALVAPGLSARKC-SLTGKWTNDLG SNMTIGAVNSKGEFTGTYT-TAVTATSNEIKESPLHGTQNTINKRTQPTFGFTV NWKFSESTTVFTGQCFIDRNGKEVLKTM-WLLRSSVNDIGDDWKATRVGINIF TRLRTQKEQL-LASLAPITRQSLDPQRRM-PQQKRSSPTEGLCPPGHHISEDS RDCISCKYGQDYSTHWNDFLFCLRCT-KCDSGEVEVSSCTTTRNTVCQCEE GTFREEDSPE-ICRKCRTGCPRGMVKVKDCTPWS-DIECVHKESGTKHTGEV PAVEKTVTTSPGTPAS (SEQ ID NO: 83).

The polynucleotide encoding amino acids 1 to 85 of mature cyno TR-2 was amplified using the forward primer GTTAGTAAGCTTGGCTCCA ATCACCCGAC (SEQ ID NO: 155) and the reverse primer GTATGAGGGATCCTC ACTGACA-CACCGTGTTTCTGG (SEQ ID NO: 158). The amino acid sequence of cyno 1-85 was MVHATSPLLLLLLLSLAL-VAPGLSARKCSLTGKWTNDLGSNMT IGAVN-SKGEFTGTYTTAVTATSNEIKESPLH-GTQNTINKRTQPTFGFTVNWK FSESTTVFTGQCFIDRNGKEVLKTMWLL-RSSVNDIGDDWKATRVGINIFTRL RTQKEQL-LASLAPITRQSLDPQR-RAAPQQKRSSPTEGLCPPGHHISEDSRD CISCKYGQDYSTHWNDFLFCLRCTKCDS-GEVEVSSCTTTRNTVCQ (SEQ ID NO: 84).

The polynucleotide encoding amino acids 16 to 85 of mature cyno TR-2 was amplified using the forward primer GTATGGAAGCTTGCCACAA CAAAAGAGATCCAGC (SEQ ID NO: 159) and the reverse primer GTATGAGGGATCCTCACTGACACACCGTGTTTCTGG (SEQ ID NO: 158). The amino acid sequence of cyno 16-85 was MVHATSPLLLLLLLSLALVAPGLSARKCSLTGKW TNDLGSNMTIGAVNSKGEFTGTYT-TAVTATSNEIKESPLHGTQNTINKRTQP TFGFTVN-WKFSESTTVFTGQCFIDRNGKEVLKTM-WLLRSSVNDIGDDWKAT RVGINIFTRLRTQKEQL-LASLPQQKRSSPIEGLCPPGHHISEDSRDCISCKYG QDYSTHWNDFLFCLRCTKCDSGEVEVSS-CTTTRNTVCQ (SEQ ID NO: 85).

Four N-avidin-fused chimeras were also made using different portions of human TR-2 and cyno TR-2, as shown in FIG. 25. Each chimera was constructed by preparing two PCR products with overlapping ends that were then amplified together using the same 5' and 3' primers. To form each of the chimeras, the amplified polynucleotide was then subcloned into the pCEP4 vector (Invitrogen) containing the chicken avidin sequence that is described above. An alignment of the human, cyno (short), and mouse TR-2 sequences is shown in FIG. 26.

Cyno/human chimera #1 was prepared by amplifying a region of mature cyno TR-2 corresponding to amino acids 1-16 using the forward primer GTTAGTAAGCTTGGCTC-CAATCACCCGAC (SEQ ID NO: 155) and the reverse primer GGACCTCTTTTGTTGTGGAGCCGCTCT-TCGCTGG (SEQ ID NO: 159) and amplifying a region of mature human TR-2 corresponding to amino acids 17-85 using the forward primer CAGCGAAGAGCGGCTCCA-CAACAAAAG AGGTCCAG (SEQ ID NO: 160) and the reverse primer GGTAGTGGATCCTCACT GACACACT-GTGTTTCTGG (SEQ ID NO: 148). Overlapping PCR of the cyno and human TR-2 fragments was performed using the forward primer for the cyno TR-2 amino acids 1-16 fragment, above (SEQ ID NO: 155) and the reverse primer for the human TR-2 amino acids 17-85 fragment, above (SEQ ID NO: 148). The amino acid sequence for cyno/human chimera #1 was MVHATSPLLLLLLLSLALVAPGLSARKC-SLTGKWT NDLGSNMTIGAVNSKGEFTGTYT-TAVTATSNEIKESPLHGTQNTINKRTQPT FGFTVN-WKFSESTTVFTGQCFIDRNGKEVLKTMWLLRSSVN DIGDDWKATR VGINIFTRLRTQKEQL-LASLAPITRQSLDPQRRAAPQQKRSSPSEGLCPPGH HISEDGRDCISCKYGQDYSTHWNDLLF-CLRCTRCDSGEVELSPCTTTRNTV CQ (SEQ ID NO: 86).

Cyno/human chimera #2 was prepared by amplifying a region of mature cyno TR-2 corresponding to amino acids 1-16 using the forward primer GTTAGTAAGCTTGGCTC-CAATCACCCGAC (SEQ ID NO: 155) and the reverse primer GGACCTCTTTTGTTGTGGAGCCGCTCT-TCGCTGG (SEQ ID NO: 159) and amplifying a region of mature human TR-2 corresponding to amino acids 17-154 using the forward primer CAGCGAAGAGCGGCTCCA-CAACAAAA GAGGTCCAG (SEQ ID NO: 160) and the reverse primer GATTAGGGATCCTCAA GAGGCAG-GAGTCCCTGG (SEQ ID NO: 146). Overlapping PCR of the cyno and human TR-2 fragments was performed using the forward primer for the cyno TR-2 amino acids 1-16 fragment, above (SEQ ID NO: 155) and the reverse primer for the human TR-2 amino acids 17-154 fragment, above (SEQ ID NO: 146). The amino acid sequence for cyno/human chimera #2 was MVHATSPLLLLLLLSLALVAPGLSARKC-SLTGKW TNDLGSNMTIGAVNSKGEFTGTYT-TAVTATSNEIKESPLHGTQNTINKRTQP TFGFTVN-WKFSESTTVFTGQCFIDRNGKEVLKTMWLLRSSV NDIGDDWKAT RVGINIFTRLRTQKEQL-LASLAPITRQSLDPQRRAAPQQKRSSPSEGLCPPG HHISEDGRDYISCKYGQDYSTHWNDLLF-CLRCTRCDSGEVELSPCTTTRNT VCQCEEGTFREED-SPEMCRKCRTGCPRGMVKVGDCTPWS-DIECVHKESG TKHSGEAPAVEETVTSSPGTPAS (SEQ ID NO: 87).

Cyno/human chimera #3 was prepared by amplifying a region of mature human TR-2 corresponding to amino acids 1-16 using the forward primer GTAAGCAAGCTTG- GCTCTGATCACCCAACAAGA (SEQ ID NO: 145) and the reverse primer GGATCTCTTTTGTTGTGGGGC-CGCTCTCTGCTGG G (SEQ ID NO: 161) and amplifying a region of mature cynoTR-2 corresponding to amino acids 17-85 using the forward primer CAGCAGAGAGCGGC-CCCACA ACAAAAGAGATCCAGC (SEQ ID NO: 162) and the reverse primer GTATGAGG GATCCTCACTGACA-CACCGTGTTTCTGG (SEQ ID NO: 158). Overlapping PCR of the cyno and human TR-2 fragments was performed using the forward primer for the human TR-2 amino acids 1-16 fragment, above (SEQ ID NO: 145) and the reverse primer for the cyno TR-2 amino acids 17-85 fragment, above (SEQ ID NO: 158). The amino acid sequence for cyno/human chimera #3 was MVHATSPLLLLLLLLSLALVAPGLSAR KCSLTGKWTNDLGSNMTIGAVNSKGEFT-GTYTTAVTATSNEIKESPLHGTQN TINKRTQPTFG-FTVNWKFSESTTVFTGQCFIDRNGKEV-LKTMWLLRSSVNDI GDDWKATRVGINIFTRLRTQKEQL-LASLALITQQDLAPQQRAAPQQKRSSPT EGLCPPGH-HISEDSRDCISCKYGQDYSTHWNDFLF-CLRCTKCDSGEVEVSS CTTTRNTVCQ (SEQ ID NO: 88).

Cyno/human chimera #4 was prepared by amplifying a region of mature human TR-2 corresponding to amino acids 1-16 using the forward primer GTAAGCAAGCTTG-GCTCTGATCACCCAACAAGA (SEQ ID NO: 145) and the reverse primer GGATCTCTTTTGTTGTGGGGC-CGCTCTCTGCTGG G (SEQ ID NO: 161) and amplifying a region of mature cyno TR-2 corresponding to amino acids 17-154 using the forward primer CAGCAGAGAGCGGC-CCCACA ACAAAAGAGATCCAGC (SEQ ID NO: 162) and the reverse primer GTAGTTGGA TCCTCAAGAAG-CAGGAGTCCCAGGG (SEQ ID NO: 157). Overlapping PCR of the cyno and human TR-2 fragments was performed using the forward primer for the human TR-2 amino acids 1-16 fragment, above (SEQ ID NO: 145) and the reverse primer for the cyno TR-2 amino acids 17-154 fragment, above (SEQ ID NO: 157). The amino acid sequence for cyno/human chimera #4 was MVHATSPLLLLLLLSLAL-VAPGLSAR KCSLTGKWTNDLGSNMTIGAVN-SKGEFTGTYTTAVTATSNEIKESPLHGTQN TINKRTQPTFGFTVNWKFSESTTVFT-GQCFIDRNGKEVLKTMWLLRSSVNDI GDDWKATRVGINIFTRLRTQKEQL-LASLALITQQDLAPQQRAAPQQKRSSPT EGLCPPGH-HISEDSRDCISCKYGQDYSTHWNDFLF-CLRCTKCDSGEVEVSS CTTTRNTVCQCEEGTFREEDSPE-ICRKCRTGCPRGMVKVKDCTPWSDIECV HKESGT-KHTGEVPAVEKTVTTSPGTPAS (SEQ ID NO: 89). Four additional modified TR-2 proteins were constructed by replacing short regions of human TR-2 with the corresponding mouse TR-2 sequence, in the context of an N-avidin fusion. Human/mouse TR-2 #1 comprised the mouse TR-2 sequence from amino acids 1-22 and the human TR-2 sequence from amino acids 23-150. Human/mouse TR-2 #2 comprised the human TR-2 sequence from amino acids 1-28 and 35-150 and the mouse TR-2 sequence from amino acids 29-34. Human/mouse TR-2 #3 comprised the human TR-2 sequence from amino acids 1-53 and 60-150 and the mouse TR-2 sequence from amino acids 54-59. Human/mouse TR-2 #4 comprised the human TR-2 sequence from amino acids 1-66 and 76-150 and the mouse TR-2 sequence from amino acids 67-75. To form each of the modified proteins, the amplified polynucleotide was then subcloned into the pCEP4 vector (Invitrogen) containing the chicken avidin sequence that is described above.

Human/mouse TR-2 #1 was prepared by amplifying a region of mature human TR-2 corresponding to amino acids 23-150 using the forward primer CAGCGGCCGGAG-GAGAGCCCCTCAGAGGGATTGT (SEQ ID NO: 163) and the reverse primer GATTGAGGATCCCTAAGAGGCAG-GAGTCCCTGG (SEQ ID NO: 164) and amplifying a region of mature mouse TR-2 corresponding to amino acids 1-22 using the forward primer TGAATGAAGCTTGGTTC-CAGTA ACAGCTAACCCA (SEQ ID NO: 165) and the reverse primer TCCCTCTGAGGG GCTCTCCTCCGGC-CGCTGTAG (SEQ ID NO: 166). Overlapping PCR of the human and mouse TR-2 fragments was performed using the forward primer for the mouse TR-2 amino acids 1-22 fragment, above (SEQ ID NO: 165) and the reverse primer for the human TR-2 amino acids 23-150 fragment, above (SEQ ID NO: 164). The amino acid sequence for human/mouse TR-2 #1 was MVHATSPLLLLLLLSLALV APGLSARKCSLT-GKWTNDLGSNMTIGAVNSKGEFTGTYT-TAVTATSNEIKES PLHGTQNTINKRTQPTFGFTVN-WKFSESTTVFTGQCFIDRNGKEVLKTMWL LRSSVNDIGDDWKATRVGINIFTRL-RTQKEQLLASLVPVTANPAHNRPAGLQ RPEESPSEG-LCPPGHHISEDGRDCISCKYGQDYSTH-WNDLLFCLRCTRCDS GEVELSPCTTTRNTVCQCEEGTFREED-SPEMCRKCRTGCPRGMVKVGDCT PWSDIECVHKES-GTKHSGEAPAVEETVTSSPGTPAS (SEQ ID NO: 90).

Human/mouse TR-2 #2 was prepared by amplifying a region of mature human TR-2 corresponding to amino acids 1-28 using the forward primer GTAAGCAAGCTTG-GCTCTGATCACCCAACAAGA (SEQ ID NO: 145) and the reverse primer CAGGTACTGGCCTGCTAGACACAATC-CCTCTGAGGGG (SEQ ID NO: 167), amplifying a region of mature human TR-2 corresponding to amino acids 35-150 using the forward primer CTAGCAGGCCAGTACCTGT-CAG AAGACGGTAGAGATTGC (SEQ ID NO: 168), and the reverse primer GATTGAG GATCCCTAAGAGGCAG-GAGTCCCTGG (SEQ ID NO: 164) and amplifying a region of mature mouse TR-2 corresponding to amino acids 29-34 using the forward primer CAGGTACTGGCCTGCTAGA-CACAATCCCTCTGAGGGG (SEQ ID NO: 169) and the reverse primer CTAGCAGGCCAGTACCTGTCAGAA-GACGG TAGAGATTGC (SEQ ID NO: 170). Overlapping PCR of the human and mouse TR-2 fragments was performed using the forward primer for the human TR-2 amino acids 1-28 fragment, above (SEQ ID NO: 145) and the reverse primer for the human TR-2 amino acids 35-150 fragment, above (SEQ ID NO: 170). The amino acid sequence for human/mouse TR-2 #2 was MVHATSPLLLLLLLSLAL-VAPGLSARKCSLTGKW TNDLGSNMTIGAVN-SKGEFTGTYTTAVTATSNEIKESPLHGTQNTINKRTQP TF GFTVNWKFSESTTVFTGQCFIDRNGKEV-LKTMWLLRSSVNDIGDDWKATRV GINIFTRL-RTQKEQLLASLALITQQD-LAPQQRAAPQQKRSSPSEGLCLAGQY LSEDGRDCISCKYGQDYSTHWNDLLFCL-RCTRCDSGEVELSPCTTTRNTVC QCEEGTFREED-SPEMCRKCRTGCPRGMVKVGDCTPWS-DIECVHKESGTK HSGEAPAVEETVTSSPGTPAS (SEQ ID NO: 91).

Human/mouse TR-2 #3 was prepared by amplifying a region of mature human TR-2 corresponding to amino acids 1-53 using the forward primer GTAAGCAAGCTTG-GCTCTGATCACCCAACAAGA (SEQ ID NO: 145) and the reverse primer TGAATCCAGAGAATGGTTGGAGT-GAGTGCTATAGTCCTG TC (SEQ ID NO: 171), and amplifying a region of mature human TR-2 corresponding to amino acids 60-154 using the forward primer TCCAACCAT-TCTCTGGATTCA TGCTTGCGCTGCACCAGG (SEQ ID NO: 172) and the reverse primer GATTG AGGATCCCTAA-GAGGCAGGAGTCCCTGG (SEQ ID NO: 173) The above primers include nucleotides encoding mouse TR-2 corresponding to amino acids 54-59. Overlapping PCR of the human and mouse TR-2 fragments was performed using the forward primer for the human TR-2 amino acids 1-53 fragment, above (SEQ ID NO: 145) and the reverse primer for the human TR-2 amino acids 60-154 fragment, above (SEQ ID NO: 173). The amino acid sequence for human/mouse TR-2 #3 was MVHATSPLLLLLLLSLALVAPGLSARKC-SLTGKWT NDLGSNMTIGAVNSKGEFTGTYT-TAVTATSNEIKESPLHGTQNTINKRTQPT FGFTVN-WKFSESTTVFTGQCFIDRNGKEVLKTMWLLRSSVN DIGDDWKATR VGINIFTRLRTQKEQLLASLALITQQD-LAPQQRAAPQQKRSSPSEGLCPPGH HISEDGRD-CISCKYGQDYSTHWNDLLFCLRCTRCDS-GEVELSPCTTTRNTV CQCEEGTFREEDSPEMCRKCRTGCPRGM-VKVGDCTPWSDIECVHKESGT KHS-GEAPAVEETVTSSPGTPAS (SEQ ID NO: 92).

Human/mouse chimera #4 was prepared by amplifying a region of mature human TR-2 corresponding to amino acids 1-66 using the forward primer GTAAGCAAGCTTG-GCTCTGATCACCCAACAAGA (SEQ ID NO: 145) and the reverse primer TCGGGTTTCTACGACTTTATCTTCCT-TACACCTGG TGCAGCGCAAG (SEQ ID NO: 174), and amplifying a region of mature human TR-2 corresponding to amino acids 76-154 using the forward primer AAGGAAG ATAAAGTCGTAGAAACCCGATGCACCAC-GACCAGAAAC AC (SEQ ID NO: 175) and the reverse primer GATTGAGGATCCCTAAGAGGCA GGAGTC-CCTGG (SEQ ID NO: 176). The above primers include nucleotides encoding mouse TR-2 corresponding to amino acids 67-75. Overlapping PCR of the human and mouse TR-2 fragments was performed using the forward primer for the human TR-2 amino acids 1-66 fragment, above (SEQ ID NO: 145) and the reverse primer for the human TR-2 amino acids 76-154 fragment, above (SEQ ID NO: 176). The amino acid sequence for human/mouse TR-2 #4 was MVHATSPLLLLLLLSLALVAPGL SARKCSLTGKWT-NDLGSNMTIGAVNSKGEFTGTYT-TAVTATSNEIKESPLHG TQNTINKRTQPTFGFTVN-WKFSESTTVFTGQCFIDRNGKEVLKTMWLLRSS VNDIGDDWKATRVGINIFTRLRTQKEQL-LASLALITQQDLAPQQRMPQQKR SSPSEGLCPPGH-HISEDGRDCISCKYGQDYSTHSNHSLD-SCLRCTRCDSGE VELSPCTTTRNTVCQCEEGTFREED-SPEMCRKCRTGCPRGMVKVGDCTP WSDIECVHKES-GTKHSGEAPAVEETVTSSPGTPAS (SEQ ID NO: 93).

Expression of avidin fusion proteins was performed by transient transfection of human 293 T adherent cells in vented T75 tissue culture flasks. Cells were grown and maintained in DMEM with 10 % dialyzed FBS and 1 × pen-step-glutamine at 37° C. with 5 % $CO_2$. To prepare for transfection, approximately $3 \times 10^6$ 293 T cells were inoculated into each of a series of clean T75 flasks containing 15 ml growth medium, and all of the flasks were grown overnight for approximately 20 hours. Each of the pCEP4 -Avidin(N)-TR-2 constructs were transfected into different cells as follows. 15 µg DNA was mixed with 75 µL Lipofectamine 2000 (Invitrogen) in the presence of Opti-MEM medium (Invitrogen) to form a DNA-Lipofectamine complex. The complex was incubated for 20 minutes. During that incubation period, the growth medium was aspirated from the T75 flasks and replaced with 15 mL Opti-MEM. Following incubation, each transfection complex was inoculated into a different flask and incubated at 37° C. for 4 to 5 hours. At the end of the incubation period, the Opti-MEM medium in each flask was replaced with fresh growth medium. Approximately 48 hours post-transfection, the conditioned media was harvested and transferred to 50 ml tubes (Falcon). The tubes were centrifuged at 2000 ×g for 10 minutes at 4° C. to remove cells and debris, and subsequently transferred to a clean 50 mL tube. A control flask lacking transfected DNA was also made following the same protocol, yielding negative control conditioned media for binding experiments.

The concentration of each N-avidin-TR-2 fusion protein was determined using a quantitative FACS-based assay. The avidin fusion proteins were captured on 6.7 µm biotin polystyrene beads (Spherotech, Inc.). Two samples were prepared for each fusion protein: 5 µL (approximately $3.5 \times 10^5$) bead suspension plus 20 µL of 1× conditioned media, and 5 µL bead suspension plus 200 µL of 1× conditioned media. All samples were incubated for 1 hour at room temperature with rotation. Conditioned media was removed from each sample by centrifugation and washing with PBS containing 0.5 % BSA (BPBS). The avidin beads were stained with 200 µL of a 0.5 µg/mL solution of a goat FITC-labeled anti-avidin antibody (Vector Labs, Burlingame, Calif.) in BPBS. The reaction was allowed to proceed at room temperature for 45 minutes with the reaction tubes covered by foil. Following incubation, the beads were collected again by centrifugation and washing with BPBS, and resuspended for analysis in 0.5 ml BPBS. The FITC fluorescence was detected using a FACScan (Becton Dickinson Bioscience). The signal was converted to protein mass using a standard curve derived with recombinant avidin.

Figure 24:
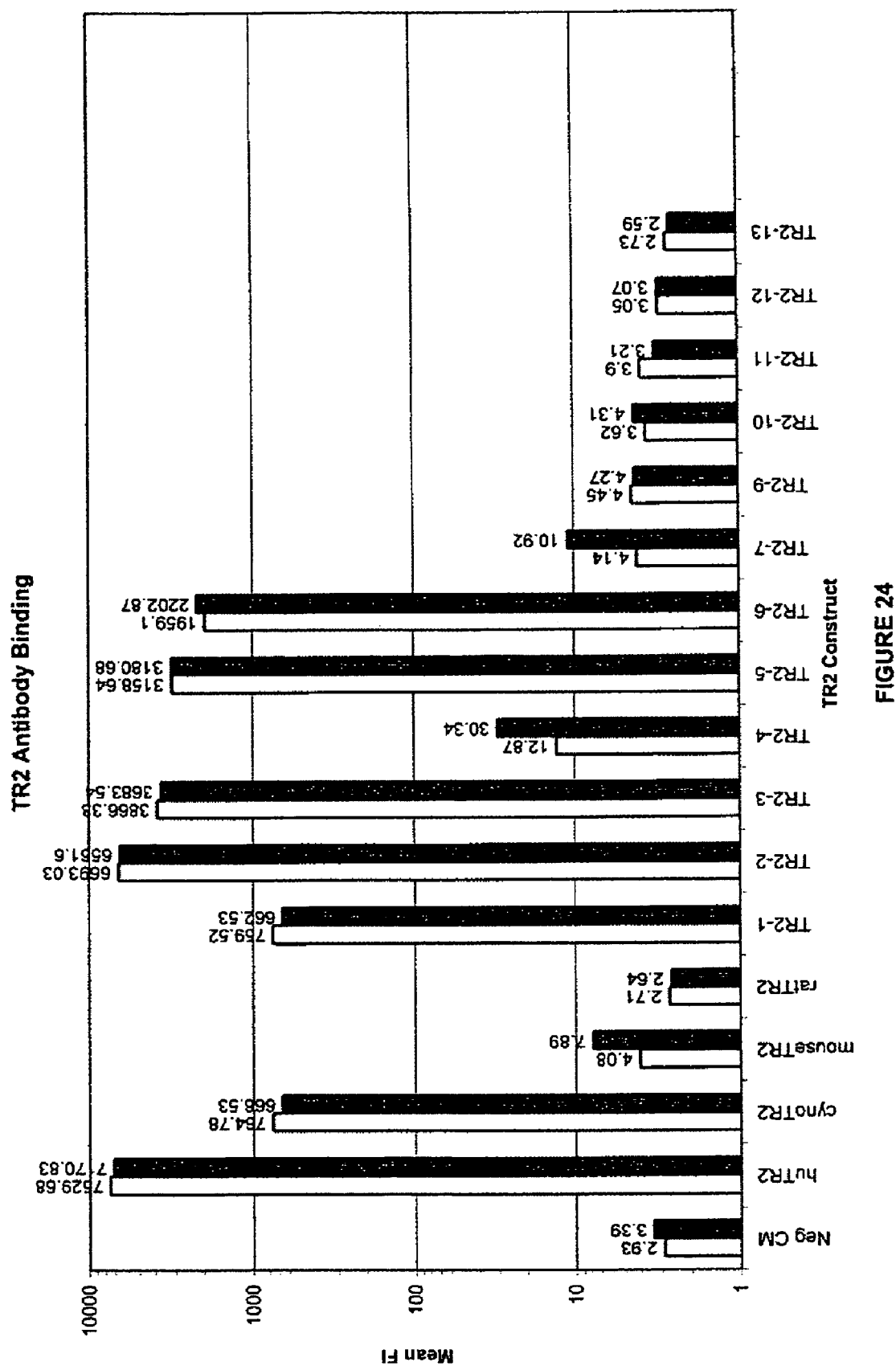
FIG. 24 is a bar graph showing the binding of certain human anti-TR-2 antibodies to the N-avidin-TR-2 truncations according to work described in Example 6.

The binding of two human anti-TR-2 antibodies to each of the human TR-2 truncations, to human TR-2, and to TR-2 from cynomolgus monkey was assessed. The binding assay was performed as follows. Biotin beads, described above, were loaded with approximately 100 ng of one of the N-Avidin TR-2 fusion proteins per $3.5 \times 10^5$ beads and brought to volume with growth medium. The beads were mixed with 1 µg of FITC-conjugated human anti-TR-2 monoclonal antibody in 0.2 mL BPBS. After incubation for 1 hour at room temperature, 3 mL BPBS was added and the antibody-bead complexes were collected by centrifugation for 5 minutes at 750 ×g. The pellet was washed in 3 mL BPBS. The antibody bound to the avidin-bead complexes was detected by FACS analysis. The mean fluorescent intensity was recorded for each sample. Binding of those antibodies to conditioned media lacking TR-2 was used as a negative control ("Neg CM"). The results are shown in FIG. 24.

The observed binding patterns of the two antibodies were similar. The strongest observed binding was to the positive control, human TR-2, with an average fluorescent intensity of 7349. Observed binding of the antibodies (as measured in fluorescent intensity) to truncation TR-2-2 was 6561-6693, to truncations TR-2-3 and TR-2-5 was 3158-3866, to truncation TR-2-6 was 1959-2202, and to truncation TR-2-1 was 662-759. Binding of the antibodies to full-length TR-2 from cynomolgus monkey (as measured in fluorescent intensity) was 666-764. The antibodies did not bind to mouse or rat TR-2, or to truncations TR-2-4, TR-2-7, TR-2-9, TR-2-10, TR-2-11, TR-2-12, or TR-2-13, as determined by the fact that the binding was similar to the background for the experiment.

TR-2-1 is a C-terminal truncation of TR-2 after amino acid 43, and TR-2-2, -3, -5, and -6 all include at least amino acids 16 to 85. Binding occurred when the entire region from amino acids 1 to 85 was present (see results for TR-2-2). The addition of amino acids 86 to 126 decreased binding by approximately two-fold (compare results for TR-2-2 to TR-2-3). The absence of amino acids 1 to 15 from the N-terminus of TR-2 in TR-2-2 decreased binding by approximately two-fold (compare results for TR-2-2 to TR-2-5). The simultaneous absence of amino acids 1 to 15 and the addition of amino acids 86 to 126 decreased binding by approximately three-fold (compare results for TR-2-2 to TR-2-6). Elimination of residues 44 to 85 (TR-2-1) reduced binding to about 11% of that observed to TR-2-2. Those results indicate that one or more residues in the regions of amino acids 1 to 15 (SEQ ID NO: 94; ALITQQDLAPQQRAA) and 44 to 85 (SEQ ID NO: 95; CKYGQDYSTHWNDLL FCLRCTRCDSGEVE LSPCTTTRNTVCQ) are important for binding of those two human anti-TR-2 antibodies and human TR-2.

The binding of a human anti-TR-2 antibody to each of the cyno TR-2 truncations, to human/cyno chimeras, and to human TR-2 comprising certain mouse TR-2 domains was also assessed. The anti-TR-2 antibody bound strongly to full-length human TR-2 (fluorescent intensity ("FI") of 5681). The binding of the anti-TR-2 antibody to the full-length long version of cyno TR-2 was about five-fold reduced (FI of 1573) from that to full-length human TR-2. Only background levels of binding were observed to the full-length short version of cyno TR-2 (FI of 209) and to cyno TR-2 truncations 17-154 (FI of 51), cyno 1-85 (FI of 11), and cyno 17-85 (FI of 8).

Figure 27:
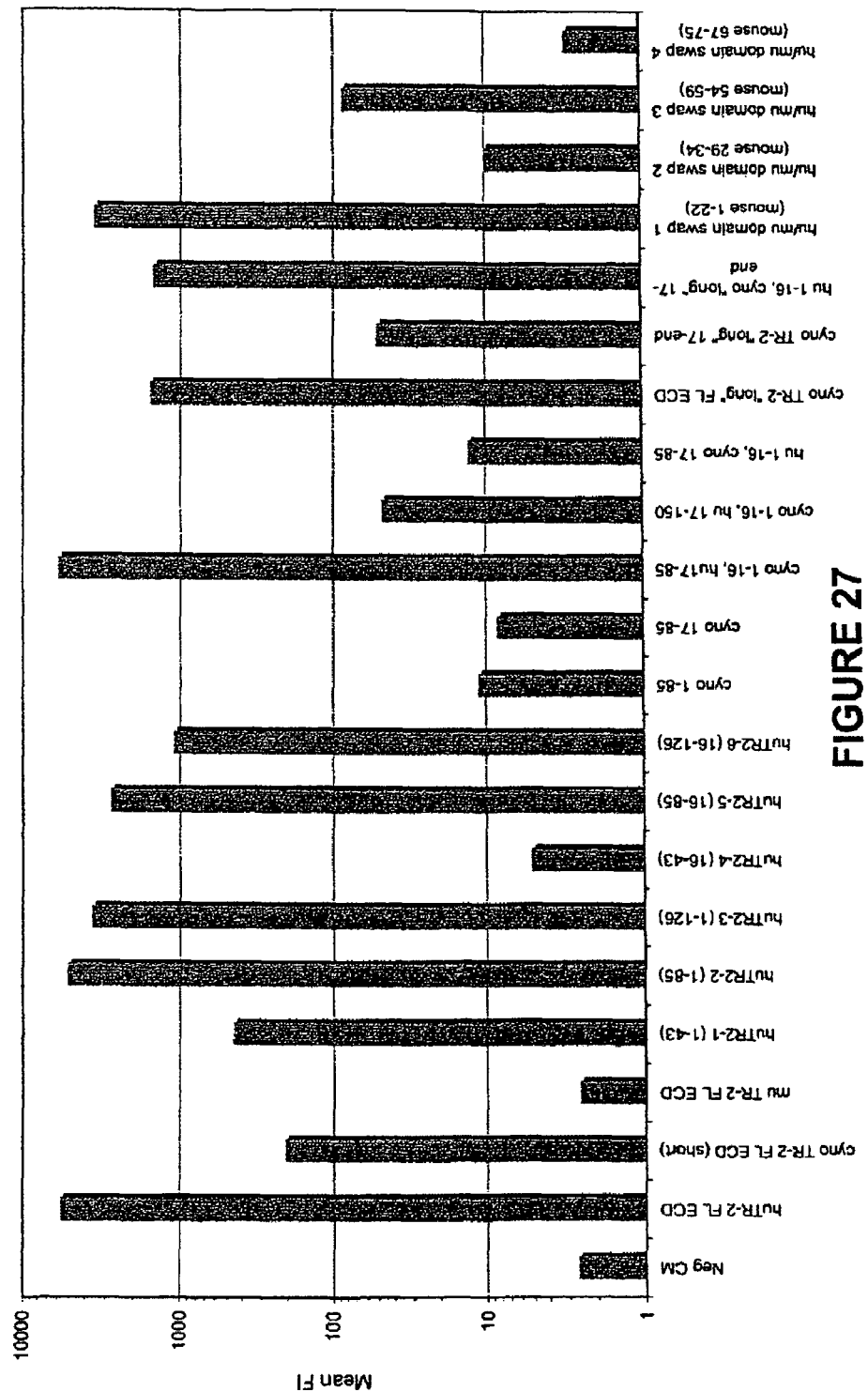
FIG. 27 is a bar graph showing the binding of certain human anti-TR-2 antibodies to the N-avidin-TR-2 truncations, chimeras, and domain replacements according to work described in Example 6.

The binding of certain human anti-TR-2 antibodies to cyno/human TR-2 chimeras was also assessed (see FIG. 27). Observed binding (FI) of the antibodies to the four chimeras was as follows: cyno/human chimera #1; FI of 5977; cyno/human chimera #2; FI of 47; cyno/human chimera #3; FI of 12; cyno/human chimera #4; FI of 1507. As above, observed binding of the antibodies to full-length human TR-2 was 5681, while binding of the antibodies to full-length cyno TR-2 was 1573 (long form) and 209 (short form).

Because the antibody binding to cyno/human chimera #1 was similar to that to the truncation TR-2-5, replacement of amino acids 1-16 with the corresponding cyno sequence apparently did not affect antibody binding in the context of human amino acids 17-85. However, replacement of amino acids 1-16 with the corresponding cyno sequence in the context of the full-length human TR-2 (cyno/human #2) significantly abrogated binding, confirming that at least one amino acid in the region from 1-16 forms part of the epitope. Binding to cyno/human chimeras #3, and #4 was significantly attenuated from that to full-length human TR-2, suggesting that amino acids 17-85 of the human sequence are important for binding. Overall, one or more of the amino acids in the region of 1-85 of the human sequence (SEQ ID NO: 96; ALITQQDLAPQQRAAPQQ KRSSPSEGLCPPGHHISEDGRDCISCKYGQDYSTHWNDLLFCLRCTRCDSG EVELSPCTTTRNTVCQ) are involved in epitope binding. Similarly, replacement of various human sequences in the region of amino acids 1-85 with the corresponding mouse sequence significantly attenuates antibody binding (see FIG. 27), further confirming that one or more amino acids in that region are involved in epitope binding.

We claim:

1. An isolated antibody comprising a heavy chain and a light chain that binds TRAIL Receptor-2 (TR-2), wherein the heavy chain comprises CDR1, CDR2, and CDR3 of SEQ ID NO: 2, and the light chain comprises CDR1, CDR2, and CDR3 of SEQ ID NO: 36.

2. An isolated antibody comprising a heavy chain and a light chain that binds TR-2, wherein the heavy chain comprises CDR1, CDR2, and CDR3 of SEQ ID NO: 4 and the light chain comprises CDR1, CDR2, and CDR3 of SEQ ID NO: 38.

3. An isolated antibody comprising a heavy chain and a light chain that binds TR-2, wherein the heavy chain comprises CDR1, CDR2, and CDR3 of SEQ ID NO: 6 and the light chain comprises CDR1, CDR2, and CDR3 of SEQ ID NO: 40.

4. An isolated antibody comprising a heavy chain and a light chain that binds TR-2, wherein the heavy chain comprises CDR1, CDR2, and CDR3 of SEQ ID NO: 8 and the light chain comprises CDR1, CDR2, and CDR3 of SEQ ID NO: 42.

5. An isolated antibody comprising a heavy chain and a light chain that binds TR-2, wherein the heavy chain comprises CDR1, CDR2, and CDR3 of SEQ ID NO: 10 and the light chain comprises CDR1, CDR2, and CDR3 of SEQ ID NO: 44.

6. An isolated antibody comprising a heavy chain and a light chain that binds TR-2, wherein the heavy chain comprises CDR1, CDR2, and CDR3 of SEQ ID NO: 12 and the light chain comprises CDR1, CDR2, and CDR3 of SEQ ID NO: 46.

7. An isolated antibody comprising a heavy chain and a light chain that binds TR-2, wherein the heavy chain comprises CDR1, CDR2, and CDR3 of SEQ ID NO: 14 and the light chain comprises CDR1, CDR2, and CDR3 of SEQ ID NO: 48.

8. An isolated antibody comprising a heavy chain and a light chain that binds TR-2, wherein the heavy chain comprises CDR1, CDR2, and CDR3 of SEQ ID NO: 16 and the light chain comprises CDR1, CDR2, and CDR3 of SEQ ID NO: 50.

9. An isolated antibody comprising a heavy chain and a light chain that binds TR-2, wherein the heavy chain comprises CDR1, CDR2, and CDR3 of SEQ ID NO: 18 and the light chain comprises CDR1, CDR2, and CDR3 of SEQ ID NO: 52.

10. An isolated antibody comprising a heavy chain and a light chain that binds TR-2, wherein the heavy chain comprises CDR1, CDR2, and CDR3 of SEQ ID NO: 20 and the light chain comprises CDR1, CDR2, and CDR3 of SEQ ID NO: 54.

11. An isolated antibody comprising a heavy chain and a light chain that binds TR-2, wherein the heavy chain comprises CDR1, CDR2, and CDR3 of SEQ ID NO: 22 and the light chain comprises CDR1, CDR2, and CDR3 of SEQ ID NO: 56.

12. An isolated antibody comprising a heavy chain and a light chain that binds TR-2, wherein the heavy chain comprises CDR1, CDR2, and CDR3 of SEQ ID NO: 24 and the light chain comprises CDR1, CDR2, and CDR3 of SEQ ID NO: 58.

13. An isolated antibody comprising a heavy chain and a light chain that binds TR-2, wherein the heavy chain comprises CDR1, CDR2, and CDR3 of SEQ ID NO: 26 and the light chain comprises CDR1, CDR2, and CDR3 of SEQ ID NO: 60.

14. An isolated antibody comprising a heavy chain and a light chain that binds TR-2, wherein the heavy chain comprises CDR1, CDR2, and CDR3 of SEQ ID NO: 28 and the light chain comprises CDR1, CDR2, and CDR3 of SEQ ID NO: 62.

15. An isolated antibody comprising a heavy chain and a light chain that binds TR-2, wherein the heavy chain comprises CDR1, CDR2, and CDR3 of SEQ ID NO: 30 and the light chain comprises CDR1, CDR2, and CDR3 of SEQ ID NO: 64.

16. An isolated antibody comprising a heavy chain and a light chain that binds TR-2, wherein the heavy chain comprises CDR1, CDR2, and CDR3 of SEQ ID NO: 32 and the light chain comprises CDR1, CDR2, and CDR3 of SEQ ID NO: 66.

17. An isolated antibody comprising a heavy chain and a light chain that binds TR-2, wherein the heavy chain comprises CDR1, CDR2, and CDR3 of SEQ ID NO: 34 and the light chain comprises CDR1, CDR2, and CDR3 of SEQ ID NO: 68.

18. An isolated antibody comprising a heavy chain and a light chain that binds TR-2, wherein the heavy chain comprises the amino acid sequence of SEQ ID NO: 2, and the light chain comprises the amino acid sequence of SEQ ID NO: 36.

19. An isolated antibody comprising a heavy chain and a light chain that binds TR-2, wherein the heavy chain comprises the amino acid sequence of SEQ ID NO: 4 and the light chain comprises the amino acid sequence of SEQ ID NO: 38.

20. An isolated antibody comprising a heavy chain and a light chain that binds TR-2, wherein the heavy chain comprises the amino acid sequence of SEQ ID NO: 6 and the light chain comprises the amino acid sequence of SEQ ID NO: 40.

21. An isolated antibody comprising a heavy chain and a light chain that binds TR-2, wherein the heavy chain comprises the amino acid sequence of SEQ ID NO: 8 and the light chain comprises the amino acid sequence of SEQ ID NO: 42.

22. An isolated antibody comprising a heavy chain and a light chain that binds TR-2, wherein the heavy chain comprises the amino acid sequence of SEQ ID NO: 10 and the light chain comprises the amino acid sequence of SEQ ID NO: 44.

23. An isolated antibody comprising a heavy chain and a light chain that binds TR-2, wherein the heavy chain comprises the amino acid sequence of SEQ ID NO: 12 and the light chain comprises the amino acid sequence of SEQ ID NO: 46.

24. An isolated antibody comprising a heavy chain and a light chain that binds TR-2, wherein the heavy chain comprises the amino acid sequence of SEQ ID NO: 14 and the light chain comprises the amino acid sequence of SEQ ID NO: 48.

25. An isolated antibody comprising a heavy chain and a light chain that binds TR-2, wherein the heavy chain comprises the amino acid sequence of SEQ ID NO: 16 and the light chain comprises the amino acid sequence of SEQ ID NO: 50.

26. An isolated antibody comprising a heavy chain and a light chain that binds TR-2, wherein the heavy chain comprises the amino acid sequence of SEQ ID NO: 18 and the light chain comprises the amino acid sequence of SEQ ID NO: 52.

27. An isolated antibody comprising a heavy chain and a light chain that binds TR-2, wherein the heavy chain comprises the amino acid sequence of SEQ ID NO: 20 and the light chain comprises the amino acid sequence of SEQ ID NO: 54.

28. An isolated antibody comprising a heavy chain and a light chain that binds TR-2, wherein the heavy chain comprises the amino acid sequence of SEQ ID NO: 22 and the light chain comprises the amino acid sequence of SEQ ID NO: 56.

29. An isolated antibody comprising a heavy chain and a light chain that binds TR-2, wherein the heavy chain comprises the amino acid sequence of SEQ ID NO: 24 and the light chain comprises the amino acid sequence of SEQ ID NO: 58.

30. An isolated antibody comprising a heavy chain and a light chain that binds TR-2, wherein the heavy chain comprises the amino acid sequence of SEQ ID NO: 26 and the light chain comprises the amino acid sequence of SEQ ID NO: 60.

31. An isolated antibody comprising a heavy chain and a light chain that binds TR-2, wherein the heavy chain comprises the amino acid sequence of SEQ ID NO: 28 and the light chain comprises the amino acid sequence of SEQ ID NO: 62.

32. An isolated antibody comprising a heavy chain and a light chain that binds TR-2, wherein the heavy chain comprises amino acid sequence of SEQ ID NO: 30 and the light chain comprises amino acid sequence of SEQ ID NO: 64.

33. An isolated antibody comprising a heavy chain and a light chain that binds TR-2, wherein the heavy chain comprises the amino acid sequence of SEQ ID NO: 32 and the light chain comprises the amino acid sequence of SEQ ID NO: 66.

34. An isolated antibody comprising a heavy chain and a light chain that binds TR-2, wherein the heavy chain comprises the amino acid sequence of SEQ ID NO: 34 and the light chain comprises the amino acid sequence of SEQ ID NO: 68.

35. The isolated antibody of any of claims 1, 2, 9, 10, 15, 16, 17, 18, 19, 26, 27, 32, 33, and 34, wherein the antibody is a fully human antibody.

36. The isolated antibody of any of claims 1, 2, 9, 10, 15, 16, 17, 18, 19, 26, 27, 32, 33, and 34, wherein the antibody is a Fab, a Fab', a F(ab')2, an Fv, or a single-chain Fv.

37. A pharmaceutical composition comprising the isolated antibody of any of claims 1, 2, 9, 10, 15, 16, 17, 18, 19, 26, 27, 32, 33, and 34 a pharmaceutically acceptable carrier.

* * * * *